(12) United States Patent
Stevens et al.

(10) Patent No.: US 6,300,363 B1
(45) Date of Patent: Oct. 9, 2001

(54) INDOLE COMPOUNDS AS COX-2 INHIBITORS

(75) Inventors: Rodney William Stevens; Kasumari Nakao; Kiyoshi Kawamura; Chikara Uchida; Shinya Fujiwara, all of Chita-gun (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/424,837

(22) PCT Filed: Jul. 3, 1998

(86) PCT No.: PCT/IB98/01026

§ 371 Date: Dec. 3, 1999

§ 102(e) Date: Dec. 3, 1999

(87) PCT Pub. No.: WO99/05104

PCT Pub. Date: Feb. 4, 1999

(30) Foreign Application Priority Data

Jul. 23, 1997 (WO) .............................. IB9700917

(51) Int. Cl.[7] .................. A61K 31/40; A61K 31/405; C07D 209/02
(52) U.S. Cl. ................... 514/415; 514/419; 548/469; 548/483; 548/484; 548/492
(58) Field of Search ................... 514/415, 419; 548/469, 484, 483, 492

(56) References Cited

FOREIGN PATENT DOCUMENTS

985666 * 3/2000 (EP) .
9713767 4/1997 (WO) .......................... C07D/409/14

OTHER PUBLICATIONS

"Syn. & Analg. acti.of . . . indole", Radl, Stanislav et al., Coll.Czech.Chem.Comm.65/2,280–296, Jan. 2000.*
"Syn. & Antimicrobial assays of 3–diazoindole. . . ", Garuti Laura et al.,Farmaco, 51/11,757–760, Jun. 1996.*
"Syn. of Disperse Dyes", Seshadri S. etal.,Indian J.Tech.,9/5, 179–183, Jan. 2000.*
Viti, et al., Journal of Heterocyclic Chem., 28 (2), 379–384 (1991).
Clarke, et al., Chemical Abstracts, 93 (13), Abstract No. 132410 p. 657 (1980).

* cited by examiner

Primary Examiner—Richard L. Raymond
Assistant Examiner—Slidhaker B. Patel
(74) Attorney, Agent, or Firm—Peter C. Richardson; Gregg C. Benson; Carl J. Goddard

(57) ABSTRACT

This invention provides a compound of the following formula:

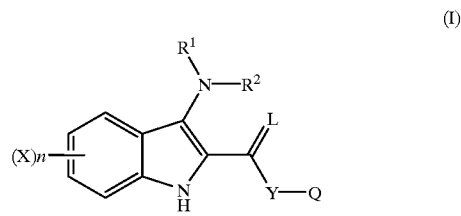

(I)

and the pharmaceutically acceptable salts thereof, wherein L is oxygen or sulfur; Y is a direct bond or $C_{1-4}$ alkylidene; Q is $C_{1-6}$ alkyl, $C_{3-7}$ cycloalkyl, phenyl, naphthyl, heteroaryl or the like; $R^1$ is hydrogen, $C_{1-6}$ alkyl or the like; $R^2$ is hydrogen, $C_{1-4}$ alkyl, $C(O)R^5$ wherein $R^5$ is $C_{1-22}$ alkyl or $C_{2-22}$ alkenyl, halosubstituted $C_{1-8}$ alkyl, halosubstituted $C_{2-8}$ alkenyl, —Y—$C_{3-7}$ cycloalkyl, —Y—$C_{3-7}$ cycloalkenyl, phenyl, naphthyl, heteroaryl or the like; X is halo, $C_{1-4}$ alkyl, hydroxy, $C_{1-4}$ alkoxy or the like; and n is 0, 1, 2 or 3, with the proviso that a group of formula —Y—Q is not methyl or ethyl when X is hydrogen; L is oxygen; $R^1$ is hydrogen; and $R^2$ is acetyl.

This invention also provides a pharmaceutical composition useful for the treatment of a medical condition in which prostaglandins are implicated as pathogens.

11 Claims, No Drawings

INDOLE COMPOUNDS AS COX-2 INHIBITORS

CROSS-REFERENCE TO RELATED APPLICATIONS

This application is the National Stage filing under 35 U.S.C. §371 based on PCT/IB98/01026, filed internationally on Jul. 3, 1998, which claims priority from PCT/IB97/00917, filed Jul. 23, 1997.

TECHNICAL FIELD

This invention relates to novel indoles cyclooxygenase inhibitors. The compounds of this invention inhibit the biosynthesis of prostaglandins by intervention of the action of the enzyme cyclooxygenase on arachidonic acid, and are therefore useful in the treatment or alleviation of inflammation and other inflammation associated disorders in mammals. This invention also relates to pharmaceutical compositions comprising such compounds.

BACKGROUND ART

Nonsteroidal antiinflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long term therapy can also result in severe side effects.

Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. *Proc. Natl. Acad. Sci. USA*, 1994, 91, 2046). COX-1 is thought to play a physiological role and to be responsible for gastrointestinal and renal protection. On the otherhand, COX-2 appears to play a pathological role and to be the predominant isoform present in inflammation conditions. A pathological role for prostaglandins has been implicated in a number of human disease states including rheumatoid and osteoarthritis, pyrexia, asthma, bone resorption, cardiovascular diseases, nephrotoxicity, atherosclerosis, hypotension, shock, pain, cancer, and Alzheimer disease. The NSAIDs currently on market inhibit both isoforms of COX with little variation for selectivity, explaining their beneficial (inhibition of COX-2) and deleterious effects (inhibition of COX-1). It is believed that compounds that would selectively inhibit the biosynthesis of prostaglandins by intervention of the induction phase of the inducible enzyme cyclooxygenase-2 and/or by intervention of the activity of the enzyme cyclooxygenase-2 on arachidonic acid would provide alternate therapy to the use of NSAIDs or corticosteriods in that such compounds would exert anti-inflammatory effects without the adverse side effects associated with COX-1 inhibition.

A variety of indole compounds are known and are disclosed in several patent applications. Specifically, the International Publication Numbers WO 96/37467 and WO 96/37469 disclose N-benzylindole compounds as cyclooxyenase-2 inhibitors. Also, a variety of indole compounds are disclosed in Khim. Geterotsikl. Soedin. 1990, 11, 1569 by Tolkunov et.al.

BRIEF DISCLOSURE OF THE INVENTION

The present invention provides a compound of the following formula:

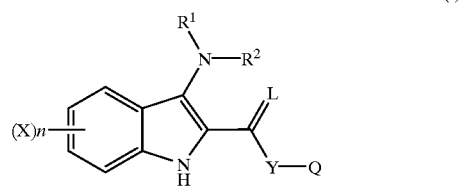

(I)

and the pharmaceutically acceptable salts thereof wherein
L is oxygen or sulfur; Y is a direct bond or $C_{1-4}$ alkylidene;
Q is
(a) $C_{1-6}$ alkyl or halosubstituted $C_{1-6}$ alkyl, said alkyl being optionally substituted with up to three substituents independently selected from hydroxy, $C_{1-4}$alkoxy, amino and mono- or di-($C_{1-4}$alkyl)amino,
(b) $C_{3-7}$ cycloalkyl optionally substituted with up to three substituents independently selected from hydroxy, $C_{1-4}$ alkyl and $C_{1-4}$ alkoxy,
(c) phenyl or naphthyl, said phenyl or naphthyl being optionally substituted with up to four substituents independently selected from
(c-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_m R^3$, $SO_2 NH_2$, $SO_2 N(C_{1-4}$ alkyl$)_2$, amino, mono- or di-($C_{1-4}$ alkyl)amino, $NHSO_2 R^3$, NHC(O)$R^3$, CN, $CO_2H$, $CO_2(C_{1-4}$ alkyl), $C_{1-4}$ alkyl-OH, $C_{1-4}$ alkylOR$^3$, $CONH_2$, CONH($C_{1-4}$ alkyl), CON($C_{1-4}$ alkyl)$_2$ and —O—Y-phenyl, said phenyl being optionally substituted with one or two substituents independently selected from halo, $C_{1-4}$ alkyl, $CF_3$, hydroxy, $OR^3$, $S(O)_m R^3$, amino, mono- or di-($C_{1-4}$ alkyl)amino and CN,
(d) a monocyclic aromatic group of 5 atoms, said aromatic group having one heteroatom selected from O, S and N and optionally containing up to three N atoms in addition to said heteroatom, and said aromatic group being substituted with up to three substitutents independently selected from
(d-1) halo, $C_{1-4}$ alkyl, halosubstituted $C_{1-4}$ alkyl, hydroxy, $C_{1-4}$ alkoxy, halosubstituted $C_{1-4}$ alkoxy, $C_{1-4}$ alkyl-OH, $S(O)_m R^3$, $SO_2 NH_2$, $SO_2 N(C_{1-4}$ alkyl$)_2$, amino, mono- or di-($C_{1-4}$ alkyl)amino, $NHSO_2 R^3$, NHC(O)$R^3$, CN, $CO_2H$, $CO_2(C_{1-4}$ alkyl), $C_{1-4}$ alkyl-OR$^3$, $CONH_2$, CONH($C_{1-4}$ alkyl), CON($C_{1-4}$ alkyl)$_2$, phenyl, and mono-, di- or tri-substituted phenyl wherein the substituent is independently selected from halo, $CF_3$, $C_{1-4}$ alkyl, hydroxy, $C_{1-4}$ alkoxy, $OCF_3$, $SR^3$, $SO_2 CH_3$, $SO_2 NH_2$, amino, $C_{1-4}$ alkylamino and $NHSO_2 R^3$,
(e) a monocyclic aromatic group of 6 atoms, said aromatic group having one heteroatom which is N and optionally containing up to three atoms in addition to said heteroatom, and said aromatic group being substituted with up to three substituents independently selected from the above group (d-1);

$R^1$ is hydrogen or $C_{1-6}$ alkyl optionally substituted with a substituent selected independently from hydroxy, $OR^3$, nitro, amino, mono- or di-($C_{1-4}$ alkyl)amino, $CO_2H$, $CO_2(C_{1-4}$ alkyl), $CONH_2$, $CONH(C_{1-4}$ alkyl) and $CON(C_{1-4}$ alkyl)$_2$;

$R^2$ is
(a) hydrogen,
(b) $C_{1-4}$alkyl,
(c) $C(O)R^5$ wherein $R^5$ is selected from
  (c-1) $C_{1-22}$ alkyl or $C_{2-22}$ alkenyl, said alkyl or alkenyl being optionally substituted with up to four substituents independently selected from
    (c-1-1) halo, hydroxy, $OR^3$, $S(O)_mR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$, $OC(O)R^3$, thienyl, naphthyl and groups of the following formulae:

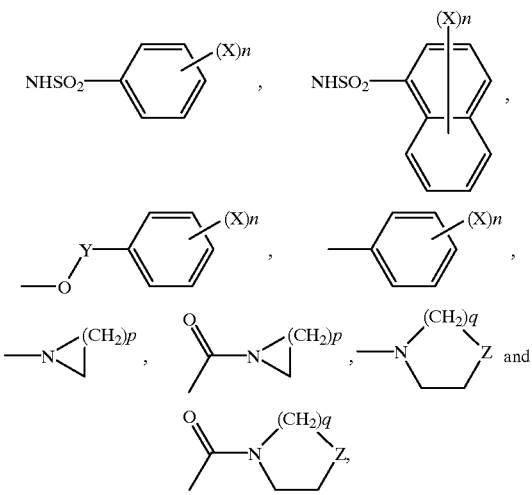

(c-2) $C_{1-22}$ alkyl or $C_{2-22}$ alkenyl, said alkyl or alkenyl being optionally substituted with five to forty-five halogen atoms,
  (c-3) —Y—$C_{3-7}$ cycloalkyl or —Y—$C_{3-7}$ cycloalkenyl, said cycloalkyl or cycloalkenyl being optionally substituted with up to three substituent independently selected from
    (c-3-1) $C_{1-4}$ alkyl, hydroxy, $OR^3$, $S(O)_mR^3$, amino, mono- or di-($C_{1-4}$ alkyl)amino, $CONH_2$, $CONH(C_{1-4}$ alkyl) and $CON(C_{1-4}$alkyl)$_2$,
  (c-4) phenyl or naphthyl, said phenyl or naphthyl being optionally substituted with up to seven (preferably up to seven) substituents independently selected from
    (c-4-1) halo, $C_{1-8}$ alkyl, $C_{1-4}$ alkyl-OH, hydroxy, $C_{1-8}$alkoxy, halosubstituted $C_{1-8}$ alkyl, halosubstituted $C_{1-8}$ alkoxy, CN, nitro, $S(O)_mR^3$, $SO_2NH_2$, $SO_2NH(C_{1-4}$ alkyl), $SO_2N(C_{1-4}$ alkyl)$_2$, amino, $C_{1-4}$ alkylamino, di-($C_{1-4}$ alkyl) amino, $CONH_2$, $CONH(C_{1-4}$ alkyl), $CON(C_{1-4}$ alkyl)$_2$, $OC(O)R_3$, and phenyl optionally substituted with up to three substituents independently selected from halo, $C_{1-4}$ alkyl, hydroxy, $OCH_3$, $CF_3$, $OCF_3$, CN, nitro, amino, mono- or di-($C_{1-4}$ alkyl)amino, $CO_2H$, $CO_2(C_{1-4}$ alkyl) and $CONH_2$,
  (c-5) a monocyclic aromatic group as defined in (d) and (e) above, said aromatic group being optionally substituted with up to three substituents independently selected from
    (c-5-1) halo, $C_{1-8}$ alkyl, $C_{1-4}$ alkyl-OH, hydroxy, $C_{1-8}$ alkoxy, $CF_3$, $OCF_3$, CN, nitro, $S(O)_mR^3$, amino, mono- or di-($C_{1-4}$ alkyl)amino, $CONH_2$, $CONH(C_{1-4}$ alkyl), $CON(C_{1-4}$ alkyl)$_2$, $CO_2H$ and $CO_2(C_{1-4}$ alkyl), and —Y-phenyl, said phenyl being optionally substituted with up to three substituents independently selected halogen, $C_{1-4}$ alkyl, hydroxy, $C_{1-4}$ alkoxy, $CF_3$, $OCF_3$, CN, nitro, $S(O)_mR^3$, amino, mono- or di-($C_{1-4}$ alkyl)amino, $CO_2H$, $CO_2(C_{1-4}$ alkyl), $CONH_2$, $CONH(C_{1-4}$ alkyl) and $CON(C_{1-4}$ alkyl)$_2$,
  (c-6) a group of the following formula:

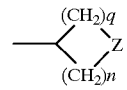

X is halo, $C_{1-4}$ alkyl, hydroxy, $C_{1-4}$ alkoxy, halosubstitued $C_{1-4}$ alkoxy, $S(O)_mR^3$, amino, mono- or di-($C_{1-4}$ alkyl)amino, $NHSO_2R^3$, nitro, halosubstitutued $C_{1-4}$ alkyl, CN, $CO_2H$, $CO_2(C_{1-4}$ alkyl), $C_{1-4}$ alkyl-OH, $C_{1-4}$ alkyl$OR^3$, $CONH_2$, $CONH(C_{1-4}$ alkyl) or $CON(C_{1-4}$ alkyl)$_2$;

$R^3$ is $C_{1-4}$ alkyl or halosubstituted $C_{1-4}$ alkyl;

m is 0, 1 or 2; n is 0, 1, 2 or 3; p is 1, 2, 3, 4 or 5; q is 2 or 3;

Z is oxygen, sulfur or $NR^4$; and $R^4$ is hydrogen, $C_{1-6}$ alkyl, halosubstitutued $C_{1-4}$ alkyl or —Y-phenyl, said phenyl being optionally substituted with up to two substituents independently selected from halo, $C_{1-4}$ alkyl, hydroxy, $C_{1-4}$ alkoxy, $S(O)_mR^3$, amino, mono- or di-($C_{1-4}$ alkyl)amino, $CF_3$, $OCF_3$, CN and nitro;

with the proviso that a group of formula —Y—Q is not methyl or ethyl when X is hydrogen; L is oxygen; $R^1$ is hydrogen; and $R^2$ is acetyl.

The indole compounds of the present invention exhibit inhibition of COX activity. Preferably compounds of this invention exhibit inhibitory activity against COX-2, with more preferable compounds having COX-2 selectivity.

Accordingly, the present invention also provides a pharmaceutical composition, useful for the treatment of a medical condition in which prostaglandins are implicated as pathogens, which comprises a compound of the formula (I): wherein L, Y, X, Q, $R^1$, $R^2$, $R^3$, $R^4$, $R^5$, m, n, p, q and z are as defined above, and the pharmaceutically acceptable salts thereof.

Further, the present invention provides a method for the treatment of a medical condition in which prostaglandins are implicated as pathogens, in a mammalian subject, which comprises administering to said subject a therapeutically effective amount of said pharmaceutical composition.

The medical conditions in which prostaglandins are implicated as pathogens, include the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis including rheumatoid arthritis, degenerative joint disease (osteoarthritis), gout and ankylosing spondylitis, bursitis, burns, injuries following surgical and dental procedures.

The compounds and pharmaceutical composition of this invention may inhibit cellular neoplastic transformations and metastic tumor growth and thus may be used in the treatment of cancer. The compounds and pharmaceutical composition of this invention were used in the treatment and/or prevention of cyclooxygenase-mediated proliferation disorders such as which occur in diabetic retinopathy and tumor angiogenesis.

The compounds and pharmaceutical composition of this invention may be of use in the treatment of dysmenorrhea, premature labor, asthma and eosinophil related disorders, use in the treatment of Alzheimer's disease, and for the treatment of bone loss (treatment of osteoarthritis) by their ability to inhibit prostaniod-induced smooth muscle contraction by preventing the synthesis of contractile prostanoids.

Furthermore, such compounds and pharmaceutical compositions which show specificity for COX-2 over COX-1, will prove useful as an alternative to conventional NSAIDs particularly where such NSAIDs may be contra-indicated such as in patients with peptic ulcers, gastritis, regional enterotis, ulcerative colitis, diverticulitis or with a redurrent history of GI lesions, GI bleeding, coagulation disorders including anemia such as hypoprothrombinemia, haemophilia or other bleeding problems; kidney disease; prior to surgery of taking of anticoagulants.

DETAILED DISCLOSURE OF THE INVENTION

As used herein, "halo" is fluoro, chloro, bromo or iodo.

As used herein, the term "alkyl" means straight or branched chain saturated radicals of 1 to 22 carbon atoms, including, but not limited to methyl, ethyl, n-propyl, isopropyl, n-butyl, iso-butyl, secondary-butyl, tertiary-butyl, pentyl, hexyl, octyl, nonyl, undecyl, dodecyl, tridecyl, tetradecyl, pentadecyl, eicosyl, and the like.

As used herein, the term "halosubstituted alkyl" refers to an alkyl radical as described above substituted with one or more halogens included, but not limited to, chloromethyl, fluoromethyl, difluoromethyl, trifluoromethyl, 2,2,2-trichloroethyl, and the like.

As used herein, the term "alkenyl" means straight or branched chain unsaturated radicals of 2 to 22 carbon atoms, including, but not limited to 1-ethenyl, 1-propenyl, 2-propenyl, 1-butenyl, 2-butenyl, 2-methyl-1-propenyl and the like.

As used herein, the term "cycloalkyl" means carbocyclic radicals, of 3 to 8 carbon atoms, including, but not limited to cyclopropyl, cyclobutyl, cyclopentyl, cyclohexyl, and the like.

As used herein, the term "cycloalkenyl" means carbocyclic unsaturated radicals, of 3 to 8 carbon atoms, including, but not limited to cyclopropenyl, cyclobutenyl, cyclopentenyl, cyclohexenyl, and the like.

As used herein, a monocyclic aromatic group of 5 atoms (in the ring) usually has one heteroatom selected from O, S and N (in the ring). In addition to said heteroatom, the monocyclic aromatic group may optionally have up to three N atoms (in the ring). For example, the monocyclic group of 5 atoms includes thienyl, furyl, thiazolyl (e.g., 1,3-thiazolyl), imidazolyl, pyrrolyl, oxazolyl (e.g., 1,3-oxazolyl, 1,2-oxazolyl), thiazolyl (e.g., 1,2-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3, 4-thiadiazolyl), isothiazolyl and the like.

As used herein, a monocyclic aromatic group of 6 atoms (in the ring) usually has one heteroatom which is N (in the ring). In addition to said heteroatom, the monocyclic aromatic group may optionally have up to three N atoms (in the ring). For example, the monocyclic group of 6 atoms includes pyridyl, pyrazinyl, pyrimidinyl, pyridazinyl, triazinyl (e.g., 1,3,5-triazinyl), tetrazinyl, and the like.

Preferred compounds of this invention are those of the formula (I) wherein

Y is a direct bond, methylene or ethylene;

Q is
(a) $C_{1-6}$ alkyl or halosubstituted $C_{1-6}$ alkyl, said alkyl being optionally substituted with up to two substituents independently selected from hydroxy, $C_{1-4}$alkoxy, amino and mono- or di-($C_{1-4}$alkyl) amino,
(b) $C_{3-7}$ cycloalkyl optionally substituted with up to two substituents independently selected from hydroxy, $C_{1-4}$ alkyl and $C_{1-4}$ alkoxy,
(c) phenyl or naphthyl, said phenyl or naphthyl being optionally substituted with up to four substituents independently selected from
(c-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_m R^3$, $SO_2NH_2$, $SO_2N(C_{1-4}$ alkyl$)_2$, amino, mono- or di-($C_{1-4}$ alkyl)amino, $NHSO_2R^3$, NHC (O)$R^3$, CN, $CO_2H$, $CO_2(C_{1-4}$ alkyl), $C_{1-4}$ alkyl-OH, $C_{1-4}$ alkylO$R^3$, $CONH_2$, $CONH(C_{1-4}$ alkyl) and $CON(C_{1-4}$ alkyl$)_2$,
(d) a monocyclic aromatic group of 5 atoms, said aromatic group having one heteroatom selected from O, S and N and optionally containing an N atom in addition to said heteroatom, and said aromatic group being substituted with up to three substitutents independently selected from
(d-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_m R^3$, $SO_2NH_2$, $SO_2$ $N(C_{1-4}$ alkyl$)_2$ , amino, mono- or di-($C_{1-4}$ alkyl)amino, $NHSO_2R^3$, NHC (O)$R^3$, CN, $CO_2H$, $CO_2(C_{1-4}$ alkyl), $C_{1-4}$ alkylOH, $C_{1-4}$ alkylO$R^3$, $CONH_2$, $CONH(C_{1-4}$ alkyl), $CON(C_{1-4}$ alkyl$)_2$, phenyl, and mono-, di- or tri-substituted phenyl wherein the substituent is independently selected from halo, $CF_3$, $C_{1-4}$ alkyl, hydroxy, $C_{1-4}$ alkoxy, $OCF_3$, $SR_3$, $SO_2CH_3$, $SO_2NH_2$, amino, mono- or di-($C_{1-4}$ alkyl)amino and $NHSO_2R^3$,
(e) a monocyclic aromatic group of 6 atoms, said aromatic group having one heteroatom which is N and optionally containing one or two N atoms in addition to said heteroatom, and said aromatic group being substituted with up to three substituents independently selected from the above group (d-1);

$R^1$ is hydrogen or $C_{1-6}$ alkyl optionally substituted with a substituent selected independently from hydroxy, $OR^3$, nitro, amino, mono- or di-($C_{1-4}$ alkyl)amino and $CO_2H$;

$R^2$ is
(a) hydrogen,
(b) $C_{1-4}$ alkyl,
(c) $C(O)R^5$ wherein $R^5$ is selected from
(c-1) $C_{1-17}$ alkyl or $C_{2-17}$ alkenyl, said alkyl or alkenyl being optionally substituted with up to four substituents independently selected from
(c-1-1) halo, hydroxy, $OR_3$, $S(O)_m R^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl$)_2$, $OC(O)$ $R^3$, and groups of the following formulae:

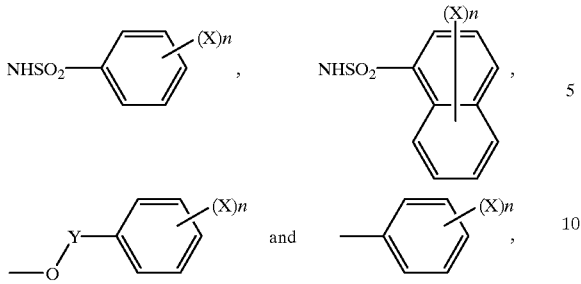

(c-2) $C_{1-17}$ alkyl or $C_{2-17}$ alkenyl, said alkyl or alkenyl being optionally substituted with five to twenty halogen atoms, (c-3) $-Y-C_{3-7}$ cycloalkyl or $-Y-C_{3-7}$ cycloalkenyl, said cycloalkyl or cycloalkenyl being optionally substituted with a substituent independently selected from $C_{1-4}$ alkyl, hydroxy and $OR^3$, (c-4) phenyl or naphthyl, said phenyl or naphthyl being optionally substituted with up to three substituents independently selected from halo, $C_{1-8}$ alkyl, $C_{1-4}$ alkyl-OH, hydroxy, $C_{1-8}$ alkoxy, halosubstituted $C_{1-8}$ alkyl, halosubstituted $C_{1-8}$ alkoxy, CN, nitro, amino and mono- or di-($C_{1-4}$ alkyl)amino, (c-5) a monocyclic aromatic group as defined in (d) and (e) above, said aromatic group being optionally substituted with up to three substituents independently selected from halo, $C_{1-8}$ alkyl, $C_{1-4}$ alkyl OH, hydroxy, $C_{1-8}$ alkoxy, $CF_3$, $OCF_3$, CN, nitro, amino and mono- or di-($C_{1-4}$ alkyl)amino, (c-6) tetrahydrofuryl, tetrahydropyrrolyl, tetrahydrothienyl or 1-methyl-tetrahydropyrrolyl;

X is halo, $C_{1-4}$ alkyl, hydroxy, $C_{1-4}$ alkoxy, halosubstitutued $C_{1-4}$ alkoxy, amino, mono- or di-($C_{1-4}$ alkyl)amino, $NHSO_2R^3$, nitro, halosubstitutued $C_{1-4}$ alkyl, CN or $CO_2H$; and $R^3$ is $C_{1-4}$ alkyl or halosubstituted $C_{1-4}$ alkyl.

Further preferred compounds of this invention are those of the formula (I) wherein L is oxygen; Y is a direct bond or methylene;

Q is (b) $C_{3-7}$ cycloalkyl optionally substituted with $C_{1-4}$ alkyl or $C_{1-4}$ alkoxy, (c) phenyl or naphthyl, said phenyl or naphthyl being optionally substituted with up to three substituents independently selected from (c-1) halo, $C_{1-4}$ alkyl, halosubstituted $C_{1-4}$ alkyl, hydroxy, $C_{1-4}$ alkoxy, halosubstituted $C_{1-4}$ alkoxy, amino, mono- or di-($C_{1-4}$ alkyl)amino, CN, $CO_2H$ and $-SR_3$, (d) a moncyclic aromatic group of 5 atoms, said aromatic group having one heteroatom selected from O, S or N and optionally containing an N atom in addition to said heteroatom, and said aromatic group being substituted with up to three substituents independently selected from (d-1) halo, $C_{1-4}$ alkyl, halosubstituted $C_{1-4}$ alkyl, hydroxy, $C_{1-4}$ alkoxy, halosubstituted $C_{1-4}$ alkoxy, amino, mono- or di-($C_{1-4}$ alkyl)amino and $C_{1-4}$ alkyl-OH, (e) a moncyclic aromatic group of 6 atoms, said aromatic group having one heteroatom which is N and optionally containing an N atom in addition to said heteroatom, and said aromatic group being substituted with up to three substituents independently selected from the above group (d-1);

$R^1$ is hydrogen or $C_{1-4}$ alkyl;

$R^2$ is (a) hydrogen, (c) $C(O)R^5$ wherein $R^5$ is selected from (c-1) $C_{1-8}$ alkyl or $C_{2-8}$ alkenyl, said alkyl or alkenyl being optionally substituted with up to three substituents independently selected from (c-1-1) halo, hydroxy, $OR_3$, $SOR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$ and $OC(O)R^3$, (c-2) $C_{1-8}$ alkyl or $C_{2-8}$ alkenyl, said alkyl or alkenyl being optionally substituted with five to seventeen halogen atoms, (c-3) $-Y-C_{3-7}$ cycloalkyl or $-Y-C_{3-7}$ cycloalkenyl, said cycloalkyl or cycloalkenyl being optionally substituted with a substituent independently selected independently from $C_{1-4}$ alkyl, hydroxy and $OR^3$, (c-4) phenyl optionally substituted with up to three substituents independently selected from halo, $C_{1-4}$ alkyl and hydroxy, (c-5) heteroaryl selected from pyridyl, quinolyl, thienyl, thiazolyl, pyrimidyl and indolyl, said heteroaryl being optionally substituted with up to two substituents independently selected from halo, $C_{1-4}$ alkyl, hydroxy, $C_{1-4}$ alkoxy and $CF_3$, (c-6) tetrahydrofuryl or tetrahydrothienyl;

X is halo, $C_{1-4}$ alkyl, hydroxy, $C_{1-4}$ alkoxy, amino, nitro or CN; and $R^3$ is $C_{1-3}$ alkyl or $CF_3$.

Further preferred compounds of this invention are those of the formula (I) wherein Y is a direct bond;

Q is phenyl, cyclohexyl optionally substituted with methyl, ethyl or methoxy, or a monocyclic aromatic group selected from pyridyl, pyrazinyl, thienyl, furyl, thiazolyl, imidazolyl and pyrrolyl, said phenyl or aromatic group being optionally substituted with up to two substituents independently selected from halo, methyl, methoxy, amino and hydroxymethyl, $R^1$ is hydrogen or methyl;

$R^2$ is (a) hydrogen, (c) $C(O)R^5$ wherein $R^5$ is selected from (c-1) $C_{1-6}$ alkyl optionally substituted with up to two substituents independently selected from hydroxy, $OR^3$, $SOR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$, $OC(O)R^3$ and phenyl, (c-2) trifluoromethyl or trichloromethyl, (c-3) cyclopropyl or cyclohexyl, (c-4) phenyl or halophenyl, (c-5) thienyl, (c-6) tetrahydrofuryl;

X is chloro, fluoro or cyano; and $R^3$ is methyl, ethyl, propyl or $CF_3$.

Further preferred compounds of this invention are those of the formula (I) wherein Y is a direct bond;

Q is phenyl, 3-methoxyphenyl, 3-methylphenyl, 2-chlorophenyl, 3-chlorophenyl, 3-bromophenyl, 2-pyridyl, 4-chloro-2-pyridyl, 4-methyl-2-pyridyl, 4-methoxy-2-pyridyl, 2-pyrazinyl, cyclohexyl, 3-methyl-cyclohexyl, 3-$NH_2$-phenyl, 3-methylcyclohexyl, 3-hydroxymethyl-2-furyl or 3-fluorophenyl;

$R^1$ is hydrogen or methyl;

$R^2$ is hydrogen, $CH_3$—C(O)—, $(CH_3)_2$C(O)—, phenyl-C(O)—, $C_2H_5$—C(O)—, $C_3H_7$—C(O)—, cyclohexyl-C(O)—, $(CH_3)_2$CH—$CH_2$—C(O)—, cyclopropyl-C(O)—, $CH_3$—O—$CH_2$—C(O)—, 2-chlorophenyl-C(O)—, $C_2H_5$—O—C(O)—$CH_2$—C(O)—, $(CH_3)_2$CH—C(O)—, 2-tetrahydrofuryl-C(O)—, $(CH_3O)(CH_3)C$—C(O)—, $CF_3$—$CH_2$—C(O)—, clopropyl-$CH_2$—C(O)—, $CH_3S$—$CH_2$—C(O)—, $(CH_3)_2N$—$CH_2$—C(O)— or $(CH_3)_2C(OH)$—C(O)—;

X is 6-chloro, 6-fluoro, 6-cyano or 6-nitro; and n is 1.

Preferred individual compounds of this invention are: 3-amino-2-benzoyl-6-chloroindole; 3-acetylamino-2-benzoyl-6-chloroindole; 2-benzoyl-6-chloro-3-(isobutyrylamino)indole; 3-(benzamido)-2-benzoyl-6-chloroindole; 2-benzoyl-6-chloro-3-(propionylamino) indole; 2-benzoyl-3-(butyrylamino)-6-chloroindole; 2-benzoyl-6-chloro-3-(cyclohexylcarboxamido)indole; 2-benzoyl-6-chloro-3-(isovalerylamino)indole; 2-benzoyl-6-chloro-3-(cyclopropylcarboxamido)indole; 2-benzoyl-6-chloro-3-(methoxyacetylamino)indole; 3-amino-6-chloro-2-(3-methoxybenzoyl)indole; 3-acetylamino-6-chloro-2-(3-methoxybenzoyl)indole; 3-amino-6-chloro-2-(3-methylbenzoyl)indole; 3-acetylamino-6-chloro-2-(3-methylbenzoyl)indole; 6-chloro-2-(3-methylbenzoyl)-3-(propionylamino)indole; 6-chloro-3-(methoxyacetylamino)-2-(3-methylbenzoyl)indole; 3-amino-6-chloro-2-(3-chlorobenzoyl)indole; 3-acetylamino-6-chloro-2-(3-chlorobenzoyl)indole; 6-chloro-2-(3-chlorobenzoyl)-3-(propionylamino)indole; 3-(butyrylamino)-6-chloro-2-(3-chlorobenzoyl)indole; 6-chloro-2-(3-chlorobenzoyl)-3-(isovalerylamino)indole; 6-chloro-2-(3-chlorobenzoyl)-3-(methoxyacetylamino)indole; 3-acetylamino-6-chloro-2-(3-fluorobenzoyl)indole; 3-amino-2-(3-bromobenzoyl)-6-chloroindole; 3-acetylamino-2-(3-bromobenzoyl)-6-chloroindole; 2-benzoyl-6-chloro-3-(2-chlorobenzamido) indole; 2-benzoyl-6-chloro-3-[(3-ethoxycarbonyl) propionylamino]indole; (s)-(+)-2-benzoyl-6-chloro-3-[(2-hydroxypropionyl)amino]indole; 3-amino-6-chloro-2-(4-chloropyridine-2-carbonyl)indole; 3-acetylamino-6-chloro-2-(4-chloropyridine-2-carbonyl)indole; 3-amino-6-chloro-2-(4-methylpyridine-2-carbonyl)indole; 3-acetylamino-6-chloro-2-(4-methylpyridine-2-carbonyl)indole; 3-amino-6-chloro-2-(4-methoxypyridine-2-carbonyl)indole; 3-acetylamino-6-chloro-2-(4-methoxypyridine-2-carbonyl) indole; 6-chloro-3-isovalerylamino-2-(4-methoxypyridine-2-carbonyl)indole; 3-acetylamino-6-chloro-2-(pyrazine-2-carbonyl)indole; 3-acetylamino-6-chloro-2-(cyclohexanecarbonyl)indole; 3-acetylamino-2-benzoyl-6-fluoroindole; 3-acetylamino-2-benzoyl-6-cyanoindole; 2-benzoyl-6-chloro-3-[(2-tetrahydrofuryl)carboxamido) indole; 2-benzoyl-6-chloro-3-[(2-methoxypropionyl)amino] indole; 2-benzoyl-6-chloro-3-(3,3,3-trifluoropropionylamino)indole; 2-benzoyl-6-chloro-3-(cyclopropaneacetylamino)indole; 2-benzoyl-6-chloro-3-(methylthioacetylamino)indole; 2-benzoyl-6-chloro-3-[(N, N-dimethylaminoacetyl)amino]indole; 3-amino-6-chloro-2-(pyridine-2-carbonyl)indole; 3-acetylamino-6-chloro-2-(pyridine-2-carbonyl)indole; 3-acetylamino-2-(3-aminobenzoyl)-6-chloroindole hydrochloride; 3-acetylamino-6-chloro-2-(3-methylcyclohexylcarbonyl) indole; 3-(N-acetyl-N-methylamino)-6-chloro-2-(3-chlorobenzoyl)indole; 2-benzoyl-6-chloro-3-(N,N-dimethylamino)indole; 3-acetylamino-2-benzoyl-6-nitroindole; 3-actetylamino-6-chloro-2-(3-hydroxymethyl-2-furoyl)indole; 6-chloro-2-(4-chloropyridine-2-carbonyl)-3-(propionylamino)indole; 6-chloro-2-(4-chloropyridine-2-carbonyl)-3-(2-hydroxyisobutyrylamino)indole;. 3-acetylamino-6-chloro-2-[2-(5-methylthiazoyl)]indole; 3-(2-acetoxyisobutyrylamino)-6-chloro-2-(4-chloropyridine-2-carbonyl)indole; 6-chloro-2-(4-chloropyridine-2-carbonyl)-3-(isovalerylamino)indole; 6-chloro-2-(4-chloropyridine-2-carbonyl)-3-[[(S)-2-hydroxypropionyl]amino]indole; 3-(N-acetyl-N-methylamino)-6-chloro-2-(4-chloropyridine-2-carbonyl) indole; and 2-(4-aminopyridine-2-carbonyl)-6-chloro-3-(propionylamino)indole hydrochloride.

More preferred individual compounds are: 3-acetylamino-2-benzoyl-6-chloroindole; 2-benzoyl-6-chloro-3-(isovalerylamino)indole; 3-acetylamino-6-chloro-2-(3-methylbenzoyl)indole; 3-acetylamino-6-chloro-2-(3-chlorobenzoyl)indole; 6-chloro-2-(3-chlorobenzoyl)-3-(propionylamino)indole; 3-acetylamino-6-chloro-2-(4-chloropyridine-2-carbonyl)indole; 3-acetylamino-6-chloro-2-(4-methylpyridine-2-carbonyl)indole; 2-benzoyl-6-chloro-3-(methylthioacetylamino)indole; 6-chloro-2-(4-chloropyridine-2-carbonyl)-3-(propionylamino)indole; 3-actetylamino-6-chloro-2-(3-hydroxymethyl-2-furoyl) indole; and 6-chloro-2-(4-chloropyridine-2-carbonyl)-3-(2-hydroxyisobutyrylamino)indole; 3-acetylamino-6-chloro-2-[2-(5-methylthiazoyl)]indole.

Most preferred individual compounds are: 3-acetylamino-2-benzoyl-6-chloroindole; 2-benzoyl-6-chloro-3-(isovalerylamino)indole; 3-acetylamino-6-chloro-2-(3-methylbenzoyl)indole; 3-acetylamino-6-chloro-2-(3-chlorobenzoyl)indole; 6-chloro-2-(3-chlorobenzoyl)-3-(propionylamino)indole; 3-acetylamino-6-chloro-2-(4-methylpyridine-2-carbonyl)indole; 2-benzoyl-6-chloro-3-(methylthioacetylamino)indole; 6-chloro-2-(4-chloropyridine-2-carbonyl)-3-(propionylamino)indole; and 6-chloro-2-(4-chloropyridine-2-carbonyl)-3-(2-hydroxyisobutyrylamino)indole.

General Synthesis

A compound of general formula (I) may be prepared by any synthetic procedure applicable to structure-related compounds known to those skilled in the art. The following representative examples as described hereinafter are illustrative of the invention in which, unless otherwise stated, L, Q, X, Y, $R^1$, $R^2$, $R^3$, $R^4$, $R^5$, Z, m, n, p, q and n are as defined herein before.

Scheme 1

In one embodiment, a compound of the formula (III) is prepared according to the reaction steps outlined in Scheme 1. The compounds of the formula (III) corresponds to those of the formula (I) wherein $R^2$ is —C(O)—$R^5$.

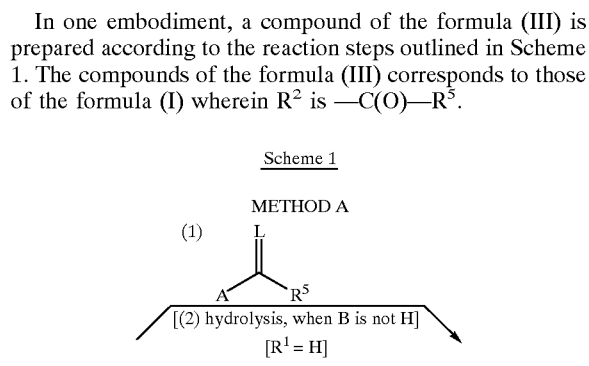

-continued

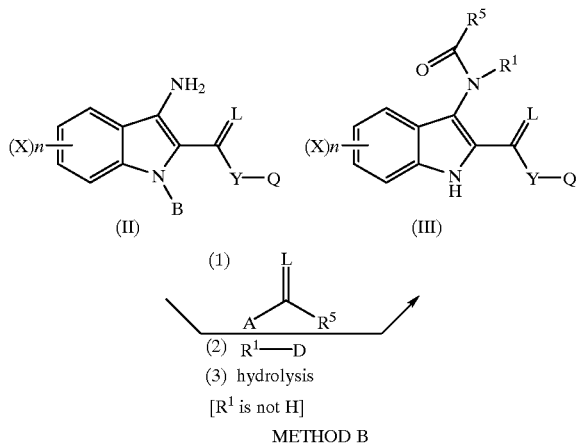

METHOD B

In the formula (II), B is hydrogen or a suitable protecting group, for example, methoxycarbonyl, ethoxycarbonyl, tert-butoxycarbonyl (Boc), benzyloxycarbonyl, phenylsulfonyl or p-toluenesulfonyl, or the like.

For example, in step 1 of Method A or Method B, a compound of formula (II) is reacted with a compound of formula $A^1$—C(O)—O—C(O)—$A^2$ or $R^5$C(O)—A wherein $A^1$ and $A^2$ are independently $C_{1-4}$ alkyl, or $A^1$ and $A^2$ together form $C_{1-4}$ alkylene or $C_{2-4}$ alkenylene, and A is defined such that the compound of $R^5$C(O)—A is, for example, a carboxylic acid halide (ex., chloride and bromide), acyl halide, carboxylic acid, carboxylic acid ester (ex., $R^5$C(O)—O—$C_{1-4}$ alkyl and $R^5$C(O)—O-aryl [an example of the aryl is phenyl, naphtyl, furyl and thienyl], a carboxylic acid anhydride, or the like. In the instant example, when a compound of formula $R^5$C(O)—A is, for example, a carboxylic acid halide (ex., chloride and bromide) or carboxylic acid anhydride the reactants may be heated together in the absence or presence of a reaction inert solvent.

Preferred reaction inert solvents include, but are not limited to, benzene, toluene, xylene, o-dichlorobenzene, nitrobenzene, 1,2-dichloroethane, or the like. Preferably, the reaction conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof.

Reaction temperatures are generally in the range of –100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

Alternatively, when a compound of formula $R^5$C(O)—A is, for example, a carboxylic acid the intermediate amide obtained from step 1 in either Method A or Method B can be readily prepared by treating the requisite carboxylic acid with a compound of formula (II) in the presence of a coupling reagent such as, but not limited to, 1-(dimethylaminopropyl)-3-ethylcarbodiimide (WSC), N,N'-dicyclohexylcarbodiimidazole (DCC), carbonyldiimidazole, cyanophosphonic acid diethyl ester, or the like. Preferred reaction inert solvents include, but are not limited to, acetone, acetonitrile, dichloromethane, 1,2-dichloroethane, N,N-dimethylformamide, N,N-dimethylacetamide, dimethylsulfoxide, dioxane, tetrahydrofuran or pyridine. Or, for example, under Mitsunobu-type reaction conditions. A suitable condensing reagent in the Mitsunobu reaction is a di-($C_{1-4}$)alkyl azodicarboxylate in the presence of a triarylphosphine, for example, diethyl azodicarboxylate in the presence of triphenylphosphine. Reaction inert solvents of choice include tetrahydrofuran, dichloromethane, dimethylformamide, benzene, toluene, or the like. The reaction temperature is preferably in the range of 0° C. to reflux temperature of the solvent, e.g. 0 to 100° C., but if necessary, temperatures lower or higher can be adopted. Reaction times are, in general, from several minutes to a day, preferably from 20 minutes to 5 hours, however shorter or longer reaction times, if necessary, can be employed.

In step 2 of Method B, the intermediate amide (the group B is a suitable protecting group as defined herein above) is reacted with a compound of formula $R^1$-D wherein D is a selected from a suitable displaceable group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of –100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

In step 2 of Method A or step 3 of Method B (the group B is a suitable protecting group as defined herein above) the group B may be removed by a number of standard procedures known to those skilled in the art (for example, see "Protection of the Amino Group", in *Protective Groups in Organic Synthesis*, 2nd Edition, T. W. Greene and P. G. M. Wuts, Ed., John Wiley and Sons, Inc. 1991, pp. 309–405).

Scheme 2

A compound of formula (III) may also be prepared according to the reaction step outlined in Scheme 2.

Scheme 2

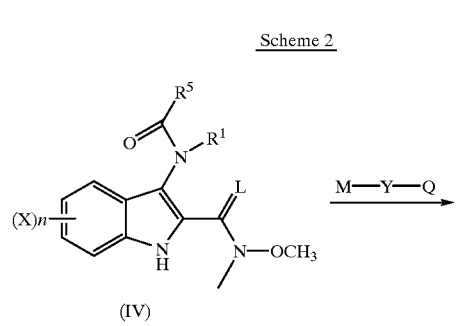

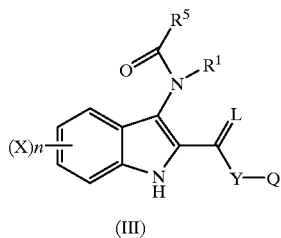

(III)

In Scheme 2, X, Y, Q, $R^1$, $R^5$ and n are as defined herein before. The compound of formula (IV) (amide) is used for illustrative purposes only and is not meant to limit the scope of the present invention. Thus, for example, a compound of formula (IV) is treated with a compound of formula M—Y—Q in a reaction inert solvent. In a compound of formula M—Y—Q, M is defined such that compound of formula M—Y—Q is, for example, the corresponding Grignard or alkali metal reagent, for example, M may be magnesium chloride (Q—Y—MgCl), magnesium bromide (Q—Y—MgBr), or magnesium iodide (Q—Y—MgI), lithium (Q—Y—Li), potassium (Q—Y—K) or sodium (Q—Y—Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof. Reaction temperatures are preferably in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula (IV) is readily accessible by conventional synthetic methods known to those skilled in the art and, of which, are adequately described within the accompanying non-limiting examples.

Scheme 3

In another embodiment, compounds of formula (I), wherein X, Y, Q and n are as defined as herein before, B is a suitable protecting group as herein before and $R^1$ and $R^2$ are both $C_{1-4}$alkyl, are prepared according to the reaction steps outlined in Scheme 3.

Scheme 3

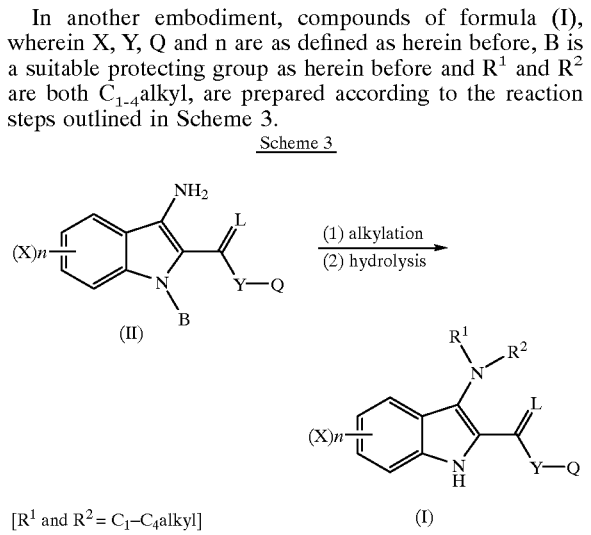

[$R^1$ and $R^2$ = $C_1$–$C_4$alkyl]

For example, a compound of formula (II) is reacted with a suitable carbaldehyde (such as formaldehyde, acetaldehyde and propionaldehyde) in the presence of a suitable reducing reagent such as, but not limited to, sodium cyanoborohydride, sodium triacetoxyborohydride, 9-borabicyclo[3.3.1]nonany(9-BBN) lithium triehtylborohydride, or the like (P. C. Unangst, D. T. Connor and S. Russell Stabler, *J. Heterocyclic Chem.*, 24, 817 (1987); R. F. Borch and A. I. Hassid, *J. Org. Chem.*, 37, 1673 (1972)). Preferred reaction inert solvents include, but are not limited to, acetic acid, N,N-dimethylformamide, N,N-dimethylacetamide, dimethylsulfoxide, dioxane or tetrahydrofuran. Reaction temperatures are preferably in the range of −40 to 200° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

Scheme 4

A compound of formula (II) may be prepared by a number of synthetic procedures known to those skilled in the art. The following representative examples as described hereinafter are illustrative and are not meant to limit the scope of the invention in anyway.

Scheme 4

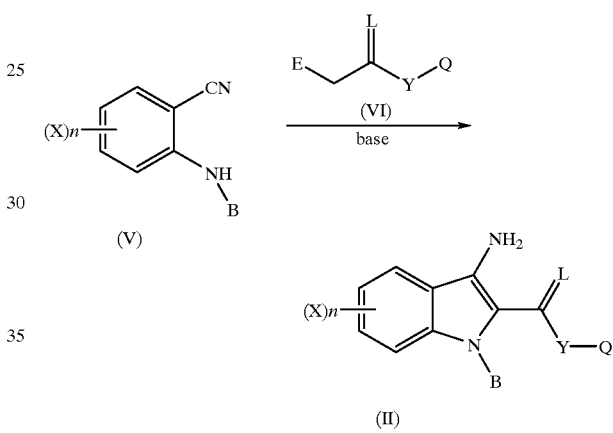

For example, a compound of formula (II), wherein B, X, Y, Q and n are as defined as herein before, is readily accessible from the appropriate 2-aminobenzonitrile (V) as illustrated in Scheme 4 (For example, see E. E. Garcia, L. E. Benjamin and R. Ian Fryer, *J Heterocycl. Chem.*, 10, 51 (1973)). Thus, the requisite 2-aminobenzonitrile (V) is reacted with a compound of formula (VI), wherein Y and Q are as defined as herein before and E is halogen, preferably, iodo, bromo or chloro, in the presence of a suitable base. A suitable base is, for example, an alkali or alkaline earth metal alkoxide, carbonate, or hydride, such as, but not limited to, sodium tert-butoxide, potassium tert-butoxide, sodium carbonate, potassium carbonate, sodium hydride or potassium hydride. Preferred reaction inert solvents include, but are not limited to, acetonitrile, N,N-dimethylformamide, N,N-dimethylacetamide, dimethylsulfoxide, dioxane or tetrahydrofuran. Reaction temperatures are preferably in the range of −40 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

Scheme 5

Alternatively, a compound of formula (II), wherein X, Y, Q and n are as defined as herein before and B is hydrogen, may be prepared according to the reaction steps depicted in Scheme 5.

Scheme 5

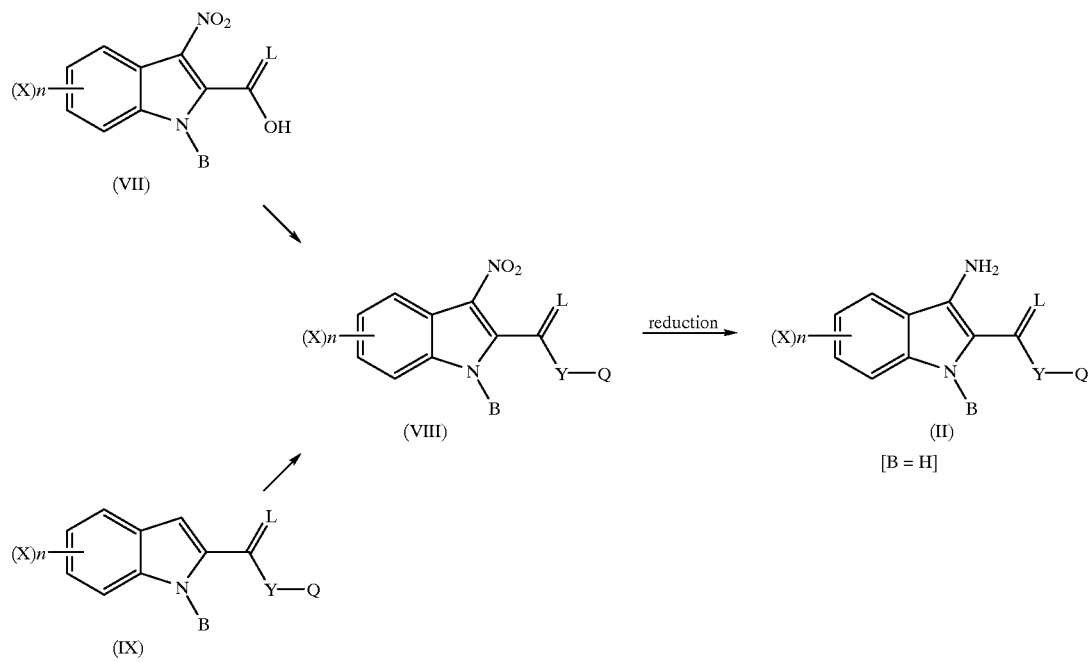

For example, the compound of formula (II) may be prepared from the requisite nitro compound of formula (VIII) by reduction in the presence of suitable reducing agent by conventional methods known to those skilled in the art. For example, tin (II) chloride in ethanol (F. D. Bellamy and K. Ou, *Tetrahedron Lett.*, 25, 839 (1984)), iron—ammonium chloride in aqueous ethanol (K. Ramadas and N. Srinivasan, *Synth. Commun.*, 22, 3189 (1992)), or zinc dust or iron in acetic acid (E. Wertheim, *Org. Synth. Coll. Vol.* 2., 160 (1943)), or by catalytic hydrogenolysis. Preferred catalysts are, for example, palladium-on-charcoal or Raney-Nickel (C. F. H. Allen and J. Vanallan, *Org. Synth. Coll. Vol.* 3., 63 (1955)). The nitro compound of formula (VIII) is readily accessible by conventional synthetic methods known to those skilled in the art and, of which, are adequately described within the accompanying non-limiting examples.

The starting material of the formulae II, IV, V, VI, VII and IX in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

The compounds of the present invention which contain one or more double bonds and/or asymmetric centers are capable of existing in various stereoisomeric forms. All such individual forms, and mixtures thereof, are included within the scope of the invention. The various isomers can be obtained by standard methods. For example, cis/trans mixtures can be separated into the individual stereoisomers by stereoselective synthesis, or by separation of the mixtures by fractional crystallization or chromatography techniques.

A number of the compounds of the present invention are capable of forming addition salts with inorganic and organic acids. The pharmaceutically acceptable acid salts of the compounds of the present invention are those which form non-toxic addition salts, such as, but not limited to, the hydrochloride, hydrobromide, hydroiodide, nitrate, sulfate or acetate, fumarate, tartrate, succinate, maleate, glucronate, saccharate, benzoate, methanesulfonate, benzenesulfonate, p-toluenesulfonate and pamoate (i.e., 1,1'-methylene-bis-(2-hydroxy-3-naphthoate)) salts.

The compounds of the invention which have also acidic groups are capable of forming base salts with various pharmaceutically acceptable cations. Examples of such salts include the alkali metal or alkaline earth metal salts and particularly, the sodium or potassium salts. These salts are all prepared by conventional techniques. For example, these salts can be easily prepared by treating the aforementioned compounds with an aqueous solution containing the desired pharmaceutically acceptable cation, and then evaporating the resulting solution to dryness, preferable under reduce pressure. Alternatively, they may be also be prepared by mixing together with a lower alkoxide, and then evaporating the resulting solution to dryness in the same manners as before. In either case, stoichiometric quantities of reagents are preferably employed in order to ensure completeness of reaction and maximum production of yields of the desired final product.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. When the compounds of the formula (I) of this invention may form solvates such as hydrates, such solvates are included within the scope of this invention.

The compounds of the formula (I) of this invention can be administered via either the oral, parenteral or topical routes to mammals. In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

Compounds of the present invention may also be used in co-administration, partially or completely, with other conventional anti-inflammatories, such as, steroids, conventional NSAIDS, 5-lipoxygenase inhibitors, $LTD_4$ antagonists, $LTB_4$ antagonists and $LTA_4$ hydrolase inhibitors. Suitable conventional anti-inflammatories include but are limited to, for example, indomethacin, diclofenac, piroxicam, nimesulide, tenidap, ebselen, masoprocol, zileuton, pranlukast, zafirlukast, montelukast, tepoxalin, rilopirox, flezelastine hydrochloride, enazadrem phosphate, and bunaprolast.

Biological Evaluation

The activity of the compounds of the formula (I) of the present invention, is demonstrated by the following assays.

Human umbilical vein endothelial cells (HUVEC), which was characterized by positive staining with von Willibrand's factor and an uptake of acetylated low-density lipoproteins, was purchased from Morinaga Bioscience Lab., Yokohama, Japan. HUVEC was maintained in E-GM UV (from Kurashikibouseki Co., Neyagawa, Japan) in 5% $CO_2$/95% air at 37° C. $PGE_2$, $TXB_2$ and 6-keto-PGF1α were from Cayman Chemical Co. (Ann Arbor, USA). Recombinant human interleukin-1β (hIL-1β) was from R&D Systems (Minneapolis, USA). RIA kits for $PGE_2$, $TXB_2$ and 6-keto-PGF1α were from Amersham (Tokyo, Japan). Indomethacin and other reagents were from Sigma Chemical Co. (St. Louis, USA). Dexamethasone (decadron[Trademark]) was from Banyu Pharmaceutical Co. (Tokyo, Japan). Vacutainer [Trademark] was from Becton Dickinson (Bedford, USA). Male Sprague-Dawley rats were purchased from Charles River (Hino, Japan).

Human Cell Based COX-1 Assay

Human peripheral blood obtained from healthy volunteers was diluted to 1/10 volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^7$ cells/ml and stored at room temperature until use. The HWP suspension (70 μl aliquots, final $2.0 \times 10^7$ cells/ml) was placed in a 96-well U bottom plate and 10 μl aliquots of 12.6 mM CaCl2 added. Platelets were incubated with A23187 (final 10 μM, Sigma) with test compound (0.1–100 μM) dissolved in DMSO (final concentration; less than 0.01%) at 37° C. for 15 min. The reaction was stopped by addition of EDTA (final 7.7 mM) and TxB2 in the supernatant quantitated by using a radioimmunoassay kit (Amersham) according to the manufacturer's procedure.

Human Cell Based COX-2 Assay

Inhibition of COX-2 Activity After Induction of COX-2 by hIL-1β

The human cell based COX-2 assay was carried out as previously described (Moore et al., 1996). Confluent human umbilical vein endothelial cells (HUVECs, Morinaga) in a 96-well U bottom plate were washed with 100 μl of RPMI1640 containing 2% FCS and incubated with hIL-1β (final concentration 300 U/ml, R & D Systems) at 37° C. for 24 hr. After washing, the activated HUVECs were stimulated with A23187 (final concentration 30 μM) in Hanks buffer containing 0.2% BSA, 20 mM Hepes and test compound (0.1 nM–100 µM) dissolved in DMSO (final concentration; less than 0.01%) at 37° C. for 15 min. 6-Keto-PGF1α, stable metabolite of PGI2, in the supernatant was quantitated after adequate dilution by using a radioimmunoassay kit (Amersham) according to the manufacturer's procedure.

Inhibition of COX-2 During the Induction Phase

Confluent human umbilical vein endothelial cells (HUVECs, Morinaga) in a 96-well U bottom plate were washed with 100 µl of RPMI1640 containing 2% FCS and test compound (0.1 nM–100 µM) dissolved in DMSO (final concentration; less than 0.01%), and incubated with hIL-1β (final concentration 300 U/ml, R & D Systems) at 37° C. for 24 hr. After washing, the HUVECs were stimulated with A23187 (final concentration 30 µM) in Hanks buffer containing 0.2% BSA and 20 mM Hepes at 37° C. for 15 min. 6-Keto-PGF1α, a stable metabolite of PGI2, in the supernatant was quantitated after adequate dilution by using a radioimmunoassay kit (Amersham) according to the manufacturer's procedure.

Carrageenan Induced Foot Edema in Rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with λ-carrageenan (0.1 ml of 1% w/v suspension in saline, Zushikagaku) into right hind paw (Winter et al., 1962; Lombardino et al., 1975) and three hours later, the paw volume (V3) was measured and the increase in volume (V3–V0) calculated. Since maximum inhibition attainable with classical NSAIDs is 60–70%, $ED_{30}$ values were calculated.

Gastric Ulceration in Rats

The gastric ulcerogenicity of test compound was assessed by a modification by the conventional method (Ezer et al., 1976; Cashin et al., 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Data Analysis

Statistical program packages, SYSTAT (SYSTAT, INC.) and StatView (Abacus Cencepts, Inc.) for Macintosh were used. Differences between test compound treated group and control group were tested for using ANOVA. The $IC_{50}$ ($ED_{30}$) values were calculated from the equation for the log-linear regression line of concentration (dose) versus percent inhibition.

Most compounds prepared in the Working Examples as described herein after were tested by these methods, and showed $IC_{50}$ values of 0.0001 µM to 15 µM with respect to inhibition of COX-2.

COX-2 selectivity can be determined by ratio in terms of $IC_{50}$ value of COX-1 inhibition to COX-2 inhibition. In general, it can be said that a compound showing a COX-2/COX-1 inhibition ratio of more than 2 has good COX-2 selectivity.

Some compounds prepared in Examples showed COX-2/COX-1 inhibition ratio of more than 10.

The following examples contain detailed descriptions of the methods of the preparation of compounds of formula (I). These detailed descriptions fall within the scope, and serve to exemplify, the above described General Synthetic Procedures which form part of the invention. These detailed descriptions are presented for illustrative purposes only and are not intended as a restriction in the scope of the invention.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or microanalysis. Yields are given for illustrative purposes only. Flash column chromatography was carried out using Merck silica gel 60 (230–400 mesh ASTM). Optical rotations were measured using a JASCO DIP-370 Digital Polarimeter (Japan Spectroscopic Co, Ltd). NMR data was determined at 270 MHz (JEOL GX 270 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, Ex.=EXAMPLE, etc.

Ex. 1

3-Amino-2-benzoyl-6-chloroindole

Step 1. 4-chloro-2-(ethoxycarbonylamino) benzonitrile

Method A

To a solution of 2-amino-4-chlorobenzonitrile (10.0 g, 65.5 mmol) in DMF (30 ml) cooled to 0° C. was added sodium hydride (60% w/w dispersion in mineral oil, 2.75 g, 68.7 mmol) portionwise over 10 min. The mixture was stirred for 1 h at 0° C. and then ethyl chloroformate (6.6 ml, 68.7 mmol) slowly added. After stirring for an additional hour at this temperature, the mixture was poured into water (300 ml) and extracted with diethyl ether (250 ml×2). The combined organic extracts were washed consecutively with water (500 ml), brine (500 ml), and then dried ($MgSO_4$). Removal of solvent gave 15.85 g (quant.) of the title compound as yellow solids. Alternatively, Method B To a suspension of 2-amino-4-chlorobenzonitrile (50 g, 0.33 mol) in a mixture of pyridine (40 ml, 0.50 mol) and dichloromethane (500 ml) cooled to 0° C., was carefully added ethyl chloroformate (35 ml, 0.37 mol). The mixture was allowed to warm to room temperature and stirred overnight. The mixture was poured into 2N aqueous HCl (300 ml) and extracted with dichloromethane (300 ml×2). Removal of solvent gave 75 g of crude product as a pale yellow solid. The solid was washed with minimal hexane to afford 64 g (86%) of the title compound as white solids.

$^1$H-NMR ($CDCl_3$) δ: 8.35 (1H, d, J=1.8 Hz), 7.47 (1H, d, J=8.4 Hz), 7.17 (1H, br s), 7.09 (1H, dd, J=8.4, 1.8 Hz), 4.28 (2H, q, J=7.0 Hz), 1.35 (3H, t, J=7.0 Hz)

Step 2. 3-Amino-2-benzoyl-6-chloro-1-(ethoxycarbonyl)indole

To a solution of 4-chloro-2-(ethoxycarbonylamino) benzonitrile (10.8 g) in DMF (50 ml) cooled to 0° C. was added sodium hydride (60% w/w dispersion in mineral oil, 2.0 g, 50 mmol). The mixture was stirred for 30 min at 0° C. and then 2-bromoacetophenone (9.9 g, 50 mmol) was carefully added. After stirring for an additional 15 h at 0° C., the mixture was poured into water (500 ml) and extracted with diethyl ether (500 ml×2). After drying (MgSO$_4$) and removal of solvent, the crude product was purified by flash chromatography eluting with ethyl acetate/hexane (1:5) to afford 11.8 g (72%) of the title compound as a brown amorphous solid.

$^1$H-NMR (CDCl$_3$) δ: 8.26 (1H, d, J=1.8 Hz), 7.78–7.70 (2H, m), 7.54 (1H, d, J=8.4 Hz), 7.50–7.39 (3H, m), 7.31 (1H, dd, J=1.8, 8.4 Hz), 5.78 (2H, br s), 3.73 (2H, q, J=7.0 Hz), 0.84 (3H, t, J=7.0 Hz).

Step 3. 3-Amino-2-benzoyl-6-chloroindole

The product of step 2 (4.5 g, 13 mmol) and K$_2$CO$_3$ (18 g, 130 mmol) was heated at reflux for 5 h in 50% aqueous ethanol. The mixture was cooled and concentrated, and the residue partitioned between water (50 ml) and dichloromethane (100 ml). The organic extract was dried (MgSO$_4$) and solvent removed. The residual solid was recrystallized from hexane/ethyl acetate to afford 3.2 g (91%) of the title compound. m.p.: 128–130° C. $^1$H-NMR (CDCl$_3$) δ: 7.85–7.76 (2H, m), 7.64 (1H, br s), 7.59–7.49 (4H, m), 7.22 (1H, d, J=1.8 Hz), 7.02 (1H, dd, J=1.8, 8.4 Hz), 5.60 (2H, br s).

Ex. 2

3-Acetylamino-2-benzoyl-6-chloroindole
Method A

Step 1. 3-Acetylamino-2-benzoyl-6-chloro-1-(ethoxycarbonyl)indole

To a solution of 3-amino-2-benzoyl-6-chloro-1-(ethoxycarbonyl)indole (300 mg, 0.88 mmol; example 1, step 2) in a mixture of dichloromethane (10 ml) and pyridine (0.08 ml, 0.96 mmol) was added acetyl chloride (0.07 ml, 0.96 mmol). After stirring for 4 h, the mixture was partitioned between 10% aqueous citric acid (50 ml) and diethyl ether (100 ml). The organic extract was washed consecutively with water (50 ml), saturated sodium bicarbonate (50 ml), water (50 ml) and brine (50 ml). After drying (MgSO$_4$) and removal of solvent, the crude product was purified by flash chromatography eluting with ethyl acetate/hexane (1:1) to afford 183 mg (54%) of the titled compound as a yellow oil.

$^1$H-NMR (CDCl$_3$) δ: 9.13 (1H, br s), 8.15 (1H, br), 7.90–7.70 (2H, m), 7.65–7.40 (4H, m), 7.30–7.20 (1H, m), 3.94 (2H, q, J=7.0 Hz), 2.22 (3H, s), 0.96 (3H, t, J=7.0 Hz).

Step 2. 3-Acetylamino-2-benzoyl-6-chloroindole

To a solution of 3-acetylamino-2-benzoyl-6-chloro-1-(ethoxycarbonyl)indole (556 mg, 1.4 mmol) in ethanol/water (3:1, 20 ml) was added KOH (85% pellets, 480 mg, 7.2 mmol) and the mixture was heated at reflux temperature for 1 h. The mixture was cooled and concentrated, and the residue partitioned between water (50 ml) and diethyl ether (100 ml). The organic extract was washed with water (100 ml) and then brine (100 ml). After drying (MgSO$_4$) and removal of solvent, the crude product was recrystallized from dichloromethane/hexane to afford 180 mg (41%) of the title compound as a yellow powder. m.p.: 212–213° C. $^1$H-NMR (CDCl$_3$) δ: 9.90 (1H, br s), 8.29–8.15 (2H, m), 7.84–7.75 (2H, m), 7.70–7.52 (3H, m), 7.32–7.27 (1H, m), 7.12 (1H, dd, J=1.83, 9.16 Hz), 2.26 (3H, s). IR (KBr) ν: 3400, 1680, 1640, 1520, 1320 cm$^{-1}$ Method B To a 0.2 M solution of pyridine in 1,2-dichloroethane (DCE, 62 μl, 12.5 μmol) was added a 0.1 M solution of 3-amino-2-benzoyl-6-chloroindole (Example 1) in DCE (50 μl, 5.0 μmol), and then a 0.1 M solution of acetyl chloride in DCE (90 μl, 9.0 μmol). The resulting homogeneous mixture was shaken for 4 h, and then left to stand overnight. After adding ethyl acetate (90 μl), the resulting mixture was filtered through a column of aminopropyl silica gel (Bond Elut®, NH$_2$, 100 mg/1.0 ml, 5010–1140) which had been treated with ethyl acetate (150 μl) prior to use. The reaction vessel was washed with ethyl acetate (150 μl×4), and each washing was filtered through the aminopropyl silica gel column. The combined filtrate was concentrated in vacuo to give the title compound in a quantitative yield (1.62 mg).

Ex. 3–Ex. 16

The compounds disclosed hereinafter were prepared from 3-amino-2-benzoyl-6-chloro-1-(ethoxycarbonyl)indole (Example 1, step 2) and the requisite commercially available acid chloride or acid anhydride according to the procedure described in Method A of Example 2.

Ex. 3

2-Benzoyl-6-chloro-3-(isobutyrylamino)indole m.p.: 197–198° C. (ethyl acetate/hexane) $^1$H-NMR (CDCl$_3$) δ: 10.16 (1H, br s), 8.31 (1H, d, J=8.8 Hz), 8.23 (1H, br s), 7.83–7.72 (2H, m), 7.69–7.50 (3H, m), 7.27 (1H, d, J=1.8 Hz), 7.08 (1H, dd, J=1.8, 8.8 Hz), 2.78–2.60 (1H, m), 1.32 (6H, d, J=7.0 Hz)

IR (KBr) ν: 3300, 1670, 1620, 1580, 1520, 1320, 1230, 980, 740 cm$^{-1}$

Ex. 4

3-(Benzamido)-2-benzoyl-6-chloroindole m.p.: 149–151° C. (ethyl acetate/hexane) $^1$H-NMR (CDCl$_3$) δ: 11.25 (1H, s), 8.52 (1H, d, J=8.8 Hz), 8.26 (1H, br s), 8.11–8.04 (2H, m), 7.87–7.79 (2H, m), 7.68–7.48 (6H, m), 7.31 (1H, d, J=1.8 Hz), 7.14 (1H, dd, J=1.8, 8.8 Hz)

IR (KBr) ν: 1660, 1600, 1580, 1540, 1460, 1345, 1250, 1050, 920, 705 cm$^{-1}$

Ex. 5

2-Benzoyl-6-chloro-3-(propionylamino)indole m.p.: 175–177° C. (ethyl acetate/hexane) $^1$H-NMR (CDCl$_3$) δ: 10.02 (1H, br s), 8.31 (1H, d, J=8.8 Hz), 8.18 (1H, br s), 7.83–7.76 (2H, m), 7.70–7.52 (3H, m), 7.30 (1H, d, J=1.8 Hz), 7.11 (1H, dd, J=1.8, 8.8 Hz), 2.52 (2H, q, J=7.3 Hz), 1.30 (3H, t, J=7.3 Hz)

IR (KBr) ν: 1660, 1620, 1570, 1540, 1320, 1240, 720 cm$^{-1}$

Ex. 6

3-(Acryloylamino)-2-benzoyl-6-chloroindole m.p.: 135–140° C. (ethyl acetate/hexane) $^1$H-NMR (CDCl$_3$) δ: 10.29 (1H, br s), 8.69 (1H, br s), 8.35–8.25 (1H, m), 7.81–7.73 (2H, m), 7.65–7.49 (3H, m), 7.25 (1H, d, J=1.8 Hz), 7.05 (1H, dd, J=1.8, 8.8 Hz), 6.50–6.30 (2H, m), 5.81 (1H, dd, J=1.8, 9.5 Hz)

IR (KBr) ν: 1660, 1620, 1570, 1540, 1320, 1240, 990, 720 cm$^{-1}$

Ex. 7

2-Benzoyl-3-(butyrylamino)-6-chloroindole m.p.: 158–161° C. (ethyl acetate/hexane) $^1$H-NMR (CDCl$_3$) δ: 10.00 (1H, br s), 8.40–8.20 (2H, m), 7.88–7.75 (2H, m), 7.69–7.50 (3H, m), 7.28 (1H, s), 7.08 (1H, d, J=8.8 Hz), 2.44 (2H, t, J=7.3 Hz), 1.90–1.70 (2H, m), 1.03 (3H, t, J=7.3 Hz)

IR (KBr) ν: 1660, 1620, 1580, 1450, 1320, 1240, 1060, 920 cm$^{-1}$

Ex. 8

2-Benzoyl-6-chloro-3-(cyclohexylcarboxamido) indole m.p.: 171–174° C. (ethyl acetate/hexane) $^1$H-NMR (CDCl$_3$) δ: 10.18 (1H, br s), 8.32 (1H, d, J=8.8 Hz), 8.23 (1H, br s), 7.85–7.76 (2H, m), 7.69–7.52 (3H, m), 7.26 (1H, s), 7.07 (1H, dd, J=1.8, 8.8 Hz), 2.52–1.20 (11H, m)

IR (KBr) ν: 1660, 1620, 1580, 1540, 1320, 1250, 1230 cm$^{-1}$

Ex. 9

2-Benzoyl-6-chloro-3-(trimethylacetylamino)indole m.p.: 189–192° C. (ethyl acetate/hexane) $^1$H-NMR (CDCl$_3$) δ: 10.49 (1H, br s), 8.35 (1H, d, J=8.8 Hz), 8.21 (1H, br s), 7.85–7.74 (2H, m), 7.68–7.52 (3H, m), 7.27 (1H, d, J=1.8 Hz), 7.08 (1H, dd, J=1.8, 8.8 Hz), 1.40 (9H, s)

IR (KBr) ν: 1655, 1600, 1580, 1490, 1480, 1350, 1250, 1200, 1010, 920 cm$^{-1}$

Ex. 10

2-Benzoyl-6-chloro-3-(isovalerylamino)indole m.p.: 187–190° C. (ethyl acetate/hexane) $^1$H-NMR (CDCl$_3$) δ: 10.01 (1H, br s), 8.28 (1H, d, J=8.8 Hz), 8.25 (1H, br s), 7.86–7.76 (2H, m), 7.70–7.52 (3H, m), 7.28 (1H, d, J=1.8 Hz), 7.09 (1H, dd, J=1.8, 8.8 Hz), 2.40–2.20 (3H, m), 1.05 (6H, d, J=6.6 Hz)

IR (KBr) ν: 1660, 1620, 1570, 1540, 1320, 1250 cm$^{-1}$

Ex. 11

2-Benzoyl-6-chloro-3-(cyclopropylcarboxamido) indole m.p.: 206–208° C. (ethyl acetate/hexane) $^1$H-NMR (CDCl$_3$) δ: 10.25 (1H, br s), 8.29 (1H, br s), 8.24 (1H, d, J=9.2 Hz), 7.84–7.76 (2H, m), 7.68–7.52 (3H, m), 7.25 (1H, d, J=1.8 Hz), 7.05 (1H, dd, J=1.8, 9.2 Hz), 1.80–1.62 (1H, m), 1.20–1.09 (2H, m), 1.00–0.88 (2H, m) IR (KBr) ν: 1660, 1620, 1580, 1450, 1320, 1240, 920 cm$^{-1}$

Ex. 12

2-Benzoyl-6-chloro-3-(valerylamino)indole m.p.: 140–143° C. (ethyl acetate/hexane) $^1$H-NMR (CDCl$_3$) δ: 10.00 (1H, br s), 8.40–8.20 (2H, m), 7.87–7.75 (2H, m), 7.68–7.50 (3H, m), 7.27 (1H, d, J=1.8 Hz), 7.07 (1H, dd, J=1.8, 8.8 Hz), 2.53–2.42 (2H, m), 1.83–1.70 (2H, m), 1.54–1.37 (2H, m), 0.98 (3H, t, J=7.4 Hz) IR (KBr) ν: 1670, 1620, 1570, 1450, 1320, 1230, 740 cm$^{-1}$

Ex. 13

2-Benzoyl-6-chloro-3-[(thiophen-2-yl)carboxamido] indole m.p.: 222–225° C. (ethyl acetate/hexane) $^1$H-NMR (CDCl$_3$) δ: 11.29 (1H, br s), 8.61–8.46 (1H, m), 8.22 (1H, br s), 7.98–7.78 (3H, m), 7.76–7.50 (3H, m), 7.42–7.08 (4H, m)

IR (KBr) ν: 1640, 1580, 1540, 1465, 1350, 1250, 720 cm$^{-1}$

Ex. 14

2-Benzoyl-6-chloro-3-(3-phenylpropionylamino) indole m.p.: 185–186° C. (ethyl acetate/hexane) $^1$H-NMR (CDCl$_3$) δ: 9.89 (1H, br s), 8.26 (1H, br s), 8.20 (1H, d, J=8.8 Hz), 7.82–7.73 (2H, m), 7.68–7.51 (3H, m), 7.34–7.16 (6H, m), 7.09 (1H, dd, J=1.8, 8.8 Hz), 3.09 (2H, t, J=7.3 Hz), 2.77 (2H, t, J=7.3 Hz)

IR (KBr) ν: 1660, 1630, 1580, 1450, 1320, 1240 cm$^{-1}$

Ex. 15

2-Benzoyl-6-chloro-3-(trifluoroacetylamino)indole m.p.: 165–168° C. (ethyl acetate/hexane) $^1$H-NMR (CDCl$_3$) δ: 11.17 (1H, br s), 8.47 (1H, br s), 8.32 (1H, d, J=8.8 Hz), 7.88–7.79 (2H, m), 7.73–7.56 (3H, m), 7.36 (1H, d, J=1.8 Hz), 7.18 (1H, dd, J=1.8, 8.8 Hz) IR (KBr) ν: 1630, 1560, 1450, 1320, 1250, 1230 cm$^{-1}$

Ex. 16

2-Benzoyl-6-chloro-3-(methoxyacetylamino)indole m.p.: 65–70° C. $^1$H-NMR (CDCl$_3$) δ: 10.42 (1H, br s), 8.55 (1H, br s), 8.23 (1H, d, J=8.8 Hz), 7.86–7.78 (2H, m), 7.68–7.50 (3H, m), 7.31 (1H, d, J=1.8 Hz), 7.11 (1H, dd, J=1.8, 8.8 Hz), 4.08(2H, s), 3.54 (3H, s)

IR (KBr) ν: 1680, 1620, 1580, 1540, 1340, 1320, 1250, .1110, 1020, 920 cm$^{-1}$

Ex. 17

3-Acetylamino-6-chloro-2-(4-methoxybenzoyl) indole

Step 1. 3-Amino-6-chloro-1-ethoxycarbonyl-2-(4-methoxybenzoyl)indole

The title compound was prepared according to the procedure described in step 2 of Example 1 from 4-chloro-2-(ethoxycarbonylamino)benzonitrile (Example 1, step 1) and 2-bromo-4'-methoxyacetophenone.

$^1$H-NMR (CDCl$_3$) δ: 8.23 (1H, d, J=1.5 Hz), 7.73 (2H, d, J=9.2 Hz), 7.54 (1H, d, J=8.4 Hz), 7.25 (1H, dd, J=1.8, 8.4 Hz), 6.92 (2H, d, J=9.2 Hz), 5.79 (2H, s), 3.84 (3H, s), 3.82 (2H, q, J=7.0 Hz), 0.88 (3H, t, J=7.0 Hz)

Step 2. 3-Acetylamino-6-chloro-1-ethoxycarbonyl-2-(4-methoxybenzoyl)indole

The title compound was prepared from 3-amino-6-chloro-1-ethoxycarbonyl-2-(4-methoxybenzoyl)indole (step 1)

according to the procedure described in step 1 of Example 2 (Method A). ¹H-NMR (CDCl₃) δ: 8.96 (1H, br s), 8.13 (1H, s), 7.80–7.71 (3H, m), 7.24 (1H, dd, J=1.8, 8.4 Hz), 6.93 (2H, d, J=8.8 Hz), 4.04 (2H, q, J=7.0 Hz), 3.86 (3H, s), 2.20 (3H, s), 1.02 (3H, t, J=7.0 Hz)

Step 3. 3-Acetylamino-6-chloro-2-(4-methoxybenzoyl)indole

The title compound was prepared according to the procedure described in step 2 of Example 2 (Method A) from 3-acetylamino-6-chloro-1-ethoxycarbonyl-2-(4-methoxybenzoyl)indole (step 2). m.p.: 137–139° C. (ethanol/hexane)

¹H-NMR (CDCl₃) δ: 9.84 (1H, br s), 8.28 (1H, br s), 8.18 (1H, d, J=8.8 Hz), 7.82 (2H, d, J=8.8 Hz), 7.30 (1H, d, J=1.8 Hz), 7.11 (1H, dd, J=1.8, 8.8 Hz), 7.05 (2H, d, J=8.8 Hz), 3.91 (3H, s), 2.25 (3H, s) IR (KBr) ν: 3450, 1650, 1620, 1600, 1570, 1540, 1320, 1260, 1250, 1170, 1020, 770 cm⁻¹.

Ex. 18

3-Amino-6-chloro-2-(3-methoxybenzoyl)indole

Step 1. 3-Amino-6-chloro-1-ethoxycarbonyl-2-(3-methoxybenzoyl)indole

The title compound was prepared according to the procedure described in step 2 of Example 1 from 4-chloro-2-(ethoxycarbonylamino)benzonitrile (Example 1, step 1) and 2-bromo-3'-methoxyacetophenone. ¹H-NMR (CDCl₃) δ: 8.25 (1H, d, J=1.5 Hz), 7.53 (1H, d, J=8.4 Hz), 7.36–7.26 (4H, m), 7.05–7.01 (1H, m), 5.78 (2H, s), 3.84 (3H, s), 3.78 (2H, q, J=7.0 Hz), 0.89 (3H, t, J=7.0 Hz).

Step 2. 3-Amino-6-chloro-2-(3-methoxybenzoyl)indole

A mixture of 3-amino-6-chloro-1-ethoxycarbonyl-2-(3-methoxybenzoyl)indole (step 1, 998 mg, 2.68 mmol) and K₂CO₃ (3.70 g, 26.8 mmol) in 70% aqueous ethanol (45 ml) was refluxed for 6.5 h and then cooled to room temperature. The mixture was concentrated to ca. 20 ml, diluted with ethyl acetate (150 ml), and the organic layer washed with water (50 ml×2) and dried (Na₂SO₄). After removal of solvent the residue was purified by flash chromatography eluting with ethyl acetate/hexane (1:4) to afford 549 mg (68%) of the title compound as a syrup. ¹H-NMR (CDCl₃) δ: 7.62 (1H, br s), 7.55–7.30 (5H, m), 7.23 (1H, d, J=1.5 Hz), 7.10 (1H, ddd, J=1.1, 2.6, and 8.1 Hz), 5.60 (2H, br s), 3.88 (3H, s)

Ex. 19

3-Acetylamino-6-chloro-2-(3-methoxybenzoyl)indole

To a solution of 3-amino-6-chloro-2-(3-methoxybenzoyl) indole (Example 18, 413 mg, 1.37 mmol) in dichloromethane (20 ml) was added pyridine (0.33 ml, 4.12 mmol) and acetyl chloride (0.14 ml, 2.06 mmol). After stirring for 0.5 h, water (1 ml) and diethyl ether (100 ml) were added, and the mixture washed consecutively with 1N aqueous HCl (50 ml×2) and saturated aqueous sodium bicarbonate (50 ml×2). The organic layer was dried (MgSO₄) and solvent removed. The resultant residue was purified by flash chromatography eluting with ethyl acetate/hexane (1:2) to afford the title compound as an oil. Crystallization from ethanol/hexane to give 260 mg (55%) of title compound. m.p.: 161–162° C. ¹H-NMR (CDCl₃) δ: 9.92 (1H, br s), 8.32 (1H, br s), 8.22 (1H, d, J=9.2 Hz), 7.47 (1H, dd, J=7.7 and 8.1 Hz), 7.37–7.26 (3H, m), 7.18–7.08 (1H, m), 7.10 (1H, dd, J=1.6 and 9.0 Hz), 3.88 (3H, s), 2.25 (3H, s)

Ex. 20

3-Acetylamino-6-chloro-2-(2-methylbenzoyl)indole

Step 1. 3-Acetylamino-6-chloro-1-ethoxycarbonyl-2-(2-methylbenzoyl)indole

The title compound was prepared according to the procedure described in step 2 of Example 1 and step 1 of Example 2 (Method A) from 4-chloro-2-(ethoxycarbonylamino)benzonitrile (Example 1, step 1) and 2-bromo-2'-methyacetophenone (Baker et al., *J.Chem.Soc.*, 1938, 445). ¹H-NMR (CDCl₃) δ: 9.32 (1H, br s), 8.14 (1H, d, J=1.8 Hz), 7.98 (1H, d, J=8.8 Hz), 7.42–7.10 (5H, m), 3.93 (2H, q, J=7.3 Hz), 2.58 (3H, s), 2.25 (3H, s), 1.03 (3H, t, J=7.3 Hz).

Step 2. 3-Acetylamino-6-chloro-2-(2-methylbenzoyl)indole

The title compound was prepared according to the procedure described in step 2 of Example 2 (Method A) from 3-acetylamino-6-chloro-1-ethoxycarbonyl-2-(2-methylbenzoyl)indole. m.p.: 140–142° C. ¹H-NMR (CDCl₃) δ: 9.59 (1H, br s), 8.29 (1H, br), 8.21 (1H, d, J=8.8 Hz), 7.50–7.35 (4H, m), 7.23 (1H, d, J=1.5 Hz), 7.07 (1H, dd, J=1.8, 8.8 Hz), 2.37 (3H, s), 2.19 (3H, s) IR(KBr)ν: 1675, 1620, 1580, 1540, 1490 cm⁻¹

Ex. 21

3-Amino-6-chloro-2-(3-methylbenzoyl)indole

Step 1. 3-Amino-6-chloro-2-(3-methylbenzoyl)-1-(ethoxycarbonyl)indole

The title compound was prepared according to the procedure described in step 2 of Example 1 from 4-chloro-2-(ethoxycarbonylamino)benzonitrile (Example 1, step 1) and 2-bromo-3'-methylacetophenone (R. Yveline, G. Gerard, and M. Geroges, *Chem.Pharm.Bull.*, 1992, 40, 1170.). tlc: Rf=0.5 (25% ethyl acetate in hexanes)

Step 2. 3-Amino-6-chloro-2-(3-methylbenzoyl)indole

The title compound was prepared according to the procedure described in step 3 of Example 1 from 3-amino-6-chloro-1-ethoxycarbonyl-2-(4-methylbenzoyl)indole (step 1). m.p.: 80–88° C. ¹H-NMR (CDCl₃) δ: 7.63 (1H, br s), 7.60–7.38 (5H, m), 7.23 (1H, d, J=1.8 Hz), 7.02 (1H, dd, J=1.8, 8.8 Hz), 5.56 (2H, br s), 2.45 (3H, s)

Ex. 22

3-Acetylamino-6-chloro-2-(3-methylbenzoyl)indole

Step 1. 3-Acetylamino-6-chloro-1-ethoxycarbonyl-2-(3-methylbenzoyl)indole

The title compound was prepared according to the procedure described in step 1 of Example 2 (Method A) from 3-amino-6-chloro-2-(3-methylbenzoyl)-1-(ethoxycarbonyl) indole (Example 21, step 1).

¹H-NMR (CDCl₃) δ: 9.06 (1H, br s), 8.20 (1H, d, J=1.5 Hz), 7.62–7.49 (2H, m), 7.40–7.24 (4H, m), 3.94 (2H, q, J=7.0 Hz), 2.39 (3H, s), 2.22 (3H, s), 0.96 (3H, t, J=7.0 Hz).

Step 2. 3-Acetylamino-6-chloro-2-(3-methylbenzoyl)indole

The title compound was prepared according to the procedure described in step 2 of Example 2 (Method A) from 3-acetylamino-6-chloro-1-ethoxycarbonyl-2-(3-methylbenzoyl)indole (step 1). m.p.: 96–100° C. $^1$H-NMR (CDCl$_3$) δ: 9.86 (1H, br s), 8.44 (1H, br s), 8.18 (1H, d, J=9.2 Hz), 7.65–7.50 (2H, m), 7.50–7.35 (2H, m), 7.27 (1H, d, J=1.5 Hz), 7.07 (1H, dd, J=1.8, 8.8 Hz), 2.45 (3H, s), 2.22 (3H, s)

IR(KBr) ν: 1670, 1620, 1580, 1540, 1320 cm$^{-1}$

Ex. 23

6-Chloro-2-(3-methylbenzoyl)-3-(propionylamino)indole

The title compound was prepared according to the procedure described in Example 19 employing 3-amino-6-chloro-2-(3-methylbenzoyl)indole (Example 21) and propionyl chloride. m.p.: 152–155° C. $^1$H-NMR (CDCl$_3$) δ: 10.02 (1H, br s), 8.36–8.20 (2H, m), 7.63–7.51 (2H, m), 7.48–7.38 (2H, m), 7.28 (1H, d, J=1.8 Hz), 7.08 (1H, dd, J=1.8, 9.2 Hz), 2.50 (2H, q, J=7.7 Hz), 2.46 (3H, s), 1.29 (3H, t, J=7.7 Hz)

Ex. 24

3-(Butyrylamino)-6-chloro-2-(3-methylbenzoyl)indole

The title compound was prepared according to the procedure described in Example 19 employing 3-amino-6-chloro-2-(3-methylbenzoyl)indole (Example 21) and butyryl chloride. m.p.: 127–130° C. $^1$H-NMR (CDCl$_3$) δ: 10.03 (1H, br s), 8.35–8.20 (2H, m), 7.62–7.54 (2H, m), 7.48–7.40 (2H, m), 7.28 (1H, d, J=1.8 Hz), 7.08 (1H, dd, J=1.8, 9.2 Hz), 2.55–2.35 (5H, m), 1.90–1.72 (2H, m), 1.04 (3H, t, J=7.3 Hz)

Ex. 25

6-Chloro-2-(3-methylbenzoyl)-3-(valerylamino)indole

The title compound was prepared according to the procedure described in Example 19 employing 3-amino-6-chloro-2-(3-methylbenzoyl)indole (Example 21) and valeryl chloride. m.p.: 124–126° C. $^1$H-NMR (CDCl$_3$) δ: 10.02 (1H, br s), 8.40–8.18 (2H, m), 7.62–7.54 (2H, m), 7.47–7.42 (2H, m), 7.28 (1H, s), 7.09 (1H, d, J=8.8 Hz), 2.55–2.45 (5H, m), 1.82–1.68 (2H, m), 1.52–1.38 (2H, m), 0.98 (3H, t, J=7.0 Hz)

Ex. 26

6-Chloro-2-(3-methylbenzoyl)-3-(isovalerylamino)indole

The title compound was prepared according to the procedure described in Example 19 employing 3-amino-6-chloro-2-(3-methylbenzoyl)indole (Example 21) and isovaleryl chloride. m.p.: 182–185° C. $^1$H-NMR (CDCl$_3$) δ: 10.05 (1H, br s), 8.42–8.17 (2H, m), 7.62–7.53 (2H, m), 7.48–7.40 (2H, m), 7.30–7.25 (1H, m), 7.12–7.03 (1H, m), 2.45 (3H, s), 2.39–2.17 (3H, m), 1.04 (6H, dd, J=6.6 Hz)

Ex. 27

6-Chloro-3-(methoxyacetylamino)-2-(3-methylbenzoyl)indole

The title compound was prepared according to the procedure described in Example 19 employing 3-amino-6-chloro-2-(3-methylbenzoyl)indole (Example 21) and methoxyacetyl chloride. m.p.: 155–157° C.

$^1$H-NMR (CDCl$_3$) δ: 10.44 (1H, br s), 8.47 (1H, br s), 8.25 (1H, d, J=8.8 Hz), 7.63–7.53 (2H, m), 7.49–7.38 (2H, m), 7.31 (1H, d, J=1.8 Hz), 7.10 (1H, dd, J=1.8, 8.8 Hz), 4.05 (2H, s), 3.52 (3H, s), 2.44 (3H, s)

Ex. 28

3-Acetylamino-6-chloro-2-(4-methylbenzoyl)indole

Step 1. 3-Acetylamino-6-chloro-1-ethoxycarbonyl-2-(4-methylbenzoyl)indole

The title compound was prepared according to the procedure described in step 2 of Example 1 and step 1 of Example 2 (Method A) from 4-chloro-2-(ethoxycarbonylamino)benzonitrile (Example 1, step 1) and 2-bromo-4'-methyacetophenone. $^1$H-NMR (CDCl$_3$) δ: 8.98 (1H, s), 8.23 (1H, d, J=1.8 Hz), 7.91 (1H, d, J=8.8 Hz), 7.67 (2H, d, J=8.1 Hz), 7.30 (1H, dd, 1.8, 8.8 Hz), 7.26 (2H, d, J=8.1 Hz), 3.93 (2H, q, J=7.3 Hz), 2.42 (3H, s), 2.22 (3H, s), 0.96 (3H, t, 7.3 Hz).

Step 2. 3-Acetylamino-6-chloro-2-(4-methylbenzoyl)indole

The title compound was prepared according to the procedure described in step 2 of Example 2 (Method A) from 3-acetylamino-6-chloro-1-ethoxycarbonyl-2-(4-methylbenzoyl)indole (step 1). m.p.: 140–143° C. $^1$H-NMR (CDCl$_3$) δ: 9.91 (1H, br s), 8.41 (1H, br s), 8.18 (1H, d, J=8.8 Hz), 7.71 (2H, d, J=8.1 Hz), 7.35 (2H, d, J=8.7 Hz), 7.27 (1H, d, J=2.2 Hz), 7.08 (1H, dd, J=1.8, 9.2 Hz), 2.46 (3H, s), 2.23 (3H, s)

IR(KBr)ν: 1670, 1580, 1535, 1320 cm$^{-1}$

Ex. 29

3-Acetylamino-6-chloro-2-(2-chlorobenzoyl)indole

Step 1. 3-Acetylamino-6-chloro-2-(2-chlorobenzoyl)-1-(ethoxycarbonyl)indole The title compound was prepared according to the procedure described in step 2 of Example 1 and step 1 of Example 2 (Method A) from 4-chloro-2-(ethoxycarbonylamino)benzonitrile (Example 1, step 1) and 2-bromo-2'-chloroacetophenone (A. Andreani, M. Rambaldi, and A. Locatelli, *Collect. Czech. Chem. Commun.*, 1991, 56, 2430–2435.).

$^1$H-NMR (CDCl$_3$) δ: 9.55 (1H, br s), 8.17 (1H, d, J=1.5 Hz), 8.08 (1H, d, J=8.4 Hz), 7.52–7.27 (5H, m), 4.00 (2H, q, J=7.0 Hz), 2.27 (3H, s), 1.10 (3H, t, J=7.0 Hz)

Step 2. 3-Acetylamino-6-chloro-2-(2-chlorobenzoyl)indole

The title compound was prepared according to the procedure described in step 2 of Example 2 (Method A) from 3-acetylamino-6-chloro-2-(2-chlorobenzoyl)-1-(ethoxycarbonyl)indole (step 1). $^1$H-NMR (CDCl$_3$) δ: 9.58 (1H, br s), 8.51 (1H, br s), 8.19 (1H, d, J=8.8 Hz), 7.52–7.03 (6H, m), 2.18 (3H, s) IR (KBr) ν: 3300, 1680, 1620, 1580, 1540, 1340, 1320, 1240, 1060, 1020, 920, 760, 740 cm$^{-1}$

Ex. 30

3-Amino-6-chloro-2-(3-chlorobenzoyl)indole

Step 1. 3-Amino-6-chloro-2-(3-chlorobenzoyl)-1-(ethoxycarbonyl)indole

The title compound was prepared according to the procedure described in step 2 of Example 1 from 4-chloro-2-

(ethoxycarbonylamino)benzonitrile (Example 1, step 1) and 2-bromo-3'-chloroacetophenone (M. Kihara, M. Kashimoto, and Y. Kobayashi, *Tetrahedron*, 1992, 48, 67–78.).

$^1$H-NMR (CDCl$_3$) δ: 8.25 (1H, d, J=1.5 Hz), 7.74 (1H, dd, J=1.5, 2.2 Hz), 7.58 (1H, dt, J=1.5, 7.7 Hz), 7.53 (1H, d, J=8.4 Hz), 7.47–7.43 (1H, m), 7.37 (1H, d, J=7.3 Hz), 7.32 (1H, dd, J=1.8, 8.4 Hz), 5.86 (2H, br s), 3.84 (2H, q, J=7.0 Hz), 0.93 (3H, t, J=7.0 Hz)

Step 2. 3-Amino-6-chloro-2-(3-chlorobenzoyl) indole

The title compound was prepared according to the procedure described in step 3 of Example 1 from 3-amino-6-chloro-2-(3-chlorobenzoyl)-1-(ethoxycarbonyl)indole (step 1). m.p.: 99–102° C.

$^1$H-NMR (CDCl$_3$) δ: 7.78 (1H, t, J=1.5 Hz), 7.68 (1H, ddd, J=1.5, 1.8, 7.3 Hz), 7.55–7.44 (4H, m), 7.25 (1H, d, J=1.8 Hz), 7.04 (1H, dd, J=1.8, 8.8 Hz), 5.68 (2H, br s)

Ex. 31

3-Acetylamino-6-chloro-2-(3-chlorobenzoyl)indole

Step 1. 3-Acetylamino-6-chloro-2-(3-chlorobenzoyl)-1-(ethoxycarbonyl)indole

The title compound was prepared according to the procedure described in step 1 of Example 2 (Method A) from 3-amino-6-chloro-2-(3-chlorobenzoyl)-1-(ethoxycarbonyl)indole (Example 30, step 1). $^1$H-NMR (CDCl$_3$) δ: 9.10 (1H, br s), 8.12–7.23 (7H, m), 4.05 (2H, q, J=7.0 Hz), 2.23 (3H, s), 1.06 (3H, t, J=7.0 Hz)

Step 2. 3-Acetylamino-6-chloro-2-(3-chlorobenzoyl) indole

The title compound was prepared according to the procedure described in step 2 of Example 2 (Method A) from 3-acetylamino-6-chloro-2-(3-chlorobenzoyl)-1-(ethoxycarbonyl)indole (step 1). m.p.: 152–154° C. (dichloromethane/hexane)

$^1$H-NMR (CDCl$_3$) δ: 9.72 (1H, br s), 8.90 (1H, br s), 8.02 (1H, d, J=8.8 Hz), 7.73–7.00 (6H, m), 2.17 (3H, s) IR (KBr) v: 3300, 1680, 1620, 1580, 1540, 1490, 1340, 1320, 1240, 1060, 1040, 920, 800, 730 cm$^{-1}$

Ex. 32

6-Chloro-2-(3-chlorobenzoyl)-3-(propionylamino) indole

The title compound was prepared according to the procedure described in Example 19 employing 3-amino-6-chloro-2-(3-chlorobenzoyl)indole (Example 30) and propionyl chloride. m.p.: 129–130° C. $^1$H-NMR (CDCl$_3$): 9.95 (1H, br s), 8.30 (1H, d, J=9.2 Hz), 8.17 (1H, br s), 7.78–7.59 (3H, m), 7.51 (1H, t, J=7.7 Hz), 7.32 (1H, d, J=1.1 Hz), 7.11 (1H, dd, J=1.8, 8.8 Hz), 4.48 (2H, q, J=7.6 Hz), 1.30 (3H, t, J=7.6 Hz)

Ex. 33

3-(Butyrylamino)-6-chloro-2-(3-chlorobenzoyl) indole

The title compound was prepared according to the procedure described in Example 19 employing 3-amino-6-chloro-2-(3-chlorobenzoyl)indole (Example 30) and butyryl chloride. m.p.: 157–158° C. $^1$H-NMR (CDCl$_3$) δ: 9.96 (1H, br s), 8.29 (1H, d, J=8.8 Hz), 8.17 (1H, br s), 7.78 (1H, dd, J=1.5, 1.8 Hz), 7.70–7.59 (2H, m), 7.51 (1H, t, J=7.7 Hz), 7.31 (1H, d, J=1.1 Hz), 7.11 (1H, dd, J=1.8, 8.8 Hz), 2.47 (2H, t, J=7.3 Hz), 1.88–1.75 (2H, m), 1.05 (3H, t, J=7.5 Hz)

Ex. 34

6-Chloro-2-(3-chlorobenzoyl)-3-(valerylamino) indole

The title compound was prepared according to the procedure described in Example 19 employing 3-amino-6-chloro-2-(3-chlorobenzoyl)indole (Example 30) and valeryl chloride. m.p.: 159–160° C. $^1$H-NMR (CDCl$_3$) δ: 9.94 (1H, br s), 8.28 (1H, d, J=9.2 Hz), 8.19 (1H, br s), 7.77 (1H, t, J=1.8 Hz), 7.70–7.58 (2H, m), 7.51 (1H, t, J=7.7 Hz), 7.31 (1H, d, J=1.8 Hz), 7.11 (1H, dd, J=1.8, 8.8 Hz), 2.49 (2H, t, J=7.3 Hz), 1.81–1.70 (2H, m), 1.51–1.37 (2H, m), 0.97 (3H, t, J=7.3 Hz)

Ex. 35

6-Chloro-2-(3-chlorobenzoyl)-3-(isovalerylamino) indole

The title compound was prepared according to the procedure described in Example 19 employing 3-amino-6-chloro-2-(3-chlorobenzoyl)indole (Example 30) and isovaleryl chloride. m.p.: 185–186° C. $^1$H-NMR (CDCl$_3$) δ: 9.94 (1H, br s), 8.28 (1H, d, J=8.8 Hz), 8.19 (1H, br s), 7.78 (1H, t, J=1.8 Hz), 7.68 (1H, dt, J=1.5, 1.5, 7.3 Hz), 7.61 (1H, ddd, J=1.5, 1.8, 8.1 Hz), 7.51 (1H, t, J=7.7 Hz), 7.31 (1H, d, J=1.5 Hz), 7.11 (1H, dd, J=1.8, 8.8 Hz), 2.37–2.20 (3H, m), 1.06 (6H, d, J=6.2 Hz)

Ex. 36

6-Chloro-2-(3-chlorobenzoyl)-3-(methoxyacetylamino)indole

The title compound was prepared according to the procedure described in Example 19 employing 3-amino-6-chloro-2-(3-chlorobenzoyl)indole (Example 30) and methoxyacetyl chloride. m.p.: 154–155° C. $^1$H-NMR (CDCl$_3$) δ: 10.22 (1H, br s), 8.41 (1H, br s), 8.21 (1H, d, J=9.2 Hz), 7.77 (1H, dd, J=1.5, 2.2 Hz), 7.68 (1H, ddd, J=1.1, 1.5, 7.7 Hz), 7.59 (1H, ddd, J=1.1, 1.8, 7.7 Hz), 7.49 (1H, dd, J=7.7, 8.1 Hz), 7.34 (1H, d, J=1.8 Hz), 7.13 (1H, dd, J=1.8, 8.8 Hz), 4.05 (2H, s), 3.53 (3H, s)

Ex. 37

3-Acetylamino-6-chloro-2-(4-chlorobenzoyl)indole

Step 1. 3-Acetylamino-6-chloro-1-ethoxycarbonyl-2-(4-chlorobenzoyl)indole

The title compound was prepared according to the procedure described in step 2 of Example 1 and step 1 of Example 2 (Method A) from 4-chloro-2-(ethoxycarbonylamino)benzonitrile (Example 1, step 1) and 2-bromo-4'-chloroacetophenone.

$^1$H-NMR (CDCl$_3$) δ: 9.06 (1H, br s), 8.11 (1H, br s), 7.82–7.69 (3H, m), 7.45–7.42 (2H, m), 7.27–7.24 (1H, m), 4.05 (2H, q, J=7.0 Hz), 2.22 (3H, s), 1.07 (3H, t, J=7.0 Hz)

Step 2. 3-Acetylamino-6-chloro-2-(4-chlorobenzoyl) indole

The title compound was prepared according to the procedure described in step 2 of Example 2 (Method A) from 3-acetylamino-6-chloro-2-(4-chlorobenzoyl)-1-(ethoxycarbonyl)indole (step 1). m.p.: 175–176° C. (ethyl acetate/hexane)

¹H-NMR (CDCl₃) δ: 9.83 (1H, br s), 8.22 (1H, br s), 8.17 (1H, br s), 7.77 (2H, d, J=8.4 Hz), 7.55 (2H, d, J=8.4 Hz), 7.30–7.26 (1H, m), 7.13 (1H, d, J=8.8 Hz), 2.27 (3H, s)

IR (KBr) ν: 3450, 1660, 1620, 1590, 1540, 1320, 1250, 1090, 850, 760 cm⁻¹

Ex. 38

3-Acetylamino-6-chloro-2-(3-fluorobenzoyl)indole

Step 1. 3-Acetylamino-6-chloro-1-ethoxycarbonyl-2-(3-fluorobenzoyl)indole

The title compound was prepared according to the procedure described in step 2 of Example 1 and step 1 of Example 2 (Method A) from 4-chloro-2-(ethoxycarbonylamino)benzonitrile (Example 1, step 1) and 2-bromo-3'-fluoroacetophenone (T. Rosen, A. A. Nagel, J. P. Rizzi, J. L. Ives, J. B. Daffeh, et al., *J. Med. Chem.*, 1990, 33, 2715–2720.).

¹H-NMR (CDCl₃) δ: 9.05 (1H, br s), 8.18 (1H, d, J=1.5 Hz), 7.88 (1H, d, J=8.4 Hz), 7.55–7.23 (5H, m), 4.01 (2H, q, J=7.0 Hz), 2.24 (3H, s), 1.03 (3H, t, J=7.0 Hz)

Step 2. 3-Acetylamino-6-chloro-2-(3-fluorobenzoyl)indole

The title compound was prepared according to the procedure described in step 2 of Example 2 (Method A) from 3-acetylamino-6-chloro-2-(3-fluorobenzoyl)-1-(ethoxycarbonyl)indole (step 1). m.p.: 201–202° C. (ethanol)

¹H-NMR (CDCl₃) δ: 9.89 (1H, br s), 8.27–8.18 (2H, m), 7.61–7.26 (5H, m), 7.12 (1H, dd, J=1.8, 8.8 Hz), 2.27 (3H, s) IR (KBr) ν: 3450, 1680, 1640, 1510, 1320, 1260, 1250, 860, 820, 520 cm⁻¹

Ex. 39

3-Acetylamino-6-chloro-2-(4-fluorobenzoyl)indole

Step 1. 3-Acetylamino-6-chloro-1-ethoxycarbonyl-2-(4-fluorobenzoyl)indole

The title compound was prepared according to the procedure described in step 2 of Example 1 and step 1 of Example 2 (Method A) from 4-chloro-2-(ethoxycarbonylamino)benzonitrile (Example 1, step 1) and 2-bromo-4'-fluoroacetophenone. m.p.: 196–198° C.

¹H-NMR (CDCl₃) δ: 8.98 (1H, br s), 8.17 (1H, d, J=1.5 Hz), 7.86–7.78 (3H, m), 7.28 (1H, dd, J=1.8, 8.8 Hz), 7.18–7.11 (2H, m), 4.02 (2H, q, J=7.0 Hz), 2.23 (3H, s), 1.03 (3H, t, J=7.0 Hz)

Step 2. 3-Acetylamino-6-chloro-2-(4-fluorobenzoyl)indole

The title compound was prepared according to the procedure described in step 2 of Example 2 (Method A) from 3-acetylamino-6-chloro-1-ethoxycarbonyl-2-(4-fluorobenzoyl)indole (step 1). m.p.: 205–207° C. (ethanol/hexane)

¹H-NMR (CDCl₃) δ: 9.79 (1H, br s), 8.24 (1H, br s), 8.19 (1H, d, J=9.2 Hz), 7.87–7.83 (2H, m), 7.30–7.22 (3H, m), 7.11 (1H, dd, J=1.8, 8.8 Hz), 2.25 (3H, s)

IR (KBr) ν: 3450, 1680, 1640, 1600, 1500, 1320, 1240, 840, 820, 600, 510 cm⁻¹

Ex. 40

3-Amino-6-chloro-2-(4-methylthiobenzoyl)indole

Step 1. 3-Amino-6-chloro-1-ethoxycarbonyl-2-(4-methylthiobenzoyl)indole

The title compound was prepared according to the procedure described in step 2 of Example 1 from 4-chloro-2-(ethoxycarbonylamino)benzonitrile (Example 1, step 1) and 2-bromo-4'-methylthioacetophenone (Cutler et al., *J. Am. Chem. Soc.*, 1952, 74, 5475). ¹H-NMR (CDCl₃) δ: 8.25 (1H, d, J=1.8 Hz), 7.67 (2H, d, J=8.4 Hz), 7.53 (1H, d, J=8.4 Hz), 7.31–7.23 (3H, m), 5.75 (2H, br s), 3.82 (2H, q, J=7.0 Hz), 2.51 (3H, s), 0.89 (3H, t, J=7.0 Hz)

Step 2. 3-Amino-6-chloro-2-(4-methylthiobenzoyl)indole

The title compound was prepared according to the procedure described in step 3 of Example 1 from 3-amino-6-chloro-1-ethoxycarbonyl-2-(4-methylthiobenzoyl)indole (step 1). m.p.: 172–173° C. ¹H-NMR (CDCl₃) δ: 7.77–7.72 (2H, m), 7.59 (1H, br s), 7.53 (1H, d, J=8.8 Hz), 7.38–7.33 (2H, m), 7.23 (1H, d, J=1.5 Hz), 7.04 (1H, dd, J=1.8, 8.4 Hz), 5.57 (2H, br s), 2.55 (3H, s)

Ex. 41

3-Acetylamino-6-chloro-2-(4-methylthiobenzoyl)indole

The title compound was prepared according to the procedure described in Example 19 from 3-amino-6-chloro-2-(4-methylthiobenzoyl)indole (Example 40).

m.p.: 187–188° C. ¹H-NMR (CDCl₃) δ: 9.87 (1H, br s), 8.24 (1H, br s), 8.20 (1H, d, J=8.4 Hz), 7.76–7.73 (2H, m), 7.39–7.35 (2H, m), 7.29 (1H, d, J=1.5 Hz), 7.11 (1H, dd, J=1.8, 8.8 Hz), 2.56 (3H, s), 2.26 (3H, s)

Ex. 42

3-Amino-2-(3-bromobenzoyl)-6-chloroindole

Step 1. 3-Amino-2-(3-bromobenzoyl)-6-chloro-1-(ethoxycarbonyl)indole

The title compound was prepared according to the procedure described in step 2 of Example 1 from 4-chloro-2-(ethoxycarbonylamino)benzonitrile (Example 1, step 1) and 2-bromo-3'-bromoacetophenone. ¹H-NMR (CDCl₃) δ: 8.25 (1H, d, J=1.5 Hz), 7.90 (1H, t, J=1.8 Hz), 7.64–7.59 (2H, m), 7.54 (1H, d, J=8.4 Hz), 7.34–7.26 (2H, m), 5.87 (2H, br s). 3.84 (2H, q, J=7.0 Hz), 0.89 (3H, t, J=7.0 Hz)

Step 2. 3-Amino-2-(3-bromobenzoyl)-6-chloroindole

The title compound was prepared according to the procedure described in step 3 of Example 1 from 3-amino-2-(3-bromobenzoyl)-6-chloro-1-(ethoxycarbonyl)indole (step 1). m.p.: 142–143° C. ¹H-NMR (CDCl₃) δ: 7.93 (1 H, dd, J=1.5, 1.8 Hz), 7.74–7.66 (2 H, m), 7.53 (1 H, d, J=8.4 Hz), 7.52 (1 H, br s), 7.41 (1 H, dd, J=7.7, 8.1 Hz), 7.26 (1 H, d, J=2.6 Hz), 7.04 (1 H, dd, J=1.7, 8.4 Hz), 5.69 (2 H, br s)

Ex. 43

3-Acetylamino-2-(3-bromobenzoyl)-6-chloroindole

The title compound was prepared according to the procedure described in Example 19 from 3-amino-2-(3-bromobenzoyl)-6-chloroindole (Example 42).

m.p.: 183–184° C. $^1$H-NMR (CDCl$_3$) δ: 9.78 (1 H, br s), 8.22 (1 H, d, J=8.8 Hz), 8.21 (1 H, br s), 7.93 (1 H, t, J=1.8 Hz), 7.78–7.70 (2 H, m), 7.44 (1 H, t, J=7.9 Hz), 7.32 (1 H, d, J=1.5 Hz), 7.12 (1 H, dd, J=1.8, 9.2 Hz), 2.26 (3 H, s)

Ex. 44

3-Acetylamino-2-(3-benzyloxybenzoyl)-6-chloroindole

Step 1. 3-Amino-2-(3-benzyloxybenzoyl)-6-chloro-1-(ethoxycarbonyl)indole

The title compound was prepared according to the procedure described in step 2 of Example 1 from 4-chloro-2-(ethoxycarbonylamino)benzonitrile (Example 1, step 1) and 2-bromo-3'-(benzyloxy)acetophenone (T. Fujii, M. Ohba, M. Tsuchida, K. Saito, Y. Hirano, and J. Sakaguchi, *Chem.Pharm.Bull.*, 1986, 34, 496–507).

$^1$H-NMR (CDCl$_3$) δ: 8.25 (1H, d, J=1.5 Hz), 7.60–7.23 (10H, m), 7.18–7.06 (1H, m), 5.76 (2H, br s), 5.11 (2H, s), 3.74 (2H, q, J=7.3 Hz), 0.85 (3H, t, J=7.3 Hz)

Step 2. 3-Acetylamino-2-(3-benzyloxybenzoyl)-6-chloro-1-(ethoxycarbonyl)indole

The title compound was prepared according to the procedure described in step 1 of Example 2 (Method A) from 3-amino-2-(3-benzyloxybenzoyl)-6-chloro-1-(ethoxycarbonyl)indole (step 1).

$^1$H-NMR (CDCl$_3$) δ: 9.02 (1H, br s), 8.20 (1H, s), 7.90 (1H, J=8.4 Hz), 7.48–7.16 (10H, m), 5.29 (2H, s), 3.91 (2H, q, J=7.0 Hz), 2.22 (3H, s), 0.95 (3H, t, J=7.0 Hz)

Step 3. 3-Acetylamino-2-(3-benzyloxybenzoyl)-6-chloroindole

The title compound was prepared according to the procedure described in step 2 of Example 2 (Method A) from 3-acetylamino-2-(3-benzyloxybenzoyl)-6-chloro-1-(ethoxycarbonyl)indole (step 2).m.p.: 159–161° C.

$^1$H-NMR (CDCl$_3$) δ: 9.88 (1H, br s), 8.25 (1H, br s), 8.21 (1H, d, J=9.2 Hz), 7.50–7.21 (10H, m), 7.08 (1H, dd, J=8.8, 1.8 Hz), 5.14 (2H, s), 2.24 (3H, s)

Ex. 45

3-Acetylamino-6-chloro-2-(3-hydroxybenzoyl)indole

3-Acetylamino-2-(3-benzyloxybenzoyl)-6-chloroindole (Example 44, 0.42 g, 1.0 mmol) was hydrogenolyzed in the presence of palladium on activated carbon (10%, 0.10 g) in a mixture of ethyl acetate (10 ml) and ethanol (1.0 ml) at atmospheric pressure overnight. The mixture was filtered and the filtrate was concentrated in vacuo. The residual solid was recrystallization from ethyl acetate/hexane to afford 0.13 g (40%) of the title compound as a pale yellow solid. m.p.: 130–145° C. $^1$H-NMR (CDCl$_3$) δ: 11.73 (1H, brs), 9.80–9.65 (2H, m), 7.62 (1H, d, J=8.4 Hz), 7.50–6.98 (5H, m), 1.76 (3H, s) The signal due to H of OH was not observed.

Ex. 46

3-Acetylamino-6-chloro-2-(3,4-dichlorobenzoyl)indole

Step 1. 3-Acetylamino-6-chloro-2-(3,4-dichlorobenzoyl)-1-(ethoxycarbonyl)indole

The title compound was prepared according to the procedure described in step 2 of Example 1 and step 1 of Example 2 (Method A) from 4-chloro-2-(ethoxycarbonylamino)benzonitrile (Example 1, step 1) and 2-bromo-3',4'-dichloroacetophenone.

$^1$H-NMR (CDCl$_3$) δ: 9.11 (1H, br s), 7.99 (1H, d, J=1.8 Hz), 7.92 (1H, d, J=1.8 Hz), 7.65 (1H, d, J=8.4 Hz), 7.57 (1H, dd, J=2.0, 8.2 Hz), 7.51 (1H, d, J=8.4 Hz), 7.20 (1H, dd, J=1.8, 8.8 Hz), 4.15 (2H, q, J=7.0 Hz), 2.21 (3H, s), 1.17 (3H, t, J=7.0 Hz)

Step 2. 3-Acetylamino-6-chloro-2-(3,4-dichlorobenzoyl)indole

The title compound was prepared according to the procedure described in step 2 of Example 2 (Method A) from 3-acetylamino-6-chloro-2-(3,4-dichlorobenzoyl)-1-(ethoxycarbonyl)indole (step 1). m.p.: 169–171° C. $^1$H-NMR (CDCl$_3$) δ: 9.74 (1H, br s), 8.25 (1H, br s), 8.19 (1H, d, J=9.2 Hz), 7.90 (1H, t, J=1.1 Hz), 7.64 (2H, br s), 7.31 (1H, d, J=1.5 Hz), 7.11 (1H, dd, J=1.8, 9.2 Hz), 2.26 (3H, s)

IR (KBr) ν: 3300, 1660, 1620, 1580, 1540, 1320, 1230, 1030, 800, 760 cm$^{-1}$

Ex. 47

3-Amino-6-chloro-2-(3,5-difluorobenzoyl)indole

Step 1. 3-Amino-6-chloro-2-(3,5-difluorobenzoyl)-1-(ethoxycarbonyl)indole

The title compound was prepared according to the procedure described in step 3 of Example 1 from 4-chloro-2-(ethoxycarbonylamino)benzonitrile (Example 1, step 1) and 2-bromo-3',5'-difluoroacetophenone (prepared according to the method of S. Kajigaeshi et al., *Bull.Chem.Soc.Jpn.*, 1987, 60, 1159–1160).

$^1$H-NMR (CDCl$_3$) δ: 8.24 (1H, d, J=1.8 Hz), 7.54 (1H, d, J=8.4 Hz), 7.33 (1H, dd, J=1.8, 8.4 Hz), 7.29–7.22 (2H, m), 6.97–6.88 (1H, m), 5.90 (2H, br s), 3.94 (2H, q, J=7.0 Hz), 1.00 (3H, t, J=7.0 Hz)

Step 2. 3-Amino-6-chloro-2-(3,5-difluorobenzoyl)indole

The title compound was prepared according to the procedure described in step 2 of Example 1 from 3-amino-6-chloro-2-(3,5-difluorobenzoyl)-1-(ethoxycarbonyl)indole (step 1). m.p.: 149–151° C.

$^1$H-NMR (CDCl$_3$) δ: 7.54 (1 H, d, J=8.4 Hz), 7.45 (1 H, br s), 7.39–7.26 (3 H, m), 7.06 (1 H, dd, J=1.8, 8.4 Hz), 7.02–6.96 (1 H, m), 5.79 (2 H, br s)

Ex. 48

3-Acetylamino-6-chloro-2-(3,5-difluorobenzoyl)indole

The title compound was prepared according to the procedure described in Example 19 from 3-amino-6-chloro-2-(3,5-difluorobenzoyl)indole (Example 47).

m.p.: 232–233° C. $^1$H-NMR (CDCl$_3$) δ: 9.87 (1 H, br s), 8.25 (1 H, d, J=8.8 Hz), 8.18 (1 H, br s), 7.38–7.32 (3 H, m), 7.12 (1 H, dd, J=1.8, 8.8 Hz), 7.09–7.04 (1 H, m), 2.28 (3 H, s)

Ex. 49

3-Amino-6-chloro-2-(3-trifluoromethylbenzoyl)indole

Step 1. 3-Amino-6-chloro-1-ethoxycarbonyl-2-(3-trifluoromethylbenzoyl)indole

The title compound was prepared according to the procedure described in step 2 of Example 1 from 4-chloro-2-

(ethoxycarbonylamino)benzonitrile (Example 1, step 1) and 2-bromo-3'-trifluoromethylacetophenone (M. Kihara, M. Kashimoto, and Y. Kobayashi, *Tetrahedron,* 1992, 48, 67–78). $^1$H-NMR (CDCl$_3$) δ: 8.25 (1H, d, J=1.8 Hz), 8.03 (1H, br s), 7.89 (1H, br d, J=7.7 Hz), 7.74 (1H, br d, J=8.1 Hz), 7.59–7.54 (2H, m), 7.33 (1H, dd, J=1.8, 8.4 Hz), 5.93 (2H, br s), 3.80 (2H, q, J=7.0 Hz), 0.88 (3H, t, J=7.0 Hz)

Step 2. 3-Amino-6-chloro-2-(3-trifluoromethylbenzoyl)indole

The title compound was prepared according to the procedure described in step 3 of Example 1 from 3-amino-6-chloro-1-(ethoxycarbonyl)-2-(3-trifluoromethybenzoyl)indole (step 1). m.p.: 84–87° C.

$^1$H-NMR (CDCl$_3$) δ: 8.07 (1 H, br s), 7.99 (1 H, br d, J=8.1 Hz), 7.82 (1 H, br d, J=7.7 Hz), 7.67 (1 H, t, J=7.7 Hz), 7.55 (1 H, d, J=8.8 Hz), 7.46 (1 H, br s), 7.46 (1 H, d, J=2.2 Hz), 7.06 (1 H, dd, J=1.8, 8.8 Hz), 5.72 (2 H, br s)

Ex. 50

6-Chloro-3-(isovalerylamino)-2-(3-trifluoromethylbenzoyl) indole

The title compound was prepared according to the procedure described in Example 19 employing 3-amino-6-chloro-2-(3-trifluoromethylbenzoyl)indole (Example 49) and isovaleryl chloride. m.p.: 179–180° C.

$^1$H-NMR (CDCl$_3$) δ: 9.87 (1H, br s), 8.27 (1H, d, J=8.8 Hz), 8.18 (1H, br s), 8.07 (1H, br s), 8.00 (1H, d, J=8.1 Hz), 7.89 (1H, d, J=7.7 Hz), 7.71 (1H, t, J=7.7 Hz), 7.31 (1H, d, J=1.8 Hz), 7.13 (1H, dd, J=1.8, 8.8 Hz), 2.37–2.20 (3H, m), 1.05 (6H, d, J=6.2 Hz)

Ex. 51

3-Amino-6-chloro-2-(4-trifluoromethoxybenzoyl)indole

Step 1. 3-Amino-6-chloro-1-ethoxycarbonyl-2-(4-trifluoromethoxybenzoyl)indole

The title compound was prepared according to the procedure described in step 2 of Example 1 from 4-chloro-2-(ethoxycarbonylamino)benzonitrile (Example 1, step 1) and 2-bromo-4'-trifluoromethoxyacetophenone.

$^1$H-NMR (CDCl$_3$) δ: 8.25 (1H, d, J=1.8 Hz), 7.82–7.77 (2H, m), 7.54 (1H, d, J=8.4 Hz), 7.33–7.26 (3H, m), 5.88 (2 H, s), 3.82 (2H, q, J=7.2 Hz), 0.87 (3H, t, J=7.2 Hz)

Step 2. 3-Amino-6-chloro-2-(4-trifluoromethoxybenzoyl)indole:

The title compound was prepared according to the procedure described in step 3 of Example 1 from 3-amino-6-chloro-1-(ethoxycarbonyl)-2-(4-trifluoromethoxybenzoyl)indole (step 1). $^1$H-NMR (CDCl$_3$) δ: 7.89–7.83 (2H, m), 7.54 (1H, d, J=8.8 Hz), 7.52 (1H, br s), 7.37 (2H, br d, J=8.8 Hz), 7.24 (1H, d, J=1.5 Hz), 7.05 (1H, dd, J=1.6, 8.8 Hz), 5.70 (2H, br s)

IR (KBr) ν: 3350, 1620, 1610, 1490, 1260, 1210, 1170 cm$^{-1}$

Ex. 52

3-Acetylamino-6-chloro-2-(4-trifluoromethoxybenzoyl)indole

The title compound was prepared according to the procedure described in Example 19 employing 3-amino-6-chloro-2-(4-trifluoromethoxybenzoyl)indole (Example 51). m.p.: 213–214° C. $^1$H-NMR (CDCl$_3$) δ: 9.75 (1H, br s), 8.23 (1H, br s), 8.19 (1H, d, J=8.8 Hz), 7.89–7.85 (2H, m), 7.41 (2H, d, J=8.1 Hz), 7.31 (1H, d, J=1.8 Hz), 7.12 (1H, dd, J=1.8, 8.8 Hz), 2.25 (3H, s) IR (KBr) ν: 3250, 1680, 1640, 1620, 1580, 1560, 1500, 1300, 1280, 1260, 1230, 1210, 1160, 920 cm$^{-1}$ Ex. 53

3-Amino-6-chloro-2-(4-chloro-3-methylbenzoyl)indole

Step 1. 3-Amino-6-chloro-2-(4-chloro-3-methylbenzoyl)-1-(ethoxycarbonyl)indole

The title compound was prepared according to the procedure described in step 2 of Example 1 from 4-chloro-2-(ethoxycarbonylamino)benzonitrile (Example 1, step 1) and 2-bromo-4'-chloro-3'-methylacetophenone.

$^1$H-NMR (CDCl$_3$) δ: 8.24 (1H, d, J=1.8 Hz), 7.63 (1H, d, J=2.2 Hz), 7.53 (1H, d, J=8.4 Hz), 7.50–7.46 (1H, m), 7.39 (1H, d, J=8.4 Hz), 7.31 (1H, dd, J=1.8, 8.4 Hz), 5.78 (2H, br s), 3.85 (2H, q, J=7.0 Hz), 2.42 (3H, s), 0.92 (3H, t, J=7.0 Hz)

Step 2. 3-Amino-6-chloro-2-(4-chloro-3-methylbenzoyl)indole

The title compound was prepared according to the procedure described in step 3 of Example 1 from 3-amino-6-chloro-1-(ethoxycarbonyl)-2-(4-chloro-3-methylbenzoyl)indole (step 1). m.p.: 142–143° C.

$^1$H-NMR (CDCl$_3$) δ: 7.68–7.40 (5H, m), 7.24 (1H, d, J=1.8 Hz), 7.04 (1H, dd, J=1.5, 8.4 Hz), 5.60 (2H, br s), 2.47 (3H, s)

Ex. 54

6-Chloro-2-(4-chloro-3-methylbenzoyl)-3-(isovalerylamino)-indole

The title compound was prepared according to the procedure described in Example 19 employing 3-amino-6-chloro-2-(4-chloro-3-methylbenzoyl)indole (Example 53). m.p.: 202–203° C. $^1$H-NMR (CDCl$_3$) δ: 9.97 (1H, br s), 8.27 (1H, d, J=9.2 Hz), 8.19 (1H, br s), 7.71–7.51 (3H, m), 7.29 (1H, d, J=1.8 Hz), 7.10 (1H, dd, J=1.8, 9.2 Hz), 2.48 (3H, s), 2.36–2.23 (3H, m), 1.05 (6H, d, J=6.2 Hz)

Ex. 55

2-Benzoyl-6-chloro-3-(2-chlorobenzamido)indole

The title compound was prepared according to the procedure described in Example 19 employing 3-amino-2-benzoyl-6-chloroindole (Example 1) and 2-chlorobenzoyl chloride. m.p.: 229–234° C. (dichloromethane/hexane)

$^1$H-NMR (DMSO-d$_6$) δ: 11.98 (1H, brs), 10.35 (1H, s), 7.86–7.38 (9H, m), 7.34–7.24 (1H, m), 7.18 (1H, dd, J=1.8, 8.8 Hz), 6.68 (1H, d, J=7.3 Hz)

Ex. 56

2-Benzoyl-6-chloro-3-[(3-ethoxycarbonyl)propionylamino]indole

The title compound was prepared according to the procedure described in Example 19 employing 3-amino-2-benzoyl-6-chloroindole (Example 1) and ethyl succinyl chloride. m.p.: 156–163° C. $^1$H-NMR (CDCl$_3$) δ: 9.96 (1H, br s), 8.39 (1H, br s), 8.20–8.12 (1H, m), 7.95–7.77 (2H, d, J=7.3 Hz), 7.68–7.52 (3H, m), 7.27 (1H, s), 7.10–7.02 (1H, m), 4.15 (2H, q, J=7.0 Hz), 2.74 (4H, s), 1.23 (3H, t, J=7.0 Hz)

Ex. 57

2-Benzoyl-6-chloro-3-(succinamoylamino)indole

A solution of 2-benzoyl-6-chloro-3-[(3-ethoxycarbonyl) propionylamino]indole (Example 56, 600 mg, 1.5 mmol) in ammonia solution (10% in ethanol, 15 ml) was stirred for 16 h. The resulting solids were collected by filtration and recrystallized from methanol to afford 150 mg (27%) of the title compound as yellow solid.

m.p.: 258–263° C. $^1$H-NMR (CDCl$_3$) δ: 11.82 (1H, br s), 9.72 (1H, br s), 7.78–7.68 (2H, m), 7.67–7.58 (2H, m), 7.57–7.46 (2H, m), 7.45 (1H, d, J=7.3 Hz), 7.24 (1H, br s), 7.10 (1H, dd, J=1.8, 8.8 Hz), 6.73 (1H, br s), 2.20–2.07 (4H, m)

Ex. 58

(S)-(−)-3-(2-Acetoxypropionyl)amino-2-benzoyl-6-chloroindole

The title compound was prepared according to the procedure described in Example 19 employing 3-amino-2-benzoyl-6-chloroindole (Example 1) and (S)-(−)-2-acetoxypropionyl chloride. m.p.: 80–85° C. $^1$H-NMR (CDCl$_3$) δ: 10.81 (1H, br s), 8.37 (1H, d, J=8.8 Hz), 8.31 (1H, br s), 7.82–7.77 (2H, m), 7.70–7.53 (3H, m), 7.29 (1H, d, J=1.5 Hz), 7.12 (1H, dd, J=1.5, 8.8 Hz), 5.44 (1H, q, J=7.0 Hz), 2.33 (3H, s), 1.61 (3H, d, J=7.0 Hz) [α]$_D^{23}$ −42.30 (MeOH, c=0.87)

Ex. 59

(S)-(+)-2-Benzoyl-6-chloro-3-[(2-hydroxypropionyl) amino]indole

A solution of (S)-(−)-3-(2-acetoxypropionylamino)-2-benzoyl-6-chloroindole (Example 58, 580 mg, 1.5 mmol) and potassium carbonate (2.0 g, 14 mmol) in ethanol (30 ml) and water (10 ml) was stirred for 2 h. The mixture was concentrated and extracted with ethyl acetate (50 ml×2). The organic extracts were dried (MgSO$_4$) and concentrated to give a yellow amorphous solid. Recrystallization from ethyl acetate/hexane gave 420 mg (81%) of the title compound as a yellow solid.

m.p.: 185–190° C. $^1$H-NMR (CDCl$_3$) δ: 11.72 (1H, br s), 10.40 (1H, br s), 7.96 (1H, d, J=8.8 Hz), 7.83–7.75 (2H, m), 7.70–7.52 (3H, m), 7.45 (1H, d, J=1.8 Hz), 7.10 (1H, dd, J=1.8, 8.8 Hz), 5.89 (1H, br s), 4.14–4.00 (1H, m), 1.12 (3H, d, J=7.0 Hz) [α]$_D^{23}$+17.53 (MeOH, c=0.73)

Ex. 60

3-(2-Acetoxyisobutyrylamino)-2-benzoyl-6-chloroindole

The title compound was prepared according to the procedure described in Example 19 employing 3-amino-2-benzoyl-6-chloroindole (Example 1) and 2-acetoxyisobutyryl chloride. m.p.: 162–165° C. $^1$H-NMR (CDCl$_3$) δ: 10.78 (1H, br s), 8.36 (1H, d, J=9.2 Hz), 8.28 (1H, br s), 7.85–7.76 (2H, m), 7.68–7.53 (3H, m), 7.26 (1H, d, J=1.8 Hz), 7.08 (1H, dd, J=1.8, 9.2 Hz), 2.21 (3H, s), 1.75 (6H, s)

Ex. 61

2-Benzoyl-6-chloro-3-(2-hydroxyisobutyrylamino) indole

The titled compound was prepared from according to the procedure described in Example 59 from 3-(2-acetoxyisobutyrylamino)-2-benzoyl-6-chloroindole (Example 60). m.p.: 234–238° C. $^1$H-NMR (DMSO-d$_6$) δ: 11.66 (1H, br s), 10.44 (1H, br s), 7.97 (1H, d, J=8.8 Hz), 7.83–7.76 (2H, m), 7.70–7.50 (3H, m), 7.45 (1H, d, J=1.5 Hz), 5.71 (1H, s), 7.08 (1H, dd, J=1.5, 8.8 Hz), 1.20 (6H, s)

Ex. 62

3-Acetylamino-6-chloro-2-(thiophene-2-carbonyl) indole

Step 1. 3-Amino-6-chloro-1-(ethoxycarbonyl)-2-(thiophene-2-carbonyl)indole

The title compound was prepared according to the procedure described in step 2 of Example 1 from 4-chloro-2-(ethoxycarbonylamino)benzonitrile (Example 1, step 1) and 2-(bromoacetyl)thiophene (Steinkopt, *Justus Liebig Ann. Chem.*, 1923, 430, 103).

$^1$H-NMR (CDCl$_3$) δ: 8.27 (1H, d, J=1.8 Hz), 7.62–7.40 (3H, m), 7.30 (1H, dd, J=1.8, 8.4 Hz), 7.15–7.05 (1H, m), 5.70 (2H, s), 3.97 (2H, q, J=7.3 Hz), 0.94 (3H, t, J=7.3 Hz)

Step 2. 3-Acetylamino-6-chloro-1-(ethoxycarbonyl)-2-(thiophene-2-carbonyl)indole The title compound was prepared according to the procedure described in step 1 of Example 2 (Method A) from 3-amino-6-chloro-1-(ethoxycarbonyl)-2-(thiophene-2-carbonyl)indole (step 1). $^1$H-NMR (CDCl$_3$) δ: 8.94 (1H, br s), 8.24 (1H, d, J=1.5 Hz), 7.90 (1H, d, J=8.4 Hz), 7.69 (1H, dd, J=1.1, 5.1 Hz), 7.55 (1H, J=1.1, 4.0 Hz), 7.31 (1H, dd, J=1.8, 8.8 Hz), 7.13 (1H, d, J=4.8, 5.1 Hz), 4.10 (2H, q, J=7.3 Hz), 2.24 (3H, s), 1.03 (3H, t, J=7.3 Hz)

Step 3. 3-Acetylamino-6-chloro-2-(thiophene-2-carbonyl)indole

The title compound was prepared according to the procedure described in step 2 of Example 2 (Method A) from 3-acetylamino-6-chloro-1-(ethoxycarbonyl)-2-(thiophene-2-carbonyl)indole (step2). m.p.: 228–231° C. $^1$H-NMR (CDCl$_3$) δ: 10.10 (1H, br s), 8.40 (1H, br s), 8.25 (1H, d, J=9.2 Hz), 7.86 (1H, dd, J=1.1, 3.7 Hz), 7.77 (1H, dd, J=1.1, 5.1 Hz), 7.34 (1H, d, J=1.8 Hz), 7.27 (1H, dd, 3.7, 5.1 Hz), 7.12 (1H, dd, J=1.8, 8.8 Hz), 2.29 (3H, m) IR (KBr) ν: 1660, 1560, 1440, 1325, 1250 cm$^{-1}$ Ex. 63

3-Acetylamino-6-chloro-2-(2-furoyl)indole)

Step 1. 3-Amino-6-chloro-1-(ethoxycarbonyl)-2-(2-furoyl)indole

The title compound was prepared according to the procedure described in step 2 of Example 1 from 4-chloro-2-(ethoxycarbonylamino)benzonitrile (Example 1, step 1) and 2-bromoacetylfuran (prepared according to the method of S. Kajigaeshi et al., *Bull. Chem. Soc. Jpn.*, 1987, 60, 1159–1160). tlc: Rf=0.4 (33% ethyl acetate in hexanes)

Step 2. 3-Acetylamino-6-chloro-1-(ethoxycarbonyl)-2-(2-furoyl)indole

The title compound was prepared according to the procedure described in step 1 of Example 2 (Method A) from 3-amino-6-chloro-1-(ethoxycarbonyl)-2-(2-furoyl)indole (step 1). $^1$H-NMR (CDCl$_3$) δ: 9.21 (1 H, br s), 8.26 (1 H, d, J=1.8 Hz), 7.97 (1 H, d, J=8.8 Hz), 7.60 (1 H, dd, J=0.7, 1.8 Hz), 7.31–7.26 (2 H, m), 6.59 (1 H, dd, J=1.5, 3.7 Hz), 4.13 (2 H, q, J=7.2 Hz), 2.26 (3 H, s), 1.07 (3 H, t, J=7.2 Hz)

Step 3. 3-Acetylamino-6-chloro-2-(2-furoyl)indole

The title compound was prepared according to the procedure described in step 2 of Example 2 (Method A) from 3-acetylamino-6-chloro-1-(ethoxycarbonyl)-2-(2-furoyl)indole (step 2). m.p.: 227–228° C. $^1$H-NMR (CDCl$_3$) δ: 10.72 (1 H, br s), 9.42 (1 H, br s), 8.42 (1 H, J=9.2 Hz), 7.78 (1 H, dd, J=0.7, 1.8 Hz), 7.47 (1 H, dd, J=0.7, 3.7 Hz), 7.37 (1 H, d, J=1.5 Hz), 7.08 (1 H, dd, J=1.8, 8.8 Hz), 6.71 (1 H,dd, J=1.6, 3.5 Hz), 2.32 (3 H, s) IR (KBr) ν: 3450, 1690, 1620, 1600, 1580, 1570, 1480, 1460, 1340, 1260, 1200, 900, 770, 630 cm$^{-1}$ Ex. 64

3-Amino-6-chloro-2-(nicotinoyl)indole

Step 1. 3-Amino-6-chloro-1-ethoxycarbonyl-2-(nicotinoyl)indole

The title compound was prepared according to the procedure described in step 2 of Example 1 from 4-chloro-2-(ethoxycarbonylamino)benzonitrile (Example 1, step 1) and 3-(bromoacetyl)pyridine hydrobromide (H. McKennis et al., J. Org. Chem., 1963, 387). $^1$H-NMR (CDCl$_3$) δ: 8.95 (1H, dd, J=0.7, 2.2 Hz), 8.70 (1H, dd, J=1.8, 4.8 Hz), 8.23 (1H, d, J=1.5 Hz), 8.03–7.99 (1H, m), 7.57 (1H, d, J=8.4 Hz), 7.41–7.28 (2H, m), 6.08 (2H, br s), 3.87 (2H, q, J=7.0 Hz), 0.92 (3H, t, J=7.0 Hz)

Step 2. 3-Amino-6-chloro-2-(nicotinoyl)indole

The title compound was prepared according to the procedure described in step 3 of Example 1 from 3-amino-6-chloro-2-(nicotinoyl)-1-(ethoxycarbonyl)indole (step 1). m.p.: 188–189° C. $^1$H-NMR (CDCl$_3$) δ: 9.09 (1 H, dd, J=0.7, 2.2 Hz), 8.72 (1 H, dd, J=1.8, 5.1 Hz), 8.12 (1 H, ddd, J=1.8, 2.2, 7.7 Hz), 8.01 (1 H, br s), 7.55 (1 H, d, J=8.4 Hz), 7.47 (1 H, ddd, J=0.7, 4.8, 7.7 Hz), 7.24 (1 H, d, J=1.1 Hz), 7.05 (1 H, dd, J=1.8, 8.8 Hz), 5.80 (2H, br s)

Ex. 65

3-Acetylamino-6-chloro-2-(nicotinoyl)indole

The title compound was prepared according to the procedure described in Example 19 employing 3-amino-6-chloro-2-(nicotinoyl)indole (Example 64). m.p.: 213–214° C. $^1$H-NMR (DMSO-d$_6$) δ: 11.90 (1H, br s), 9.83 (1H, br s), 8.82 (1H, d, J=2.2 Hz), 8.76 (1H, dd, J=1.7, 4.9 Hz), 8.09–8.01 (1H, m), 7.64 (1H, d, J=8.8 Hz), 7.54 (1H, dd, J=4.9, 7.9 Hz), 7.47 (1H, d, J=1.5 Hz), 7.13 (1H, dd, J=1.8, 8.8 Hz), 1.64 (3H, s) IR (KBr) ν: 3300, 1730, 1680, 1590, 1580, 1540, 1440, 1310, 1250, 1230, 920, 750 cm$^{-1}$ Ex. 66

3-Amino-6-chloro-2-(isonicotinoyl)indole

Step 1. 3-Amino-6-chloro-1-(ethoxycarbonyl)-2-(isonicotinoyl)indole

The title compound was prepared according to the procedure described in step 2 of Example 1 from 4-chloro-2-(ethoxycarbonylamino)benzonitrile (Example 1, step 1) and 4-(bromoacetyl)pyridine hydrobromide (A. Taurins and A. Blage, J. Heterocycl. Chem., 1970, 7, 1137–1141). $^1$H-NMR (CDCl$_3$) δ: 8.75–8.73 (2H, m), 8.24 (1H, d, J=1.5 Hz), 7.57–7.54 (3H, m), 7.33 (1H, dd, J=1.8, 8.4 Hz), 6.04 (2H, br s), 3.82 (2H, q, J=7.0 Hz), 0.93 (3H, t, J=7.0 Hz)

Step 2. 3-Amino-6-chloro-2-(isonicotinoyl)indole

The title compound was prepared according to the procedure described in step 3 of Example 1 from 3-amino-6-chloro-1-(ethoxycarbonyl)-2-(isonicotinoyl)indole (step 1). m.p.: 266–267° C.

$^1$H-NMR (CDCl$_3$) δ: 8.96–8.82 (2H, m), 7.64–7.62 (2H, m), 7.55 (1H, d, J=8.4 Hz), 7.44 (1H, br s), 7.24 (1H, d, J=1.5 Hz), 7.06 (1H, dd, J=1.8, 8.8 Hz), 5.80 (2H, br s)

Ex. 67

3-Acetylamino-6-chloro-2-(isonicotinoyl)indole

The title compound was prepared according to the procedure described in Example 19 employing 3-amino-6-chloro-2-(isonicotinoyl)indole (Example 66).

m.p.: 262–264° C. $^1$H-NMR (DMSO-d$_6$): 11.90 (1H, br s), 9.79 (1H, br s), 8.77–8.74 (2H, m), 7.66 (1H, d, J=8.8 Hz), 7.58–7.55 (2H, m), 7.46 (1H, d, J=1.8 Hz), 7.13 (1H, dd, J=1.8, 8.8 Hz), 1.64 (3H, s)

Ex. 68

3-Amino-6-chloro-2-(4-chloropyridine-2-carbonyl)indole

Step 1. 3-Amino-6-chloro-2-(4-chloropyridine-2-carbonyl)-1-(ethoxycarbonyl)indole The title compound was prepared according to the procedure described in step 2 of Example 1 from 4-chloro-2-(ethoxycarbonylamino)benzonitrile (Example 1, step 1) and 2-(bromoacetyl)-4-chloropyridine hydrobromide*.

$^1$H-NMR (CDCl$_3$) δ: 8.50 (1H, d, J=5.5 Hz), 8.20 (1H, d, J=1.8 Hz), 8.06 (1H, d, J=2.6 Hz), 7.52 (1H, d, J=8.4 Hz), 7.38 (1H, dd, J=1.8, 5.1 Hz), 7.25 (1H, dd, J=1.8, 8.4 Hz), 6.06 (2H, br s), 3.86 (2H, q, J=7.0 Hz), 0.96 (3H, t, J=7.0 Hz)
*2-(Bromoacetyl)-4-chloropyridine hydrobromide was prepared as follows;

4-Chloro 2-pyridinecarbonitrile: To a mixture of 4-chloropiridine-N-oxide (5.00 g, 38.6 mmol) and trimethylsilyl cyanide (4.84 g, 46.3 mmol) in dichloromethane (60 ml) cooled to 0° C. was added dropwise N,N-dimethylcarbamoyl chloride (3.8 ml, 40.5 mmol). The mixture was allowed to warm to ambient temperature and stirred for 16 h. The mixture was cooled to 0° C. and a 30% aqueous solution of K$_2$CO$_3$ (100 ml) was added. The crude product was extracted with dichloromethane (100 ml×2), the organic extracts dried (MgSO$_4$) and evaporated to give 4-chloro-2-pyridinecarbonitrile (5.35 g, 100%). $^1$H-NMR (CDCl$_3$) δ: 8.63 (1 H, d, J=4.8 Hz), 7.72 (1 H, d, J=2.6 Hz), 7.55 (1 H, dd, J=1.8, 5.1 Hz).

2-Acetyl-4-chloropyridine: To a solution of 4-chloro-2-pyridinecarbonitrile (5.35 g, 38.6 mmol) in benzene (50 ml) and ether (50 ml) cooled to 0° C. was added dropwise over 20 min a 2M solution of MeMgI in ether (23 ml, 46.3 mmol). After 0.5 h, the mixture was allowed to warm to ambient temperature, and stirring continued for 2 h. The mixture was cooled to 0° C. and 2M aqueous HCl (100 ml) added. The mixture was made basic with saturated aqueous sodium bicarbonate (~80 ml) and the organic layer separated and dried (MgSO$_4$). After removal of solvent, the residue was purified by flash chromatography eluting with ethyl acetate/hexane (1:5) to afford 3.60 g (60%) of 2-acetyl-4'-chloropyridine. $^1$H-NMR (DMSO-d$_6$) δ: 8.59 (1 H, d, J=5.1 Hz), 8.04 (1 H, d, J=1.8 Hz), 7.47 (1 H, dd, J=1.8, 5.1 Hz), 2.72 (3 H, s).

2-(Bromoacetyl)-4-chloropyridine hydrobromide: 2-(Bromoacetyl)-4-chloropyridine hydrobromide was prepared from 2-acetyl-4'-chloropyridine according to the method of H. McKennis, Jr., L. B. Turnbull, E. R. Bowman, and E. Tamaki (in *J. Org. Chem.,* 1963, 28, 383–387). $^1$H-NMR (DMSO-d$_6$) δ: 8.74 (1 H, d, J=5.5 Hz), 8.05 (1 H, d, J=1.8 Hz), 7.88 (1 H, dd, J=2.2 and 5.5 Hz), 5.02 (2 H, s)

Step 2. 3-Amino-6-chloro-2-(4-chloropyridine-2-carbonyl)indole

The title compound was prepared according to the procedure described in step 3 of Example 1 from 3-amino-6-chloro-2-(4-chloropyridine-2-carbonyl)-1-(ethoxycarbonyl)indole (step 1). m.p.: 234–235° C. $^1$H-NMR (DMSO-d$_6$) δ: 10.94 (1H, br s), 8.78 (1H, d, J=5.5 Hz), 8.14 (1H, d, J=2.2 Hz), 7.92 (1H, d, J=8.4 Hz), 7.80 (1H, dd, J=1.5, 5.1 Hz), 7.51 (1H, d, J=1.8 Hz), 6.93 (1H, dd, J=1.8, 8.8 Hz)

The signal due to NH$_2$ was not observed.

Ex. 69

3-Acetylamino-6-chloro-2-(4-chloropyridine-2-carbonyl)indole

The title compound was prepared according to the procedure described in Example 19 employing 3-amino-6-chloro-2-(4-chloropyridine-2-carbonyl)indole (Example 68). m.p.: 201–202° C. $^1$H-NMR (DMSO-d$_6$): 11.97 (1H, br s), 10.22 (1H, br s), 8.75 (1H, d, J=5.1 Hz), 8.04 (1H, d, J=1.5 Hz), 7.86–7.79 (2H, m), 7.59 (1H, d, J=1.8 Hz), 7.09 (1H, dd, J=1.8, 8.8 Hz), 1.96 (3H, s)

Ex. 70

3-Amino-6-chloro-2-(4-methylpyridine-2-carbonyl)indole

Step 1. 3-Amino-6-chloro-1-(ethoxycarbonyl)-2-(4-methylpyridine-2-carbonyl)indole The title compound was prepared according to the procedure described in step 2 of Example 1 from 4-chloro-2-(ethoxycarbonylamino)benzonitrile (Example 1, step 1) and 2-(bromoacetyl)-4-methylpyridine hydrobromide (F. H. Case et al., J. Am. Chem. Soc., 1956, 78, 5842). $^1$H-NMR (CDCl$_3$) δ: 8.46 (1H, d, J=4.8 Hz), 8.22 (1H, d, J=1.8 Hz), 7.89 (1H, s), 7.51 (1H, d, J=8.4 Hz), 7.24 (1H, dd, J=1.8, 8.4 Hz), 7.20 (1H, br d, J=4.8 Hz), 5.97 (2H, br s), 3.80 (2H, q, J=7.0 Hz), 2.46 (3H, s), 0.90 (3H, t, J=7.0 Hz)

Step 2. 3-Amino-6-chloro-2-(4-methylpyridine-2-carbonyl)indole

The title compound was prepared according to the procedure described in step 3 of Example 1 from 3-amino-6-chloro-1-(ethoxycarbonyl)-2-(4-methylpyridine-2-carbonyl)indole (step 1). m.p.: 195–196° C. $^1$H-NMR (DMSO-d$_6$) δ: 11.11 (1H, br s), 8.59 (1H, d, J=5.1 Hz), 8.17 (1H, s), 7.52 (1H, d, J=8.8 Hz), 7.33 (1H, d, J=1.5 Hz), 7.29 (1H, d, J=4.8 Hz), 6.96 (1H, dd, J=1.8, 8.4 Hz), 6.03 (2H, br s), 2.48 (3H, s)

Ex. 71

3-Acetylamino-6-chloro-2-(4-methylpyridine-2-carbonyl)indole

The title compound was prepared according to the procedure described in Example 19 employing 3-amino-6-chloro-2-(4-methylpyridine-2-carbonyl)indole (Example 70). m.p.: 187–188° C. $^1$H-NMR (DMSO-d$_6$): 12.05 (1H, br s), 10.48 (1H, br s), 8.68 (1H, d, J=4.8 Hz), 7.94 (1H, s), 7.85 (1H, d, J=8.8 Hz), 7.63 (1H, d, J=1.5 Hz), 7.56 (1H, dd, J=0.9, 5.0 Hz), 7.07 (1H, dd, J=1.8, 8.8 Hz), 2.47 (3H, s), 2.04 (3H, s)

Ex. 72

3-Amino-6-chloro-2-(4-methoxypyridine-2-carbonyl)indole

Step 1. 3-Amino-6-chloro-1-(ethoxycarbonyl)-2-(4-methoxypyridine-2-carbonyl)indole The title compound was prepared according to the procedure described in step 2 of Example 1 from 4-chloro-2-(ethoxycarbonylamino)benzonitrile (Example 1, step 1) and 2-(bromoacetyl)-4-methoxypyridine hydrobromide*.

$^1$H-NMR (CDCl$_3$) δ: 8.42 (1H, d, J=5.9 Hz), 8.22 (1H, d, J=1.8 Hz), 7.61 (1H, d, J=2.9 Hz), 7.51 (1H, d, J=8.4 Hz), 7.27–7.23 (1H, m), 6.89 (1H, dd, J=2.6, 5.9 Hz), 5.96 (2H, br s), 3.95 (3H, s), 3.84 (2H, q, J=7.0 Hz), 0.95 (3H, t, J=7.0 Hz)

*2-(Bromoacetyl)-4-methoxypyridine hydrobromide was prepared as follows;

4-Methoxy-2-pyridinecarbonitrile: To a mixture of 4-methoxypiridine-N-oxide (5.00 g, 38.6 mmol) and trimethylsilyl cyanide (4.84 g, 46.3 mmol) in dichloromethane (60 ml) cooled to 0° C. was added dropwise N,N-dimethylcarbamoyl chloride (3.8 ml, 40.5 mmol). The mixture was allowed to warm to ambient temperature and stirred for 16 h. The mixture was cooled to 0° C. and a 30% aqueous solution of K$_2$CO$_3$ (100 ml) was added. The crude product was extracted with dichloromethane (100 ml×2), the organic extracts dried (MgSO$_4$) and evaporated to give 4-methoxy-2-pyridinecarbonitrile (5.35 g, 100%). $^1$H-NMR (CDCl$_3$) δ: 8.51 (1 H, d, J=5.9 Hz), 7.22 (1 H, d, J=2.6 Hz), 7.01 (1 H, dd, J=2.6, 5.9 Hz), 3.91 (3H, s)

2-Acetyl-4-methoxypyridine: To a solution of 4-methoxy-2-pyridinecarbonitrile (5.35 g, 38.6 mmol) in benzene (50 ml) and ether (50 ml) cooled to 0° C. was added dropwise over 20 min a 2M slution of MeMgI in ether (23 ml, 46.3 mmol). After 0.5 h, the mixture was allowed to warm to ambient temperature, and stirring continued for 2 h. The mixture was cooled to 0° C. and 2M aqueous HCl (100 ml) added. The mixture was made basic with saturated aqueous sodium bicarbonate (~80 ml) and the organic layer separated and dried (MgSO$_4$). After removal of solvent, the residue was purified by flash chromatography eluting with ethyl acetate/hexane (1:5) to afford 3.60 g (60%) of 2-acetyl-4-methoxypyridine.

$^1$H-NMR (CDCl$_3$) δ: 8.49 (1 H, d, J=5.5 Hz), 7.58 (1 H, d, J=2.6 Hz), 6.98 (1 H, dd, J=2.6, 5.5 Hz), 3.91 (3H, s), 2.72 (3 H, s)

2-(Bromoacetyl)-4-methoxypyridine hydrobromide: 2-(Bromoacetyl)-4-methoxypyridine hydrobromide was prepared from 2-acetyl-4-methoxypyridine according to the method of H. McKennis, Jr., L. B. Turnbull, E. R. Bowman, and E. Tamaki (in *J. Org. Chem.,* 1963, 28, 383–387).

$^1$H-NMR (DMSO-d$_6$) δ: 8.61 (1 H, d, J=5.9 Hz), 7.66 (1 H, dd, J=2.6 Hz), 7.37 (1 H, dd, J=2.6, 5.9 Hz), 5.03 (2H, s), 3.97 (3H, s)

Step 2. 3-Amino-6-chloro-2-(4-methoxypyridine-2-carbonyl)indole

The title compound was prepared according to the procedure described in step 3 of Example 1 from 3-amino-6- chloro-1-(ethoxycarbonyl)-2-(4-methoxypyridine-2-carbonyl)indole (step 1). m.p.: 195–196° C. (ethyl acetate)

$^1$H-NMR (DMSO-d$_6$) δ: 11.08 (1H, br s), 8.63 (1H, d, J=5.5 Hz), 7.90 (1H, d, J=8.8 Hz), 7.67 (1H, d, J=2.6 Hz), 7.52 (1H, d, J=1.5 Hz), 7.22 (1H, dd, J=2.6, 5.5 Hz), 6.92 (1H, dd, J=1.8, 8.4 Hz), 4.02 (3H, s); The signal due to NH2 group was not observed.

Ex. 73

3-Acetylamino-6-chloro-2-(4-methoxypyridine-2-carbonyl)indole

The title compound was prepared according to the procedure described in Example 19 employing 3-amino-6-chloro-2-(4-methoxypyridine-2-carbonyl)indole (Example 72). m.p.: 207–208° C. (ethyl acetate)

$^1$H-NMR (DMSO-d$_6$) δ: 12.09 (1H, br s), 10.54 (1H, br s), 8.66 (1H, d, J=5.5 Hz), 7.87 (1H, d, J=8.8 Hz), 7.64 (1H, d, J=1.8 Hz), 7.62 (1H, d, J=2.6 Hz), 7.31 (1H, dd, J=2.6, 5.9 Hz), 7.06 (1H, dd, J=1.8, 8.8 Hz), 3.96 (3H, s), 2.07 (3H, s)

Ex. 74

6-Chloro-3-isovalerylamino-2-(4-methoxypyridine-2-carbonyl)indole

The title compound was prepared according to the procedure described in Example 19 employing 3-amino-6-chloro-2-(4-methoxy-pyridine-2-carbonyl)indole (Example 72) and isovaleryl chloride. m.p.: 162–163° C. (ethyl acetate/hexane)

$^1$H-NMR (DMSO-d$_6$) δ: 12.08 (1H, br s), 10.54 (1H, br s), 8.66 (1H, d, 5.5 Hz), 7.88 (1H, d, J=8.8 Hz), 7.64 (1H, d, J=1.5 Hz), 7.63 (1H, d, J=2.6 Hz), 7.31 (1H, dd, J=2.6, 5.5Hz), 7.07 (1H, dd, J=1.8, 8.8 Hz), 3.95 (3H, s), 2.24 (2H, d, J=7.3 Hz), 2.09–2.00 (1H, m), 0.93 (6H, d, J=6.6 Hz)

Ex. 75

3-Amino-6-chloro-2-(2-thiazoyl)indole

Step 1. 3-Amino-6-chloro-1-(ethoxycarbonyl)-2-(2-thiazoyl)indole

The title compound was prepared according to the procedure described in step 2 of Example 1 from 4-chloro-2-(ethoxycarbonylamino)benzonitrile (Example 1, step 1) and-2-(bromoacetyl)thiazole hydrobromide (A. Dondoni, A. Marra, and P. Merino, *J. Am. Chem. Soc.*, 1994, 116, 3324–3336). $^1$H-NMR (CDCl$_3$) δ: 8.22 (1H, d, J=1.8 Hz), 7.99 (1H, d, J=3.3 Hz), 7.60 (1H, d, J=3.3 Hz), 7.52 (1H, d, J=8.4 Hz), 7.23 (1H, dd, J=1.8, 8.4 Hz), 6.21 (2H, s), 4.00 (2H, q, J=7.1 Hz), 0.94 (3H, t, J=7.1 Hz)

Step 2. 3-Amino-6-chloro-2-(2-thiazoyl)indole

The title compound was prepared according to the procedure described in step 3 of Example 1 from 3-amino-6-chloro-1-(ethoxycarbonyl)-2-(2-thiazoyl)indole (step 1). m.p.: 233–234° C.

$^1$H-NMR (CDCl$_3$) δ: 10.64 (1H, br s), 8.22 (1H, d, J=3.3 Hz), 8.16 (1H, d, J=3.0 Hz), 7.93 (1H, d, J=8.4 Hz), 7.60–7.35 (3H, br s), 6.94 (1H, dd, J=1.8, 8.8 Hz)

Ex. 76

3-Acetylamino-6-chloro-2-(2-thiazoyl)indole

The title compound was prepared according to the procedure described in Example 19 employing 3-amino-6-chloro-2-(2-thiazoyl)indole (Example 75).

m.p.: 220–221° C. $^1$H-NMR (DMSO-d$_6$) δ: 11.87 (1H, s), 10.60 (1H, s), 8.34–8.31 (2H, m), 7.91 (1H, d, J=8.8 Hz), 7.71 (1H, d, J=1.8 Hz), 7.08 (1H, dd, J=1.8, 8.8 Hz), 2.15 (3H, s)

Ex. 77

3-Amino-6-chloro-2-[2-(5-methylfuroyl)]indole

Step 1. 3-Amino-6-chloro-1-(ethoxycarbonyl)-2-[2-(5-methylfuroyl)]indole

The title compound was prepared according to the procedure described in step 2 of Example 1 from 4-chloro-2-(ethoxycarbonylamino)benzonitrile (Example 1, step 1) and 2-(bromoacetyl)-5-methylfuran (K. Y. Novitskii et al., *J. Org. Chem. USSR*, 1965, 1, 377–379). $^1$H-NMR (CDCl$_3$) δ: 8.25 (1H, d, J=1.5 Hz), 7.52 (1H, d, J=8.4 Hz), 7.24 (1H, dd, J=1.8, 8.4 Hz), 7.11 (1H, d, J=3.3 Hz), 6.15 (1H, dd, J=0.9, 3.3 Hz), 5.82 (2H, br s), 4.05 (2H, q, J=7.0 Hz), 2.36 (3H, s), 1.03 (3H, t, J=7.0 Hz)

Step 2. 3-Amino-6-chloro-2-[2-(5-methylfuroyl)]indole

The title compound was prepared according to the procedure described in step 3 of Example 1 from 3-amino-6-chloro-1-(ethoxycarbonyl)-2-[2-(5-methylfuroyl)]indole (step 1). m.p.: 140–141° C. $^1$H-NMR (CDCl$_3$) δ: 8.69 (1H, br s), 7.50 (1H, d, J=8.4 Hz), 7.31 (1H, d, J=1.1 Hz), 7.26 (1H, d, J=2.9 Hz), 6.97 (1H, dd, J=1.5, 8.4 Hz), 6.22 (1H, dd, J=1.1, 3.7 Hz), 5.91 (2H, br s), 2.50 (3H,s)

Ex. 78

3-Acetylamino-6-chloro-2-[2-(5-methylfuroyl)]indole

The title compound was prepared according to the procedure described in Example 19 employing 3-amino-6-chloro-2-[2-(5-methylfuroyl)]indole (Example 77) and acetyl chloride. m.p.: 208–209° C. $^1$H-NMR (CDCl$_3$) δ: 10.73 (1H, br s), 9.30 (1H, br s), 8.42 (1H, d, J=9.2 Hz), 7.39 (2H, d, J=1.8 Hz), 7.09 (1H, dd, J=1.8, 9.2 Hz), 6.33 (1H, d, J=3.3 Hz), 2.57 (3H, s), 2.31 (3H, s)

Ex. 79

3-Amino-6-chloro-2-(3-furoyl)indole

Step 1. 3-Amino-6-chloro-1-ethoxycarbonyl-2-(3-furoyl)indole

The title compound was prepared according according to the procedure described in step 2 of Example 1 from 4-chloro-2-(ethoxycarbonylamino)benzonitrile (Example 1, step 1) and 3-bromoaceylfuran (R. A. Massy-Westropp and G. D. Reynolds, *Aust. J. Chem.*, 1966, 19, 891–892.) $^1$H-NMR (CDCl$_3$) δ: 8.24 (1H, d, J=1.8 Hz), 7.93 (1H, s), 7.51 (1H, d, J=8.4 Hz), 7.45 (1H, dd, J=1.5, 1.8 Hz), 7.30 (1H, dd, J=1.8, 8.4 Hz), 6.78 (1H, dd, J=0.7, 1.1 Hz), 5.72 (2H, br s), 4.06 (2H, q, J=7.3 Hz), 1.05 (3H, t, J=7.3 Hz)

Step 2. 3-Amino-6-chloro-2-(3-furoyl)indole

The title compound was prepared according to the procedure described in step 3 of Example 1 from 3-amino-6-chloro-1-ethoxycarbonyl-2-(3-furoyl)indole (step 1).

m.p.: 113–114° C. (dichloromethane/hexane) $^1$H-NMR (CDCl$_3$) δ: 8.08 (1H, dd, J=0.7, 1.5 Hz), 7.70 (1H, br s), 7.51

(1H, d, J=8.8 Hz), 7.51 (1H, dd, J=1.5, 1.8 Hz), 7.27 (1H, d, J=2.2 Hz), 7.03 (1H, dd, J=1.8, 8.8 Hz), 6.87 (1H, dd, J=1.8, 0.7 Hz), 5.70 (2H, br s)

Ex. 80

3-Acetylamino-6-chloro-2-(3-furoyl)indole

The title compound was prepared according to the procedure described in Example 19 from 3-amino-6-chloro-2-(3-furoyl)indole (Example 79) and acetyl chloride. m.p.:217–219° C. (ethyl acetate/hexane)

$^1$H-NMR (CDCl$_3$) δ: 10.04 (1H, br s), 8.25 (1H, br s), 8.21 (1H, br s), 8.12 (1H, dd, J=1.1, 1.5 Hz), 7.59 (1H, dd, J=1.5, 1.8 Hz), 7.32 (1H, d, J=1.8 Hz), 7.12 (1H, dd, J=1.8, 8.8 Hz), 6.89 (1H, dd, J=0.7, 1.8 Hz), 2.29 (3 H, s)

Ex. 81

3-Amino-6-chloro-2-(3-phenyl-5-isoxazoyl)indole

Step 1. 3-Amino-6-chloro-1-(ethoxycarbonyl)-2-(3-phenyl-5-isoxazoyl)indole

The title compound was prepared according to the procedure described in step 2 of Example 1 from 4-chloro-2-(ethoxycarbonylamino)benzonitrile (Example 1, step 1) and 5-(bromoacetyl)-3-phenylisoxazole. $^1$H-NMR (CDCl$_3$) δ: 8.27 (1H, d, J=1.8 Hz), 7.89–7.84 (2H, m), 7.56–7.47 (5H, m), 7.30 (1H, dd, J=1.8, 8.4 Hz), 6.18 (2H, s), 4.13 (2H, q, J=7.2 Hz), 1.10 (3H, t, J=7.2 Hz)

Step 2. 3-Amino-6-chloro-2-(3-phenyl-5-isoxazoyl)indole

The title compound was prepared according to the procedure described in step 3 of Example 1 from 3-amino-6-chloro-1-(ethoxycarbonyl)-2-(5-phenyl-3-isoxazoyl)indole (step 1). m.p.: 241–242° C.

$^1$H-NMR (CDCl$_3$) δ: 8.81 (1H, br s), 7.91–7.86 (2H, m), 7.56–7.49 (4H, m), 7.38 (1H, s), 7.32 (1H, d, J=1.5 Hz), 7.03 (1H, dd, J=1.5, 8.8 Hz), 6.23 (2H, br s)

Ex. 82

3-Acetylamino-6-chloro-2-(3-phenyl-5-isoxazoyl)indole

The title compound was prepared according to the procedure described in Example 19 employing 3-amino-6-chloro-2-(3-phenyl-5-isoxazoyl)indole (Example 81). m.p.: 209 –210° C. $^1$H-NMR (CDCl$_3$) δ: 10.65 (1H, br s), 9.52 (1H, br s), 8.49 (1H, d, J=9.2 Hz), 7.92–7.86 (2H, m), 7.56–7.52 (3H, m), 7.45 (1H, s), 7.40 (1H, d, J=1.8 Hz), 7.11 (1H, dd, J=1.8, 9.2 Hz), 2.36 (3H, s)

Ex. 83

3-Amino-6-chloro-2-(phenylacetyl)indole

Step 1. 3-Amino-6-chloro-1-(ethoxycarbonyl)-2-(phenylacetyl)indole

The title compound was prepared according to the procedure described in step 2 of Example 1 from 4-chloro-2-(ethoxycarbonylamino)benzonitrile (Example 1, step 1) and 2-chloro-2'-phenylacetone (J. Barluenga, M. Yus, J. M. Concellon, P. Bernad, *J. Org. Chem.*, 1983, 48, 3116–3118). $^1$H-NMR (CDCl$_3$) δ: 8.07 (1H, d, J=1.8 Hz), 7.41 (1H, d, J=8.4 Hz), 7.34 (1H, d, J=4.4 Hz), 7.31–7.16 (5H, m), 5.89 (2H, br s), 4.43 (2H, q, J=7.2 Hz), 4.02 (2H, s), 1.42 (3H, t, J=7.2 Hz)

Step 2. 3-Amino-6-chloro-2-(phenylacetyl)indole

The title compound was prepared according to the procedure described in step 3 of Example 1 from 3-amino-6-chloro-1-(ethoxycarbonyl)-2-(phenylacetyl)indole (step 1). m.p.: 204–205° C. $^1$H-NMR (CDCl$_3$) δ: 7.46 (1H, d, J=8.4 Hz), 7.40–7.26 (6H, m), 7.17 (1H, br s), 6.99 (1H, br d, J=8.4 Hz), 5.51 (2H, br s), 4.07 (2H, s)

Ex. 84

3-Acetylamino-6-chloro-2-(phenylacetyl)indole

The title compound was prepared according to the procedure described in Example 19 employing 3-amino-6-chloro-2-(phenylacetyl)indole (Example 83).

m.p.: 258–259° C. $^1$H-NMR (DMSO-d$_6$) δ: 11.76 (1H, br s), 9.98 (1H, br s), 7.63 (1H, d, J=8.8 Hz), 7.43 (1H, d, J=1.5 Hz), 7.36–7.22 (5H, m), 7.09 (1H, dd, J=1.8, 8.8 Hz), 4.27 (2H, s), 2.16 (3H, s)

Ex. 85

2-Acetyl-3-amino-6-chloroindole

Step 1. 2-Acetyl-3-amino-6-chloro-1-(ethoxycarbonyl)indole

The title compound was prepared according to the procedure described in step 2 of Example 1 from 4-chloro-2-(ethoxycarbonylamino)benzonitrile (Example 1, step 1) and 2-bromoacetone. $^1$H-NMR (DMSO-d$_6$) δ: 8.02 (1H, d, J=8.4 Hz), 7.98 (1H, d, J=1.8 Hz), 7.40 (1H, dd, J=1.8, 8.4 Hz), 7.22 (2H, br s), 7.44 (2H, q, J=7.3 Hz) 2.27 (3H, s), 1.40 (3H, t, J=7.3 Hz)

Step 2. 2-Acetyl-3-amino-6-chloroindole

The title compound was prepared according to the procedure described in step 3 of Example 1 from 2-acetyl-3-amino-6-chloro-1-(ethoxycarbonyl)indole (step 1).

$^1$H-NMR (DMSO-d$_6$) δ: 10.60 (1H, br s), 7.83 (1H, d, J=8.4 Hz), 7.24 (1H, d, J=1.8 Hz), 6.92 (1H, J=1.8 Hz), 6.44 (2H, br s), 2.40 (3H, s)

Ex. 86

2-Acetyl-3-acetylamino-6-chloroindole

The title compound was prepared according to the procedure described in Example 19 employing 2-acetyl-3-amino-6-chloroindole (Example 85).

m.p.: 262–267° C.

$^1$H-NMR (DMSO-d$_6$) δ: 11.71 (1H, br s), 9.90 (1H, br s), 7.60 (1H, d, J=8.8 Hz), 7.41 (1H, d, J=1.8 Hz), 7.09(1H, dd, J=1.8, 8.8 Hz), 2.51 (3H, s), 2.16 (3H, s)

Ex. 87

3-Amino-6-chloro-2-propionylindole

Step 1. 3-Amino-6-chloro-1-(ethoxycarbonyl)-2-propionylindole

The title compound was prepared according to the procedure described in step 2 of Example 1 from 4-chloro-2-(ethoxycarbonylamino)benzonitrile (Example 1, step 1) and 2-bromomethyl ethyl ketone.

$^1$H-NMR (CDCl$_3$) δ: 7.75–7.67 (2H, m), 7.35 (1H, dd, J=8.4, 2.2 Hz), 4.45 (2H, br s), 4.30–4.10 (2H, m), 2.60–2.40 (2H, m), 1.35–1.1(6H, m)

Step 2. 3-Amino-6-chloro-2-propionylindole

The title compound was prepared according to the procedure described in step 3 of Example 1 from 3-amino-6-chloro-1-(ethoxycarbonyl)-2-propionylindole (step 1).

m.p.: 144–146° C. $^1$H-NMR (DMSO-d$_6$) δ: 9.15 (1H, br s), 7.52 (1H, d, J=8.4 Hz), 7.27 (1H, d, J=1.8 Hz), 6.95 (1H, dd, J=1.8, 8.4Hz), 5.53 (2H, br s), 2.80 (2H, q, J=7.3 Hz), 1.25 (3H, t, J=7.3 Hz)

Ex. 88

3-Acetylamino-6-chloro-2-propionylindole

The title compound was prepared according to the procedure described in Example 19 employing 3-amino-6-chloro-2-propionylindole (Example 87) and acetyl chloride. m.p.: >270° C. $^1$H-NMR (DMSO-d$_6$) δ: 11.72 (1H, br s), 9.93 (1H, br s), 7.59 (1H, d, J=8.4 Hz), 7.43 (1H, s), 7.07 (1H, d, J=8.4 Hz), 2.94 (2H, q, J=7.0 Hz), 2.15 (3H, s), 1.09 (3H, t, J=7.0 Hz)

Ex. 89

3-Amino-6-chloro-2-trimethylacetylindole

Step 1. 3-Amino-6-chloro-1-(ethoxycarbonyl)-2-trimethylacetylindole

The title compound was prepared according to the procedure described in step 2 of Example 1 from 4-chloro-2-(ethoxycarbonylamino)benzonitrile (Example 1, step 1) and 2-bromomethyl tert-butyl ketone. $^1$H-NMR (CDCl$_3$) δ: 7.60 (1H, d, J=8.8 Hz), 7.37 (1H, dd, J=1.8, 8.8 Hz), 7.28 (1H, d, J=1.8 Hz), 4.59 (2H, brs), 4.28–4.10 (2H, m), 1.31–1.19 (12H, m)

Step 2. 3-Amino-6-chloro-2-trimethylacetylindole

The title compound was prepared according to the procedure described in step 3 of Example 1 from 3-amino-6-chloro-1-(ethoxycarbonyl)-2-trimethylacetylindole (step 1). m.p.: 132–134° C. $^1$H-NMR (CDCl$_3$) δ: 7.60 (1H, br s), 7.47 (1H, d, J=8.4 Hz), 7.26 (1H, d, J=1.8 Hz), 7.00 (1H, dd, J=1.8, 8.4 Hz), 5.76 (2H, br s), 1.40 (9H, s)

Ex. 90

3-Acetylamino-6-chloro-2-trimethylacetylindole

The title compound was prepared according to the procedure described in Example 19 employing 3-amino-6-chloro-2-trimethylacetylindole (Example 89) and acetyl chloride. m.p.: 190–193° C. $^1$H-NMR (CDCl$_3$) δ: 10.46 (1H, br s), 8.40 (1H, br s), 8.22 (1H, d, J=9.2 Hz), 7.29 (1H, s), 7.05 (1H, d, J=9.2 Hz), 2.29 (3H, s), 1.42 (9H, s)

Ex. 91

3-Acetylamino-6-chloro-2-(pyrazine-2-carbonyl)indole

Step 1. 3-Amino-6-chloro-1-(ethoxycarbonyl)-2-(pyrazine-2-carbonyl)indole

The title compound was prepared according to the procedure described in step 2 of Example 1 from 4-chloro-2-(ethoxycarbonylamino)benzonitrile (Example 1, step 1) and 2-(bromoacetyl)pyrazine (prepared according to the method of F. H. Case et al., *J. Am.Chem.Soc.*, 1956, 78, 5842).

$^1$H-NMR (CDCl$_3$) δ: 9.26 (1H, d, J=1.5 Hz), 8.67 (1H, d, J=2.6 Hz), 8.56 (1H, dd, J=1.5, 2.6 Hz), 8.21 (1H, d, J=1.8 Hz), 7.55 (1H, d, J=8.4 Hz), 7.27 (1H, dd, J=1.5, 8.4 Hz), 6.18 (2H, br s), 3.87 (2H, q, J=7.0 Hz), 0.93 (3H, t, J=7.0 Hz)

Step 2. 3-Acetylamino-6-chloro-1-(ethoxycarbonyl)-2-(pyrazine-2-carbonyl)indole The title compound was prepared according to the procedure described in step 1 of Example 2 (Method A) from 3-amino-6-chloro-1-(ethoxycarbonyl)-2-(pyrazine-2-carbonyl)indole (step 1). tlc: Rf=0.4 (50% acetone in hexanes)

Step 3. 3-Acetylamino-6-chloro-2-(pyrazine-2-carbonyl)indole

The title compound was prepared according to the procedure described in step 2 of Example 2 (Method A) from 3-acetylamino-6-chloro-1-(ethoxycarbonyl)-2-(pyrazine-2-carbonyl)indole (step 2). m.p.: 269–271° C.

$^1$H-NMR (DMSO-d$_6$): 11.92 (1H, br s), 10.10 (1H, br s), 9.10 (1H, d, J=1.5 Hz), 8.89 (1H, d, J=2.2 Hz), 8.79 (1H, dd, J=1.5, 2.2 Hz), 7.77 (1H, d, J=8.8 Hz), 7.54 (1H, d, J=1.5 Hz), 7.11 (1H, dd, J=1.8, 8.8 Hz), 1.84 (3H, s)

Ex. 92

3-Acetylamino-6-chloro-2-(2-naphthoyl)indole

Step 1. 3-Amino-6-chloro-1-(ethoxycarbonyl)-2-(2-naphthoyl)indole

The title compound was prepared according to the procedure described in step 2 of Example 1 from 4-chloro-2-(ethoxycarbonylamino)benzonitrile (Example 1, step 1) and 2-bromo-2'-acetonaphthone. tlc: Rf=0.8 (50% ethyl acetate in hexanes)

Step 2. 3-Acetylamino-6-chloro-1-(ethoxycarbonyl)-2-(2-naphthoyl)indole

The title compound was prepared according to the procedure described in step 1 of Example 2 (Method A) from 3-amino-6-chloro-1-(ethoxycarbonyl)-2-(2-naphthoyl)indole (step 1). tlc: Rf =0.6 (50% ethyl acetate in hexanes)

Step 3. 3-Acetylamino-6-chloro-2-(2-naphthoyl)indole

The title compound was prepared according to the procedure described in step 2 of Example 2 (Method A) from 3-acetylamino-6-chloro-1-(ethoxycarbonyl)-2-(2-naphthoyl)indole (step 2). m.p.: 167–169° C.

$^1$H-NMR (CDCl$_3$) δ: 9.87 (1H, br s), 8.32 (2H, br), 8.24 (1H, d, J=8.8 Hz), 8.07–7.80 (4H, m), 7.70–7.56 (2H, m), 7.30 (1H, br), 7.12 (1H, dd, J=1.8, 8.8 Hz), 2.23 (3H, s)

Ex. 93

3-Amino-6-chloro-2-(cyclohexanecarbonyl)indole

Step 1. 3-Amino-6-chloro-2-(cyclohexanecarbonoyl)-1-(ethoxycarbonyl)indole The title compound was prepared according to the procedure described in step 2 of Example 1 from 4-chloro-2-(ethoxycarbonylamino)benzonitrile (Example 1, step 1) and 2-bromoacetylcyclohexane (Lotfield, Schaad, *J.Am. Chem.Soc.*, 1954, 76, 35).

$^1$H-NMR (CDCl$_3$) δ: 8.14 (1H, d, J=1.8 Hz), 7.45 (1H, d, J=8.4 Hz), 7.26 (1H, dd, J=1.8, 8.4 Hz), 5.66 (2H, br), 4.44 (2H, q, J=7.0 Hz), 2.95–2.72 (1H, m), 2.00–1.10 (13H, m)

Step 2. 3-Amino-6-chloro-2-
(cyclohexanecarbonoyl)indole

The title compound was prepared according to the procedure described in step 3 of Example 1 from 3-amino-6-chloro-2-(cyclohexanecarbonoyl)-1-(ethoxycarbonyl)indole (step 1).

$^1$H-NMR (CDCl$_3$) δ: 7.66 (1H, br s), 7.49 (1H, d, J=8.4 Hz), 7.26 (1H, s),7.02 (1H, d, J=8.4 Hz), 5.50 (2H, br s), 2.88–2.72 (1H, m), 2.00–1.20 (10H, m)

Ex. 94

3-Acetylamino-6-chloro-2-(cyclohexanecarbonyl) indole

The title compound was prepared according to the procedure described in Example 19 from 3-amino-6-chloro-2-(cyclohexanecarbonoyl)indole (Example 93) and acetyl chloride. m.p.: 198° C. $^1$H-NMR (CDCl$_3$) δ: 9.96 (1H, br s), 8.49 (1H, br), 8.21 (1H, d, J=8.4 Hz), 7.28 (1H, s), 7.06 (1H, d, J=8.1 Hz), 3.05–2.85 (1H, m), 2.29 (3H, s), 2.15–1.20 (10H, m) IR (KBr) v: 1655, 1630, 1570, 1540, 1440 cm$^{-1}$ Ex. 95

6-Chloro-2-cyclohexanecarbonyl-3-
(isovalerylamino)indole

The title compound was prepared according to the procedure described in Example 19 from 3-amino-6-chloro-2-(cyclohexanecarbonoyl)indole (Example 93) and isovaleryl chloride. m.p.: 209–215° C.

$^1$H-NMR (DMSO-d$_6$) δ: 11.66 (1H, br s), 9.86 (1H, br s), 7.52 (1H, d, J=8.8 Hz), 7.42 (1H, d, J=1.8 Hz), 7.07 (1H, dd, J=1.8, 8.8 Hz), 3.40–3.19 (1H, m), 2.32 (2H, d, J=7.0 Hz), 2.29–2.08 (1H, m), 1.92–1.13 (10H, m), 1.01 (6H, d, J=6.6 Hz)

Ex. 96

3-Acetylamino-2-benzoyl-5-nitroindole

Step 1. 2-(Ethoxycarbonylamino)-5-
nitrobenzonitrile

The title compound was prepared according to the procedure described in step 1 of Example 1 (Method A) from 2-amino-5-nitrobenzonitrile. tlc: Rf=0.4 (33% ethyl acetate in hexanes)

Step 2. 3-Amino-2-benzoyl-1-(ethoxycarbonyl)-5-
nitroindole

The title compound was prepared according to the procedure described in step 2 of Example 1 from 2-(ethoxycarbonylamino)-5-nitrobenzonitrile (step 1).

$^1$H-NMR (CDCl$_3$) δ: 8.60 (1H, d, J=2.2 Hz), 8.42 (1H, dd, J=2.2, 9.2 Hz), 8.33 (1H, d, J=9.2 Hz), 7.7–7.8 (2H, m), 7.4–7.5 (3H, m), 5.84 (2H, br s), 3.77 (2H, q, J=7.0 Hz), 0.87 (3H, t, J=7.0 Hz)

Step 3. 3-Acetylamino-2-benzoyl-1-
(ethoxycarbonyl)-5-nitroindole

The title compound was prepared according to the procedure described in step 1 of Example 2 (Method A) from 3-amino-2-benzoyl-1-(ethoxycarbonyl)-5-nitroindole (step 2). tlc: Rf=0.2 (50% ethyl acetate in hexanes)

Step 4. 3-Acetylamino-2-benzoyl-5-nitroindole

The title compound was prepared according to the procedure described in step 2 of Example 2 (Method A) from 3-acetylamino-2-benzoyl-1-(ethoxycarbonyl)-5-nitroindole (step 3). m.p.: 210–212° C. $^1$H-NMR (CDCl3+CDOD3) δ: 9.14 (1H, d, J=1.8 Hz), 8.19 (1H, dd, J=2.6, 9.2 Hz), 7.84 (1H, d, J=8.8 Hz), 7.4–7.8 (5H, m), 2.20 (3H, s) IR (KBr) v: 1665, 1620, 1435, 1345, 1265, 1020, 915, 820 cm$^{-1}$ Ex. 97

2-(3-Chlorobenzoyl)-3-(isovalerylamino)-5-
nitroindole

Step 1. 3-Amino-2-(3-chlorobenzoyl)-1-
(ethoxycarbonyl)-5-nitroindole

The title compound was prepared according to the procedure described in step 2 of Example 1 from 2-(ethoxycarbonylamino)-5-nitrobenzonitrile (Example 96, step 1) and 2-bromo-3'-chloroacetophenone.

$^1$H-NMR (CDCl$_3$) δ: 9.19 (1H, d, J=2.2 Hz), 8.44 (1H, dd, J=2.2, 9.2 Hz), 8.21 (1H, d, J=9.2 Hz), 7.65–7.48 (6H, m), 3.81 (2H, q, J=7.3 Hz), 0.86 (3H, t, J=7.3 Hz)

Step 2. 3-Amino-2-(3-chlorobenzoyl)-5-nitroindole

The title compound was prepared according to the procedure described in step 3 of Example 1 from 3-amino-2-(3-chlorobenzoyl)-1-(ethoxycarbonyl)-5-nitroindole (step 1). tlc: Rf=0.3 (33% ethyl acetate in hexanes)

Step 3. 2-(3-Chlorobenzoyl)-3-(isovalerylamino)-5-
nitroindole

The title compound was prepared according to the procedure described in Example 19 employing 3-amino-2-(3-chlorobenzoyl)-5-nitroindole (step 2) and isovaleryl chloride. m.p.: 197–199° C. $^1$H-NMR (CDCl$_3$) δ: 9.91 (1H, br s), 9.37 (1H, d, J=2.2 Hz), 8.73 (1H, br.s), 8.24 (1H, dd, J=2.2, 9.2 Hz), 7.51–7.80 (4H, m), 7.38 (1H, d, J=9.2 Hz),2.37 (2H, br.s), 2.24–2.29 (1H, m), 1.07 (3H, s), 1.05 (3H, s)

Ex. 98

3-Methoxyacetylamino-2-(3-methylbenzoyl)-5-
nitroindole

Step 1. 3-Amino-1-(ethoxycarbonyl)-2-(3-
methylbenzoyl)-5-nitroindole

The title compound was prepared according to the procedure described in step 2 of Example 1 from 2-(ethoxycarbonylarnino)-5-nitrobenzonitrile (Example 96, step 1) and 2-bromo-3'-methylacetophenone. tlc: Rf=0.6 (33% ethyl acetate in hexanes)

Step 2. 1-(Ethoxycarbonyl)-3-methoxyacetylamino-
2-(3-methylbenzoyl)-5-nitroindole The title compound was prepared according to the procedure described in step 1 of Example 2 (Method A) from 3-amino-2-(3-chlorobenzoyl)-1-(ethoxycarbonyl)-5-nitroindole (step 1) and methoxyacetyl chloride.

tlc: Rf=0.6 (14% ethyl acetate in toluene)

Step 3. 3-Methoxyacetylamino-2-(3-
methylbenzoyl)-5-nitroindole

The title compound was prepared according to the procedure described in step 2 of Example 2 (Method A) from 1-(ethoxycarbonyl)-3-methoxyacetylamino-2-(3-methylbenzoyl)-5-nitroindole (step 2). m.p.: 155–157° C.

$^1$H-NMR (CDCl$_3$) δ: 10.4 (1H, br s, J=1.8 Hz), 9.36 (1H, d, J=2.2 Hz), 8.77 (1H, br s), 8.25 (1H, dd, J=2.2, 9.2 Hz), 7.59–7.63(2H, m), 7.46–7.48 (2H, m), 7.40 (1H, d, J=9.2 Hz), 4.09 (2H, s), 3.54 (3H, s), 2.47 (S, 3H)

Ex. 99

3-Acetylamino-5-amino-2-benzoylindole

Step 1. 3-Acetylamino-5-amino-2-benzoyl-1-(ethoxycarbonyl)indole

3-Acetylamino-2-benzoyl-1-(ethoxycarbonyl)-5-nitroindole (Example 96, step 3; 200 mg, 0.51 mmol) was hydrogenolyzed in the presence of palladium on activated carbon (5%, 50 mg) in ethyl acetate (40 ml) at atmospheric pressure for 4 h. Catalyst was removed by filtration and the filtrate was concentrated to afford the title compound.

$^1$H-NMR (CDCl$_3$) δ: 8.99 (1H, br s), 7.93 (1H, d, J=8.8 Hz), 7.76–7.69 (3H, m), 7.40–7.56 (3H, m), 7.09 (1H, br s), 4.77 (2H, br s), 3.91 (2H, q, J=7.0 Hz), 1.64 (3H, s), 0.93 (3H, t, J=7.0 Hz)

Step 2. 3-Acetylamino-5-amino-2-benzoylindole

The title compound was prepared according to the procedure described in step 2 of Example 2 (Method A) from 3-acetylamino-5-amino-2-benzoyl-1-(ethoxycarbonyl)indole (step 1) as a yellow solid. m.p.: 254–256° C.

$^1$H-NMR (DMSO-d$_6$) δ: 11.2 (1H, s), 9.33 (1H, s), 7.45–7.69 (5H, m), 7.16 (1H, d, 8.4 Hz), 6.74 (1H, dd, J=2.2, 8.4 Hz), 6.58 (1H, d, J=2.2 Hz), 4.76 (2H, br s), 4.76 (2H, br, s), 1.62 (3H, s)

Ex. 100

3-Acetylamino-2-benzoyl-5-(methanesulfonylamino)indole

To a solution of 3-acetylamino-5-amino-2-benzoyl-1-ethoxycarbonylindole (Example 99, step 1: 100 mg, 0.27 mmol) in dichloromethane (5 ml) and pyridine (33 μl, 0.41 mmol) was added methanesulfonyl chloride (25 μl, 0.32 mmol) and the mixture was stirred for 1 h. The mixture was partitioned between 2N aqueous HCl (30 ml) and ethyl acetate (30 ml), the organic layer separated and washed cocnsecutively with brine (10 ml), saturated aqueous sodium bicarbonate (10 ml), brine (10 ml) and dried (MgSO$_4$). After removal of solvent the residue was diluted with ethanol (10 ml) and water (5 ml), and potassium hydroxide (0.5 g) added. The mixture was stirred for 4 h, poured into a saturated aqueous ammonium chloride (30 ml) and extracted with ethyl acetate (50 ml×2). The organic layer was washed with brine (50 ml), dried (MgSO$_4$), and solvent removed by evaporation. The residue was recrystallized from methanol/dichloromethane/hexane to give 66 mg of the title compound as a yellow solid. m.p.: 260–261° C. $^1$H-NMR (DMSO-d$_6$) δ: 11.7 (1H, br s), 9.63 (1H, s), 7.81–8.22 (2H, m), 7.40–7.64 (7H, m), 2.90 (3H, s), 164 (3H, s).

IR (KBr) ν: 3640, 1665, 1610, 1545, 1325, 1270, 1140, 1010, 770 cm$^{-1}$

Ex. 101

3-Acetylamino-2-benzoyl-6-trifluoromethylindole

Step 1. 2-(Ethoxycarbonylamino)-4-trifluoromethylbenzonitrile

The title compound was prepared according to the procedure described in step 1 of Example 1 (Method B) from 2-amino-4-trifluoromethylbenzonitrile (Y. Tomioka, K. Ohkubo and M. Yamazaki, *Chem. Pharm. Bull.*, 1985, 33, 1360–1366).

$^1$H-NMR (CDCl$_3$) δ: 6.95–7.88 (3H, m), 4.65 (1H, br s), 4.31 (2H, q, J=7.3 Hz), 1.28 (3H, t, J=7.3 Hz)

Step 2. 3-Amino-2-benzoyl-1-(ethoxycarbonyl)-6-trifluoromethylindole

The title compound was prepared according to the procedure described in step 2 of Example 1 from 2-(ethoxycarbonylamino)-4-trifluoromethylbenzonitrile (step 1).

$^1$H-NMR (CDCl$_3$) δ: 8.54 (1H, s), 7.77–7.72 (3H, m), 7.57–7.41 (4H, m), 5.79 (2H, br s), 3.77 (2H, q, J=7.3 Hz), 0.86 (3H, t, J=7.3 Hz)

Step 3. 3-Acetylamino-2-benzoyl-1-(ethoxycarbonyl)-6-trifluoromethylindole

The title compound was prepared according to the procedure described in step 1 of Example 2 (Method A) from 3-amino-2-benzoyl-1-(ethoxycarbonyl)-6-trifluoromethylnitroindole (step 2). tlc: Rf=0.6 (50% ethyl acetate in hexanes)

Step 4. 3-Acetylamino-2-benzoyl-6-trifluoromethylindole

The title compound was prepared according to the procedure described in step 2 of Example 2 (Method A) from 3-acetylamino-2-benzoyl-1-(ethoxycarbonyl)-6-trifluoromethylindole (step 3). m.p.: 177–179° C.

$^1$H-NMR (CDCl$_3$) δ: 9.88 (1H, s), 9.45 (1H, s), 7.99 (1H, s), 7.72–7.70 (1H, m), 7.70 (1H, d, J=8.8 Hz), 7.38–7.54 (4H, m), 7.08 (1H, d, J=8.8 Hz), 2.01 (3H, s)

Ex. 102

3-Acetylamino-2-benzoyl-5-bromoindole

Step 1. 5-bromo-2-(ethoxycarbonylamino)benzonitrile

The title compound was prepared according to the procedure described in step 1 of Example 1 (Method B) from 2-amino-5-bromobenzonitrile (M. Hird, G. W. Gray and K. J. Toyne, *Mol. Cryst. Liq. Cryst.*, 1991, 206, 205–221).

tlc: Rf=0.7 (33% ethyl acetate in hexanes)

Step 2. 3-Amino-2-benzoyl-5-bromo-1-(ethoxycarbonyl)indole

The title compound was prepared according to the procedure described in step 2 of Example 1 from 5-bromo-2-(ethoxycarbonylamino)benzonitrile (step 1).

tlc: Rf=0.55 (33% ethyl acetate in hexanes)

Step 3. 3-Acetylamino-2-benzoyl-5-bromo-1-(ethoxycarbonyl)indole

The title compound was prepared according to the procedure described in step 1 of Example 2 (Method A) from 3-amino-2-benzoyl-5-bromo-1-(ethoxycarbonyl)indole (step 2). tlc: Rf=0.3 (33% ethyl acetate in hexanes)

Step 4. 3-Acetylamino-2-benzoyl-5-bromoindole

The title compound was prepared according to the procedure described in step 2 of Example 2 (Method A) from 3-acetylamino-2-benzoyl-5-bromo-1-(ethoxycarbonyl) indole (step 3). m.p.: 192–194° C.

$^1$H-NMR (DMSO-d$_6$) δ: 11.8 (1H, br s), 9.65 (1H, s),7.35–7.79 (8H, m), 1.69 (3H, s)

Ex. 103

3-Acetylamino-2-benzoyl-5-chloroindole

Step 1. 3-Amino-2-benzoyl-5-chloro-1-(ethoxycarbonyl)indole

The title compound was prepared according to the procedure described in step 2 of Example 1 from 5-chloro-2-(ethoxycarbonylamino)benzonitrile (K. O. Geolotte et al, *J. Heterocyclic Chem.*, 1990, 27, 1549) and 2-bromoacetophenone.

$^1$H-NMR (CDCl$_3$) δ: 8.15 (1H, d, J=9 Hz), 7.74 (2H, dd, J=8, 2 Hz), 7.58 (1H, d, J=2 Hz), 7.52–7.43 (4H, m), 5.70 (2H, br s), 3.73 (2H, q, J=7 Hz), 0.84 (3H, t, J=7 Hz)

Step 2. 3-Acetylamino-2-benzoyl-5-chloro-1-(ethoxycarbonyl)indole

The title compound was prepared according to the procedure described in step 1 of Example 2 (Method A) and from 3-amino-2-benzoyl-5-chloro-1-(ethoxycarbonyl) indole (step 1) and acetyl chloride.

$^1$H-NMR (CDCl$_3$) δ: 8.84 (1H, br s), 8.14 (1H, d, J=9 Hz), 7.96 (1H, s), 7.76 (2H, d, J=8 Hz), 7.57–7.44 (4H, m), 3.92 (2H, q, J=7 Hz), 2.23 (3H, s), 0.93 (3H, t, J=7 Hz)

Step 3. 3-Acetylamino-2-benzoyl-5-chloroindole

The title compound was prepared according to the procedure described in step 2 of Example 2 (Method A) and from 3-acetylamino-2-benzoyl-5-chloro-1-(ethoxycarbonyl) indole (step 2). m.p.: 200–201° C. (ethyl acetate)

$^1$H-NMR (CDCl$_3$) δ: 9.70 (1H, br s), 8.28 (1H, br s), 8.25 (1H, s), 7.80 (2H, dd, J=8,1.5 Hz), 7.65–7.56 (3H, m), 7.33 (1H, dd, J=8, 1.5 Hz), 7.23 (1H, d, J=8 Hz), 2.24 (3H, s)

IR (KBr) ν: 3250, 1670, 1535, 1270, 800, 730 cm$^{-1}$

Ex. 104

5-Chloro-2-(3-chlorobenzoyl)-3-(propionylamino) indole

Step 1. 3-Amino-5-chloro-2-(3-chlorobenzoyl)-1-(ethoxycarbonyl)indole

The title compound was prepared according to the procedure described in step 2 of Example 1 from 5-chloro-2-(ethoxycarbonylamino)benzonitrile (K. O. Geolotte et al, *J. Heterocyclic Chem.*, 1990, 27, 1549) and 2-bromo-3'-chloroacetophenone (M. Kihara et al., *Tetrahedron*, 1992, 48, 67–78).

$^1$H-NMR (CDCl$_3$) δ: 8.15 (1H, dd, J=10, 1 Hz), 7.75 (1H, t, J=1.5 Hz), 7.60–7.43 (4H, m), 7.36 (1H, t, J=8 Hz), 5.78 (2H, br s), 3.83 (2H, q, J=7 Hz), 0.92 (3H, t, J=7 Hz)

Step 2. 5-Chloro-2-(3-chlorobenzoyl)-3-(propionylamino)indole

The title compound was prepared according to the procedure described in Example 2 (Method A) from 3-amino-5-chloro-2-(3-chlorobenzoyl)-1-(ethoxycarbonyl)indole (step 1) and propionyl chloride. m.p.: 206.5–207.5° C. (ethyl acetate) $^1$H-NMR (CDCl$_3$) δ: 9.78 (1H, br s), 8.31 (1H, s), 8.28 (1H, br s), 7.78 (1H, s), 7.70–7.59 (2H, m), 7.51 (1H, t, J=8 Hz), 7.34 (1H, dd, J=8, 1.5 Hz), 7.25 (1H, d, J=8 Hz), 2.51 (2H, q, J=7 Hz), 1.30 (3H, t, J=7 Hz)

IR (KBr) ν: 3300, 1680, 1580, 1540, 700 cm$^{-1}$

Ex. 105

3-Acetylamino-2-benzoylindole

Step 1. 3-Acetylamino-2-benzoyl-1-(ethoxycarbonal)indole

The title compound was prepared according to the procedure described in step 1 of Example 2 (Method A) from 3-amino-2-benzoyl-1-(ethoxycarbonyl)indole (E. E. Garcia, L. E. Benjamin and R. Ian Fryer, *J. Heterocyclic Chem.*, 1973, 10, 51–53) and acetyl chloride. m.p.: 112–113° C. (ethyl acetate/isopropyl ether)

$^1$H-NMR (CDCl$_3$) δ: 9.05 (1H, br s), 8.21 (1H, d, J=8 Hz), 7.98 (1H, d, J=8 Hz), 7.79 (2H, d, J=8 Hz), 7.60–7.43 (4H, m), 7.34 (1H, t, J=8 Hz), 3.90 (2H, q, J=7 Hz), 2.24 (3H, s), 0.94 (3H, t, J=7 Hz)

Step 2. 3-Acetylamino-2-benzoylindole

The title compound was prepared according to the procedure described in step 2 of Example 2 (Method A) from 3-acetylamino-2-benzoyl-1-(ethoxycarbonyl)indole (step 1). $^1$H-NMR (CDCl$_3$) δ: 9.78 (1H, br s), 8.24 (1H, d, J=8 Hz), 8.22 (1H, br s), 7.82 (2H, d, J=8 Hz), 7.64–7.52 (3H, m), 7.42–7.25 (2H, m), 7.16 (1H, t, J=8 Hz), 2.26 (3H, s) IR (KBr) ν: 3360, 1670, 1620, 1540, 730 cm$^{-1}$

Ex. 106

3-Acetylamino-2-benzoyl-4-chloroindole

Step 1. 6-Chloro-2-(ethoxycarbonylamino) benzonitrile

The title compound was prepared according to the procedure described in step 1 of Example 1 (Method B) from 2-amino-6-chlorobenzonitrile. m.p.: 144.5–145.1 (ethyl acetate/hexane) $^1$H-NMR (CDCl$_3$) δ: 8.21 (1H, d, J=8 Hz), 7.49 (1H, t, J=8 Hz), 7.16 (1H, d, J=8 Hz), 7.17 (1H, br s), 4.27 (2H, q, J=7 Hz), 1.35 (3H, t, J=7 Hz)

Step 2. 3-Amino-2-benzoyl-4-chloro-1-(ethoxycarbonyl)indole

The title compound was prepared according to the procedure described in step 2 of Example 1 from 6-chloro-2-(ethoxycarbonylamino)benzonitrile (step 1) and 2-bromoacetophenone. m.p.: 118–119° C. (isopropyl ether)

$^1$H-NMR (CDCl$_3$) δ: 8.15 (1H, d, J=8 Hz), 7.73 (2H, dd, J=7, 2 Hz), 7.46–7.40 (4H, m), 7.24 (1H, d, J=7 Hz), 6.54 (2H, br s), 3.69 (2H, q, J=7 Hz), 0.83 (3H, t, J=7 Hz)

Step 3. 3-Acetylamino-2-benzoyl-4-chloro-1-(ethoxycarbonyl)indole

The title compound was prepared according to the procedure described in step 1 of Example 2 (Method A) from 3-amino-2-benzoyl-4-chloro-1-(ethoxycarbonyl)indole (step 2). $^1$H-NMR (CDCl$_3$) δ: 8.16 (1H, d, J=8 Hz), 7.85 (2H, d, J=7 Hz), 7.63–7.25 (6H, m), 4.08 (2H, q, J=7 Hz), 2.08 (3H, s), 0.99 (3H, t, J=7 Hz)

Step 4. 3-Acetylamino-2-benzoyl-4-chloroindole

The title compound was prepared according to the procedure described in step 2 of Example 2 (Method A) from 3-acetylamino-2-benzoyl-4-chloro-1-(ethoxycarbonyl) indole (step 3). m.p.: 221–222° C. (ethyl acetate/hexane) $^1$H-NMR (CDCl$_3$) δ: 9.12 (1H, br s), 7.82 (2H, d, J=7 Hz), 7.60–7.20 (6H, m), 7.12 (1H, d, J=7 Hz), 1.79 (3H, s) IR (KBr) ν: 3400, 3150, 1670, 1630, 1507, 1270, 780, 730 cm$^{-1}$ Ex. 107

3-Acetylamino-2-benzoyl-4-fluoroindole

Step 1. 2-(Ethoxycarbonylamino)-6-fluorobenzonitrile

The title compound was prepared according to the procedure described in step 1 of Example 1 (Method B) from 2-amino-6-fluorobenzonitrile.

tlc: Rf=0.75 (33% ethyl acetate in hexanes)

Step 2. 3-Amino-2-benzoyl-1-(ethoxycarbonyl)-4-fluoroindole

The title compound was prepared according to the procedure described in step 2 of Example 1 from 2-(ethoxycarbonylamino)-6-fluorobenzonitrile (step 1) and 2-bromoacetophenone. tlc: Rf=0.3 (33% ethyl acetate in hexanes)

Step 3. 3-Acetylamino-2-benzoyl-1-(ethoxycarbonyl)-4-fluoroindole

The title compound was prepared according to the procedure described in step 1 of Example 2 (Method A) from 3-amino-2-benzoyl-1-(ethoxycarbonyl)-4-fluoroindole (step 2). $^1$H-NMR (CDCl$_3$) δ: 8.70 (1H, s), 7.72 (1H, d, J=8.4 Hz), 7.55–7.38 (5H, m), 7.20 (1H, dd, J=8.1, 13.6 Hz), 6.78 (1H, dd, J=8.4, 9.9 Hz), 4.05 (2H, q, J=7.3 Hz), 2.12 (3H, s), 0.99 (3H, t, J=7.3 Hz)

Step 4. 3-Acetylamino-2-benzoyl-4-fluoroindole

The title compound was prepared according to the procedure described in step 2 of Example 2 (Method A) from 3-acetylamino-2-benzoyl-1-(ethoxycarbonyl)-4-fluoroindole (step 3). m.p.: 131–133° C.

$^1$H-NMR (CDCl$_3$) δ: 8.92 (1H, br s), 7.81 (1H, d, J=8.4 Hz), 7.80 (1H, br s), 7.61–7.46 (3H, m), 7.29–7.15 (2H, m), 6.80 (1H, dd, J=7.7, 10.7 Hz), 1.91 (3H, s)

Ex. 108

3-Acetylamino-2-benzoyl-6-fluoroindole

Step 1. 2-(Ethoxycarbonylamino)-4-fluorobenzonitrile

The title compound was prepared according to the procedure described in step 1 of Example 1 (Method B) from 2-amino-4-fluorobenzonitrile.

tlc: Rf=0.7 (25% ethyl acetate in hexanes)

Step 2. 3-Amino-2-benzoyl-1-(ethoxycarbonyl)-6-fluoroindole

The title compound was prepared according to the procedure described in step 2 of Example 1 from 2-(ethoxycarbonylamino)-4-fluorobenzonitrile (step 1) and 2-bromoacetophenone. $^1$H-NMR (CDCl$_3$) δ: 7.94 (1H, dd, J=2.7, 10.3 Hz), 7.76–7.72 (2H, m), 7.57 (1H, dd, J=5.5, 8.8 Hz), 7.51–7.39 (3H, m), 7.06 (1H, ddd, J=2.7, 8.8, 10.3 Hz), 5.87 (2H, br s), 3.74 (2H, q, J=7.3 Hz), 0.84 (3H, t, J=7.3 Hz)

Step 3. 3-Acetylamino-2-benzoyl-1-(ethoxycarbonyl)-6-fluoroindole

The title compound was prepared according to the procedure described in step 1 of Example 2 (Method A) from 3-amino-2-benzoyl-1-(ethoxycarbonyl)-6-fluoroindole (step 2). tlc: Rf=0.2 (33% ethyl acetate in hexanes)

Step 4. 3-Acetylamino-2-benzoyl-6-fluoroindole

The title compound was prepared according to the procedure described in step 2 of Example 2 (Method A) from 3-acetylamino-2-benzoyl-1-(ethoxycarbonyl)-6-fluoroindole (step 3). m.p.: 144–145° C.

$^1$H-NMR (CDCl$_3$) δ: 9.96 (1H, br s), 8.44 (1H, br s), 8.25 (1H, dd, J=5.5, 8.8 Hz), 7.80–7.71 (2H, m), 7.65–7.51 (3H, m), 6.94–6.85 (2H, m), 2.22 (3H, s)

Ex. 109

3-Acetylamino-2-benzoyl-6-methylindole

Step 1. 2-(Ethoxycarbonylamino)-4-methylbenzonitrile

The title compound was prepared according to the procedure described in step 1 of Example 1 (Method B) from 2-amino-4-methylbenzonitrile.

$^1$H-NMR (CDCl$_3$) δ: 8.06 (1H, s), 7.43 (1H, d, J=7.7 Hz), 7.10 (1H, br. s), 6.92 (1H, d, 7.7 Hz), 4.25 (2H, q, J=7.3 Hz), 2.40 (3H, s), 1.35 (3H, t, J=7.3 Hz)

Step 2. 3-Amino-2-benzoyl-1-(ethoxycarbonyl)-6-methylindole

The title compound was prepared according to the procedure described in step 2 of Example 1 from 2-(ethoxycarbonylamino)-4-methylbenzonitrile (step 1) and 2-bromoacetophenone. tlc: Rf=0.6 (25% ethyl acetate in hexanes)

Step 3. 3-Acetylamino-2-benzoyl-1-(ethoxycarbonyl)-6-methylindole

The title compound was prepared according to the procedure described in step 1 of Example 2 (Method A) from 3-amino-2-benzoyl-1-(ethoxycarbonyl)-6-methylindole (step 2). $^1$H-NMR (CDCl$_3$) δ: 9.29 (1H, br.s), 7.78–7.38 (5H, m), 7.84 (1H, s), 7.77 (1H, d, J=8.4 Hz), 7.02 (1H, d, J=8.4 Hz), 3.92 (2H, q, J=7.3 Hz), 2.46 (3H, s), 2.18 (3H, s), 0.94 (3H, t, J=7.3 Hz)

Step 4. 3-Acetylamino-2-benzoyl-6-methylindole

The title compound was prepared according to the procedure described in step 2 of Example 2 (Method A) from 3-acetylamino-2-benzoyl-1-(ethoxycarbonyl)-6-methylindole (step 3). m.p.: 136–138° C.

$^1$H-NMR (CDCl$_3$) δ: 9.92 (1H, br s), 8.16–8.13 (2H, br s), 7.81–7.78 (2H, m), 7.52–7.65 (3H, m), 7.05 (1H, br s), 6.97 (1H, dd, J=1.1, 8.4 Hz), 2.44 (3H, s), 2.23 (3H, s)

Ex. 110

3-Acetylamino-2-benzoyl-6-cyanoindole

Step 1. 4-Cyano-2-(ethoxycarbonylamino)benzonitrile

The title compound was prepared according to the procedure described in step 1 of Example 1 (Method B) from 2-amino-4-cyanobenzonitrile.

tlc: Rf=0.6 (25% ethyl acetate in hexanes)

Step 2. 3-Amino-2-benzoyl-6-cyano-1-(ethoxycarbonyl)indole

The title compound was prepared according to the procedure described in step 2 of Example 1 from 4-cyano-2-(ethoxycarbonylamino)benzonitrile (step 1) and 2-bromoacetophenone. tlc: Rf=0.2 (25% ethyl acetate in hexanes)

Step 3. 3-Acetylamino-2-benzoyl-6-cyano-1-(ethoxycarbonyl)indole

The title compound was prepared according to the procedure described in step 1 of Example 2 (Method A) from 3-amino-2-benzoyl-6-cyano-1-(ethoxycarbonyl)indole (step 2). tlc: Rf=0.1 (33% ethyl acetate in hexanes)

Step 4. 3-Acetylamino-2-benzoyl-6-cyanoindole

The title compound was prepared according to the procedure described in step 2 of Example 2 (Method A) from 3-acetylamino-2-benzoyl-6-cyano-1-(ethoxycarbonyl)indole (step 3). m.p.: 244–246° C.

$^1$H-NMR (DMSO-d$_6$) δ: 12.3 (1H, br s), 9.80 (1H, s), 7.90 (1H, d, J=1.5 Hz), 7.79–7.49 (6H, m), 7.42 (1H, dd, J=1.5, 8.4 Hz),1.68 (3H, s)

Ex. 111

3-Acetylamino-5-bromo-6-chloro-2-(6-methylpyridine-2-carbonyl)indole

Step 1. 3-Amino-6-chloro-1-(ethoxycarbonyl)-2-(6-methylpyridine-2-carbonyl)indole and,

3-Amino-5-bromo-6-chloro-1-(ethoxycarbonyl)-2-(6-methylpyridine-2-carbonyl)indole The title compounds were prepared according to the procedure described in step 2 of Example 1 from 4-chloro-2-(ethoxycarbonylamino)benzonitrile and 2-bromoacetyl-6-methylpyridine hydrobromide (H. Erlenmeyer, J. Jenni, and B. Prijs, *J. Med. Pharm. Chem.*, 1961, 3, 561–566).

3-Amino-5-bromo-6-chloro-1-(ethoxycarbonyl)-2-(6-methylpyridine-2-carbonyl)indole (3%): $^1$H-NMR (CDCl$_3$) δ: 8.36 (1H, s), 7.90 (1H, d, J=7.7 Hz), 7.86 (1H, s), 7.77 (1H, t, J=7.7 Hz), 7.26 (1H, d, J=7.3 Hz), 5.90 (2H, br s), 3.74 (2H, q, J=7.2 Hz), 2.56 (3H, s), 0.84 (3H, t, J=7.2 Hz), 3-Amino-6-chloro-1-(ethoxycarbonyl)-2-(6-methylpyridine-2-carbonyl)indole (46%):

$^1$H-NMR (CDCl$_3$) δ: 8.23 (1H, d, J=1.8 Hz), 7.90 (1H, d, J=7.7 Hz), 7.76 (1H, t, J=7.7 Hz), 7.52 (1H, d, J=8.1 Hz), 7.26–7.22 (2H, m), 6.00 (2H, br s), 3.73 (2H, q, J=7.0 Hz), 2.56 (3H, s), 0.85 (3H, t, J=7.0 Hz)

Step 2. 3-Acetylamino-5-bromo-6-chloro-1-(ethoxycarbonyl)-2-(6-methylpyridine-2-carbonyl)indole The title compound was prepared according to the procedure described in step 1 of Example 2 (Method A) from 3-amino-5-bromo-6-chloro-1-(ethoxycarbonyl)-2-(6-methylpyridine-2-carbonyl)indole (step 1).

tlc: Rf=0.1 (33% ethyl acetate in hexanes)

Step 3. 3-Acetylamino-5-bromo-6-chloro-2-(6-methylpyridine-2-carbonyl)indole The title compound was prepared according to the procedure described in step 2 of Example 2 (Method A) from 3-acetylamino-5-bromo-6-chloro-1-(ethoxycarbonyl)-2-(6-methylpyridine-2-carbonyl)indole (step 2). m.p.: 234–236° C. (dichloromethane/methanol) $^1$H-NMR (DMSO-d$_6$) δ: 12.01 (1H, br s), 10.26 (1H, br s), 8.21 (1H, s), 7.98 (1H, t, J=7.7 Hz), 7.86 (1H, d, J=7.7 Hz), 7.85 (1H, s), 7.57 (1H, d, J=7.7 Hz), 2.66 (3H, s), 1.99 (3H, s).

Ex. 112

3-Amino-6-chloro-2-(6-methylpyridine-2-carbonyl)indole

The title compound was prepared according to the procedure described in step 2 of Example 1 from 3-amino-6-chloro-1-(ethoxycarbonyl)-2-(6-methylpyridine-2-carbonyl)indole (Example 111, step 1). m.p.: 210–211° C. (ethyl acetate)

$^1$H-NMR (DMSO-d$_6$) δ: 10.85 (1H, br s), 7.97–7.90 (3H, m), 7.59 (1H, br s), 7.50 (1H, t, J=4.4 Hz), 7.34 (2H, br s), 6.93 (1H, dd, J=1.8, 8.4 Hz), 2.73 (3H, s).

Ex. 113

3-Acetylamino-6-chloro-2-(6-methylpyridine-2-carbonyl)indole

The title compound was prepared according to the procedure described in Example 19 employing 3-acetylamino-6-chloro-2-(6-methylpyridine-2-carbonyl)indole (Example 112). m.p.: 195–196° C. (ethyl acetate)

$^1$H-NMR (CDCl$_3$) δ: 11.88 (1H, br s), 10.24 (1H, br s), 7.97 (1H, t, J=7.7 Hz), 7.85 (1H, d, J=7.7 Hz), 7.81 (1H, d, J=8.8 Hz), 7.63 (1H, d, J=1.8 Hz), 7.56 (1H, d, J=7.7 Hz), 7.08 (1H, dd, J=1.8, 8.8 Hz), 2.67 (3H, s), 1.97 (3H, s)

Ex. 114

2-Benzoyl-6-chloro-3-[(2-tetrahydrofuryl)carboxamido)indole

A mixture of 3-amino-2-benzoyl-6-chloroindole (Example 1; 380 mg, 1.4 mmol), tetrahydro-2-furancarboxylic acid (490 mg, 4.2 mmol) and 1-ethoxycarbonyl-2-ethoxy-1,2-dihydroquinoline (EEDQ, 1.04 g, 4.2 mmol) in THF (20 ml) was heated at reflux stirred for 20 h. The mixture was cooled, poured into 2N aqueous HCl (30 ml) and extracted with diethyl ether (50 ml). The organic extract was washed with saturated sodium bicarbonate (30 ml), dried (MgSO$_4$) and solvent evaporated. The residue was purified by flash chromatography eluting with ethyl acetate/hexane (1:1) to afford 500 mg (97%) of the titled compound as clear brown liquid.

$^1$H-NMR (CDCl$_3$) δ: 10.56 (1H, br s), 8.62 (1H, br s), 8.23 (1H, d, J=8.8 Hz), 7.82–7.75 (2H, m), 7.65–7.48 (3H, m), 7.30 (1H, d, J=1.8 Hz), 7.08 (1H, dd, J=8.8, 1.8 Hz), 4.55–4.38 (1H, m), 4.25–3.85 (3H, m), 2.40–1.85 (3H, m).

Ex. 115

2-Benzoyl-6-chloro-3-[(2-methoxypropionyl)amino]indole

The title compound was prepared according to the procedure described in Example 114 employing 3-amino-2-benzoyl-6-chloroindole (Example 1) and 2-methoxypropionic acid. m.p.: 169–171° C. (ethyl acetate/hexane)

$^1$H-NMR (CDCl$_3$) δ: 10.43 (1H, br s), 8.49 (1H, br s), 8.20 (1H, d, J=8.8 Hz), 7.83–7.76 (2H, m), 7.65–7.50

(3H,m), 7.30 (1H, d, J=1.8 Hz), 7.09 (1H, dd, J=1.8, 8.8 Hz), 3.88 (1H, q, J=7.0 Hz), 3.48 (3H,s), 1.45 (3H, d, J=7.0 Hz).

Ex. 116

2-Benzoyl-6-chloro-3-(3,3,3-trifluoropropionylamino)indole

The title compound was prepared according to the procedure described in Example 114 employing 3-amino-2-benzoyl-6-chloroindole (Example 1) and 3,3,3-trifluoropropionic acid. m.p.: 201–204° C. (ethyl acetate/hexane)

$^1$H-NMR (CDCl$_3$) δ: 10.35 (1H, br s), 8.34 (1H, br s), 8.22 (1H, d, J=8.8 Hz), 7.88–7.75 (5H, m), 7.31 (1H, d, J=1.8 Hz), 7.13 (1H, dd, J=8.8, 1.8 Hz), 3.46–3.30 (2H, m)

Ex. 117

2-Benzoyl-6-chloro-3-(cyclopropaneacetylamino)indole

The title compound was prepared according to the procedure described in Example 114 employing 3-amino-2-benzoyl-6-chloroindole (Example 1) and cyclopropylacetic acid. m.p.: 72–75° C.

$^1$H-NMR (CDCl$_3$): 10.33 (1H, br s), 8.34 (1H, br s), 8.27 (1H, d, J=9.2 Hz), 7.83–7.75 (2H, m), 7.67 (3H, m), 7.27 (1H, d, J=1.8 Hz), 7.09 (1H, dd, J=9.2, 1.8 Hz), 2.38 (2H, d, J=7.3 Hz), 1.21–1.05 (1H, m), 0.80–0.70 (2H, m), 0.38–0.27 (2H, m)

Ex. 118

2-Benzoyl-6-chloro-3-[(3-hydroxy-3-methyl)butyrylamino]indole

The title compound was prepared according to the procedure described in Example 114 employing 3-amino-2-benzoyl-6-chloroindole (Example 1) and 3-hydroxyisovaleric acid. m.p.: 179–182° C. $^1$H-NMR (CDCl$_3$) δ: 10.07 (1H, br s), 8.37 (1H, br s), 8.16 (1H, d, J=9.2 Hz), 7.86–7.77 (2H, m), 7.70–7.53 (3H, m), 7.30 (1H, d, J=1.8 Hz), 7.12 (1H, dd, J=9.2, 1.8 Hz), 3.98 (1H, brs), 2.62 (2H, s), 1.36 (6H, s)

Ex. 119

2-Benzoyl-6-chloro-3-(methylthioacetylamino)indole

The title compound was prepared according to the procedure described in Example 114 employing 3-amino-2-benzoyl-6-chloroindole (Example 1) and methylthioacetic acid. m.p.: 63–70° C. $^1$H-NMR (CDCl$_3$) δ: 10.78 (1H, br s), 8.42 (1H, br s), 8.16 (1H, d, J=9.2 Hz), 7.86–7.79 (2H, m), 7.68–7.53 (3H, m), 7.31 (1H, d, J=1.8 Hz), 7.12 (1H, dd, J=9.2, 1.8 Hz), 3.39 (2H, s), 2.23 (3H, s)

Ex. 120 and Ex. 121

2-Benzoyl-6-chloro-3-(methylsulfinylacetylamino)indole (EXAMPLE 120) and,

2-benzoyl-6-chloro-3-(methylsulfonylacetylamino)indole (EXAMPLE 121)

A mixture of 2-benzoyl-6-chloro-3-(methylthioacetylamino)indole (Example 119; 0.87 g, 2.4 mmol) in methanol (20 ml) and oxone (2.9 g, 4.8 mmol) in water (10 ml) was stirred together for 10 min, poured into aqueous sodium thiosulfate (50 ml) and extracted with dichloromethane (30 ml×2). The combined organic extract was dried (MgSO$_4$) and solvent removed by evaporation. The residue was purified by flash chromatography eluting with ethyl acetate/hexane (1:1) to afford 280 mg (31%) of the sulfoxide (less polar) and 130 mg (14%) of sulfone (more polar), respectively. Recrystallization from ethyl acetate and n-hexane afforded 220 mg (24%) of sulfoxide as yellow solids and recrystallization from ethyl acetate afforded 90 mg (10%) of the sulfone as yellow solids.

2-Benzoyl-6-chloro-3-(methylsulfinylacetylamino)indole (Example 120)

m.p.: 191–192° C. (ethyl acetate/hexane, yellow solids)

$^1$H-NMR (CDCl$_3$) δ: 10.29 (1H, br s), 10.06 (1H, br s), 7.94 (1H, d, J=8.8 Hz), 7.88–7.82 (2H, m), 7.65–7.49 (3H, m), 7.43 (1H, d, J=1.8 Hz), 7.09 (1H, dd, J=8.8, 1.8 Hz), 3.73 (1H, d, J=13.6 Hz), 3.57 (1H, d, J=13.6 Hz), 2.75 (3H, s) and,

2-Benzoyl-6-chloro-3-(methylsulfonylacetylamino)indole (Example 121)

m.p.: 217–220° C. (ethyl acetate, yellow solids)

$^1$H-NMR (CDCl$_3$) δ: 10.27 (1H, br s), 8.50 (1H, br s), 8.06 (1H, d, J=8.8 Hz), 7.88–7.79 (2H, m), 7.72–7.52 (3H, m), 7.34 (1H, d, J=1.8 Hz), 7.13 (1H, dd, J=8.8, 1.8 Hz), 4.10 (2H, s), 3.19 (3H,s).

Ex. 122

2-Benzoyl-6-chloro-3-[(n,n-dimethylaminoacetyl)amino]indole

Step 1. 2-Benzoyl-6-chloro-3-chloroacetylamino-1-(ethoxycarbonyl)indole

The titled compound was prepared according to the procedure described in step 1 of Example 2 (Method A) from 3-amino-2-benzoyl-6-chloro-1-(ethoxycarbonyl)indole (Example 1, step 2) and chloroacetyl chloride.

$^1$H-NMR (CDCl$_3$) δ: 9.86 (1H, br s), 8.27 (1H, d, J=1.8 Hz), 7.92 (1H, d, J=8.8 Hz), 7.81–7.72 (2H, m), 7.62–7.42 (3H, m), 7.33 (1H, dd, J=1.8, 8.8 Hz), 4.20 (2H, s), 3.92 (2H, q, J=7.0 Hz), 0.94 (3H, t, J=7.0 Hz).

Step 2. 2-Benzoyl-6-chloro-3-[(N,N-dimethylaminoacetyl)amino]indole

A mixture of 2-benzoyl-6-chloro-3-(chloroacetylamino)-1-(ethoxycarbonyl)indole (step 1, 890 mg, 2.12 mmol) and dimethylamine hydrochloride (520 mg, 6.36 mmol) in DMF (30 ml) was stirred for 2 h. Water (80 ml) was added and the mixture extracted with an ethyl acetate-toluene mixture (2:1 v/v, 30 ml×2). The combined organic extracts were washed consecutively with water (50 ml) and brine (50 ml), dried (MgSO$_4$) and evaporated. The residue was treated with a solution of 1N aqueous KOH (20 ml) and EtOH (40 ml) for 1 h, volatiles removed by evaporation and the residue extracted with ethyl acetate (30 ml×2). The combined organic extracts were dried (MgSO$_4$) and evaporated. The crude product was recrystallized from ethyl acetate/hexane to give 350 mg (47%) of the title compound as a yellow solid. m.p.: 175–176° C. $^1$H-NMR (CDCl$_3$) δ: 10.60 (1H, br s), 8.83 (1H, br s), 8.08 (1H, d, J=8.8 Hz), 7.88–7.70 (2H, m), 7.68–7.42 (3H, m), 7.29 (1H, d, J=1.8 Hz), 7.07 (1H, dd, J=1.8, 8.8 Hz), 3.04 (2H, s), 2.33 (6H, s)

IR (KBr) ν: 1660, 1620, 1570, 1540, 1250, 1240, 1050, 920 cm$^{-1}$

Ex. 123

3-Acetylamino-2-benzoyl-5,6-dimethoxyindole

Step 1. 4,5-Dimethoxy-2-(ethoxycarbonylamino)benzonitrile

The title compound was prepared according to the procedure described in step 1 of Example 1 (Method B) from 2-amino-4,5-dimethoxybenzonitrile.

tlc: Rf=0.7 (33% ethyl acetate in hexanes)

Step 2. 3-Amino-2-benzoyl-5,6-dimethoxy-1-(ethoxycarbonyl)indole

The title compound was prepared according to the procedure described in step 2 of Example 1 from 4,5-dimethoxy-2-(ethoxycarbonylamino)benzonitrile (step 1).

tlc: Rf=0.2 (33% ethyl acetate in hexanes)

Step 3. 3-Acetylamino-2-benzoyl-4,5-dimethoxy-1-(ethoxycarbonyl)indole

The title compound was prepared according to the procedure described in step 1 of Example 2 (Method A) from 3-amino-2-benzoyl-5,6-dimethoxy-1-(ethoxycarbonyl)indole (step 2). tlc: Rf=0.6 (50% ethyl acetate in hexanes)

Step 4. 3-Acetylamino-2-benzoyl-4,5-dimethoxyindole

The title compound was prepared according to the procedure described in step 2 of Example 2 (Method A) from 3-acetylamino-2-benzoyl-4,5-dimethoxy-1-(ethoxycarbonyl)indole (step 3). m.p.: 118–120° C.

$^1$H-NMR (CDCl$_3$) δ: 10.2 (1H, br s), 8.44 (1H, br s), 7.74–7.78 (3H, m), 7.47–7.57 (3H, m), 6.64 (1H, s), 3.91 (3H, s), 3.84 (3H, s), 2.23 (3H, s)

IR (KBr) ν: 1665, 1540, 1495, 1265, 1220, 11120, 1015, 835 cm$^{-1}$

Ex. 124

3-Acetylamino-6-chloro-2-[(1-methylimidazol-2-yl)carbonyl]indole

Step 1. Methyl 3-amino-6-chloro-1-(ethoxycarbonyl)indole-2-carboxylate

The title compound was prepared according to the procedure described in step 2 of Example 1 from 4-chloro-2-(ethoxycarbonylamino)benzonitrile (Example 1, step 2) and methyl bromoacetate. $^1$H-NMR (CDCl$_3$) δ: 8.08 (1H, d, J=1.8 Hz), 7.42 (1H, d, J=8.8 Hz), 7.22 (1H, dd, J=8.8, 1.8 Hz), 5.17 (2H, br s), 4.40 (2H, q, J=7.3 Hz), 3.88 (3H, s), 1.40 (3H, t, J=7.3 Hz)

Step 2. Methyl 3-acetylamino-6-chloro-1-(ethoxycarbonyl)indole-2-carboxylate The title compound was prepared according to the procedure described in step 1 of Example 2 (Method A) from methyl 3-amino-6-chloro-1-(ethoxycarbonyl)indole-2-carboxylate (step 1). $^1$H-NMR (CDCl$_3$) δ: 8.80 (1H, br s), 8.05 (1H, d, J=1.8 Hz), 7.92 (1H, d, J=8.4 Hz), 7.23 (1H, dd, J=8.8, 1.8 Hz), 4.44 (2H, q, J=7.3 Hz), 3.92 (3H, s), 2.27 (3H, s), 1.43 (3H, t, J=7.3 Hz)

Step 3. 3-Acetylamino-6-chloroindole-2-carboxylic acid

Methyl 3-acetylamino-6-chloro-1-(ethoxycarbonyl)indole-2-carboxylate (step 2; 1.48 g, 4.37 mmol) dissolved in ethanol (20 ml) and 1N aqueous KOH (10 ml) were heated together at reflux for 1 h. The mixture was cooled and concentrated, and the residue diluted with 1N aqueous HCl (20 ml) and extracted with ethyl acetate (30 ml×2). The organic extract was dried (MgSO$_4$) and evaporated to afford 0.95 g (86%) of the title compound as a white solid.

$^1$H-NMR (CDCl$_3$) δ: 11.69 (1H, s), 9.58 (1H, s), 7.63 (1H, dd, J=8.8, 1.5 Hz), 7.38 (1H, d, J=1.5 Hz), 7.03 (1H, d, J=8.4 Hz), 2.11 (3H, s).

Step 4. 3-Acetylamino-6-chloro-2-[(N-methoxy-N-methylamino)carbonyl]indole To a mixture of (3-acetylamino-6-chloroindole)-2-carboxylic acid (step 3; 280 mg, 1.11 mmol), diphenyl phosphoryl azide (365 mg, 1.33 mmol) and N,O-dimethylhydroxylamine hydrochloride (162 mg, 1.66 mmol) in dimethylformamide (5 ml) was added triethylamine (0.58 ml, 4.16 mmol). After stirring for 1 h, the mixture was poured into water (10 ml) and extracted with diethyl ether (30 ml×2). The combined organic extracts were washed consecutively with water (20 ml×2), saturated sodium bicarbonate (20 ml), brine (20 ml), then dried (MgSO$_4$). Removal of solvent gave the title compound as a brown solid (ca. 20%) which was used in the next step without further purification.

$^1$H-NMR (CDCl$_3$) δ: 10.00 (1H, brs), 8.12 (1H, m), 7.42–7.12 (3H, m), 3.80 (3H, s), 3.40 (3H, s), 2.23 (3H, s)

Step 5. 3-Acetylamino-6-chloro-2-[(1-methylimidazol-2-yl)carbonyl]indole

To a solution of 3-acetylamino-6-chloro-2-[(N-methoxy-N-methylamino)carbonyl]indole (step 4; 50 mg, 0.175 mmol) in tetrahydrofuran (3.0 ml) cooled to −70° C. was added a tetrahydrofuran (2.0 ml) solution of 2-lithiated-1-methylimidazole (prepared according to the method of Fraser, Robert R et. al., Can. J Chem., 1985, 63, 3505). The reaction mixture was allowed to warm to ambient temperature and stirred for 2 h. The mixture was poured into water (20 ml) and extracted with dichloromethane (20 ml×2). The organic extract was dried (MgSO$_4$) and concentrated. The residual solid was purified by flash column chromatography eluting with ethyl acetate to afford 20 mg (36%) of the title compound as a yellow solid. m.p.: 205–207° C. $^1$H-NMR (CDCl$_3$) δ: 11.69 (1H, br s), 10.67 (1H, br s), 8.40 (1H, d, J=8.8 Hz), 7.36 (1H, d, J=1.8 Hz), 7.26 (1H, s), 7.11 (1H, s), 7.03 (1H, dd, J=8.8, 1.8 Hz), 4.15 (3H, s), 2.33 (3H, s)

IR (KBr) ν: 1695, 1580, 1540, 1470, 1400, 1360, 1240, 1200, 1160, 1025 cm$^{-1}$

Ex. 125

3-Amino-6-chloro-2-(pyridine-2-carbonyl)indole

Step 1. 6-chloro-3-nitroindole-2-carboxylic acid

To an ice-cooled soluton of acetic anhydride (90 ml) and concentrated nitric acid (70%, 10.3 ml) was added 6-chloroindole-2-carboxylic acid (H. W. Ridon and J. C. Tweddle, J. Chem.Soc., 1955, 3499: 18.16 g, 92.84 mmol) portion wise over 20 min. The mixture was stirred for 2 h at 0° C. and the resulting precipitates collected by filtration and washed with a mixture of dichloromethane/hexane (1:1) to give 12.6 g (56%) of the title compound as a yellow solid. $^1$H-NMR (DMSO-$d_6$) δ: 13.41(1H, br s), 8.04 (1H, d, J=8.8 Hz), 7.62 (1H, d, 1.8 Hz), 7.44 (1H, dd, J=1.8, 8.8 Hz)

Step 2: 6-Chloro-2-(N-methoxy-N-methylamino)carbonyl-3-nitroindole

To a mixture of 6-chloro-3-nitroindole-2-carboxylic acid (step 1, 2.35 g, 9.77 mmol) and N,O-dimethylhydroxylamine hydrochloride (3.81 g, 39.1 mmol) in DMF (50 ml) was added dropwise a dimethylformamide (15 ml) solution of WSC (5.61 g, 29.3 mmol) over 10 min. After stirring for 4 h the mixture was diluted with diethyl ether (200 ml) and washed with water (100 ml×4). The organic extract was dried (MgSO$_4$) and solvent removed by evaporation. The crude product was recystallized from ethyl acetate to afford 1.55 g (56%) of the title compound.

$^1$H-NMR (DMSO-$d_6$) δ: 13.48 (1H, br s), 8.09 (1H, d, J=8.4 Hz), 7.68 (1H, d, J=1.5 Hz), 7.46 (1H, dd, J=1.8, 8.8 Hz), 3.51 (3H, s), 3.38 (3H, s)

Step 3. 6-Chloro-3-nitro-2-(pyridine-2-carbonyl)indole

To a solution of 2-bromopyridine (548 mg, 3.47 mmol) in diethyl ether (8 ml) cooled to −70° C. was added dropwise 1.66 M n-BuLi (2.1 ml in hexane). After stirring for 30 min, a solution of 6-chloro-2-(N-methoxy-N-methylamino)carbonyl-3-nitroindole (step 2, 328 mg, 1.16 mmol) in THF (8 ml) was added. The mixture was allowed to warm to ambient temperature and stirring continued for 5 h. Saturated ammonium chloride (20 ml) was then added and the mixture basified with saturated sodium bicarbonate (50 ml). The mixture was extracted with ethyl acetate (150 ml) and the extract was washed with brine (80 ml) and dried (Na$_2$SO$_4$). After removal of solvent by evaporation, the residue was purified by flash column chromatography eluting with ethyl acetate/hexane (1:3) to afford 150 mg (43%) of the title compound.

$^1$H-NMR (CDCl$_3$) δ: 8.67 (1H, br d, J=4.0 Hz), 8.24 (1H, d, J=8.1 Hz), 8.12 (1H, d, J=8.8 Hz), 7.98 (1H, dt, J=1.8, 7.7 Hz), 7.57 (1H, ddd, J=1.1, 4.8, 7.7 Hz), 7.54 (1H, d, J=1.5 Hz), 7.38 (1H, dd, J=1.5, 8.8 Hz). The signal due to NH was not observed.

Step 4: 3-Amino-6-chloro-2-(pyridine-2-carbonyl)indole

A mixture of 6-chloro-3-nitro-2-(pyridine-2-carbonyl)indole (step 3, 92 mg, 0.30 mmol), ammonium chloride (8 mg, 0.15 mmol) and iron powder (89 mg, 1.52 mmol) in 70% aqueous ethanol (6 ml) was heated at reflux for 2 h, and then cooled and filtered through a pad of Celite. The pad was washed copiously with a mixture of ethanol/ethyl acetate (1:1 v/v) and the combined washing evaporated. The residue was diluted with ethyl acetate (50 ml), washed with saturated aqueous sodim bicarbonate (30 ml) and dried (Na$_2$SO$_4$). Removal of solvent gave product as crystals.

m.p.: 186–187° C. $^1$H NMR (CDCl$_3$) δ: 11.02 (1H, br s), 8.76–8.74 (1H, m), 8.35 (1H, d, J=8.8 Hz), 7.94 (1H, dt, J=1.8, 7.7 Hz), 7.53 (1H, d, J=8.8 Hz), 7.48 (1H, ddd, J=1.5, 4.8, 7.7 Hz), 7.34 (1H, d, J=1.8 Hz), 6.97 (1H, dd, J=1.8, 8.4 Hz), 6.06 (2H, br s)

Ex. 126

3-Acetylamino-6-chloro-2-(pyridine-2-carbonyl)indole

The title compound was prepared according to the procedure described in Example 19 employing 3-amino-6-chloro-2-(pyridine-2-carbonyl)indole (Example 125) and acetyl chloride. m.p.: 211–212° C. (ethanol) $^1$H-NMR (DMSO-$d_6$) δ: 12.02 (1H, br s), 10.34 (1H, br s), 8.82 (1H, d, J=4.4 Hz), 8.15–8.07 (2H, m), 7.85 (1H, d, J=8.8 Hz), 7.75–7.70 (1H, m), 7.63 (1H, d, J=1.8 Hz), 7.07 (1H, dd, J=1.8, 8.8 Hz), 2.02 (3H, s) IR (KBr) ν: 3450, 1690, 1620, 1580, 1570, 1480, 1350, 1240, 1180, 1160, 1030, 760 cm$^{-1}$ Ex. 127 and Ex. 128

3-Amino-6-chloro-2-(3-cyanobenzoyl)indole (EXAMPLE 127) and, 3-amino-2-(3-aminocarbonylbenzoyl)-6-chloroindole (EXAMPLE 128)

Step 1. 3-Amino-6-chloro-2-(3-cyanobenzoyl)-1-(ethoxycarbonyl)indole

The title compound was prepared according to the procedure described in step 2 of Example 1 from 4-chloro-2-(ethoxycarbonylamino)benzonitrile (Example 1, step 1) and 2-bromo-3'-cyanoacetophenone. $^1$H-NMR (CDCl$_3$) δ: 8.21 (1H, d, J=1.8 Hz), 8.03 (1H, s), 7.94 (1H, m), 7.80–7.72 (1H, m), 7.63–7.52 (2H, m), 7.32 (1H, dd, J=8.4, 1.8 Hz), 6.10 (2H, brs), 3.88 (2H, q, J=7.3 Hz), 0.95 (3H, t, J=7.3 Hz).

Step 2. 3-Amino-6-chloro-2-(3-cyanobenzoyl)indole (Example 127) and, 3-amino-2-(3-aminocarbonylbenzoyl)-6-chloroindole (Example 128)

A mixture of 3-amino-6-chloro-2-(3-cyanobenzoyl)-1-(ethoxycarbonyl)indole (step 1, 10.4 g, 28 mmol) and potassium carbonate (20 g, 140 mmol) in ethanol (100 ml) and water (100 ml) was heated at reflux for 4 h. The mixture was cooled and concentrated, and the residue partitioned between water (100 ml) and ethyl acetate (250). The organic layer was dried (MgSO$_4$) and concentrated. The residual oil was purified by flash column chromatography eluting with hexane/ethyl acetate (2/1) to give; 3-Amino-6-chloro-2-(3-cyanobenzoyl)indole (Example 127):

yellow solid: 4.0 g (48%) m.p.: 228–231° C. $^1$H-NMR (DMSO-$d_6$) δ: 10.33 (1H, br s), 8.15 (1H, s), 8.09–8.02 (2H, m), 7.92 (1H, d, J=8.4 Hz), 7.77 (1H, t, J=7.3 Hz), 7.25 (1H, d, J=1.8 Hz), 7.04 (2H, br s), 6.96 (1H, dd, J=8.4, 1.8 Hz) and, 3-Amino-2-(3-aminocarbonylbenzoyl)-6-chloroindole (Example 128):

yellow solid: 0.7 g (8%) m.p.: 132–150° C. $^1$H-NMR (DMSO-$d_6$) δ: 10.30 (1H, br s), 8.23 (1H, s), 8.28–8.02 (2H, m), 7.95–7.85 (2H, m), 7.65 (1H, t, J=7.7 Hz), 7.48 (1H, brs), 7.25 (1H, d, J=1.8 Hz), 6.95 (1H, dd, J=8.4, 1.8 Hz), 6.90 (2H, br s).

Ex. 129

3-Acetylamino-2-(3-aminocarbonylbenzoyl)-6-chloroindole

The title compound was prepared according to the procedure described in Example 19 employing 3-amino-2-(3-aminocarbonylbenzoyl)-6-chloroindole (Example 128) and acetyl chloride. m.p.: 243–247° C. (ethyl acetate/hexane)

$^1$H-NMR (DMSO-$d_6$) δ: 11.85 (1H, s), 9.79 (1H, s), 8.22 (1H, s), 8.18–8.03 (2H, m), 7.83 (1H, d, J=7.7 Hz), 7.70–7.44 (4H, m), 7.12 (1H, dd, J=8.4, 1.8 Hz), 1.63 (3H, s)

Ex. 130

3-Acetylamino-6-chloro-2-(3-cyanobenzoyl)indole

The title compound was prepared according to the procedure described in Example 19 employing 3-amino-6-chloro-2-(3-cyanobenzoyl)indole (Example 127) and acetyl chloride. m.p.: 185–187° C. (ethyl acetate/hexane) $^1$H-NMR (DMSO-$d_6$) δ: 11.91 (1H, br s), 9.85 (1H, brs), 8.12–8.04 (2H, m), 8.03–7.95 (1H, m), 7.77–7.62 (2H, m), 7.46 (1H, d, J=1.8 Hz), 7.12 (1H, dd, J=1.8, 8.8 Hz), 1.64 (3H, s)

Ex. 131

3-Amino-2-(3-carboxybenzoyl)-6-chloroindole

A mixture of 3-acetylamino-6-chloro-2-(3-cyanobenzoyl) indole (Example 130, 2.7 g, 7.99 mmol) and potassium hydroxide (2.2 g, 40 mmol) in ethanol (100 ml) and water (100 ml) was heated at reflux for 5 h. The mixture was cooled and concentrated, and the residue partitioned between water (100 ml) and ethyl acetate (100 ml). The aqueous layer was separated and acidified with 2N aqueous hydrochloric acid, extracted with ethyl acetate (100 ml×2) and the combined extracts dried (MgSO$_4$). After removal of solvent the residual solids were recrystallization from ethyl acetate to afford 1.8 g (72%) of the title compound as brown solids.

m.p.: 263–270° C. $^1$H-NMR (DMSO-$d_6$) δ: 13.15 (1H, s), 10.33 (1H, s), 8.27 (1H, s), 8.20–8.11 (1H, m), 8.03–7.96 (1H, m), 7.92 (1H, d, J=8.8 Hz), 7.70 (1H, t, J=7.6 Hz), 7.25 (1H, d, J=1.8 Hz), 6.96 (1H, dd, J=8.8, 1.8 Hz), 6.94 (2H, br s)

Ex. 132

3-Acetylamino-2-(3-carboxybenzoyl)-6-chloroindole

The title compound was prepared according to the procedure described in Example 19 employing 3-amino-2-(3-carboxybenzoyl)-6-chloroindole (Example 131) and acetyl chloride. m.p.: >290° C. (ethyl acetate) $^1$H-NMR (DMSO-$d_6$) δ: 11.85 (1H, s), 9.90 (1H, s), 8.39 (1H, br s), 8.20 (1H, d, J=7.7 Hz), 7.77 (1H, d, J=7.7 Hz), 7.65 (1H, d, J=8.8 Hz), 7.54–7.43 (2H, m), 7.09 (1H, dd, J=1.8, 8.4 Hz), 1.67 (3H, s)

Ex. 133

3-Amino-6-chloro-2-(3-methoxycarbonylbenzoyl) indole

A mixture of 3-acetylamino-6-chloro-2-(3-carboxybenzoyl)indole (Example 132, 0.9 g, 2.5 mmol) and 10% HCl—MeOH (30 ml) was heated at 60° C. for 8 h. The mixture was cooled and concentrated, and the residue partitioned between water (100 ml) and ethyl acetate (100 ml). The organic layer was separated and washed with brine (50 ml), and dried (MgSO$_4$) and solvent removed by evaporation. The residual solid was purified by flash column chromatography eluting with hexane/ethyl acetate (2/1) to afford 0.5 g of a title compound as a yellow solid. m.p.: 187–189° C. (ethyl acetate/hexane) $^1$H-NMR (DMSO-$d_6$) δ: 9.14 (1H, br s), 8.47 (1H, dd, J=1.8, 1.1 Hz), 8.20 (1H, ddd, J=7.7, 1.8, 1.1 Hz), 8.03 (1H, ddd, J=7.7, 1.8, 1.1 Hz), 7.69–7.58 (2H, m), 7.28 (1H, d, J=1.8 Hz), 6.97 (1H, dd, J=1.4, 8.4 Hz), 6.04 (2H, br s), 3.95 (3H, s)

Ex. 134

3-Acetylamino-6-chloro-2-(3-methoxycarbonylbenzoyl)indole

The title compound was prepared according to the procedure described in Example 19 employing 3-amino-6-chloro-2-(3-methoxycarbonylbenzoyl)indole (Example 133) and acetyl chloride. m.p.: 190–193° C. (ethyl acetate)

$^1$H-NMR (DMSO-$d_6$) δ: 9.80 (1H, s), 8.52–8.41 (2H, m), 8.26 (1H, d, J=7.7 Hz), 8.19 (1H, d, J=9.2 Hz), 8.98 (1H, d, J=7.7 Hz), 7.70–7.62 (1H, m), 7.30 (1H, d, J=1.8 Hz), 7.09 (1H, dd, J=9.2, 1.8 Hz), 3.95 (3H, s), 2.23 (3H, s)

Ex. 135

3-Acetylamino-2-(3-aminobenzoyl)-6-chloroindole

Step 1. 3-Amino-6-chloro-1-ethoxycarbonyl-2-(3-nitrobenzoyl)indole

The title compound was prepared according to the procedure described in step 2 of Example 1 from 4-chloro-2-(ethoxycarbonylamino)benzonitrile (Example 1, step 1) and 2-bromo-3'-nitroacetophenone.

$^1$H-NMR (CDCl$_3$) δ: 8.62–8.54 (1H, m), 8.38–8.28 (1H, m), 8.21 (1H, d, J=1.8 Hz), 8.04 (1H, d, J=7.7 Hz), 7.63 (1H, dd, J=1.8, 8.1 Hz), 7.57 (1H, d, J=8.4 Hz), 7.33 (1H, dd, J=1.8, 8.1 Hz), 6.03 (2H, br s), 3.88 (2H, q, J=7.0 Hz), 0.94 (3H, t, J=7.0 Hz)

Step 2. 3-Acetylamino-6-chloro-1-(ethoxycarbonyl)-2-(3-nitrobenzoyl)indole

The title compound was prepared according to the procedure described in step 1 of Example 2 (Method A) from 3-amino-6-chloro-1-ethoxycarbonyl-2-(3-nitrobenzoyl) indole (step 1) and acetyl chloride. $^1$H-NMR (CDCl$_3$) δ: 9.18 (1H, br s), 8.65–8.69 (1H, m), 8.38–8.42 (1H, m), 8.02–8.10 (1H, m), 7.98 (1H, s), 7.61–7.71 (2H, m), 7.18–7.25 (1H, m), 4.15 (2H, q, J=7.0 Hz), 2.24 (3H, s), 1.17 (3H, t, J=7.0 Hz)

Step 3. 3-Acetylamino-6-chloro-2-(3-nitrobenzoyl) indole

The title compound was prepared according to the procedure described in step 2 of Example 2 (Method A) from 3-acetylamino-6-chloro-1-(ethoxycarbonyl)-2-(3-nitrobenzoyl)indole (step 2). m.p.: 246–250° C.

$^1$H-NMR (CDCl$_3$) δ: 11.24 (1H, br s), 9.87 (1H, br s), 8.62 (1H, s), 8.46–8.36 (1H, m), 8.17 (1H, d, J=7.7 Hz), 7.90 (1H, d, J=8.4 Hz), 7.72 (1H, dd, J=7.7, 8.1 Hz), 7.46 (1H, d, J=1.5 Hz), 7.05 (1H, dd, J=1.5, 8.8 Hz), 1.98 (3H, s)

Step 4. 3-Acetylamino-2-(3-aminobenzoyl)-6-chloroindole

A mixture of 3-acetylamino-6-chloro-2-(3-nitrobenzoyl) indole (step 3, 2.68 g, 7.5 mmol), iron powder (1.7 g, 30 mmol) and ammonium chloride (0.8 g, 17 mmol) in 70% aqueous ethanol (70 ml) was heated at reflux for 1 h, and then cooled and filtered through a pad of Celite. The filtrate was concentrated and the residue partitioned between water (50 ml) and ethyl acetate (150 ml). The organic layer was separated, dried (MgSO$_4$) and slovent removed by evaporation to afford 2.6 g (quant.) of the title compound as yellow amorphous solids. $^1$H-NMR (CDCl$_3$) δ: 9.83 (1H, br s), 8.63 (1H, brs), 8.16 (1H, d, J=8.8 Hz), 7.35–7.21 (2H, m), 7.15–6.98 (3H, m), 6.88 (1H, dd, J=8.8, 1.8 Hz), 2.25 (3H, s) The signal due to NH$_2$ was not observed.

Ex. 136

3-Acetylamino-2-(3-aminobenzoyl)-6-chloroindole hydrochloride

3-Acetylamino-2-(3-aminobenzoyl)-6-chloroindole (Example 135, 0.41 g, 1.3 mmol) was stirred in 10%

HCl—MeOH (3.0 ml) for 10 min and then solvent removed by evaporation. The residual solid was recrystallized from ethanol/diethyl ether to afford 320 mg (70%) of the title compound as a yellow solid. m.p.:>300° C.

$^1$H-NMR (DMSO-d$_6$) δ: 11.87 (1H, br s), 9.85 (1H, br s), 7.78–7.40 (6H, m), 7.12 (1H, d, J=8.4 Hz), 1.70 (3H, s).

Ex. 137

3-Acetylamino-2-(3-acetylaminobenzoyl)-6-chloroindole

The title compound was prepared according to the procedure described in Example 19 employing 3-acetylamino-2-(3-aminobenzoyl)-6-chloroindole (Example 135) and acetyl chloride. m.p.: 225–228° C. (ethyl acetate/hexane) $^1$H-NMR (DMSO-d$_6$) δ: 10.59 (1H, br s), 9.75 (1H, br s), 9.45 (1H, br s), 7.96 (1H, d, J=8.8 Hz), 7.93–7.82 (2H, m), 7.58–7.40 (3H, m), 7.04 (1H, d, J=8.8 Hz), 2.17 (3H, s), 2.10 (3H, s)

Ex. 138

3-Acetylamino-6-chloro-2-(3-methanesulfonylaminobenzoyl)-indole

The title compound was prepared according to the procedure described in Example 19 employing 3-acetylamino-2-(3-aminobenzoyl)-6-chloroindole (Example 135) and methanesulfonyl chloride. m.p.: 133–142° C. (ethyl acetate/hexane)

$^1$H-NMR (DMSO-d$_6$) δ: 11.80 (1H, br s), 9.90 (1H, br s), 9.70 (1H, br s), 7.65 (1H, d, J=8.8 Hz), 7.58 (1H, br s), 7.49–7.40 (4H, m), 7.08 (1H, d, J=8.8 Hz), 3.03 (3H, s), 0.86 (3H, s)

Ex. 139

3-Acetylamino-6-chloro-2-(3-n,n-dimethylaminobenzoyl)indole

To a solution of 3-acetylamino-2-(3-aminobenzoyl)-6-chloroindole (Example 135, 0.89 g, 2.7 mmol) in acetonitrile (10 ml) was added aqueous formaldehyde (37%; 1.1 ml) and sodium cyanoborohydride (0.28 g, 4.4 mmol). After stirring for 30 min acetic acid (1.0 ml) was added and stirring was continued a further 1.5 h. The mixture was concentrated, saturated aqueous sodium bicarbonate (30 ml) added and the mixture extracted with ethyl acetate (50 ml×3). The organic layer was extracted with 2N aqueous hydrochloric acid (40 ml×3). The acidic extract and aqueous layer were combined, basified with 2N aqueous sodium hydroxide (120 ml) and extracted with ethyl acetate (50 ml×3). The organic layer was dried (MgSO$_4$) and concentrated and the residue purified by flash column chromatography eluting with hexane/ethyl acetate (2/1) to give 720 mg (67%) of the title compound which was recrystallization from hexane/ethyl acetate (440 mg, 41%) as a yellow solid. $^1$H-NMR (CDCl$_3$) δ: 10.00 (1H, br s), 8.45 (1H, br s), 8.23 (1H, d, J=8.4 Hz), 8.44–8.36 (1H, m), 7.28 (1H, d, J=1.8 Hz), 7.13–7.03 (3H, m), 7.00–6.93 (1H, m), 3.02 (6H, s), 2.30 (3H, s)

Ex. 140

3-Acetylamino-6-chloro-2-(3-n,n-dimethylaminobenzoyl)indole hydrochloride

The title compound was prepared from 3-acetylamino-6-chloro-2-(3-N,N-dimethylaminobenzoyl)indole (Example 139) according to the procedure described in Example 136. m.p.: 245–247° C. (ethanol/diethyl ether)

$^1$H-NMR (DMSO-d$_6$) δ: 11.85 (1H, br s), 9.84 (1H, br s), 7.75–7.40 (6H, m), 7.10 (1H, dd, J=8.8, 1.8 Hz), 3.10 (6H, s), 1.69 (3H, s)

Ex. 141

3-Acetylamino-6-chloro-2-(3,4-dihydroxybenzoyl)indole

Step 1. [3,4-Bis(methoxymethoxy)]phenacyl chloride 4-(Chloroacetyl)catechol (4.1 g, 22 mmol), chloromethylmethylether (3.7 ml, 44 mmol) and triethylamine (12 ml) in tetrahydrofuran (50 ml) were stirred together for 1 h, the mixture poured into water (80 ml) and extracted with diethyl ether (80 ml×2). The organic extract was washed consecutively with 2N aqueous sodium hydroxide (50 ml×2) and water (50 ml), dried (MgSO$_4$), and solvent evaporated to give 4.7 g (78%) of the title compound as a pale brown solid. (The crude product was used in the next step without further purification.)

$^1$H-NMR (CDCl$_3$) δ: 7.78 (1H, d, J=2.2 Hz), 7.60 (1H, dd, J=8.4, 2.2 Hz), 7.23 (1H, d, J=8.4 Hz), 5.32 (2H, s), 5.29 (2H, s), 4.65 (2H, s), 3.53 (3H, s), 3.52 (3H, s)

Step 2. 3-Amino-6-chloro-1-ethoxycarbonyl-2-[[3,4-bis(methoxymethoxy)]benzoyl]indole The title compound was prepared according to the procedure described in step 2 of Example 1 from 4-chloro-2-(ethoxycarbonylamino)benzonitrile (Example 1, step 1) and [3,4-bis(methoxymethyloxy)]phenacyl chloride (step 1).

$^1$H-NMR (CDCl$_3$) δ: 8.25 (1H, d, J=1.8 Hz), 7.61 (1H, d, J=2.2 Hz), 7.52 (1H, d, J=8.0 Hz), 7.39 (1H, dd, J=8.4, 1.8 Hz), 7.29 (1H, dd, J=8.4, 1.8 Hz), 7.18 (1H, d, J=8.4 Hz), 5.72 (2H, br s), 5.29 (2H, s), 5.25 (2H, s), 3.86 (2H, q, J=7.3 Hz), 3.52 (6H, s), 0.91 (3H, t, J=7.3 Hz).

Step 3. 3-Amino-6-chloro-2-[[3,4-bis(methoxymethyloxy)]benzoyl]indole

The title compound was prepared according to the procedure described in step 3 of Example 1 from 3-amino-6-chloro-1-ethoxycarbonyl-2-[[3,4-bis(methoxymethyloxy)]benzoyl]indole (step 2).

$^1$H-NMR (CDCl$_3$) δ: 7.73 (1H, br s), 7.63 (1H, d, J=1.8 Hz), 7.52 (1H, d, J=8.8 Hz), 7.47 (1H, dd, J=8.8, 1.8 Hz), 7.28 (1H, d, J=8.4 Hz), 7.22 (1H, d, J=1.8 Hz), 7.02 (1H, dd, J=8.4, 1.8 Hz), 5.59 (2H, br s), 5.32 (2H, s), 5.30 (2H, s), 3.54 (6H, s).

Step 4. 3-Acetylamino-6-chloro-2-[(3,4-dihydroxy)benzoyl]indole

To a solution of 3-amino-6-chloro-2-[[3,4-bis(methoxymethyloxy)]benzoyl]indole (step 3, 0.50 g, 1.3 mmol) in pyridine (1.0 ml) and dichloromethane (20 ml) cooled to 0° C. was added acetyl chloride (0.10 ml, 1.40 mmol). After stiiring for 1 h at room temperature, the reaction mixture was poured into water (20 ml) and extracted with dichloromethane (30 ml×2). The organic extracts were dried (MgSO$_4$) and solvent removed by evaporation. The residue was dissolved in dichloromethane (30 ml), trifluoroacetic acid (0.50 ml) added and the mixture heated at reflux for 5 h. The mixture was cooled, poured into water and extracted with ethyl acetate (80 ml×2). The organic extracts were dried (MgSO$_4$) and solvent removed by evaporation. The residual oil was purified by flash column chromatography eluting with hexane/ethyl acetate (1/3) to give 80 mg (20%) of the title compound. Recrystallization from ethyl acetate/hexane afforded the title compound as a yellow solid. m.p.: 193–200° C. $^1$H-NMR (CDCl$_3$) δ: 11.64 (1H, br s), 9.66 (1H, br s), 7.58 (1H, d, J=8.4 Hz), 7.41 (1H, J=1.5 Hz), 7.24 (1H, d, J=2.2 Hz), 7.15 (1H, dd, J=8.8, 1.8 Hz), 7.08 (1H, dd, J=8.8, 1.5 Hz), 6.80 (1H, d, J=8.4 Hz), 1.98 (3H, s)

The signal due to OH was not observed.

Ex. 142

3-(3-Amino-6-chloroindole-2-carbonyl) benzenesulfonamide

Step 1. 3-[3-Amino-6-chloro-1-(ethoxycarbonyl) indole-2-carbonyl]benzenesulfonamide The title compound was prepared according to the procedure described in step 2 of Example 1 from 4-chloro-2-(ethoxycarbonylamino)benzonitrile (Example 1, step 1) and 3-bromoacetylbenzensulfonamide (T. Fujikura, K. Nigata, S. Hashimoto, K. Imai, and T. Takenaka, Chem. Pharm. Bull., 1982, 30, 4092–4101).

$^1$H-NMR (DMSO-d$_6$) δ: 8.14–8.07 (3H, m), 7.94 (1H, br d, J=7.7 Hz), 7.78 (1H, br d, J=7.7 Hz), 7.65 (1H, t, J=7.7 Hz), 7.47 (2H, br s), 7.45 (1H, dd, J=1.8, 8.4 Hz), 7.38 (2H, br s), 3.75 (2H, q, J=7.0 Hz), 0.79 (3H, t, J=7.0 Hz)

Step 2. 3-(3-Amino-6-chloroindole-2-carbonyl) benzenesulfonamide

The title compound was prepared according to the procedure described in step 2 of Example 1 employing 3-[3-amino-6-chloro-1-(ethoxycarbonyl)indole-2-carbonyl] benzenesulfonamide (step 1). m.p.: 125–127° C. (2-propanol/toluene)

$^1$H-NMR (DMSO-d$_6$) δ: 10.31 (1H, br s), 8.15 (1H, br s), 8.02–7.93 (2H, m), 7.92 (1H, d, J=8.8 Hz), 7.75 (1H, t, J=7.7 Hz), 7.46 (2H, br s), 7.24 (1H, d, J=1.5 Hz), 6.96 (1H, dd, J=1.8, 8.4 Hz), 6.98–6.94 (2H, m)

Ex. 143

3-(3-Acetylamino-6-chloroindole-2-carbonyl) benzenesulfonamide

The title compound was prepared according to the procedure described in Example 19 employing 3-(3-amino-6-chloroindole-2-carbonyl)benzenesulfonamide (Example 142) and acetyl chloride. m.p.: 250–251° C. (ethanol/toluene)

$^1$H-NMR (DMSO-d$_6$) δ: 11.89 (1H, br s), 9.83 (1H, br s), 8.14 (1H, br s), 8.03 (1H, br d, J=8.1 Hz), 7.90 (1H, br d, J=7.7 Hz), 7.69 (1H, t, J=7.7 Hz), 7.68 (1H, d, J=8.8 Hz), 7.46 (2H, s), 7.45 (1H, d, J=1.8 Hz), 7.13 (1H, dd, J=1.8, 8.8 Hz), 1.64 (3H, s)

Ex. 144

3-Amino-6-chloro-2-(3-methylcyclohexylcarbonyl) indole

Step 1. 1-Bromoacetyl-3-methylcyclohexane (a mixture of cis and trans)

The title compound was prepared according to the procedure described in H. McKennis, Jr., L. B. Turnbull, E. R. Bowman, and E. Tamaki, J. Org. Chem., 1963, 28, 383–387 from 1-acetyl-3-methylcyclohexane (N. Dufort et al., Can. J. Chem., 1968, 46, 1073) $^1$H NMR (CDCl$_3$) δ: 3.98 (2H, s), 2.80–2.65 (1H, m), 1.95–1.20 (9H, m), 1.92 (3H, d, J=6.6 Hz)

Step 2. 3-Amino-6-chloro-1-ethoxycarbonyl-2-(3-methylcyclohexylcarbonyl)indole

The title compound was prepared according to the procedure described in step 2 of Example 1 from 4-chloro-2-(ethoxycarbonylamino)benzonitrile (Example 1, step 1) and 1-bromoacetyl-3-methylcyclohexane (step 1).

$^1$H NMR (CDCl$_3$) δ: 8.14 (1H, d, J=1.8 Hz), 7.45 (1H, d, J=8.4 Hz), 7.26 (1H, dd, J=1.8, 8.4 Hz), 5.66 (2H, br s), 4.43 (2H, q, J=7.0 Hz), 2.90–2.75 (1H, m), 1.89–0.90 (9H, m), 1.42 (3 H, t, J=7.0 Hz), 0.88 (3H, d, J=6.6 Hz)

Step 3. 3-Amino-6-chloro-2-(3-methylcyclohexylcarbonyl)indole

The title compound was prepared according to the procedure described in step 3 of Example 1 from 3-amino-6-chloro-1-ethoxycarbonyl-2-(3-methylcyclohexylcarbonyl) indole (step 2). m.p.: 140–142° C. (hexane/ethyl acetate)

$^1$H-NMR (CDCl$_3$) δ: 7.57 (1H, br s), 7.48 (1H, d, J=8.4 Hz), 7.26 (1H, d, J=1.5 Hz), 7.02 (1H, dd, J=1.5, 8.4 Hz), 5.46 (2H, br s), 2.84–2.75 (1H, m), 1.93–1.03 (9H, m), 0.95 (3H, d, J=6.6 Hz)

Ex. 145

3-Acetylamino-6-chloro-2-(3-methylcyclohexylcarbonyl)indole

The title compound was prepared according to the procedure described in Example 19 employing 3-amino-6-chloro-2-(3-methylcyclohexylcarbonyl)indole (Example 144) and acetyl chloride. m.p.: 202–203° C. (ethyl acetate/hexane)

$^1$H-NMR (CDCl$_3$) δ: 9.98 (1H, br s), 8.27 (1H, br s), 8.25 (1H, d, J=9.2 Hz), 7.31 (1H, s), 7.08 (1H, d, J=7.7 Hz), 2.94 (1H, br t, J=8.2 Hz), 2.29 (3H, s), 1.94–1.00 (9H, m), 0.96 (3H, d, J=6.2 Hz)

Ex. 146

3-(N-Acetyl-n-methylamino)-2-benzoyl-6-chloroindole

To a solution of 3-acetylamino-2-benzoyl-6-chloro-1-(ethoxycarbonyl)indole (Example 2, step 1, 900 mg, 2.34 mmol) in dimethylformamide (10 ml) was added sodium hydride (60% w/w dispersion in mineral oil, 94 mg, 2.34 mmol). The mixture was stirred for 0.5 h and then iodomethane (0.22 ml, 3.51 mmol) was added dropwise, and stirring continued for 19 h. The reaction mixture was poured into water (50 ml) and extracted with diethyl ether (100 ml×2). The extracts were washed consecutively with water (50 ml) and brine (50 ml), dried (MgSO$_4$) and solvent removed by evaporation. The residual oil was dissolved in ethanol/water (1:1, 20 ml) and KOH (85% pellets, 264 mg, 4.0 mmol) added. After stirring for 3 h, the mixture was concentrated and the residue partitioned between water (100 ml) and diethyl ether (100 ml). The organic layer was separated and washed consecutively with water (100 ml) and brine (100 m), dried (MgSO$_4$) and solvent removed by evaporation. The residual solids were recrystallized from dichloromethane/hexane to afford 165 mg (63%) of the title compound as a yellow powder. m.p.: 232–235° C.

¹H-NMR (CDCl₃) δ: 9.18 (1H, br s), 7.74–7.35 (7H, m), 7.22 (1H, dd, J=1.5, 8.4 Hz), 2.97 (3H, s), 1.86 (3H, s) IR (KBr) v: 1620, 1320, 1240 cm⁻¹

Ex. 147

3-(N-Acetyl-n-methylamino)-6-chloro-2-(3-methylbenzoyl)indole

The title compound was prepared from 3-acetylamino-6-chloro-1-ethoxycarbonyl-2-(3-methylbenzoyl)indole (Example 22, step 1) according to the procedure described in Example 146. m.p.: 166–171° C. (ethanol/diethyl ether)

¹H-NMR (CDCl₃) δ: 9.48 (1H, br s), 7.65–7.35 (6H, m), 7,21 (1H, dd, J=8.8, 1.8 Hz), 2.96 (3H, s), 2.42 (3H, s), 1.88 (3H, s)

Ex. 148

3-(N-Acetyl-n-methylamino)-6-chloro-2-(3-chlorobenzoyl)indole

The title compound was prepared from 3-acetylamino-6-chloro-2-(3-chlorobenzoyl)-1-(ethoxycarbonyl)indole (Example 31, step 1) according to the procedure described in Example 146. m.p.: 202–203° C. (ethyl acetate)

¹H-NMR (CDCl₃) δ: 9.16 (1 H, br s), 7.79–7.39 (6 H, m), 7.23 (1 H, dd, J=1.8, 8.4 Hz), 3.02 (3 H, s), 1.86 (3 H, s)

Ex. 149

3-(N-Acetyl-n-methylamino)-6-chloro-2-(cyclohexylcarbonyl)indole

Step 1. 3-Acetylamino-6-chloro-2-(cyclohexanecarbonyl)-1-(ethoxycarbonyl)indole

The title compound was prepared according to the procedure described in step 1 of Example 2 (Method A) from 3-acetylamino-6-chloro-2-cyclohexylcarbonyl-1-(ethoxycarbonyl)indole (Example 93, step1).

¹H-NMR (CDCl₃) δ: 8.80 (1H, br s), 8.12 (1H, d, J=1.5 Hz), 7.87 (1H, d, J=8.8 Hz), 7.27 (1H, dd, J=1.5, 8.8 Hz), 4.50 (2H, q, J=7.0 Hz), 2.77 (1H, tt, J=2.6, (0.4 Hz), 2.22 (3H, s), 1.80–1.23 (10H, m), 1.47 (3H, t, J=7.0 Hz)

Step 2. 3-(N-acetyl-N-methylamino)-6-chloro-2-(cyclohexanecarbonyl)indole

The title compound was prepared from 3-acetylamino-6-chloro-2-cyclohexylcarbonyl-1-(ethoxycarbonyl)indole (step 1) according to the procedure described in Example 146. m.p.: 162–163° C. (ethyl acetate/hexane)

¹H-NMR (CDCl₃) δ: 9.07 (1H, br s), 7.46–7.43 (2H, m), 7.20 (1H, dd, J=1.8, 8.8 Hz), 3.37 (3H, s), 3.07–2.96 (1H, m), 1.88 (3H, s), 1.88–1.25 (10H, m)

Ex. 150

3-(N-Acetyl-n-carboxymethylamino)-2-benzoyl-6-chloroindole

Step 1: 3-(N-Acetyl-N-methoxycarbonylmethylamino)-2-benzoyl-6-chloro-1-(ethoxycarbonyl)indole The title compound was prepared according to the procedure described in Example 146 from 3-acetylamino-2-benzoyl-6-chloro-1-(ethoxycarbonyl)indole (Example 2, step 2) and methyl bromoacetate.

¹H-NMR (CDCl₃) δ: 8.30 (1H, d, J=1.8 Hz), 7.89 (1H, d, J=8.4 Hz), 7.77–7.55 (2H, m), 7.52–7.36 (4H, m), 4.64 (1H, d, J=17.7 Hz), 4.18 (2H, d, J=7.0 Hz), 3.98 (1H, J=17.7 Hz), 3.59 (3H, s), 1.97 (3H, s), 1.02 (3H, t, J=7.0 Hz)

Step 2: 3-(N-Acetyl-N-carboxymethylamino)-2-benzoyl-6-chloroindole

The title compound was prepared according to the procedure described in step 2 of Example 2 (Method A) from 3-(N-acetyl-N-methoxycarbonylmethylamino)-2-benzoyl-6-chloro-1-(ethoxycarbonyl)indole (step 1). m.p.: 148–154° C. (dichloromethane) ¹H-NMR (DMSO-d₆) δ: 12.53 (1H, br s), 12.17 (1H, br s), 7.85 (1H, d, J=8.8 Hz), 7.78–7.62 (3H, m), 7.62–7.51 (3H, m), 7.22 (1H, dd, J=1.8, 8.8 Hz), 3.96 (1H, d, J=17.2 Hz), 3.66 (1H, d, J=17.2 Hz), 1.80 (s, 3H)

Ex. 151

2-Benzoyl-6-chloro-3-(n,n-dimethylamino)indole

Step 1. 2-Benzoyl-6-chloro-1-ethoxycarbonyl-3-(N,N-dimethylamino)indole

To a solution of 3-amino-2-benzoyl-6-chloro-1-(ethoxycarbonyl)indole (Example 1, step 2, 1.0 g, 2.9 mmol) in acetonitrile (20 ml) was added formaldehyde (37% wt. % solution in water, 1.2 g, 14.5 mmol) and sodium borohydride (380 mg, 5.8 mmol) and the mixture made acidic (pH 6) with glacial acetic acid. After stirring for 19 h, the reaction mixture was concentrated and the residue partitioned between 4N aqueous NaOH (20 ml) and diethyl ether (100 ml). The organic extract was separated and washed consecutively with water (100 ml) and brine (100 ml), and dried (MgSO₄). After removal of solvent the residue was purified by flash column chromatography eluting with ethyl acetate/hexane (1:10) to give 590 mg of title compound as a yellow oil. tlc: Rf=0.6 (33% ethyl acetate in hexanes)

Step 2. 2-Benzoyl-6-chloro-3-(N,N-dimethylamino)indole

The title compound was prepared according to the procedure described in step 2 of Example 2 from 2-benzoyl-6-chloro-1-ethoxycarbonyl-3-(N,N-dimethylamino)indole (step 1). m.p.: 178–180° C. (diethyl ether/hexane)

¹H-NMR (CDCl₃) δ: 8.36 (1H, br s), 7.88–7.75 (3H, m), 7.60–7.42 (3H, m), 7.29 (1H, d, J=1.8 Hz), 7.00 (1H, dd, J=1.8, 8.8 Hz), 2.81 (6H, s)

IR (KBr) v: 1600, 1560, 1320, 980 cm⁻¹

Ex. 152

3-Acetylamino-2-benzoyl-6-nitroindole

Step 1. 2-(Ethoxycarbonylamino)-4-nitrobenzonitrile

The title compound was prepared according to the procedure described in step 1 of Example 1 (Method B) from 2-amino-4-nitrobenzonitrile.

tlc: Rf=0.45 (33% ethyl acetate in hexanes)

Step 2. 3-Amino-2-benzoyl-1-(ethoxycarbonyl)-6-nitroindole

The title compound was prepared according to the procedure described in step 2 of Example 1 from 2-(ethoxycarbonylamino)-4-nitrobenzonitrile (step 1) and 2-bromoacetophenone. ¹H-NMR (CDCl₃) δ: 9.13 (1H, d, J=1.8 Hz), 8.20 (1H, dd, J=1.8, 8.6 Hz), 7.74 (1H, d, J=8.6 Hz), 7.77–7.43 (5H, m), 5.67 (2H, br. s), 3.83 (2H, q, J=7.3 Hz), 0.89 (3H, t, J=7.3 Hz)

Step 3. 3-Acetylamino-2-benzoyl-1-(ethoxycarbonyl)-6-nitroindole

The title compound was prepared according to the procedure described in step 1 of Example 2 (Method A) from 3-amino-2-benzoyl-1-(ethoxycarbonyl)-6-nitroindole (step 2). tlc: Rf=0.2 (50% ethyl acetate in hexanes)

Step 4. 3-Acetylamino-2-benzoyl-6-nitroindole

The title compound was prepared according to the procedure described in step 2 of Example 2 (Method A) from 3-acetylamino-2-benzoyl-1-(ethoxycarbonyl)-6-nitroindole (step 3). m.p.: 234–236° C.

$^1$H-NMR (DMSO-d$_6$) δ: 12.3 (1H, br s), 9.87 (1H, s), 8.34 (1H, d, J=2.2 Hz), 7.95 (1H, dd, J=2.2, 8.8 Hz), 7.81 (1H, d, J=8.8 Hz), 7.78–7.51 (5H, m), 1.69 (3H, s)

IR (KBr) ν: 1675, 1605, 1540, 1355, 1250, 1020, 970, 850, 840 cm$^{-1}$

Ex. 153

3-Acetylamino-6-amino-2-benzoylindole

3-Acetylamino-2-benzoyl-6-nitroindole (Example 152, 180 mg. 0.56 mmol) was hydrogenolyzed in the presence of palladium on activated carbon (5%, 18 mg) in ethanol (30 ml) at atmospheric pressure for 4 h. Catalyst was removed by filtration and the filtrate was concentrated. The residue was purified by flash column chromatography eluting with 0 to 50% ethyl acetate in hexanes and the product recrystallized from a mixture of methanol/ethyl acetate/hexane to give 85 mg of the title compound. m.p.: 219–221° C. $^1$H-NMR (DMSO-d$_6$) δ: 10.9 (1H, br s), 9.54 (1H, s), 7.44–7.66 (5H, m), 7.38(1H, d, J=9.2 Hz), 6.47–6.45 (2H, m), 5.35 (2H, s), 1.69 (3H, s)

Ex. 154

3-Acetylamino-2-benzoyl-5-methoxyindole

Step 1. 5-Methoxy-3-nitroindole-2-carboxylic acid

The title compound was prepared according to the procedure described in step 1 of Example 125 employing 5-methoxyindole-2-carboxylic acid.

Step 2. 5-Methoxy-2-(N-methoxy-N-methylamino) carbonyl-3-nitroindole

The title compound was prepared according to the procedure described in step 2 of Example 125 employing 5-methoxy-3-nitroindole-2-carboxylic acid (step 1).

$^1$H NMR (CDCl$_3$) δ: 9.64 (1H, br s), 7.62 (1H, d, J=8.8 Hz), 7.49 (1H, d, J=2.2 Hz), 7.14 (1H, dd, J=2.2, 8.8 Hz), 4.02 (3H, s), 3.87 (3H, s), 3.45 (3H, s)

Step 3. 3-Amino-5-methoxy-2-[(N-methoxy-N-methylamino)carbonyl]indole

A mixture of 5-methoxy-2-(N-methoxy-N-methylamino) carbonyl-3-nitroindole (step 2, 110 mg, 0.39 mmol), ammonium chloride (11 mg, 0.20 mmol) and iron powder (115 mg, 1.97 mmol) in 70% aqueous ethanol (10 ml) was heated at reflux for 2 h, and then cooled and filtered through a pad of Celite. The pad was washed copiously with a mixture of ethanol/ethyl acetate (1:1 v/v) and the combined washing evaporated. The residue was diluted with ethyl acetate (50 ml), washed with saturated aqueous sodim bicarbonate (30 ml) and dried (Na$_2$SO$_4$). Removal of solvent gave product as an oil. tlc: Rf=0.5 (50% ethyl acetate in hexanes)

Step 4. 3-Acetyamino-5-methoxy-2-(N-methoxy-N-methylamino)carbonyl indole

The title compound was prepared according to the procedure described in Example 19 employing 3-amino-5-methoxy-2-(N-methoxy-N-methylamino)carbonylindole (step 3) and acetyl chloride. MS m/z: 291 [M$^+$]

Step 5. 3-Acetylamino-2-benzoyl-5-methoxyindole

The title compound was prepared in an analogous manner to the procedure described in step 3 of Example 125 employing 3-acetylamino-5-methoxy-2-(N-methoxy-N-methylamino)carbonyl indole (step 4) and phenylmagnesium bromide.

m.p: 258–260° C. $^1$H NMR (CDCl$_3$) δ: 9.12 (1H, br. s), 7.99 (1H, d, J=8.4 Hz), 7.98 (1H, s), 7.50–7.61 (4H, m), 7.11–7.36 (3H, m), 3.91 (3H, s), 1.57 (3H, s)

Ex. 155

3-Acetylamino-2-benzoyl-6-methoxyindole

Step 1. Methyl 6-methoxy-3-nitroindole-2-carboxylate

The title compound was prepared according to the procedure described in step 1 of Example 125 employing methyl 6-methoxyindole-2-carboxylate.

1H NMR (DMSO-d$_6$) δ: 7.89 (1H, d, J=9.2 Hz), 7.06 (1H, dd, J=2.2, 9.2 Hz), 7.01 (1H, d, J=2.2 Hz), 3.96 (3H, s), 3.83 (3H, s). The signal due to NH of indole was not observed.

Step 2. 6-Methoxy-3-nitroindole-2-carboxylic acid

To a solution of methyl 6-methoxy-3-nitroindole-2-carboxylate (step 1) in ethanol (10 ml) and water(5 ml) was added K$_2$CO$_3$ and the mixture was stirred for 4 hr at 40° C. The mixture was acidified with 2N HCl and extracted with ethyl acetate (20 ml×2). The organic layer was washed with brine (10 ml) and dried (MgSO$_4$). Removal of solvent gave product as an oil. tlc: Rf=0.1 (50% ethyl acetate in hexanes)

Step 3. 3-Acetylamino-2-benzoyl-6-methoxyindole

The title compound was prepared according to the procedure described in Example 154 employing 6-methoxy-3-nitroindole-2-carboxylic acid (step 2). m.p: 144–146° C. $^1$H NMR (CDCl$_3$) δ: 10.16 (1H, br.s), 8.32 (1H, br.s), 8.20 (1H, d, J=9.2 Hz), 7.33–7.79 (5H, m), 6.76 (1H, dd, J=2.2, 9.2 Hz), 6.63 (1H, d, J=2.2 Hz), 3.80 (3H, s), 1.58 (3H, s)

Ex. 156

3-Acetylamino-2-benzoyl-5-fluoroindole

The title compound was prepared according to the procedures described in Example 154 employing 5-fluoroindole-2-carboxylic acid. m.p.: 80–82° C.

$^1$H NMR (CDCl$_3$) δ: 9.68 (1H, br s), 8.30 (1H, br s), 7.93 (1H, d, J=9.9 Hz), 7.79–7.83 (2H, m), 7.53–7.65 (3H, m), 7.10–7.25 (2H, m), 2.24 (3H, s)

Ex. 157–Ex. 353

The compounds disclosed hereinafter were prepared from 3-amino-2-benzoyl-6-chloroindole (Example 1) and the requisite commercially available acid chloride or acid anhydride according to the procedure described in Method B of Example 2.

Ex. 157

2-Benzoyl-6-chloro-3-(tert-butylacetylamino)indole, MS m/z: 367 [(M−H)⁻]

Ex. 158

2-Benzoyl-3-(2-bromobenzamido)-6-chloroindole, MS m/z: 453 [(M−H)⁻]

Ex. 159

2-Benzoyl-3-(3-bromobenzamido)-6-chloroindole, MS m/z: 453 [(M−H)⁻]

Ex. 160

2-Benzoyl-3-(bromoacetylamino)-6-chloroindole, MS m/z: 389 [(M−H)⁻]

Ex. 161

2-Benzoyl-3-(4-bromobenzamido)-6-chloroindole, MS m/z: 453 [(M−H)⁻]

Ex. 162

2-Benzoyl-6-chloro-3-(heptadecanoylamino)indole, MS m/z: 521 [(M−H)⁻]

Ex. 163

2-Benzoyl-6-chloro-3-(lauroylamino)indole, HPLC [Column: SHISEIDO CAPCELLPAK C18 UG120, 150×2.0 mm; Eluent: MeCN:50 mM $KH_2PO_4$ (pH 3 with 2M HCl)=10/90–60/40]: Rt=11.58 min

Ex. 164

2-Benzoyl-6-chloro-3-(3,4-dichlrobenzamido)indole, MS m/z: 443 [(M−H)⁻]

Ex. 165

2-Benzoyl-6-chloro-3-(3,5-dichlrobenzamido)indole, MS m/z: 441 [(M−H)⁻]

Ex. 166

2-Benzoyl-6-chloro-3-(decanoylamino)indole, MS m/z: 423 [(M−H)⁻]

Ex. 167

2-Benzoyl-6-chloro-3-(2-furoylamino)indole, MS m/z: 363 [(M−H)⁻]

Ex. 168

2-Benzoyl-6-chloro-3-(4-fluorobenzamido)indole, MS m/z: 391 [(M−H)⁻]

Ex. 169

2-Benzoyl-6-chloro-3-(2-iodobenzamido)indole, MS m/z: 499 [(M−H)⁻]

Ex. 170

2-Benzoyl-6-chloro-3-(heptafluorobutyrylamino)indole, MS m/z: 465 [(M−H)⁻]

Ex. 171

2-Benzoyl-6-chrolo-3-(4-trifluoromethylbenzamido)indole, MS m/z: 441 [(M−H)⁻]

Ex. 172

2-Benzoyl-6-chloro-3-[n-(4-methylphenylsulfonyl)-1-phenylalanylamino]indole, MS m/z: 521 [(M−H)⁻]

Ex. 173

2-Benzoyl-6-chloro-3-(hexanoylamino)indole, MS m/z: 367 [(M−H)⁻]

Ex. 174

2-Benzoyl-6-chloro-3-(octanoylamino)indole, MS m/z: 395 [(M−H)⁻]

Ex. 175

2-Benzoyl-6-chloro-3-(2-ethylhexanoylamino)indole, MS m/z: 395 [(M−H)⁻]

Ex. 176

2-Benzoyl-6-chloro-3-(3-fluorobenzamido)indole, MS m/z: 391 [(M−H)⁻]

Ex. 177

2-Benzoyl-6-chloro-3-(heptanoylamino)indole, MS m/z: 381 [(M−H)⁻]

Ex. 178

2-Benzoyl-6-chloro-3-(phenoxyacetylamino)indole, MS m/z: 403 [(M−H)⁻]

Ex. 179

2-Benzoyl-6-chloro-3-(2-propylvalerylamino)indole, MS m/z: 395 [(M−H)⁻]

Ex. 180

2-Benzoyl-6-chloro-3-(cinnamoylamino)indole, MS m/z: 399 [(M−H)⁻]

Ex. 181

2-Benzoyl-6-chloro-3-(phenylacetylamino)indole, MS m/z: 387 [(M−H)⁻]

Ex. 182

2-Benzoyl-6-chloro-3-(4-methoxybenzamido)indole, MS m/z: 403 [(M−H)⁻]

Ex. 183

2-Benzoyl-6-chloro-3-(3-methylthiopropionylamino)indole, MS m/z: 371 [(M−H)⁻]

Ex. 184

2-Benzoyl-6-chloro-3-(2-methoxybenzamido)indole, MS m/z: 403 [(M−H)⁻]

Ex. 185

2-Benzoyl-6-chloro-3-(palmitoylamino)indole, MS m/z: 507 [(M−H)⁻]

Ex. 186

2-Benzoyl-6-chloro-3-(2-phenoxypropionylamino)indole, MS m/z: 417 [(M−H)⁻]

Ex. 187

2-Benzoyl-6-chloro-3-(3-methacryloylamino)indole, MS m/z: 337 [(M−H)⁻]

Ex. 188

2-Benzoyl-6-chloro-3-(3,5-dinitrobenzamido)indole, MS m/z: 463 [(M−H)⁻]

Ex. 189

2-Benzoyl-6-chloro-3-(2-chloro-2-phenylacetylamino)indole, MS m/z: 421 [(M−H)⁻]

Ex. 190

2-Benzoyl-6-chloro-3-(4-tert-butylbenzamido)indole, MS m/z: 429 [(M−H)⁻]

Ex. 191

2-Benzoyl-6-chloro-3-(5-chlorovalerylamino)indole, MS m/z: 387 [(M−H)⁻]

Ex. 192

2-Benzoyl-3-(2-bromopropionylamino)-6-chloroindole, MS m/z: 402 [(M−H)⁻]

Ex. 193

2-Benzoyl-6-chloro-3-(2-chloro-4-nitrobenzamido)indole, MS m/z: 452 [(M−H)⁻]

Ex. 194

2-Benzoyl-6-chloro-3-(4-chlromethylbenzamido)indole, MS m/z: 421 [(M−H)⁻]

Ex. 195

2-Benzoyl-6-chloro-3-(3-chloropropionylamino)indole, MS m/z: 359 [(M−H)⁻]

Ex. 196

2-Benzoyl-6-chloro-3-(3-trans-crotonylamino)indole, MS m/z: 337 [(M−H)⁻]

Ex. 197

2-Benzoyl-6-chloro-3-(2-chloropropionylamino)indole, MS m/z: 359 [(M−H)⁻]

Ex. 198

2-Benzoyl-6-chloro-3-(4-chlorobutyrylamino)indole, MS m/z: 373 [(M−H)$^-$]

Ex. 199

2-Benzoyl-6-chloro-3-(3-chloro-2,2-dimethylpropionylamino)indole, MS m/z: 387 [(M−H)$^-$]

Ex. 200

2-Benzoyl-6-chloro-3-(10-undecenoylamino)indole, MS m/z: 435 [(M−H)$^-$]

Ex. 201

2-Benzoyl-6-chloro-3-(undecanoylamino)indole, MS m/z: 437 [(M−H)$^-$]

Ex. 202

2-Benzoyl-6-chloro-3-(4-cyanobenzamido)indole, MS m/z: 398 [(M−H)$^-$]

Ex. 203

2-Benzoyl-6-chloro-3-(4-chlorophenoxyacetylamino)indole, MS m/z: 437 [(M−H)$^-$]

Ex. 204

2-Benzoyl-6-chloro-3-(4-chlorobenzamido)indole, MS m/z: 407 [(M−H)$^-$]

Ex. 205

2-Benzoyl-6-chloro-3-(nonanoylamino)indole, MS m/z: 409 [(M−H)$^-$]

Ex. 206

2-Benzoyl-6-chloro-3-(3-nitrobenzamido)indole, MS m/z: 418 [(M−H)$^-$]

Ex. 207

2-Benzoyl-6-chloro-3-(pentafluorobenzamido)indole, MS m/z: 463 [(M−H)$^-$]

Ex. 208

2-Benzoyl-6-chloro-3-(trichloroacetylamino)indole, MS m/z: 423 [(M−H)$^-$]

Ex. 209

2-Benzoyl-6-chloro-3-(3-nitrophenoxyacetylamino)indole, MS m/z: 448 [(M−H)$^-$]

Ex. 210

2-Benzoyl-6-chloro-3-(4-nitrobenzamido)indole, MS m/z: 418 [(M−H)$^-$]

Ex. 211

2-Benzoyl-6-chloro-3-(1-naphthoylamino)indole, MS m/z: 423 [(M−H)$^-$]

Ex. 212

2-Benzoyl-6-chloro-3-(2-naphthoylamino)indole, MS m/z: 423 [(M−H)$^-$]

Ex. 213

2-Benzoyl-6-chloro-3-[n-(1-naphthylsulfonyl)-1-phenylalanylamino]indole, MS m/z: 606 [(M−H)$^-$]

Ex. 214

2-Benzoyl-6-chloro-3-[n-(4-nitrophenylsulfonyl)-1-phenylalanylamino]indole, MS m/z: 601 [(M−H)$^-$]

Ex. 215

2-Benzoyl-6-chloro-3-(stearoylamino)indole, MS m/z: 535 [(M−H)$^-$]

Ex. 216

Ethyl 3-[[(2-benzoyl-6-chloro)indol-3-yl]aminocarbonyl]butanoate, MS m/z: 411 [(M−H)$^-$]

Ex. 217

2-Benzoyl-6-chloro-3-(2-trifluoromethylbenzamido)indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=5.52 min

Ex. 218

2-Benzoyl-6-chloro-3-(3-trifluoromethylbenzamido)indole, MS m/z: 441 [(M−H)$^-$]

Ex. 219

2-Benzoyl-6-chloro-3-(2,4,6-trichlorobenzamido)indole, MS m/z: 475 [(M−H)$^-$]

Ex. 220

2-Benzoyl-6-chloro-3-(3-methylbenzamido)indole, MS m/z: 387 [(M−H)⁻]

Ex. 221

2-Benzoyl-6-chloro-3-(4-methylbenzamido)indole, MS m/z: 387 [(M−H)⁻]

Ex. 222

2-Benzoyl-6-chloro-3-(2-methylbenzamido)indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=5.31 min

Ex. 223

2-Benzoyl-6-chloro-3-(myristoylamino)indole, MS m/z: 479 [(M−H)⁻]

Ex. 224

2-Benzoyl-6-chloro-3-(3,5,5-trimethylhexanoylamino)indole, MS m/z: 409 [(M−H)⁻]

Ex. 225

2-Benzoyl-6-chloro-3-(4-phenylbenzamido)indole, MS m/z: 449 [(M−H)⁻]

Ex. 226

2-Benzoyl-6-chloro-3-(3,3-dimethylacryloylamino)indole, MS m/z: 351 [(M−H)⁻]

Ex. 227

2-Benzoyl-6-chloro-3-(3-fluoro-5-trifluoromethylbenzamido)indole, MS m/z: 459 [(M−H)⁻]

Ex. 228

2-Benzoyl-6-chloro-3-(2-fluoro-3-trifluoromethylbenzamido)indole, MS m/z: 459 [(M−H)⁻]

Ex. 229

2-Benzoyl-6-chloro-3-[2,4-di(trifluoromethyl)benzamido]indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=6.30 min

Ex. 230

2-Benzoyl-6-chloro-3-(4-fluoro-2-trifluoromethylbenzamido)indole, MS m/z: 459 [(M−H)⁻]

Ex. 231

2-Benzoyl-6-chloro-3-(3,4,5-trifluorobenzamido)indole, MS m/z: 428 [(M−H)⁻]

Ex. 232

2-Benzoyl-6-chloro-3-(octafluorovalerylamino)indole, MS m/z: 497 [(M−H)⁻]

Ex. 233

2-Benzoyl-6-chloro-3-[(2-chlorophenyl)acetylamino]indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=6.03 min

Ex. 234

2-Benzoyl-6-chloro-3-(4-fluoro-3-trifluoromethylbenzamido)indole, MS m/z: 459 [(M−H)⁻]

Ex. 235

2-Benzoyl-6-chloro-3-(3,5-dimethoxylbenzamido)indole, MS m/z: 433 [(M−H)⁻]

Ex. 236

2-Benzoyl-6-chloro-3-(2,4-difluorobenzamido)indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=5.55 min

Ex. 237

2-Benzoyl-6-chloro-3-(2-methylbutyrylamino)indole, MS m/z: 353 [(M−H)⁻]

Ex. 238

2-Benzoyl-6-chloro-3-(linolenoylamino)indole, MS m/z: 529 [(M−H)⁻]

Ex. 239

2-Benzoyl-6-chloro-3-(4-decylbenzoylamino)indole, MS m/z: 513 [(M−H)⁻]

Ex. 240

2-Benzoyl-6-chloro-3-(neodecanoylamino)indole, MS m/z: 423 [(M−H)⁻]

Ex. 241

2-Benzoyl-6-chloro-3-(4-methylvalerylamino) indole, MS m/z: 367 [(M−H)⁻]

Ex. 242

2-Benzoyl-6-chloro-3-(4-methyl-4-nitrohexanoylamino)indole, MS m/z: 426 [(M−H)⁻]

Ex. 243

2-Benzoyl-6-chloro-3-(trichloroacryloylamido) indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=5.74 min

Ex. 244

2-Benzoyl-6-chloro-3-(2,4,6-trifluorobenzamido) indole, MS m/z: 427 [(M−H)⁻]

Ex. 245

2-Benzoyl-6-chloro-3-[3-(2-chloro-6-fluorophenyl)-5-methylisoxazole-4-carboxamido]indole, MS m/z: 506 [(M−H)⁻]

Ex. 246

2-Benzoyl-6-chloro-3-(2-fluoro-5-trifluoromethylbenzamido)indole, MS m/z: 459 [(M−H)⁻]

Ex. 247

2-Benzoyl-6-chloro-3-(5-nitro-2-furoylamino)indole, MS m/z: 408 [(M−H)⁻]

Ex. 248

2-Benzoyl-6-chloro-3-(2-phenoxybutyrylamino) indole, MS m/z: 431 [(M−H)⁻]

Ex. 249

2-Benzoyl-6-chloro-3-(6-chlorohexanoylamino) indole, MS m/z: 401 [(M−H)⁻]

Ex. 250

2-Benzoyl-6-chloro-3-(2-ethoxy-2-naphthoylamino) indole, MS m/z: 467 [(M−H)⁻]

Ex. 251

2-Benzoyl-6-chloro-3-(2-chloronicotinoylamino) indole, MS m/z: 408 [(M−H)⁻]

Ex. 252

2-Benzoyl-6-chloro-3-[3-(2,6-dichlorophenyl)-5-methylisoxazole-4-carboxamido]indole, MS m/z: 522 [(M−H)⁻]

Ex. 253

2-Benzoyl-6-chloro-3-(2-fluoro-4-trifluoromethylbenzamido)indole, MS m/z: 459 [(M−H)⁻]

Ex. 254

2-Benzoyl-6-chloro-3-(3-trifluoromethoxybenzamido)indole, MS m/z: 459 [(M−H)⁻]

Ex. 255

2-Benzoyl-6-chloro-3-(2-methylvalerylamino) indole, MS m/z: 367 [(M−H)⁻]

Ex. 256

Methyl 4-[[(2-benzoyl-6-chloro)indol-3-yl]-aminocarbonyl]pentanoate, MS m/z: 411 [(M−H)⁻]

Ex. 257

2-Benzoyl-6-chloro-3-(2-phenylbutyrylamino) indole, MS m/z: 415 [(M−H)⁻]

Ex. 258

2-Benzoyl-6-chloro-3-[3-(2-chlorophenyl)-5-methylisoxazole-4-carboxamido]indole,

Ex. 259

2-Benzoyl-6-chloro-3-[(4-chlorophenyl) acetylamino]indole, MS m/z: 421 [(M−H)⁻]

Ex. 260

2-Benzoyl-6-chloro-3-[(4-methylphenyl) acetylamino]indole, MS m/z: 401 [(M−H)⁻]

Ex. 261

2-Benzoyl-6-chloro-3-(1-methylcyclohexylcarboxamido)indole, MS m/z: 393 [(M−H)⁻]

Ex. 262

2-Benzoyl-3-(4-bromobutyrylamino)-6-chloroindole, MS m/z: 417 [(M−H)⁻]

Ex. 263

Methyl 2-[[(2-benzoyl-6-chloro)indol-3-yl]aminocarbonyl]butanoate, MS m/z: 383 [(M−H)⁻]

Ex. 264

2-Benzoyl-6-chloro-3-(3,4,5-trimethoxybenzamido)indole, MS m/z: 463 [(M−H)⁻]

Ex. 265

Methyl 4-[[(2-benzoyl-6-chloro)indol-3-yl]aminocarbonyl]pentanoate, MS m/z: 397 [(M−H)⁻]

Ex. 266

2-Benzoyl-6-chloro-3-(2,3,4-trifluorobenzamido)indole, MS m/z: 427 [(M−H)⁻]

Ex. 267

2-Benzoyl-6-chloro-3-(4-chloro-3-nitrobenzamido)indole, MS m/z: 452 [(M−H)⁻]

Ex. 268

2-Benzoyl-6-chloro-3-(4-propylbenzamido)indole, MS m/z: 415 [(M−H)⁻]

Ex. 269

3-(2-Acetoxy-2-phenylacetylamino)-2-benzoyl-6-chloroindole, MS m/z: 445 [(M−H)⁻]

Ex. 270

2-Benzoyl-6-chloro-3-(2,3-dichloropropionylamino)indole, MS m/z: 393 [(M−H)⁻]

Ex. 271

2-Benzoyl-6-chloro-3-(5-bromovalerylamino)indole, MS m/z: 431 [(M−H)⁻]

Ex. 272

2-Benzoyl-6-chloro-3-[(4-methoxyphenyl)acetylamino]indole, MS m/z: 417 [(M−H)⁻]

Ex. 273

2-Benzoyl-3-(benzyloxyacetylamino)-6-chloroindole, MS m/z: 417 [(M−H)⁻]

Ex. 274

2-Benzoyl-6-chloro-3-(2-thiopheneacetylamino)indole, MS m/z: 393 [(M−H)⁻]

Ex. 275

2-Benzoyl-6-chloro-3-(2,3-difluorobenzamido)indole, MS m/z: 409 [(M−H)⁻]

Ex. 276

2-Benzoyl-6-chloro-3-(2,5-difluorobenzamido)indole, MS m/z: 409 [(M−H)⁻]

Ex. 277

2-Benzoyl-3-(6-bromohexanoylamino)-6-chloroindole, MS m/z: 445 [(M−H)⁻]

Ex. 278

2-Benzoyl-6-chloro-3-(3,4-dimethoxybenzamido)indole, HPLC [Column: SHISEIDO CAPCELLPAK C1 UG120, 150×2.0 mm; Eluent: MeCN:0.01M CH₃CO₂NH₄=50/50–90/10]: Rt=4.60 min

Ex. 279

2-Benzoyl-6-chloro-3-(cyclobutylcarboxamido)indole, MS m/z: 351 [(M−H)⁻]

Ex. 280

2-Benzoyl-6-chloro-3-(3-methoxybenzamido)indole, MS m/z: 403 [(M−H)⁻]

Ex. 281

2-Benzoyl-6-chloro-3-(2,6-difluorobenzamido)indole, MS m/z: 409 [(M−H)⁻]

Ex. 282

2-Benzoyl-3-(3-bromopropionylamino)-6-chloroindole, MS m/z: 403 [(M−H)⁻]

Ex. 283

2-Benzoyl-6-chloro-3-(2,3,6-trifluorobenzamido)
indole, MS m/z: 427 [(M−H)⁻]

Ex. 284

2-Benzoyl-6-chloro-3-[3-(dichloromethyl)
benzamido]indole, MS m/z: 455 [(M−H)⁻]

Ex. 285

2-Benzoyl-6-chloro-3-[3-(cyclopentyl)
propionylamino]indole, MS m/z: 433 [(M−H)⁻]

Ex. 286

2-Benzoyl-3-(4-butylbenzamido)-6-chloroindole,
MS m/z: 439 [(M−H)⁻]

Ex. 287

3-(2-Acetoxybenzamido)-2-benzoyl-6-chloroindole,
MS m/z: 431 [(M−H)⁻]

Ex. 288

2-Benzoyl-6-chloro-3-[3-(chloromethyl)benzamido]
indole, MS m/z: 421 [(M−H)⁻]

Ex. 289

2-Benzoyl-6-chloro-3-[2-nitrobenzamido]indole,
MS m/z: 418 [(M−H)⁻]

Ex. 290

2-Benzoyl-6-chloro-3-(3,5-difluorobenzamido)
indole, MS m/z: 409 [(M−H)⁻]

Ex. 291

2-Benzoyl-6-chloro-3-[(3,5-dimethoxyphenyl)
acetylamino]indole, MS m/z: 447 [(M−H)⁻]

Ex. 292

2-Benzoyl-6-chloro-3-(diphenylacetylamino)indole,
MS m/z: 463 [(M−H)⁻]

Ex. 293

2-Benzoyl-6-chloro-3-[3,5-di(trifluoromethyl)
benzamido]indole, MS m/z: 509 [(M−H)⁻]

Ex. 294

2-Benzoyl-6-chloro-3-(2,4-dichloro-5-
fluorobenzamido)indole, MS m/z: 459 [(M−H)⁻]

Ex. 295

2-Benzoyl-6-chloro-3-[(3-methoxyphenyl)
acetylamino]indole, MS m/z: 417 [(M−H)⁻]

Ex. 296

2-Benzoyl-6-chloro-3-(perfluorooctanoylamino)
indole, MS m/z: 665 [(M−H)⁻]

Ex. 297

2-Benzoyl-6-chloro-3-(2-chloro-2,2-
diphenylacetylamino)indole, HPLC [Column:
SHISEIDO CAPCELLPAK C1 UG120, 150×2.0
mm; Eluent: MeCN:0.01M $CH_3CO_2NH_4$=50/
50–90/10]: Rt=6.68 min

Ex. 298

2-Benzoyl-6-chloro-3-(4-hexylbenzamido)indole,
MS m/z: 457 [(M−H)⁻]

Ex. 299

2-Benzoyl-6-chloro-3-(4-heptyloxybenzamido)
indole, MS m/z: 487 [(M−H)⁻]

Ex. 300

2-Benzoyl-6-chloro-3-[2,5-di(trifluoromethyl)
benzamido]indole, MS m/z: 509 [(M−H)⁻]

Ex. 301

Methyl 4-[[(2-benzoyl-6-chloro)indol-3-yl]-
aminocarbonyl]heptanoate, MS m/z: 439 [(M−H)⁻]

Ex. 302

2-Benzoyl-6-chloro-3-(4-ethylbenzamido)indole,
MS m/z: 401 [(M−H)⁻]

Ex. 303

2-Benzoyl-6-chloro-3-(2,3,4,5-
tetrafluorobenzamido)indole, MS m/z: 445 [(M−H)⁻]

Ex. 304

Methyl 4-[[(2-benzoyl-6-chloro)indol-3-yl]-aminocarbonyl]nanoate, MS m/z: 467 [(M–H)⁻]

Ex. 305

2-Benzoyl-6-chloro-3-(cyclopentylcarboxamido)indole, MS m/z: 365 [(M–H)⁻]

Ex. 306

2-Benzoyl-6-chloro-3-(3,4-difluorobenzamido)indole, MS m/z: 409 [(M–H)⁻]

Ex. 307

2-Benzoyl-6-chloro-3-(4-trifluoromethoxybenzamido)indole, MS m/z: 457 [(M–H)⁻]

Ex. 308

2-Benzoyl-6-chloro-3-(2,4,5-trifluorobenzamido)indole, MS m/z: 427 [(M–H)⁻]

Ex. 309

2-Benzoyl-3-(4-butoxybenzamido)-6-chloroindole, MS m/z: 445 [(M–H)⁻]

Ex. 310

2-Benzoyl-6-chloro-3-[(2,5-dimethoxyphenyl)acetylamino]indole, MS m/z: 447 [(M–H)⁻]

Ex. 311

3-[Acetoxyacetylamino]-2-benzoyl-6-chloroindole, MS m/z: 369 [(M–H)⁻]

Ex. 312

2-Benzoyl-6-chloro-3-(4-pentylbenzamido)indole, MS m/z: 443 [(M–H)⁻]

Ex. 313

2-Benzoyl-6-chloro-3-(4-iodobenzamido)indole, MS m/z: 499 [(M–H)⁻]

Ex. 314

2-Benzoyl-6-chloro-3-(4-hexyloxylbenzamido)indole, MS m/z: 473 [(M–H)⁻]

Ex. 315

2-Benzoyl-6-chloro-3-(cyclohex-3-enylcarboxamido)indole, MS m/z: 377 [(M–H)⁻]

Ex. 316

(R)-2-Benzoyl-6-chloro-3-(alpha-methoxy-alpha-trifluoromethylphenylacetylamino)indole, MS m/z: 485 [(M–H)⁻]

Ex. 317

(S)-2-Benzoyl-6-chloro-3-(alpha-methoxy-alpha-trifluoromethylphenylacetylamino)indole, MS m/z: 485 [(M–H)⁻]

Ex. 318

2-Benzoyl-6-chloro-3-(2-fluorobenzamido)indole, MS m/z: 391 [(M–H)⁻]

Ex. 319

2-Benzoyl-6-chloro-3-[(r)-(–)-phenylglycinoyl]indole, HPLC [Column: SHISEIDO CAPCELLPAK C1 UG120, 150×2.0 mm; Eluent: MeCN:0.01M CH₃CO₂NH₄=50/50–90/10]: Rt=4.27 min

Ex. 320

2-Benzoyl-6-chloro-3-(4-ethoxybenzamido)indole, MS m/z: 417 [(M–H)⁻]

Ex. 321

2-Benzoyl-6-chloro-3-(3-chlorobenzamido)indole, MS m/z: 407 [(M–H)⁻]

Ex. 322

(2-Benzoyl-6-chloroindol-3-ylamino)-n,n-diethylbenzenesulfonamide, MS m/z: 536 [(M–H)⁻]

Ex. 323

2-Benzoyl-6-chloro-3-[(1-naphthyl)acetylamino]indole, MS m/z: 437 [(M–H)⁻]

Ex. 324

2-Benzoyl-6-chloro-3-(2-fluoro-6-trifluorobenzamido)indole, HPLC [Column: SHISEIDO CAPCELLPAK C1 UG120, 150×2.0 mm; Eluent: MeCN:0.01M CH₃CO₂NH₄=50/50–90/10]: Rt=5.71 min

Ex. 325

Methyl 2-[[(2-benzoyl-6-chloro)indol-3-yl]-aminocarbonyl]acetate, MS m/z: 369 [(M−H)$^-$]

Ex. 326

2-Benzoyl-6-chloro-3-(2-trifluoromethoxybenzamido)indole, MS m/z: 457 [(M−H)$^-$]

Ex. 327

2-Benzoyl-6-chloro-3-[isoxazole-5-carboxamido]indole, MS m/z: 364 [(M−H)$^-$]

Ex. 328

2-Benzoyl-6-chloro-3-(2-chloro-6-fluorobenzamido)indole, MS m/z: 425 [(M−H)$^-$]

Ex. 329

2-Benzoyl-3-[5-tert-butyl-2-methylpyrazole-3-carboxamido]-6-chloroindole, MS m/z: 433 [(M−H)$^-$]

Ex. 330

2-Benzoyl-6-chloro-3-(2,3-dimethylbenzamido)indole, MS m/z: 401 [(M−H)$^-$]

Ex. 331

2-Benzoyl-6-chloro-3-(2-chloro-4-fluorobenzamido)indole, MS m/z: 425 [(M−H)$^-$]

Ex. 332

2-Benzoyl-3-[4-bromo-2-ethyl-5-methylpyrazole-3-carboxamido]-6-chloroindole, MS m/z: 483 [(M−H)$^-$]

Ex. 333

2-Benzoyl-6-chloro-3-[4-methyl-1,2,3-thiadiazole-5-carboxamdo]indole, MS m/z: 395 [(M−H)$^-$]

Ex. 334

2-Benzoyl-6-chloro-3-[5-methyl-3-phenylisoxazole-4-carboxamido]indole, MS m/z: 454 [(M−H)$^-$]

Ex. 335

2-Benzoyl-6-chloro-3-(6-chloronicotinoylamino)indole, MS m/z: 408 [(M−H)$^-$]

Ex. 336

2-Benzoyl-3-[2-benzyl-5-tert-butylpyrazole-3-carboxamido]-6-chloroindole, MS m/z: 509 [(M−H)$^-$]

Ex. 337

2-Benzoyl-6-chloro-3-(2-chloro-3-methoxy-4-thiophenecarboxamido)indole, TLC [Merk Kieselgel 60, Art 1.05719; AcOEt-PhMe (1:8)] Rf 0.55

Ex. 338

2-benzoyl-6-chloro-3-(3-chloro-4-methanesulfonyl-2-thiophenecarboxamido)indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=4.67 min

Ex. 339

2-Benzoyl-6-chloro-3-[3-trifluoromethyl-2-(4-chlorophenyl)pyrazole-4-carboxamido]indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=6.28 min

Ex. 340

2-Benzoyl-6-chloro-3-[5-methylisoxazole-3-carboxamido]indole, MS m/z: 378 [(M−H)$^-$]

Ex. 341

2-Benzoyl-6-chloro-3-(3-chloro-2-thiophenecarboxamido)indole, MS m/z: 413 [(M−H)$^-$]

Ex. 342

2-Benzoyl-6-chloro-3-(2,2,3,3-tetrafluoropropionylamino)indole, MS m/z: 397 [(M−H)$^-$]

Ex. 343

2-Benzoyl-6-chloro-3-(3,4-dichloro-2,2,3,4,4-pentafluorobutyrylamino)indole, MS m/z: 497 [(M−H)$^-$]

Ex. 344

2-Benzoyl-6-chloro-3-(9h-hexadecafluorononanoylamino)indole, HPLC [Column: SHISEIDO CAPCELLPAK C1 UG120, 150×2.0 mm; Eluent: MeCN:0.01M CH$_3$CO$_2$NH$_4$=50/50–90/10]: Rt=7.18 min

Ex. 345

2-Benzoyl-6-chloro-3-(3-chloro-2,2,3,3-tetrafluoropropionylamino)indole, MS m/z: 431 [(M–H)⁻]

Ex. 346

2-Benzoyl-6-chloro-3-[2-(4-chlorophenyl)-3-propylpyrazole-4-carboxamido]indole, MS m/z: 515 [(M–H)⁻]

Ex. 347

2-Benzoyl-6-chloro-3-(trans-3-trifluoromethylcinnamoylamino)indole, MS m/z: 467 [(M–H)⁻]

Ex. 348

2-Benzoyl-6-chloro-3-(4-pentoxybenzamido)indole, HPLC [Column: SHISEIDO CAPCELLPAK C1 UG120, 150×2.0 mm; Eluent: MeCN:0.01M CH₃CO₂NH₄=50/50–90/10]: Rt=5.75 min

Ex. 349

2-Benzoyl-6-chloro-3-(4-heptylbenzamido)indole, MS m/z: 471 [(M–H)⁻]

Ex. 350

2-Benzoyl-6-chloro-3-(2,5-dichlorothiophene-3-carboxamido)indole, HPLC [Column: SHISEIDO CAPCELLPAK C1 UG120, 150×2.0 mm; Eluent: MeCN:0.01M CH₃CO₂NH₄=50/50–90/10]: Rt=6.11 min

Ex. 351

2-Benzoyl-6-chloro-3-(3-cyanobenzamido)indole, MS m/z: 398 [(M–H)⁻]

Ex. 352

2-Benzoyl-6-chloro-3-(iodoacetylamino)indole, HPLC [Column: SHISEIDO CAPCELLPAK C1 UG120, 150×2.0 mm; Eluent: MeCN:0.01M CH₃CO₂NH₄=50/50–90/10]: Rt=4.39 min

Ex. 353

2-Benzoyl-6-chloro-3-[5,6-dichloronicotinoylamino]indole, MS m/z: 442 [(M–H)⁻]

Ex. 354

3-[[(2-Benzoyl-6-chloro)indole-3-yl]aminocarbonyl] propionic acid

A mixture of 2-benzoyl-6-chloro-3-[(3-ethoxycarbonyl)propionylamino]indole (Example 56) (500 mg, 1.25 mmol), 2N aqueous potassium hydroxide (5 ml) and ethanol (15 ml) was stirred at room temperature for 2 h. The mixture was concentrated and 2N aqueous HCl (10 ml) was added, and then extracted with diethyl ether (80 ml×2), dried (MgSO₄) and concentrated to gave a pale yellow solid. Recrystallization from ethyl acetate/hexane afforded 150 mg (32%) of the titled compound as a pale yellow solid. m.p.: 204–207° C. ¹H-NMR (CDCl₃) δ: 9.94 (1H, br s), 9.81 (1H, br s), 8.12 (1H, d, J=8.8 Hz), 7.88–7.78 (2H, m), 7.67–7.48 (3H, m), 7.36 (1H, d, J=1.8 Hz), 7.04 (1H, dd, J=1.8, 8.8 Hz), 2.72 (4H, s).

Ex. 355

2-Benzoyl-6-chloro-3-(3-oxobutyrylamino)indole

A mixture of 3-amino-2-benzoyl-6-chloroindole (Example 1) (850 mg, 4.07 mmol) and tert-butyl acetoacetate (1.3 ml, 8.15 mmol) in xylene (10 ml) was heated at 120° C. for 5 h. The mixture was concentrated and purified by flash column chromatography eluting with hexane/ethyl acetate (2/1) to give a yellow amorphous solid. Recrysalization from ethyl acetate/hexane afforded 450 mg (31%) of the titled compound as a pale yellow solid. m.p.: 170–173° C. ¹H-NMR (CDCl₃) δ: 10.22 (1H, br s), 8.47 (1H, br s), 8.01 (1H, d, J=8.8 Hz), 7.83–7.77 (2H, m), 7.65–7.50 (3H, m), 7.32 (1H, d, J=1.5 Hz), 7.11 (1H, dd, J=1.5, 8.8 Hz), 3.56 (2H, s), 2.32 (3H, s).

Ex. 356

2-Benzoyl-6-chloro-3-(3-hydroxybutyrylamino)indole

Step 1. 2-Benzoyl-3-(3-benzyloxybutyrylamino)-6-chloroindole

The titled compound was prepared according to the procedure described in Example 19 employing 3-amino-2-benzoyl-6-chloroindole (Example 1) and 3-benzyloxybutyryl chloride (Eberlein, T. H. et al., J. Org. Chem. 1992, 57, 3479).

¹H-NMR (CDCl₃) δ: 10.22 (1H, br s), 8.47 (1H, br s), 8.01 (1H, d, J=8.8 Hz), 7.83–7.77 (2H, m), 7.65–7.50 (3H, m), 7.50–7.15 (6H, m), 7.11 (1H, dd, J=1.5, 8.8 Hz), 4.60–4.45 (2H, m), 4.02–3.97 (1H, m), 2.70–2.50 (2H, m), 1.40 (3H, d, J=6.2 Hz)

Step 2. 2-Benzoyl-6-chloro-3-(3-hydroxybutyrylamino)indole

A mixture of 2-benzoyl-3-(3-benzyloxybutyrylamino)-6-chloroindole (Step 1) (2.3 g, 5.1 mmol) and 10% Pd—C (0.2 g) in ethyl acetate (50 ml) was stirred at room temperature for 24 h under a hydrogen atmosphere. The mixture was filtered through a pad of Celite and the filtrate was concentrated. Purification by flash column chromatography eluting with hexane/ethyl acetate (1/1) gave a yellow amorphous solid. Recrystallization from ethyl acetate/hexane afforded 290 mg (16%) of the titled compound as a pale yellow solid. m.p.: 159–162° C.

¹H-NMR (CDCl₃) δ: 9.95 (1H, br s), 8.70 (1H, br s), 8.16 (1H, d, J=8.8 Hz), 7.81–7.77 (2H, m), 7.68–7.51 (3H, m), 7.30 (1H, d, J=1.5 Hz), 7.11 (1H, dd, J=1.5, 8.8 Hz), 4.29 (1H, br s), 3.43 (1H, br s), 2.62–2.55 (2H, m), 1.28 (3H, d, J=6.2 Hz).

Ex. 357

6-Chloro-2-(3-furoyl)-3-(isovalerylamino)indole

The title compound was prepared according to the procedure described in Ex. 19 from 3-amino-6-chloro-2-(3- furoyl)indole (Example 79) and isovaleryl chloride. m.p.: 202–203° C. (recrystallized from ethyl acetate) $^1$H-NMR (CDCl$_3$) δ: 10.10 (1 H, br s), 8.28 (1 H, d, J=8.8 Hz), 8.23 (1 H, br s), 8.11 (1 H, dd, J=0.7, 1.5 Hz), 7.59 (1 H, dd, J=1.5, 1.8 Hz), 7.31 (1 H, d, J=1.8 Hz), 7.10 (1 H, dd, J=1.8, 8.8 Hz), 6.89 (1 H, dd, J=0.7, 1.8 Hz), 2.39–2.22 (3 H, m), 1.06 (6 H, d, J=6.6 Hz).

Ex. 358

6-Chloro-2-(4-chloropyridine-2-carbonyl)-3-(propionylamino)indole

The title compound was prepared according to the procedure described in Example 19 from 3-amino-6-chloro-2-(4-chloropyridine-2-carbonyl)indole (Example 68) and propionyl chloride. m.p.: 188–190° C. (recrystallized from ethyl acetate) $^1$H-NMR (CDCl$_3$) δ: 11.68 (1 H, br s), 10.88 (1 H, br s), 8.70 (1 H, d, J=5.4 Hz), 8.54 (1 H, d, J=9.1 Hz), 8.37 (1 H, d, J=2.0 Hz), 7.58 (1 H, dd, J=2.1, 5.3 Hz), 7.40 (1 H, d, J=2.0 Hz), 7.06 (1 H, dd, J=1.1, 9.1 Hz), 2.63 (2 H, q, J=7.6 Hz), 1.37 (3 H, t, J=7.6 Hz).

Ex. 359

6-Chloro-2-(4-chloropyridine-2-carbonyl)-3-(isovalerylamino)indole

The title compound was prepared according to the procedure described in Example 19 from 3-amino-6-chloro-2-(4-chloropyridine-2-carbonyl)indole (Example 68) and isovaleryl chloride. m.p.: 183–184° C. (recrystallized from ethyl acetate) $^1$H-NMR (DMSO-d$_6$) δ: 11.67 (1 H, br s), 10.08 (1 H, br s), 8.69 (1 H, d, J=5.3 Hz), 8.52 (1 H, d, J=9.2 Hz), 8.37 (1 H, d, J=2.1 Hz), 7.57 (1 H, dd, J=2.0, 5.3 Hz), 7.39 (1 H, d, J=2.0 Hz), 7.06 (1 H, dd, J=2.0, 9.6 Hz), 2.46–2.30 (3 H, m), 1.09 (6 H, d, J=6.4 Hz).

Ex. 360

3-(2-Acetoxyisobutyrylamino)-6-chloro-2-(4-chloropyridine-2-carbonyl)indole The title compound was prepared according to the procedure described in Example 19 employing 3-amino-6-chloro-2-(4-chloropyridine-2-carbonyl)indole (Exampe 68) and 2-acetoxyisobutyryl chloride. m.p.: 228–229° C. (recrystallized from ethyl acetate) IR(KBr)ν: 3500, 3250, 1740, 1710, 1620, 1600, 1570, 1540, 1480, 1350, 1230, 1180, 1150, 740 cm$^{-1}$.

$^1$H-NMR (DMSO-d$_6$) δ: 12.07 (1 H, br s), 10.71 (1 H, br s), 8.80 (1 H, d, J=5.3 Hz), 8.15 (1 H, d, J=2.1 Hz), 8.04 (1 H, dd, J=8.8, 3.7 Hz), 7.90 (1 H, dd, J=5.4, 1.9 Hz), 7.65 (1 H, d, J=2.0 Hz), 7.09 (1 H, dd, J=9.0, 1.4 Hz), 2.14 (3 H, s), 1.55 (6 H, s).

Ex. 361

6-Chloro-2-(4-chloropyridine-2-carbonyl)-3-(2-hydroxyisobutyrylamino)indole To a suspension of 3-(2-acetoxyisobutyrylamino)-6-chloro-2-(4-chloropyridine-2-carbonyl)indole (Example 360, 251.4 mg, 0.5789 mmol) in methanol (8 ml) and DMSO (20 ml) was added potassium carbonate (45.0 mg, 0.3259 mmol) in water (1 ml) at room tempetature. After stirring for 30 h, the mixture was diluted with diethyl ether (150 ml), and then washed with water (25 ml×3), brine (25 ml) and dried (MgSO$_4$). Removal of solvent gave a crystalline residue, which was recrystallized from ethyl acetate to afford 103.9 mg (45.8%) of the title compound.

m.p.: 207–208° C. (recrystallized from ethyl acetate) IR(KBr)ν: 3346, 3285, 1665, 1626, 1570, 1531, 1483, 1348, 1232, 741 cm$^{-1}$. $^1$H-NMR (DMSO-d$_6$) δ: 11.75 (1 H, br s), 11.69 (1 H, br s), 8.68 (1 H, dd, J=5.3 and 0.5 Hz), 8.56 (1 H, d, J=9.1 Hz), 8.40 (1 H, dd, J=2.1, 0.5 Hz), 7.56 (1 H, dd, J=5.3, 2.1 Hz), 7.40 (1 H, dd, J=1.9, 0.6 Hz), 7.06 (1 H, dd, J=9.1, 1.8 Hz), 2.77 (1 H, s), 1.56 (6 H, s).

Ex. 362

3-[[(S)-2-Acetoxypropionyl]amino]-6-chloro-2-(4-chloropyridine-2-carbonyl)indole The title compound was prepared according to the procedure described in Example 19 employing 3-amino-6-chloro-2-(4-chloropyridine-2-carbonyl)indole (Exampe 68) and (S)-(–)-2-acetoxypropionyl chloride. m.p.: 236–238° C. (recrystallized from ethyl acetate) IR(KBr)ν: 3287, 1738, 1693, 1624, 1585, 1570, 1545, 1489, 1236, 1188, 739 cm$^{-1}$. $^1$H-NMR (DMSO-d$_6$) δ: 12.09 (1 H, br s), 10.67 (1 H, br s), 8.77 (1 H, dd, J=5.5 and 1.8 Hz), 8.10 (1 H, t, J=1.9 Hz), 7.93 (1 H, dd, J=9.1, 1.8 Hz), 7.88 (1 H, dt, J=5.4, 2.3 Hz), 7.64 (1 H, t, J=1.9 Hz), 7.12 (1 H, dt, J=9.1, 2.1 Hz), 5.13 (1 H, q, J=6.8 Hz), 2.18 (3 H, s), 1.35 (3 H, d, J=6.9 Hz).

Ex. 363

6-Chloro-2-(4-chloropyridine-2-carbonyl)-3-[[(s)-2-hydroxypropionyl]amino]indole To a suspension of 3-[(S)-2-acetoxypropionylamino]-6-chloro-2-(4-chloropyridine-2-carbonyl)indole (Example 362, 316.7 mg, 0.7536 mmol) in DMSO (10 ml) was added potassium carbonate (104.2 mg, 0.7536 mmol) in water (1 ml) at room temperature. After stirring for 30 h, the mixture was diluted with diethyl ether (200 ml), and then washed with water (50 ml×3), brine (50 ml), and dried (MgSO$_4$). Removal of solvent gave a crystalline residue, which was recrystallized from ethyl acetate to afford 213.0 mg (74.7%) of the title compound. m.p.: 244–246° C. (recrystallized from ethyl acetate) IR(KBr)ν: 3483, 3288, 1690, 1570, 1553, 1533, 1481, 1348, 1240, 1186, 737 cm$^{-1}$. $^1$H-NMR (DMSO-d$_6$) δ: 12.07 (1 H, br s), 11.43 (1 H, br s), 8.82 (1 H, dd, J=5.3 and 0.5 Hz), 8.26 (1 H, d, J=9.1 Hz), 8.20 (1 H, dd, J=2.1, 0.5 Hz), 7.91 (1 H, dd, J=5.4, 2.1 Hz), 7.67 (1 H, dd, J=2.0, 0.5 Hz), 7.07 (1 H, dd, J=8.9, 2.0 Hz), 6.18 (1H, d, J=4.9 Hz), 4.23 (1 H,dd, J=6.8, 4.9 Hz), 134 (3 H, d, J=6.8 Hz).

Ex. 364

3-(N-Acetyl-n-methylamino)-6-chloro-2-(4-chloropyridine-2-carbonyl)indolE

STEP 1. 6-Chloro-2-(4-chloropyridine-2-carbonyl)-1-ethoxycarbonyl-3-(N-acetyl-N-methylamino)indole To a solution of 3-amino-6-chloro-2-(4-chloropyridine-2-carbonyl)-1-ethoxycarbonylindole (step 1 of Example 68, 407 mg, 1.08 mmol) in dichloromethane (10 ml) was added pyridine (0.42 ml, 5.38 mmol) and acetyl chloride (0.09 ml, 1.29 mmol) at room temperature. After stirring for 1 h, methanol (1 ml) was added to the mixture at room temperature. The mixture was concentrated and the residue was diluted with ethyl acetate (100 ml) The resulting mixture was washed with 2N aqueous HCl (50 ml×2) and saturated aqueous sodium bicarbonate (50 ml), and dried (Na$_2$SO$_4$). Removal of solvent gave a crystalline residue (413 mg). The residue was dissolved in DMF (5 ml), and then sodium hydride (60% in oil) (43 mg, 1.08 mmol) was added at room temperature. After stirring 0.5 h, MeI (0.07 ml, 1.08 mmol) was added and the mixture was stirred for an additional 1 h. The mixture was diluted with diethyl ether (100 ml), washed with water (50 ml×2) and brine (50 ml), and dried (MgSO$_4$). Removal of solvent gave an oily residue, which was purified by flash column chromatography eluting with ethyl acetate/hexane (1:3) to afford 111 mg (26%) of the title compound as an oil. $^1$H-NMR (CDCl$_3$) δ: 8.46 (1 H, dd, J=5.1, 0.6 Hz), 8.25 (1 H, dd, J=1.8, 0.6 Hz), 8.18 (1 H, dd, J=2.1, 0.6 Hz), 7.48 (1 H, dd, J=5.1, 2.1 Hz), 7.44 (1 H, d, J=0.7 Hz), 7.39 (1 H, d, J=1.8 Hz), 4.21 (2 H, q, J=7.2 Hz), 3.19 (3 H, s), 1.91 (3 H, s), 1.14 (3H, t, J=7.2 Hz).

Step 2. 3-(N-Acetyl-N-methylamino)-6-chloro-2-(4-chloropyridine-2-carbonyl)indole The title compound was prepared according to the procedure described in step 2 of Example 2 (Method A) employing 6-Chloro-2-(4-chloropyridine-2-carbonyl)-1-ethoxycarbonyl-3-(N-acetyl-N-methylamino)indole (step 1).

m.p.: 236–237° C. (recrystallized from ethyl acetate) IR(KBr)ν: 3250, 1649, 1522, 1375, 1350, 1296, 1238, 1213, 1180, 1055, 1007, 781, 740 cm$^{-1}$.

$^1$H-NMR (DMSO-d$_6$) δ: 12.37 (1 H, br s), 8.72 (1 H, dd, J=5.3 and 0.5 Hz), 8.10 (1 H, dd, J=2.1, 0.5 Hz), 7.86 (1 H, dd, J=5.3, 2.1 Hz), 7.68 (1 H, dd, J=1.8, 0.5 Hz), 7.62 (1 H, dd, J=8.6, 0.5 Hz), 7.21 (1 H, dd, J=8.6, 1.8 Hz), 2.95 (3 H, s), 1.70 (3 H, s).

Ex. 365

6-Chloro-2-(3-chlorobenzoyl)-3-(n-methyl-n-propionylamino)indole

Step 1. 6-Chloro-2-(3-chlorobenzoyl)-1-ethoxycarbonyl-3-(propionylamino)indole

The title compound was prepared according to the procedure described in step 1 of Example 2 (Method A) from 3-amino-6-chloro-2-(3-chlorobenzoyl)-1-(ethoxycarbonyl) indole (step 1 of Example 30) and propionyl chloride.

m.p.: 189–191° C. (recrystallized from ethyl acetate)

$^1$H-NMR (CDCl$_3$) δ: 9.14 (1 H, br s), 8.21 (1 H, d, J=1.8 Hz), 7.99 (1 H, d, J=8.7 Hz), 7.79 (1 H, t, J=2.0 Hz), 7.58 (1 H, dt, J=1.5, 1.5, 7.7 Hz), 7.53 (1 H, ddd, J=1.5, 2.1, 8.7 Hz), 7.39 (1 H, t, J=7.8 Hz), 7.31 (1 H, dd, J=2.0, 8.7 Hz), 3.99 (2 H, q, J=7.2 Hz), 2.50 (2 H, q, J=7.5 Hz), 1.26 (3 H, t, J=7.5 Hz), 1.02 (3 H, t, J=7.2 Hz).

Step 2. 6-Chloro-2-(3-chlorobenzoyl)-3-(N-methyl-N-propionylamino)indole

The title compound was prepared according to the procedure described in Example 146 employing 6-chloro-2-(3-chlorobenzoyl)-1-ethoxycarbonyl-3-(propionylmino)indole (step 1). m.p.: 194–195° C. (recrystallized from ethyl acetate/hexane) $^1$H-NMR (CDCl$_3$) δ: 9.10 (1 H, br s), 7.66–7.41 (6 H, m), 7.22 (1 H, dd, J=1.8, 8.7 Hz), 3.03 (3 H, s), 2.07 (2 H, q, J=7.7 Hz), 0.99 (3 H, t, J=7.7 Hz).

Ex. 366

3-Acetylamino-6-chloro-2-(5-pyrimidinylcarbonyl)indole

Step1. 5-Bromoacetylpyrimidine

A mixture of 5-bromopyrimidine (2.20 g, 13.85 mmol), (1-ethoxyvinyl)tributyltin (5.00 g, 13.85 mmol), and tetrakis(triphenylphosphine)palladium (1.60 g, 1.38 mmol) in toluene (20 ml) was refluxed for 29 h, and then cooled to room temperature. The mixture was filtered through a pad of Celite and the filtrate was concentrated to give an oily residue. The residue was diluted with THF (30 ml) and water (8 ml). N-Bromosuccinimide (2.96 g, 16.61 mmol) was added at 0° C. The resulting mixture was stirred at 0° C. for 0.5 h and concentrated to ca. 10 ml. The residue was diluted with ethyl acetate (200 ml) and washed with water (100 ml×2), then dried (MgSO$_4$). Removal of solvent gave an oily residue, which was purified by flash column chromatography eluting with ethyl acetate-hexane (1:3) to afford 2.60 g (94%) of the title compound as an oil.

$^1$H-NMR (CDCl$_3$) δ: 9.41 (1 H, s), 9.29 (2 H, s), 4.40 (2 H, s).

Step 2. 3-Amino-6-chloro-1-ethoxycarbonyl-2-(5-pyrimidinylcarbonyl)indole

The title compound was prepared according to the procedure described in step 2 of Example 1 from 4-chloro-2-(ethoxycarbonylamino)benzonitrile (Example 1, step 1) and 5-bromoacetylpyrimidine (step 1). $^1$H-NMR (CDCl$_3$) δ: 9.29 (1 H, s), 9.03 (2 H, s), 8.02 (1 H, d, J=1.6 Hz), 7.57 (1 H, d, J=8.4 Hz), 7.35 (1 H, dd, J=1.6, 8.4 Hz), 6.13 (2 H, br s), 4.01 (2 H, q, J=7.1 Hz), 1.02 (3 H, t, J=7.1 Hz).

Step 3. 3-Acetylamino-6-chloro-1-ethoxycarbonyl-2-(5-pyrimidinylcarbonyl)indole

The title compound was prepared according to the procedure described in step 1 of Example 2 (Method A) employing 3-amino-6-chloro-1-ethoxycarbonyl-2-(5-pyrimidinylcarbonyl)indole (step 2) and acetyl chloride.

$^1$H-NMR (CDCl$_3$) δ: 9.34 (1 H, s), 9.23 (1 H, br s), 9.07 (2 H, s), 7.96 (1 H, d, J=1.6 Hz), 7.72 (1 H, d, J=6.7 Hz), 7.23 (1 H, dd, J=1.8, 8.7 Hz), 4.21 (2 H, q, J=7.1 Hz), 2.25 (3 H, s), 1.23 (3 H, t, J=7.1 Hz).

Step 4. 3-Acetylamino-6-chloro-1-ethoxycarbonyl-2-(5-pyrimidinylcarbonyl)indole

The title compound was prepared according to the procedure described in step 2 of Example 2 (Method A) from 3-acetylamino-6-chloro-1-ethoxycarbonyl-2-(5-pyrimidinylcarbonyl)indole (step 3). m.p.: 214–215° C. (recrystallized from ethyl acetate) $^1$H-NMR (DMSO-d$_6$) δ: 12.00 (1 H, br s), 10.00 (1 H, br s), 9.35 (1 H, s), 8.99 (2 H, s), 7.67 (1 H, d, J=9.2 Hz), 7.48 (1 H, s), 7.15 (1 H, d, J=8.6 Hz), 1.65 (3 H, s).

Ex. 367

3-Amino-6-chloro-2-(3-methylpyridine-2-carbonyl) indole

Step 1. 2-Bromoacetyl-3-methylpyridine

The title compound was prepared according to the procedure described in step 1 of Example 366 employing 2-bromo-3-methylpyridine.

$^1$H-NMR (CDCl$_3$) δ: 8.51 (1 H, br d, J=4.0 Hz), 7.63 (1 H, br d, J=7.7 Hz), 7.38 (1 H, dd, J=4.4, 7.7 Hz), 4.88 (2 H, s), 2.62 (3 H, s).

Step 2. 3-Amino-6-chloro-1-ethoxycarbonyl-2-(3-methylpyridine-2-carbonyl)indole

The title compound was prepared according to the procedure described in step 2 of Example 1 from 4-chloro-2-

(ethoxycarbonylamino)benzonitrile (Example 1, step 1) and 2-bromoacetyl-3-methylpyridine (step 1). $^1$H-NMR (CDCl$_3$) δ: 8.36 (1 H, dd, J=1.1, 4.8 Hz), 8.14 (1 H, d, J=1.8 Hz), 7.64 (1 H, ddd, J=0.7, 1.5, 7.0 Hz), 7.51 (1 H, dd, J=0.7, 8.4 Hz), 7.24 (1 H, d, J=1.8, 8.8 Hz), 7.22 (1 H, d, J=7.7 Hz), 6.05 (2 H, br s), 3.78 (2 H, q, J=7.3 Hz), 2.63 (3 H, s), 1.01 (3 H, t, J=7.3 Hz).

Step 3. 3-Amino-6-chloro-2-(3-methylpyridine-2-carbonyl)indole

The title compound was prepared according to the procedure described in step 3 of Example 1 from 3-amino-6-chloro-1-ethoxycarbonyl-2-(3-methylpyridine-2-carbonyl)indole (step 2). m.p.: 171–172° C. (recrystallized from ethyl acetate)

$^1$H-NMR (DMSO-d$_6$) δ: 10.25 (1 H, br s), 8.56 (1 H, d, J=4.4 Hz), 7.88 (1 H, d, J=8.8 Hz), 7.82 (1 H, d, J=7.0 Hz), 7.49 (1 H, dd, J=4.8, 7.7 Hz), 7.32 (1 H, d, J=1.8 Hz), 6.91 (1 H, dd, J=1.8, 8.4 Hz), 2.44 (3 H, s). The signal due to NH$_2$ was not observed.

Ex. 368

3-Acetylamino-6-chloro-2-(3-methylpyridine-2-carbonyl)indole

The title compound was prepared according to the procedure described in Example 19 from 3-amino-6-chloro-2-(3-methylpyridine-2-carbonyl)indole (Example 367) and acetyl chloride. m.p.: 173–175° C. (recrystallized from ethyl acetate)

$^1$H-NMR (DMSO-d$_6$) δ: 11.79 (1 H, br s), 9.53 (1 H, br s), 8.46 (1 H, d, J=4.4 Hz), 7.80 (1 H, d, J=7.0 Hz), 7.61 (1 H, d, J=8.4 Hz), 7.47 (1 H, dd, J=4.4, 7.0 Hz), 7.47 (1 H, d, J=1.5 Hz), 7.09 (1 H, dd, J=1.8, 8.8 Hz), 2.37 (3 H, s), 1.65 (3 H, s).

Ex. 369

6-Chloro-3-(isovalerylamino)-2-(3-methylpyridine-2-carbonyl)indole

The title compound was prepared according to the procedure described in Example 19 from 3-amino-6-chloro-2-(3-methylpyridine-2-carbonyl)indole (Example 367) and isovaleryl chloride. m.p.: 142–144° C. (recrystallized from ethyl acetate)

$^1$H-NMR (DMSO-d$_6$) δ: 11.77 (1 H, br s), 9.50 (1 H, br s), 8.46 (1 H, d, J=4.8 Hz), 7.79 (1 H, d, J=7.7 Hz), 7.60 (1 H, d, J=8.8 Hz), 7.50–7.45 (2 H, m), 7.09 (1 H, dd, J=1.8, 8.8 Hz), 2.38 (3 H, s), 1.86–1.74 (3 H, m), 0.81 (6 H, d, J=6.2 Hz).

Ex. 370

3-Acetylamino-6-chloro-2-[4-(hydroxymethyl)pyridine-2-carbonyl]indole

Step 1. 2-Cyano-4-(hydroxymethyl)pyridine

To a solution of 4-pyridylcarbinol-N-oxide (5.00 g, 39.96 mmol) and TMSCN (8.35 g, 79.92 mmol) in dichloromethane (60 ml) was added dropwise N,N-dimethylcarbamoyl chloride (7.4 ml, 79.92 mmol) at room temperature over 30 min. After stirring for 24 h, potassium carbonate (30 g) in water (100 ml) was added carefully. The organic layer was separated and dried over potassium carbonate. Removal of the solvent gave an oily residue, which was crystallized from ethanol/hexane to afford 3.63 g (68%) of the title compound.

$^1$H-NMR (CDCl$_3$) δ: 8.67 (1 H, d, J=4.9 Hz), 7.74 (1 H, t, J=0.8 Hz), 7.52 (1 H, dd, J=0.8, 4.9 Hz), 4.83 (2 H, s), 2.29 (1 H, br s).

Step 2. 4-(tert-Butyldimethylsilyloxy)methyl-2-cyanopyridine

To a solution of 2-cyano-4-hydroxymethylpyridine (step 1, 3.63 g, 27.06 mmol) in DMF (50 ml) were added imidazole (4.42 g, 64.95 mmol) and TBDMSCl (4.89 g, 32.47 mmol) at room temperature. After stirring for 1 h, the mixture was diluted with diethyl ether (300 ml), washed with water (100 ml×4), and dried (MgSO$_4$). Removal of solvent gave the title compound. $^1$H-NMR (CDCl$_3$) δ: 8.65 (1 H, d, J=5.1 Hz), 7.68 (1 H, s), 7.46 (1 H, d, J=4.9 Hz), 4.78 (2 H, s), 0.96 (9 H, s), 0.13 (6 H, s).

Step 3. 2-Acetyl-4-[(tert-butyldimethylsilyloxy)methyl]pyridine

To a solution of 4-(tert-butyldimethylsilyloxymethyl)-2-cyanopyridine (step 2, 6.72 g, 27.06 mmol) in benzene (50 ml) and diethyl ether (50 ml) was added dropwise 2M MeMgI in diethyl ether (19 ml, 37.89 mmol) at 0° C. over 30 min. After stirring for 1 h at room temperature, saturated aqueous ammonium chloride (50 ml) was added at 0° C. The organic layer was separated, dried (MgSO$_4$) and concentrated. The residue was purified by flash column chromatography eluting with ethyl acetate-hexane (1:12) to afford 1.03 g (14%) of the title compound.

$^1$H-NMR (CDCl$_3$) δ: 8.62 (1 H, d, J=5.1 Hz), 7.94 (1 H, s), 7.48 (1 H, dd, J=4.9, 1.8 Hz), 4.78 (2 H, s), 2.71 (3 H, s), 0.94 (9 H, s), 0.11 (6 H, s).

Step 4. 2-Bromoacetyl-4-[(tert-butyldimethylsilyloxy)methyl]pyridine

To a solution of 2-acetyl-4-[(tert-butyldimethylsilyloxy)methyl]pyridine (step 3, 736 mg, 2.77 mmol) in THF (15 ml) was added dropwise lithium bis(trimethylsilyl)amide (1.0 M in hexane, 3.3 ml, 3.32 mmol) at −78° C. over 20 min. After stirring for 1 h, triethylsilyl chloride (0.7 ml, 4.16 mmol) was added to the mixture at −78° C. The mixture was stirred for an additional 1 h at the same temperature, and then allowed to warm to room temperature. After stirring for 1 h, the mixure was poured into saturated aqueous ammonium chloride (20 ml). The organic layer was separated and dried (MgSO$_4$). Removal of solvent gave an oily residue, which was dissolved in THF (10 ml) and water (2 ml). To the mixture was added N-bromoscuccinimide (592 mg, 3.32 mmol) at 0° C. After stirring for 15 min, the mixture was diluted with diethyl ether (100 ml), washed with water (50 ml×2), and dried (MgSO$_4$). Removal of solvent gave an oily residue, which was purified by flash column chromatography eluting with ethyl acetate/hexane (1:10) to afford 1.52 g (quantitative yield) of the title compound.

$^1$H-NMR (CDCl$_3$) δ: 8.63 (1 H, d, J=4.9 Hz), 8.02 (1 H, s), 7.53 (1 H, d, J=5.4 Hz), 4.87 (2 H, s), 4.81 (2 H, s), 0.96 (9 H, s), 0.13 (6 H, s).

Step 5. 3-Amino-6-chloro-1-ethoxycarbonyl-2-[4-[(tert-butyldimethylsilyloxy)methyl]pyridine-2-carbonyl]indole The title compound was prepared according to the procedure described in step 2 of Example 1 from 4-chloro-2-(ethoxycarbonylamino)benzonitrile (Example 1, step 1) and 2-bromoacetyl-4-[(tert-butyldimethylsilyloxy)methyl]
pyridine (step 4).

$^1$H-NMR (CDCl$_3$) δ: 8.56 (1 H, d, J=4.9 Hz), 8.22 (1 H, d, J=2.0 Hz), 7.98 (1 H, br s), 7.51 (1 H, d, J=8.4 Hz), 7.40 (1 H, br d, J=4.9 Hz), 7.23 (1 H, dd, J=1.8, 8.4 Hz), 6.00 (2 H, br s), 4.83 (2 H, s), 3.78 (2 H, q, J=7.2 Hz), 0.97 (9 H, s), 0.88 (3 H, t, J=7.2 Hz), 0.14 (6 H, s).

Step 6. 3-Acetylamino-6-chloro-2-[4-[(tert-butyldimethylsilyloxy)methyl]pyridine-2-carbonyl] indole The title compound was prepared according to the procedure described in step 1 of Example 2 (Method A) from 3-amino-6-chloro-1-ethoxycarbonyl-2-[4-[(tert-butyldimethylsilyloxy)methyl]pyridine-2-carbonyl]indole (step 5) and acetyl chloride.

$^1$H-NMR (CDCl$_3$) δ: 9.49 (1 H, br s), 8.58 (1 H, d, J=4.9 Hz), 8.19 (1H, d, J=1.8 Hz), 8.06 (1 H, s), 7.98 (1 H, d, J=8.4 Hz), 7.45 (1 H, d, J=4.9 Hz), 7.25 (1H, dd, J=1.8, 8.4 Hz), 4.84 (2 H, s), 3.95 (2 H, q, J=6.9 Hz), 2.24 (3 H, s), 1.01–0.93 (3H, m), 0.97 (9 H, s), 0.14 (6 H, s).

Step 7. 3-Acetylamino-6-chloro-2-[4-(hydroxymethyl)pyridine-2-carbonyl]indole

To a solution of 3-acetylamino-6-chloro-2-[4-[(tert-butyldimethylsilyloxy)methyl]pyridine-2-carbonyl]indole (step 6, 240 mg, 0.454 mmol) in THF (10 ml) was added 1M TBAF in THF (0.7 ml, 0.681 mmol) at 0° C. After stirring for 30 min, potassium hydroxide (90 mg, 1.36 mmol) in water (2 ml) was added at 0° C. The mixture was stirred for an additional 1 h at room temperature and concentrated. The residue was diluted with ethyl acetate (100 ml), and then washed with water (30 ml×2) and dried (MgSO$_4$). Removal of solvent gave a crystalline residue, which was recrystallized from dichloromethane to afford 52 mg (33%) of the title compound. m.p.: 216–218° C. (recrystallized from dichloromethane)

$^1$H-NMR (DMSO-d$_6$) δ: 12.06 (1 H, br s), 10.49 (1 H, br s), 8.76 (1 H, d, J=4.9 Hz), 8.07 (1 H, s), 7.86 (1 H, d, J=8.6 Hz), 7.67–7.64 (2 H, m), 7.07 (1 H, dd, J=1.8, 8.7 Hz), 5.62 (1 H, t, J=5.5 Hz), 4.69 (2 H, d, J=5.1 Hz), 2.04 (3 H, s).

Ex. 371

2-(4-Aminopyridine-2-carbonyl)-6-chloro-3-(propionylamino)indole hydrochloride

Step 1. 4-[N,N-bis(tert-butoxycarbonyl)amino]-2-chloropyridine

A mixture of 4-amino-2-chloropyridine (1.50 g, 11.67 mmol) and di-tert-butyl dicarbonate (10.7 ml, 46.67 mmol) in dichloromethane (30 ml) was stirred at room temperature for a week. After evaporation, the residue was purified by flash column chromatography eluting with ethyl acetate/hexane (1:10) to afford 3.09 g (81%) of the title compound as a solid. $^1$H-NMR (CDCl$_3$) δ: 8.38 (1 H, d, J=5.4 Hz), 7.19 (1 H, d, J=1.8 Hz), 7.05 (1 H, dd, J=1.8, 5.4 Hz), 1.47 (18 H, s).

Step 2. 3-Amino-2-[4-[N,N-bis(tert-butoxycarbonyl) amino]pyridine-2-carbonyl]-6-chloro-1-(ethoxycarbonyl)indole The title compounds were prepared according to the procedure described in step 1 of Example 366 and step 2 of Example 1 employing 4-[N,N-bis(tert-butoxycarbonyl) amino]-2-chloropyridine (step 1).

$^1$H-NMR (CDCl$_3$) δ: 8.59 (1 H, d, J=5.3 Hz), 8.24 (1 H, d, J=1.6 Hz), 7.88 (1 H, d, J=2.1 Hz), 7.52 (1 H, d, J=8.4 Hz), 7.27–7.23 (1 H, m), 7.20 (1 H, dd, J=2.0, 5.2 Hz), 5.97 (2 H, br s), 3.82 (2 H, q, J=7.1 Hz), 1.49 (18 H, s), 0.95 (3 H, t, J=7.1 Hz).

Step 3. 2-[4-[N,N-Bis(tert-butoxycarbonyl)amino] pyridine-2-carbonyl]-6-chloro-1-ethoxycarbonyl-3-(propionylamino)indole The title compound was prepared according ot the procedure described in step 1 of Example 2 (Method A) employing 3-amino-2-[4-[N,N-bis(tert-butoxycarbonyl) amino]pyridine-2-carbonyl]-6-chloro-1-(ethoxycarbonyl) indole (step 2) and propionyl chloride. $^1$H-NMR (CDCl$_3$) δ: 9.52 (1 H, br s), 8.61 (1 H, d, J=5.1 Hz), 8.21 (1 H, d, J=1.8 Hz), 8.05 (1 H, d, J=8.7 Hz), 7.95 (1 H, d, J=2.1 Hz), 7.28–7.23 (2 H, m), 3.93 (2 H, q, J=7.1 Hz), 2.51 (2 H, q, J=7.4 Hz), 1.50 (18 H, s), 1.26 (3 H, t, J=7.4 Hz), 1.02 (3 H, t, J=7.1 Hz).

Step 4. 2-[4-(t-Butoxycarbonyl)aminopyridine-2-carbonyl]-6-chloro-3-(propionylamino)indole To a solution of 2-[4-[N,N-bis(tert-butoxycarbonyl) amino]-2-pyridine-2-carbonyl]-6-chloro-1-ethoxycarbonyl-3-(propionylmino)indole (step 3, 240 mg, 0.391 mol) in ethanol (10 ml) was added a solution of potassium carbonate (260 mg, 3.91 mmol) in water (5 ml) at room temperature. After stirring for 8 h, the mixture was concentrated. The residue was diluted with ethyl acetate (100 ml) and washed with (50 ml×2), dried (Na$_2$SO$_4$). Removl of solvent gave an oily residue, which was purified by flash column chromatography eluting with ethyl acetate/hexane (1/3) to afford 118 mg (68%) of the title compound as an oil.

$^1$H-NMR (CDCl$_3$) δ: 11.97 (1 H, br s), 10.87 (1 H, br s), 8.55 (1 H, d, J=5.8 Hz), 8.49 (1 H, d, J=9.1 Hz), 8.08 (1 H, d, J=2.0 Hz), 7.79 (1 H, dd, J=2.1, 5.8 Hz), 7.36 (1 H, d, J=1.3 Hz), 7.02 (1 H, dd, J=1.8, 5.8 Hz), 6.75 (1 H, br s), 2.60 (2 H, q, J=7.5 Hz), 1.56 (9 H, s), 1.36 (3 H, t, J=7.5 Hz).

Step 5. 2-(4-Aminopyridine-2-carbonyl)-6-chloro-3-(propionylamino)indole hydrochloride 2-[4-(tert-Butoxycarbonyl)aminopyridine-2-carbonyl]-6-chloro-3-(propionylamino)indole (step 4, 118 mg, 0.266 mmol) was treated with trifluoroacetic acid (4 ml) at room temperature for 1 h. The mixture was concentrated and azeotroped with toluene to give an oily residue. The residue was basified with saturated aqueous sodium bicarbonate (30 ml) and extracted with dichloromethane (30 ml×3). The organic phase was dried (K$_2$CO$_3$), and concentrated to afford the free base of title compound. The free base was dissolved in 10% HCl—MeOH (4 ml) and then evaporated. The residue obtained was crystallized from ethanol-diethyl ether to give the title compound. m.p.: 199–204° C. (decomposition) $^1$H-NMR (DMSO-d$_6$) δ: 12.03 (1 H, br s), 10.41 (1 H, br s), 8.17 (1 H, d, J=7.3 Hz), 7.93 (1 H, d, J=8.9 Hz), 7.48 (1 H, d, J=1.6 Hz), 7.18 (1 H, dd, J=1.6, 8.7 Hz), 7.12 (1 H, d, J=1.8 Hz), 6.88 (1H, dd, J=7.4, 2.0 Hz), 2.18 (1 H, q, J=7.4 Hz), 0.82 (3 H, t, J=7.4 Hz).

A signal due to NH$_2$ was not observed.

Ex. 372

3-Acetylamino-6-chloro-2-(3-hydroxymethyl-2-furoyl)indole

Step 1. 3-Acetoxymethyl-2-(bromoacetyl)furan

3-Acetoxymethyl-2-acetylfuran (1.7 g, 9.3 mmol, prepared according to the procedure described in Acta.

Chemica. Scandinavia, 1990, 44, 916) was dissolved in acetic acid (30 ml). To the solution was added pyridinium tribromide (3.3 g, 10.2 mmol) and the resulting mixture was stirred at room temperature for 3 h. The mixture was cooled to 0° C. and saturated aqueous sodium bicarbonate added dropwise until the solution was basic. The mixture was extracted with ethyl acetate (100 ml). The organic extract was washed with brine (100 ml), dried (MgSO$_4$) and concentrated to give 2.3 g (95%) of the title compound. $^1$H-NMR (CDCl$_3$) δ: 7.54 (1 H, d, J=1.6 Hz), 6.65 (1 H, d, J=1.6 Hz), 5.38 (2 H, s), 4.37 (2 H, s), 2.09 (3 H, s).

Step 2. 3-Amino-6-chloro-1-ethoxycarbonyl-2-(3-hydroxymethyl-2-furoyl)indole

To a suspension of sodium hydride (60% w/w dispersion in mineral oil, 390 mg, 8.8 mmol) in DMF (20 ml) was added a solution of 4-chloro-2-(ethoxycarbonylamino) benzonitrile (step 1, 2 g, 8.8 mmol) in DMF (5 ml) at 0° C. After stirring for 1 h at 0° C., 3-acetoxymethyl-2-(bromoacetyl)furan (step 1, 2.3 g, 8.8 mmol) was added and the resulting mixture was stirred at room temperature for an additional 6 h. The mixture was poured into water (100 ml), and extracted with ethyl acetate (300 ml). The organic extract was washed with saturated aqueous sodium bicarbonate (100 ml), brine (100 ml), and then dried (MgSO$_4$) and concentrated. The residue was diluted with a mixture of ethanol (20 ml) and water (10 ml), and then potassium carbonate (ca. 2 g) was added. After stirring for 6 h, the mixture was poured into a saturated aqueous ammonium chloride (100 ml) and the mixture extracted with ethyl acetate (300 ml). The organic extract was washed with brine (100 ml), dried (MgSO$_4$) and concentrated. The residue was purified by flash column chromatography eluting with ethyl acetate/hexane (2/1) to give 505 mg (16%) of the titled compound as yellow solids. Mass; M$^+$=362

Step 3. 3-Acetylamino-6-chloro-1-ethoxycarbonyl-2-(3-acetoxymethyl-2-furoyl)indole To a solution of 3-amino-6-chrolo-1-ethoxycarbonyl-2-(3-hydroxymethyl-2-furoyl) indole (step 2, 330 mg, 0.91 mmol) in dichloromethane (10 ml) was added pyridine (2 ml) and acetic anhydride (0.19 ml, 2.0 mmol) at room temperature. After stirring for 5 h, the mixture was poured into 2N aqueous HCl (30 ml) and extracted with ethyl acetate (100 ml). The organic layer was washed with water (50 ml), saturated aqueous sodium bicarbonate (50 ml) and brine (50 ml), and then dried (MgSO$_4$) and concentrated. The residue was purified by flash column chromatography eluting with ethyl acetate/hexane (1/1) to give 382 mg (94%) of the title compound as a yellow solid. $^1$H-NMR (CDCl$_3$) δ: 10.2 (1H, br s), 8.11 (1H, d, J=1.1 Hz), 7.48 (1H, d, J=4.8 Hz), 7.05–7.33 (2H, m), 6.70 (1H, d, J=4.8 Hz), 5.41 (2H, s), 4.25 (2H, q, J=7.0 Hz), 2.36 (6H, s), 1.33 (3H, t, J=7.0 Hz).

Step 4. 3-Acetylamino-6-chloro-2-(3-hydroxymethyl-2-furoyl)indole

To a solution of 3-acetylamino-6-chloro-1-ethoxycarbonyl-2-(3-acetoxymethyl-2-furoyl) indole (step 3, 180 mg, 0.4 mmol) in a mixture of ethanol (10 ml) and water (5 ml) was added 2N aqueous sodium hydroxide (2 ml) at room temperture. After stirring for 1.5 h, the mixture was poured into saturated aqueous ammonium chloride (50 ml) and extracted with ethyl acetate (100 ml). The organic layer was washed with brine (50 ml), dried (MgSO$_4$) and concentrated. The residue was purified by flash column chromatography eluting with ethyl acetate/hexane (1/1), and the product recrystalized from acetone/hexane to give 98 mg (73%) of the titled compound as a yellow crystalline solid. m.p.: 196–198° C. $^1$H-NMR (CDCl$_3$) δ: 10.6 (1H, br s), 9.52 (1H, br s), 8.33 (1H, d, J=9.2 Hz), 7.66 (1H, br s), 7.30 (1H,br s), 7.01 (1H, d, J=9.2 Hz), 6.66 (1H, br s), 4.81 (2H, s), 2.32 (3H, s). The signal due to H of OH was not observed.

Ex. 373

6-Chloro-2-(4-hydroxymethyl-2-furoyl)-3-(isovalerylamino)indole

Step 1. 4-Acetoxymethyl-2-(bromoacetyl)furan

The title compound was prepared according to the procedure described in step 1 of Example 372 employing 4-acetoxymethyl-2-acetylfuran (prepared according to the procedure described in Acta. Chemica. Scandinavia, 1990, 44, 916).

$^1$H-NMR (CDCl$_3$) δ: 7.67 (1H, s), 7.34 (1H, s), 5.00 (2H, s), 4.29 (2H, s), 2.09 (3H, s).

Step 2. 2-(4-Acetoxymethyl-2-furoyl)-3-amino-6-chloro-1-(ethoxycarbonyl)indole

The title compound was prepared according to the procedure described in step 2 of Example 1 employing 4-chloro-2-(ethoxycabonylamino)benzonitrile (Exampe 1, step 1) and 4-acetoxymethyl-2-(bromoacetyl)furan (step 1).

$^1$H-NMR (CDCl$_3$) δ: 8.26 (1H, d, J=1.8 Hz), 7.55 (1 H, s), 7.50 (1H, d, J=8.4 Hz), 7.27 (1H, dd, J=1.8, 8.4 Hz), 7.20 (1H, s), 5.84 (2H, br s), 4.99 (2H, s), 4.08 (2H, q, J=7.1 Hz), 2.07 (3H, s), 1.03 (3H, t, J=7.1 Hz).

Step 3. 2-(4-Acetoxymethyl-2-furoyl)-6-chloro-1-ethoxycarbonyl-3-(isovalerylamino)indole The title compound was prepared according to the procedure described in step 1 of Example 2 (Method A) employing 2-(4-acetoxymethyl-2-furoyl)-3-amino-6-chloro-1-(ethoxycarbonyl)indole (step 2) and isovaleryl chloride.

$^1$H-NMR (CDCl$_3$) δ: 9.24 (1H, br s), 8.25 (1H, d, J=1.8 Hz), 8.00 (1H, d, J=8.7 Hz), 7.61 (1H, s), 7.29 (1H, dd, J=1.8, 8.7 Hz), 7.26 (1H, s), 4.99 (2H, s), 4.15 (2H, q, J=7.1 Hz), 2.34 (2H, d, J=6.6 Hz), 2.17–2.27 (1H, m), 2.08 (3H, s), 1.09 (3H, t, J=7.1 Hz), 1.05 (6H, d, J=6.4 Hz)

Step 4. 6-Chloro-2-(4-hydroxymethyl-2-furoyl)-3-(isovalerylamino)indole

To a solution of 2-(4-acetoxymethyl-2-furoyl)-6-chloro-1-ethoxycarbonyl-3-(isovalerylamino)indole (step 3, 213.5 mg, 0.437 mmol) in ethanol (1.5 ml) was added 2N aqueous sodium hydroxide (1.5 ml). After stirring for 5.5 h, the mixture was poured into saturated aqueous ammonium chloride (20 ml) and extracted with ethyl acetate (80 ml). The organic layer was washed with brine (20 ml), dried (MgSO$_4$) and cocentrated. The residue was purified by flash column chromatography eluting with ethyl acetate/hexane (1/3) and recrystallization from 2-propanol/isopropyl ether to give 119 mg (88%) of the titled compound as yellow solids. m.p: 200–201° C.

$^1$H-NMR (CDCl$_3$) δ: 10.7 (1H,br s), 9.37 (1H, br s), 8.47 (1H, d, J=8.74 Hz), 7.74 (1H, s), 7.45 (1H, s), 7.38 (1H, d, J=1.81 Hz), 7.08 (1H, dd, J=1.81 Hz), 8.74 Hz), 4.70 (2H, d, J=4.78 Hz), 2.41 (2H, d, J=6.38 Hz), 2.35–2.27 (1H, m), 1.08 (3H, s), 1.06 (3H, s).

The signal due to H of OH was not observed.

Ex. 374

6-Chloro-2-(4-hydroxymethyl-2-furoyl)-3-(propionylamino)indole

Step 1. 2-(4-Acetoxymethyl-2-furoyl)-6-chloro-1-ethoxycarbonyl-3-(propionylamino)indole The title compound was prepared according to the procedure described in step 1 of Example 2 (Method A) employing 2-(4-acetoxymethyl-2-furoyl)-3-amino-6-chloro-1-(ethoxycarbonyl)indole (Exampe 373, step 2) and propionyl chloride.

$^1$H-NMR (CDCl$_3$) δ: 9.29 (1H, br s),8.23 (1H, d, J=1.65 Hz), 8.00 (1H, d, J=8.73 Hz), 7.61 (1H, s), 7.29–7.28 (2H, m), 4.99 (2H, s), 4.15 (2H, q, J=7.08 Hz), 2.51 (2H, q, J=7.58 Hz), 2.08 (3H, s), 1.27 (3H, t, J=7.58 Hz), 1.09 (3H, t, J=7.08 Hz).

Step 2. 6-chloro-2-(4-hydroxymethyl-2-furoyl)-3-(propionylamino)indole

To a solution of 2-(4-acetoxymethyl-2-furoyl)-6-chloro-1-ethoxycarbonyl-3-(propionylamino)indole (step 1, 114 mg, 0.313 mmol) in ethanol (2 ml) was added 2N aqueous sodium hydroxide (2 ml). After stirring for 3 h, the mixture was poured into saturated aqueous ammonium chloride (20 ml) and extracted with ethyl acetate (80 ml). The organic layer was washed with brine (20 ml), dried (MgSO$_4$) and concentrated. The residue was purified by flash column chromatography eluting with ethyl acetate/hexane (1/1) and recrystalization from 2-propanol/isopropyl ether to give 46 mg (40%) of the titled compound as yellow solids. m.p.: 171–172° C. $^1$H-NMR (CDCl$_3$) δ: 10.74 (1H, br s), 9.37 (1H, br s), 8.45 (1H, d, J=9.06 Hz), 7.08 (1H, s), 7.42 (1H, s), 7.36 (1H, d, J=1.81 Hz), 7.06 (1H, dd, J=9.06 Hz, 1.81 Hz), 4.67 (2H, s), 2.58 (2H, q, J=7.58 Hz), 1.33 (3H, t, J=7.58 Hz).

The signal due to H of OH was not observed.

Ex. 375

6-Chloro-2-(4-hydroxymethyl-2-furoyl)-3-[[(s)-2-hydroxypropionyl]amino]indole

Step 1. 2-(4-Acetoxymethyl-2-furoyl)-6-chloro-1-ethoxycarbonyl-3-[[(S)-2-acetoxypropionyl]amino]indole The title compound was prepared according to the procedure described in step 1 of Example 2 (Method A) employing 2-(4-acetoxymethyl-2-furoyl)-3-amino-6-chloro-1-(ethoxycarbonyl)indole (Example 373, step 2) and (S)-(−)-2-acetoxypropionyl chloride. $^1$H-NMR (CDCl$_3$) δ: 10.03 (1H, br s), 8.26 (1H, d, J=1.81 Hz), 8.21 (1H, d, J=8.74 Hz), 7.62 (1H, s),7.30 (1H, dd, J=8.74 Hz, 1.81 Hz), 7.28 (1H, s), 5.38 (1H, q, J=6.92 Hz), 4.99 (2H, s), 4.12 (2H, q, J=7.09 Hz), 2.08 (3H, s), 2.04 (3H, s), 1.59 (3H, d, J=6.92 Hz), 1.26 (3H, t, J=7.09 Hz).

Step 2. 6-chloro-2-(4-hydroxymethyl-2-furoyl)-3-[[(S)-2-hydroxypropionyl]amino]indole To a solution of 2-(4-acetoxymethyl-2-furoyl)-6-chloro-1-ethoxycarbonyl-3-[(S)-2-acetoxypropionylamino]indole (step 1, 267 mg, 0.494 mmol) in ethanol (2 ml) was added 2N aqueous sodium hydroxide (2 ml). After stirrig for 3 h, the mixture was poured into saturated aqueous ammonium chloride (20 ml) and extracted with ethyl acetate (80 ml). The organic layer was washed with brine (20 ml), dried (MgSO$_4$) and concentrated. The residue was purified by flash column chromatography eluting with dichloromethane/methanol (50/1) and recrystallized from 2-propanol/isopropyl ether to give 43 mg (24%) of the titled compound as yellow solids. m.p.: 213–214° C. $^1$H-NMR (CDCl$_3$) δ: 11.4 (1H, br s), 10.8 (1H, br s), 8.35 (1H, d, J=8.90 Hz), 7.76 (1H, s), 7.53 (1H, d, J=1.81 Hz), 7.45 (1H, s), 7.01 (1H, dd, J=8.90 Hz, 1.81 Hz), 4.58 (2H, d, J=5.11 Hz), 4.36 (1H, q, J=6.92 Hz), 1.52 (3H, d, J=6.92 Hz).

Ex. 376

3-Amino-6-chloro-2-[2-(5-methylthiazoyl)]indole

Step 1. 2-Bromoacetyl-5-methylthiazole

The title compound was prepared according to the procedure described in step 4 of Example 370 employing 2-acetyl-5-methylthiazole (Bull. Soc. Chim.Fr., 1953, 702).
$^1$H-NMR (CDCl$_3$) δ: 7.70 (1H, s), 4.65 (2H, s), 2.59 (3H, s).

Step 2. 3-Amino-6-chloro-1-ethoxycarbonyl-2-[2-(5-methylthiazoyl)]indole

The title compound was prepared according to the procedure described in step 2 of Example 1 employing 4-chloro-2-(ethoxycarbonylamino)benzonitrile (Example 1, step 1) and 2-bromoacetyl-5-methylthiazole (step 1).
$^1$H-NMR (CDCl$_3$) δ: 8.23 (1H, d, J=1.81 Hz), 7.64 (1H, d, J=0.82 Hz), 7.50 (1H, d, J=8.4 Hz), 7.25 (1H, dd, J=1.8,8.4 Hz), 6.02 (2H, br s), 4.07 (2H, q, J=7.08 Hz), 2.57 (3H, d, J=0.82 Hz), 1.00 (3H, d, J=0.82 Hz).

Step 3. 3-Amino-6-chloro-2-[2-(5-methylthiazoyl)]indole

The title compound was prepared according to the procedure described in step 3 of Example 1 employing 3-amino-6-chloro-1-ethoxycarbonyl-2-[2-(5-methylthiazoyl)]indole. $^1$H-NMR (CDCl$_3$) δ: 10.4 (1H, br s), 7.71 (1H, d, J=0.82 Hz), 7.51 (1H, d, J=8.74 Hz), 7.31 (1H, d, J=1.81 Hz), 6.97 (1H, dd, J=1.81, 8.74 Hz), 5.95 (2H, br s), 2.60 (3H, d, J=0.82 Hz).

Ex. 377

6-Chrolo-3-isovalerylamino-2-[2-(5-methylthiazoyl)]indole

The title compound was prepared according to the procedure described in Example 19 from 3-amino-6-chloro-2-[2-(5-methylthiazoyl)]indole (Example 376) and isovaleryl chloride. $^1$H-NMR (CDCl$_3$) δ: 11.1 (1H, br s), 10.6 (1H, br s), 8.52 (1H, d, J=8.9 Hz), 7.78 (1H, d, J=1.2 Hz), 7.37 (1H, d, J=1.8 Hz), 7.05 (1H, dd, J=1.8, 8.9 Hz), 2.63 (3H, d, J=1.2 Hz), 2.43 (2H, m), 2.35–2.24 (1H, m), 1.07 (6H, d, J=6.4 Hz).

Ex. 378

3-Acetylamino-6-chloro-2-[2-(5-methylthiazoyl)]indole

To a suspension of sodium hydride (60% w/w dispersion in mineral oil, 900 mg, 22.5 mmol) in DMF (30 ml) was added a solution of 4-chloro-2-(ethoxycarbonylamino)benznitrile (5 g, 22.5 mmol) in DMF (10 ml) at 0° C. After stirring for 1 h at 0° C., 2-bromoacetyl-5-methylthiazole was added and the resulting mixture was stirred at room temperature for 18 h, and then quenched with ethyl acetate (1 ml). The mixture was poured into water (50 ml), and extracted with ethyl acetate (100 ml). The organic layer was washed with saturated aqueous sodium bicarbonate (50 ml) and brine (50 ml). The organic layer was dried (MgSO$_4$) and solvent removed. The residue was diluted with ethanol (10 ml) and water (5 ml), and then potassium carbonate (ca. 1 g) was added. The mixture was stirred at room temperature for 4 h, and then poured into saturated aqueous ammonium chloride and extracted with ethyl acetate (100 ml). The organic layer was washed with brine (50 ml), dried (MgSO$_4$) and concentrated. The residue was purified by flash column chromatography eluting with ethyl acetate/hexane (1/5) and recrystallization from methanol/dichloromethane/hexane to give 100 mg (4%) of the title compound as yellow solids. m.p.: 215–217° C. $^1$H-NMR (CDCl$_3$) δ: 11.07 (1H, br s), 10.5 (1H, br s), 8.44 (1H, d, J=9.2 Hz), 7.75 (1H, d, J=1.1 Hz), 7.34 (1H, d, J=1.8 Hz), 7.03 (1H, dd, J=1.8,9.2 Hz), 2.62 (3H, s), 2.32 (3H, s).

Ex. 379

3-Acetylamino-6-chloro-2-[3-(1-methylpyrrolyl) carbonyl]indole

Step 1. 3-Bromoacetyl-1-methylpyrrole

The title compound was prepared according to the procedure described in step 4 of Example 370 employing 3-acetyl-1-methylpyrrole (Synthesis, 1990, 212).

$^1$H-NMR (CDCl$_3$) δ: 7.34(1H,s), 6.61(2H,br.s), 4.19(2H, d,J=0.66 Hz), 3.71(3H,s)

Step 2. 3-Amino-6-chloro-1-ethoxycarbonyl-2-[3-(1-methylpyrrolyl)carbonyl]indole The title compound was prepared according to the procedure described in step 2 of Example 1 employing 4-chloro-2-(ethoxycarbonylamino)benzonitrile and 3-bromoacetyl-1-methylpyrrole (step 1). $^1$H-NMR (CDCl$_3$) δ: 8.22 (1H, d, J=1.3 Hz), 7,47 (1H, d, J=8.4 Hz), 7.27 (1H, dd, J=1.8, 8.4 Hz), 7.18 (1H, d, J=1.8 Hz), 6.57–6.55 (2H, m), 5.38 (2H, br s), 4.02 (2H, q, J=7.1 Hz), 3.67 (3H, s), 0.98 (3H, t, J=7.1 Hz)

Setp 3. 6-Chloro-3-diacetylamino-1-ethoxycarbonyl-2-[3-(1-methylpyrrolyl)carbonyl] indole To a mixture of 3-amino-6-chloro-1-ethoxycarbonyl-2-[3-(1-methylpyrrolyl)carbonyl]indole (step 2, 337 mg, 0.95 mmol) and pyridine (89 ml, 1.1 mmol) in dichloromethane (5 ml) was added acetyl chloride (75 ml, 1.05 mmol) at room temperature. After stirring for 1 h, the mixture was poured into 2N aqueous HCl (20 ml)and extracted with ethyl acetate (80 ml). The organic layer was washed with water (20 ml), saturated aqueous sodium bicarbonate (20 ml) and brine (20 ml), and then dried (MgSO$_4$). Removal of solvent gave 208 mg (93%) of the title compound as a yellow oil . $^1$H-NMR (CDCl$_3$) δ: 8.30 (1H, d, J=1.65 Hz), 7.34 (1H, dd, J=1.65, 7.91 Hz), 7.27 (1H, d, J=7.91 Hz), 7.07 (1H, s), 6.58 (2H, br s), 4.30 (2H, q, J=7.25 Hz), 3.63 (3H, s), 2,32 (6H, s), 1.22 (3H, t, J=7.25 Hz).

Step 4. 3-Acetylamino-6-chloro-2-[3-(1-methylpyrrolyl)carbonyl]indole

6-Chloro-3-diacetylamino-1-ethoxycarbonyl-2-[3-(1-methylpyrrolyl)carbonyl]indole (step 3, 200 mg) was diluted with a mixture of ethanol (20 ml) and water (10 ml), and then potassium hydroxide (ca. 1 g) was added. After stirring for 4 h at room temperature, the mixture was poured into saturated aqueous ammonium chloride (20 ml) and extracted with ethyl acetate (80 ml). The organic layer was washed with brine (29 ml), dried (MgSO$_4$) and concentrated. The residue was purified by flash column chromatography eluting with ethyl acetate/hexane (1/2) to give 45 mg (27%) of the titled compound as yellow solids. m.p.: 205–206° C.

$^1$H-NMR (CDCl$_3$) δ: 10.7 (1H, br s), 10.2 (1H, br s), 8.07 (1H, d, J=8.7 Hz), 7.49–7.46 (2H, m), 7.01 (1H, d, J=8.7 Hz), 6.73 (2H, m), 3.77 (3H, s), 2.23 (3H, s).

Ex. 380

3-(2-Acetoxyisobutyrylamino)-6-chloro-2-(4-methylpyridine-2-carbonyl)indole

The title compound was prepared according to the procedure described in Example 19 employing 3-amino-6-chloro-2-(4-methylpyridine-2-carbonyl)indole (Example 70) and 2-acetoxyisobutyryl chloride. m.p.: 222–223° C.

H-NMR (CDCl$_3$) δ: 12.03 (1 H, br s), 11.45 (1 H, br s), 8.63 (1 H, d, J=4.6 Hz), 8.56 (1 H, d, J=9.2 Hz), 8.17 (1 H, t, J=0.8 Hz), 7.40 (1 H, d, J=1.5 Hz), 7.37 (1 H, dt, J=4.9, 0.8 Hz), 7.04 (1 H, dd, J=8.9, 1.9 Hz), 2.51 (3 H, s), 2.29 (3 H, s), 1.81 (6 H, s).

Ex. 381

6-Chloro-3-(2-hydroxyisobutyrylamino)-2-(4-methylpyridine-2-carbonyl)indole

The title compound was prepared according to the procedure described in Example 361 employing 3-(2-acetoxyisobutyrylamino)-6-chloro-2-(4-methylpyridine-2-carbonyl)indole (Example 380). m.p.: 217–219° C. $^1$H-NMR (CDCl$_3$) δ: 12.07 (1H, br s), 11.70 (1 H, br s), 8.62 (1 H, dd, J=4.9, 0.5 Hz), 8.55 (1 H, d, J=9.1 Hz), 8.21 (1 H, dd, J=1.0, 0.7 Hz), 7.40 (1 H, dd, J=2.0, 0.5 Hz), 7.36 (1 H, ddd, J=5.1, 1.8, 0.7 Hz), 7.05 (1 H, dd, J=9.1, 1.8 Hz), 2.86 (1 H,br s), 2.48 (3H, s), 1.67 (6 H, s).

Ex. 382

3-[[(S)-2-Acetoxypropionyl]amino]-6-chloro-2-(4-methylpyridine-2-carbonyl)indole The title compound was prepared according to the procedure described in Example 19 employing 3-amino-6-chloro-2-(4-methylpyridine-2-carbonyl)indole (Example 70) and (S)-(−)-2-acetoxypropionyl chloride. m.p.: 213–214° C.

$^1$H-NMR (CDCl$_3$) δ: 12.06 (1 H, br s), 11.53 (1 H, br s), 8.61 (1 H, d, J=4.9 Hz), 8.57 (1 H, d, J=9.1 Hz), 8.16 (1 H, t, J=0.9 Hz), 7.40 (1 H, dd, J=1.8, 0.9 Hz), 7.36 (1 H, ddd, J=4.9, 1.8, 0.8 Hz), 7.05 (1 H, dd, J=8.9, 1.8 Hz), 5.49 (1 H, q, J=6.9 Hz), 2.51 (3 H, s), 2.42 (3 H, s), 1.67 (3 H, d, J=6.9 Hz).

Ex. 383

6-Chloro-3-[[(s)-2-hydroxypropionyl]amino]-2-(4-methylpyridine-2-carbonyl)indole The title compound was prepared according to the procedure described in Example 361 employing 3-[[(S)-2-acetoxypropionyl]amino]-6-chloro-2-(4-methylpyridine-2-carbonyl)indole (Example 382). m.p.: 206–207° C.

¹H-NMR (CDCl₃) δ: 12.07 (1 H, br s), 11.52 (1 H, br s), 8.64 (1 H, d, J=5.1 Hz), 8.54 (1 H, d, J=9.2 Hz), 8.21 (1 H, s), 7.42 (1 H, d, J=1.8 Hz), 7.38 (1H, ddd, J=4.9, 1.7, 0.9 Hz), 7.07 (1 H, dd, J=9.0, 1.9 Hz), 4.55 (1 H, br s), 2.89 (1 H, d, J=4.3 Hz), 2.50 (3H, s), 1.66 (3 H, d, J=6.8 Hz).

Ex. 384

6-Chloro-3-(2-chloroacetylamino)-2-(4-methylpyridine-2-carbonyl)indole

The title compound was prepared, according to the procedure described in Example 19 employing 3-amino-6-chloro-2-(4-methylpyridine-2-carbonyl)indole (Example 70) and chloroacetyl chloride. m.p.: 224–225° C.

¹H-NMR (CDCl₃) δ: 12.12 (1 H, br s), 11.65 (1 H, br s), 8.64 (1 H, d, J=5.1 Hz), 8.43 (1 H, d, J=8.7 Hz), 8.23 (1 H, s), 7.43 (1 H, d, J=1.8 Hz), 7.39 (1 H, ddd, J=4.4, 1.0, 0.6 Hz), 7.07 (1 H, dd, J=9.2, 2.0 Hz), 4.32 (2H, s), 2.50 (3H, s).

Ex. 385

6-Chloro-3-[2-(N,N-dimethylamino)acetylamino]-2-(4-methylpyridine-2-carbonyl)indole The title compound was prepared according to the procedure in step 2 of Example 122 employing 6-chloro-3-(2-chloroacetylamino)-2-(4-methylpyridine-2-carbonyl)indole (Example 384). m.p.: 193–194° C. ¹H-NMR (CDCl₃) δ: 12.08 (1 H, br s), 11.67 (1 H, br s), 8.62 (1 H, d, J=4.9 Hz), 8.48 (1 H, d, J=9.1 Hz), 8.22 (1 H, t, J=0.8 Hz), 7.41 (1 H, dd, J=2.0, 0.5 Hz), 7.36 (1 H, ddd, J=5.0, 1.8, 0.7 Hz), 7.05 (1 H, dd, J=9.1, 2.0 Hz), 3.24 (2 H, s), 2.51 (6 H, s), 2.50 (3 H, s).

Ex. 386

6-Chloro-3-(3-chloropropionylamino)-2-(4-methylpyridine-2-carbonyl)indole

The title compound was prepared according to the procedure described in Example 19 employing 3-amino-6-chloro-2-(4-methylpyridine-2-carbonyl)indole (Example 70) and 3-chloropropionyl chloride.

¹H-NMR (CDCl₃) δ: 11.96 (1 H, br s), 10.97 (1 H, br s), 8.60 (1 H, d, J=4.9 Hz), 8.44 (1 H, d, J=8.9 Hz), 8.14 (1 H, s), 7.35–7.39 (2 H, m), 7.04 (1 H, dd, J=9.1, 1.5 Hz), 3.96 (2 H, t, J=6.7 Hz), 3.03 (2 H, t, J=6.7 Hz), 2.50 (3H, s).

Ex. 387

6-Chloro-3-[3-(N,N-dimethylamino)propionylamino]-2-(4-methylpyridine-2-carbonyl)indole The title compound was prepared according to the procedure described in step 2 of Example 122 employing 6-chloro-3-(3-chloropropionylamino)-2-(4-methylpyridine-2-carbonyl)indole (Example 386). m.p.: 170–171° C.

¹H-NMR (CDCl₃) δ: 12.04 (1 H, br s), 11.37 (1 H, br s), 8.62 (1 H, d, J=5.1 Hz), 8.33 (1 H, d, J=9.1 Hz), 8.17 (1 H, t, J=0.8 Hz), 7.40 (1 H, dd, J=1.9, 0.6 Hz), 7.36 (1 H, ddd, J=4.9, 1.8, 0.8 Hz), 7.32 (1 H, dd, J=9.0, 1.9 Hz), 2.78–2.84 (2 H, m), 2.68–2.74 (2 H, m), 2.51 (3 H, s), 2.39 (6 H, s).

Ex. 388

6-Chloro-2-(3-hydroxymethyl-2-furoyl)-3-(2-isobutyrylamino)indole

Sep 1. 2-(3-acetoxymethyl-2-furoyl)-3-amino-6-chloro-1-(ethoxycarbonyl)indole

The title compound was prepared according to the procedure described in Step 2 of Example 1 from 4-chloro-2-(ethoxycarbonylamino)benzonitrile (Example 1, step 1) and 3-acetoxymethyl-2-(bromoacetyl)furan (Example 372, step 1).

¹H-NMR (CDCl₃) δ: 8.27 (1H, d, J=1.3 Hz), 7.51 (1H, d, J=8.2), 7.43 (1H, d, J=1.6 Hz), 7.27 (1H, dd, J=2.0, 8.4 Hz), 6.60 (1H, d, J=1.6 Hz), 5.50 (2H, s), 4.03 (2H, q, J=7.1 Hz), 2.14 (3H, s), 1.03 (3H, t, J=7.1 Hz).

Step 2. 2-(3-Acetoxymethyl-2-furoyl)-6-chloro-1-ethoxycarbonyl-3-(isobutyrylamino)indole The title compound was prepared according to the procedure described in step 1 of Example 2 employing 2-(3-acetoxymethyl-2-furoyl)-3-amino-6-chloro-1-(ethoxycarbonyl)indole (step 1) and isobutyryl chloride.

Step 3. 6-Chloro-2-(3-hydroxymethyl-2-furoyl)-3-(isobutyrylamino)indole

The title compound was prepared, according to the procedure described in step 4 of Example 373 employing 2-(3-acetoxymethyl-2-furoyl)-6-chloro-1-ethoxycarbonyl-3-(isobutyrylamino)indole (step 2). m.p.: 170–171 ° C.

¹H-NMR (CDCl₃) δ: 10.87 (1 H, br s), 9.47 (1 H, br s), 8.52 (1 H, d, J=8.9 Hz), 7.71 (1 H, d, J=1.6 Hz), 7.37 (1 H, d, J=1.3 Hz), 7.08 (1 H, dd, J=9.0, 1.8 Hz), 6.68 (1 H, d, J=1.8 Hz), 4.83 (2 H, d, J=6.8 Hz), 4.57 (1 H, t, J=6.9 Hz), 2.71–2.82 (1 H, m), 1.37 (6 H, d, J=6.9 Hz).

EXAMPE 389

2-(2-Amino-5-chlorobenzoyl)-6-chloro-3-(propionylamino)indole

Step 1. 3-Amino-6-chloro-2-(5-chloro-2-nitrobenzoyl)-1-(ethoxycarbonyl)indole

The title compound was prepared according to the procedure described in step 2 of Example 1 from 4-chloro-2-(ethoxycarbonylamino)benzonitrile (Example 1, step 1) and 5-chloro-2-nitrophenacyl bromide (Schofield, K.; and Simpson, J. C. E.; *J. Chem. Soc.*, 1947, 1170–1174.).

¹H-NMR (CDCl₃) δ: 8.12 (1 H, d, J=1.8 Hz), 7.95 (1 H, d, J=8.4 Hz), 7.56–7.48 (3 H, m), 7.31 (1 H, dd, J=1.6, 8.4 Hz), 6.32 (2 H, br s), 3.99 (2 H, q, J=7.1 Hz), 1.09 (3 H, t, J=7.1 Hz).

Step 2. 3-Amino-6-chloro-2-(5-chloro-2-nitrobenzoyl)indole

The title compound was prepared according to the procedure described in step 3 of Example 1 from 3-amino-6-chloro-2-(5-chloro-2-nitrobenzoyl)-1-(ethoxycarbonyl)indole (step 1). m.p.: 233–234° C.

IR (KBr) ν: 3439, 1626, 1512, 1337, 1312, 1267, 1242, 1061, 880 cm⁻¹

¹H-NMR (DMSO-d₆) δ: 10.26 (1 H, br s), 8.25 (1 H, d, J=8.7 Hz), 7.92 (1 H, d, J=8.7 Hz), 7.86 (1 H, dd, J=2.3, 8.7 Hz), 7.77 (1 H, d, J=2.3 Hz), 7.15 (1 H, d, J=1.6 Hz), 6.97 (2 H, br s), 6.95 (1 H, dd, J=1.6, 8.6 Hz).

Step 3. 6-Chloro-2-(5-chloro-2-nitrobenzoyl)-3-(propionylamino)indole

The title compound were prepared according to the procedure described in Example 19 from 3-amino-6-chloro-2-(5-chloro-2-nitrobenzoyl)indole (step 2) and propionyl chloride. m.p.: 245–246° C. IR (KBr) ν: 3078, 1665, 1628, 1580, 1526, 1497, 1340, 1313, 1238, 1022, 843 cm⁻¹ ¹H-NMR (DMSO-d₆) δ: 12.09 (1 H, br s), 9.26 (1 H, br s), 8.29 (1 H, d, J=8.7 Hz), 7.87 (1 H, dd, J=2.3, 8.7 Hz), 7.66 (1 H, d, J=2.0 Hz), 7.49 (1 H, d, J=8.6 Hz), 7.46 (1 H, d, J=2.0 Hz), 7.11 (1 H, dd, J=1.8, 8.7 Hz), 1.89 (2 H, q, J=7.9 Hz), 0.84 (3 H, t, J=7.9 Hz).

Step 4. 2-(2-Amino-5-chlorobenzoyl)-6-chloro-3-(propionylamino)indole

A suspension of 6-chloro-2-(5-chloro-2-nitrobenzoyl)-3-(propionylamino)indole (step 3, 540 mg, 1.33 mmol), ammonium chloride (35.6 mg, 0.665 mmol), iron powder (391 mg, 6.65 mmol), ethanol (20 ml) and water (10 ml) was heated at reflux temperature for 1 h. After cooling to room temperature, the mixture was filtered through a pad of Celite. The filtrate was concentrated to give a crystalline residue. Purification by flash column chromatography eluting with ethyl acetate/hexane (1:3) afforded 394 mg (79%) of 2-(2-amino-5-chlorobenzoyl)-6-chloro-3-(propionylamino)indole. $^1$H-NMR (CDCl$_3$) δ: 11.67 (1H, br s), 9.76 (1H, br s), 7.58 (1H, d, J=8.6 Hz), 7.43 (1H, d, J=1.5 Hz), 7.35 (1H, d, J=2.5 Hz), 7.26 (1H, dd, J=2.5, 8.9 Hz), 7.09 (1H, dd, J=1.8, 8.6 Hz), 6.99 (2H, br s), 6.83 (1H, d, J=8.9 Hz), 2.12 (2H, q, J=7.6 Hz), 0.90 (3H, t, J=7.6 Hz).

Ex. 390

2-(2-Amino-5-chlorobenzoyl)-6-chloro-3-(propionylamino)indole hydrochloride 2-(2-Amino-5-chlorobenzoyl)-6-chloro-3-(propionylamino)indole (Example 389, 394 mg) was dissolved in 10% HCl-methanol (10 ml) and the solvent was removed. The residue was crystallized from ethyl acetate/ethanol to give 175 mg (41%) of the title compound. m.p.: 184–185° C. IR(KBr)ν: 3200, 1618, 1541, 1491, 1321, 1232, 1061, 920 cm$^{-1}$ $^1$H-NMR (DMSO-d$_6$) δ: 11.70 (1 H, br s), 9.79 (1 H, br s), 7.59 (2 H, br d, J=8.6 Hz), 7.44 (1 H, d, J=1.6 Hz), 7.36 (1 H, d, J=2.5 Hz), 7.28 (1 H, dd, J=2.5, 8.7 Hz), 7.10 (1 H, dd, J=1.6, 8.6 Hz), 6.85 (1 H, d, J=8.7 Hz), 2.12 (2 H, q, J=7.6 Hz), 0.89 (3 H, t, J=7.6 Hz).

Ex. 391

2-(2-Acetylamino-5-chlorobenzoyl)-6-chloro-3-(propionylamino)indole

To a solution of 2-(2-amino-5-chlorobenzoyl)-6-chloro-3-(propionylamino)indole (Example 389, 217 mg, 0.576 mmol) and pyridine (0.12 ml, 1.50 mmol) in dichloromethane (10 ml) was added acetyl chloride (53 μl, 0.749 mmol) at 0° C. After stirring at room temperature for 1 h, the mixture was concentrated and the residue was diluted with ethyl acetate (100 ml). The solution was washed with 2N aqueous HCl (30 ml×2), saturated aqueous sodium bicarbonate (30 ml), and dried (MgSO$_4$). Removal of solvent gave a crystalline residue. Recrystallization from ethyl acetate gave 163 mg (68%) of the title compound. m.p.: 264–266° C. IR (KBr) ν: 3260, 1676, 1655, 1578, 1547, 1508, 1313, 1234, 1205, 1006, 918, 841 cm$^{-1}$ $^1$H-NMR (DMSO-d$_6$) δ: 11.77 (1 H, br s), 10.09 (1 H, br s), 9.39 (1 H, br s), 7.77 (1 H, d, J=8.4 Hz), 7.63 (1 H, d, J=8.7 Hz), 7.60 (1 H, dd, J=1.5, 8.1 Hz), 7.44 (1 H, s), 7.40 (1 H, d, J=2.6 Hz), 7.09 (1 H, d, J=8.7 Hz), 2.02 (2 H, q, J=7.7 Hz), 1.93 (3 H, s), 0.84 (3 H, t, J=7.7 Hz).

Ex. 392

6-Chloro-2-[3-(hydroxmethyl)pyridine-2-carbonyl]-3-(propioalamino)indole

Step 1. 3-tert-Butyldimethylsilyloxymethyl-2-chloropyridine

To a solution of 2-chloro-3-(hydroxymethyl)pyridine (Read, M. W; and Ray, P. S.; *J. Heterocyclic. Chem.*, 1995, 32, 1595–1597., 2.81 g, 19.1 mmol) and imidazole (3.25 g, 47.7 mmol) in N,N-dimethylformamide (30 ml) was added tert-butyldimethylsilyl chloride (3.74 g, 24.8 mmol) at 0° C. The mixture was allowed to warm to room temperature and stirred for 17 h. The solution was diluted with diethyl ether (200 ml), and the resulting solution was washed with water (100 ml×3), and dried (MgSO$_4$). Removal of solvent gave an oily residue. Purification by flash column chromatography eluting with ethyl acetate/hexane (1:15) afforded 3.61 g (73%) of the title compound.

$^1$H-NMR (CDCl$_3$) δ: 8.28 (1 H, dd, J=2.0, 4.7 Hz), 7.91 (1 H, dd, J=2.0, 8.1 Hz), 7.28 (1 H, dd, J=4.8, 8.1 Hz), 4.75 (2 H, s), 0.97 (9 H, s), 0.15 (6 H, s).

Step 2. 2-Bromoacetyl-3-(tert-butyldimethylsilyloxymethyl)pyridine

The title compound was prepared according to the procedure described in step 1 of Example 366 employing 3-(tert-butyldimethylsilyloxy)methyl-2-chloropyridine (step 1).

$^1$H-NMR (CDCl$_3$) δ: 8.56 (1 H, dd, J=1.8, 4.6 Hz), 8.27 (1 H, dd, J=1.8, 7.9 Hz), 7.54 (1 H, dd, J=4.7, 7.8 Hz), 5.13 (2 H, s), 4.92 (2 H, s), 0.97 (9 H, s), 0.14 (6 H, s).

Step 3. 3-Amino-2-[3-(tert-butyldimethylsilyloxymethyl)pyridine-2-carbonyl]-6-chloro-1-(ethoxycarbonyl)indole The title compound was prepared according to the procedure described in step 2 of Example 1 employing 4-chloro-2-(ethoxycarbonylamino)benzonitrile (Example 1, step 1) and 2-bromoacetyl-3-(tert-butyldimethylsilyloxymethyl)pyridine (step 2).

$^1$H-NMR (CDCl$_3$) δ: 8.42 (1 H, br d, J=4.6 Hz), 8.21–8.16 (2 H, m), 7.50 (1 H, d, J=8.4 Hz), 7.38 (1 H, dd, J=4.7, 7.7 Hz), 7.24 (1 H, dd, J=1.8, 8.4 Hz), 5.96 (2 H, br s), 5.17 (2 H, s), 3.69 (2 H, q, J=7.1 Hz), 0.99 (9 H, s), 0.93 (3 H, t, J=7.1 Hz), 0.17 (6 H, s).

Step 4. 2-[3-(tert-Butyldimethylsilyloxymethyl)pyridine-2-carbonyl]-6-chloro-1-ethoxycarbonyl-3-(propionylamino)indole The title compound was prepared according to the procedure described in step 1 of Example 2 employing 3-amino-2-[3-(tert-butyldimethylsilyloxymethyl)pyridine-2-carbonyl]-6-chloro-1-(ethoxycarbonyl)indole (step 3) and propionyl chloride. $^1$H-NMR (CDCl$_3$) δ: 9.48 (1 H, br s), 8.45 (1 H, dd, J=1.5, 4.5 Hz), 8.25 (1 H, dd, J=1.5, 8.1 Hz), 8.16 (1 H, d, J=1.8 Hz), 8.08 (1 H, d, J=8.9 Hz), 7.44 (1 H, dd, J=4.6, 7.9 Hz), 7.25 (1 H, dd, J=1.8, 8.8 Hz), 5.20 (2 H, s), 3.86 (2 H, q, J=7.1 Hz), 2.50 (2 H, q, J=7.6 Hz), 1.26 (3 H, t, J=7.6 Hz), 1.00 (9 H, s), 1.00 (3 H, t, J=7.0 Hz), 0.18 (6 H, s).

Step 5. 2-[3-(tert-Butyldimethylsilyloxymethyl)pyridine-2-carbonyl]-6-chloro-3-(propionylamino)indole To a solution of 2-[3-(tert-butyldimethylsilyloxymethyl)pyridine-2-carbonyl]-6-chloro-1-ethoxycarbonyl-3-(propionylamino)indole (step 4, 890 mg, 1.64 mmol) in ethanol-THF (2:1, 30 ml) was added 2N aqueous NaOH (5 ml) at 0° C. After stirring for 1.5 h, the mixture was neutralized with 2N aqueous HCl (5 ml). The mixture was concentrated and the residue was diluted with ethyl acetate (200 ml). The organic solution was washed with water (50 ml×2), dried (MgSO$_4$), and concentrated. The residue was purified by flash column chromatography eluting with ethyl acetate/hexane (1:15) to afford 663 mg (82%) of the title compound.

$^1$H-NMR (CDCl$_3$) δ: 11.53 (1 H, br s), 10.75 (1 H, br s), 8.67 (1 H, d, J=3.8 Hz), 8.45 (1 H, d, J=8.9 Hz), 8.41 (1 H, d, J=8.1 Hz), 7.59 (1 H, dd, J=4.8, 8.2 Hz), 7.37 (1 H, d, J=2.0 Hz), 7.04 (1 H, dd, J=1.8, 8.9 Hz), 5.26 (2 H, s), 2.63 (2 H, q, J=7.7 Hz), 1.36 (3 H, t, J=7.7 Hz), 0.99 (9 H, s), 0.18 (6 H, s).

Step 6. 6-Chloro-2-[3-(hydroxymethyl)pyridine-2-carbonyl]-3-(propionylamino)indole To a solution of 2-[(3-tert-butyldimethylsilyloxymethyl)pyridine-2-carbonyl]-6-chloro-3-(propionylamino)indole (step 5, 544 mg, 1.15 mmol) and acetic acid (0.20 ml, 3.50 mmol) in THF (30 ml) was added tetra(n-butylammonium)fluoride (1M in THF, 3.5 ml, 3.50 mmol) at 0° C. The mixture was stirred for 4.5 h at the same temperature and diluted with diethyl ether (200 ml). This solution was washed with saturated aqueous sodium bicarbonate (50 ml), water (50 ml×2), and dried (MgSO$_4$). Removal of solvent gave a crystalline residue. Recrystallization from ethyl acetate afforded 361 mg (88%) of the title compound. m.p.: 198–199° C. IR (KBr) ν: 3250, 1663, 1624, 1607, 1578, 1541, 1472, 1352, 1211, 1178, 1153, 1074, 1045, 1013, 833, 808, 716 cm$^{-1}$ $^1$H-NMR (CDCl$_3$) δ: 11.33 (1 H, br s), 10.74 (1 H, br s), 8.75 (1 H, dd, J=1.6, 4.8 Hz), 8.47 (1 H, d, J=9.1 Hz), 8.00 (1 H, dd, J=1.5, 7.7 Hz), 7.57 (1 H, dd, J=4.8, 7.7 Hz), 7.36 (1 H, d, J=1.8 Hz), 7.05 (1 H, dd, J=1.8 and 9.1 Hz), 4.87 (2 H, d, J=7.3 Hz), 4.00 (1 H, t, J=7.1 Hz), 2.62 (2 H, q, J=7.6 Hz), 1.36 (3 H, t, J=7.6 Hz).

Example 393

3-Acetylamino-2-benzoyl-7-chloroindole

Step 1. 7-Chloro-3-nitroindole-2-carboxylic acid

Seventy percent nitric acid (3.4 ml) was added to dropwise to acetic anhydride (35 ml) with stirring at room temperature. The mixture was then cooled in an ice bath and 7-chloroindole-2-carboxylic acid (EP 0 622 356 A1, 1.71 g, 8.74 mmol) was added carefully. After stirring for an additional 1.5 h, the suspension was filtered and the filter cake washed with hexane and air-dried. The yield of 7-chloro-3-nitroindole-2-carboxylic acid , yellow solids, was 283 mg (14%). $^1$H-NMR (DMSO-d$_6$) δ: 13.66 (1H, br s), 8.04 (1H, dd, J=1.1, 8.1 Hz), 7.53 (1H, dd, J=1.1, 7.7 Hz), 7.42 (1H, dd, J=7.7, 8.1 Hz).

Step 2. 7-Chloro-2-[(N-methoxy-N-methylamino)carbonyl]-3-nitroindole

A solution of 7-chloro-3-nitroindole-2-carboxylic acid (step 1, 400 mg, 1.7 mmol) in thionyl chloride (2 ml) was heated at 70° C. for 3 h, the mixture cooled and concentrated. The residue was dissolved in dichloromethane (20 ml). To the solution was added N,O-dimethylhydroxylamine hydrochloride (326 mg, 3.4 mmol) and pyridine (0.27 ml, 3.4 mmol). After stirring for 16 h, the mixture was poured into water (100 ml) and extracted with ethyl acetate (200 ml). The organic layer was washed with 2N aqueous HCl (100 ml), water (100 ml), saturated aqueous sodium bicarbonate (100 ml), brine (100 ml), and dried (MgSO$_4$). After removal of solvent, the residue was purified by flash column chromatography eluting with ethyl acetate/hexane (1:10~1:1) to give 420 mg (87%) of the title compound. tlc: Rf=0.55 (25% ethyl acetate in hexanes)

Step 3. 3-Amino-7-chloro-2-[(N-methoxy-N-methylamino)carbonyl]indole

To a solution of 7-chloro-2-[(N-methoxy-N-methylamino)carbonyl]-3-nitroindole (step 2, 420 mg, 1.5 mmol) in ethanol-water (2:1, 30 ml) was added iron powder (168 mg, 3 mmol) and ammonium chloride (160 mg, 3 mmol). The mixture was heated at 50° C. for 2 h, and then cooled to room temperature. After filtration through a pad of Celite, the filtrate was concentrated. The residue was purified by flash column chromatography eluting with ethyl acetate/hexane (1:10~1:1) to give 287 mg (75%) of the title compound.

$^1$H-NMR (CDCl$_3$) δ: 8.56 (1H, br s), 7.46 (1H, d, J=7.9 Hz), 7.28 (1H, d, J=7.6 Hz), 6.94 (1H, t, J=7.6, 7.9 Hz), 5.27 (1H, br s), 3.82 (3H, s), 3.36 (3H, s)

Step 4. 3-Acetylamino-7-chloro-2-[(N-methoxy-N-methylamino)carbonyl]indole

To a solution of 3-amino-7-chloro-2-[(N-methoxy-N-methylamino)carbonyl]indole (step 3, 287 mg, 1.1 mmol) in dichloromethane (10 ml) was added pyridine (2 ml) and acetic anhydride (0.16 ml, 1.7 mmol) at room temperature. After stirring for 3 h, the mixture was poured into water (100 ml) and extracted with ethyl acetate (150 ml). The organic layer was washed with 2N aquous HCl (100 ml), water (100 ml), saturated aqueous sodium bicarbonate (100 ml), brine (100 ml), and dried (MgSO$_4$). After removal of solvent, the residue was purified by flash column chromatography eluting with ethyl acetate/hexane (1:10l:1) to give 320 mg (98%) of the title compound.

$^1$H-NMR (CDCl$_3$) δ: 9.95 (1H,br s), 9.19 (1H,d,J=7.6 Hz), 8.08 (1H,d,J=8.4 Hz), 7.31 (1H, d, J=7.6 Hz), 7.04 (1H, dd, J=7.6, 8.4 Hz), 3.82 (3H, s), 3.41 (3H, s)

Step 5. 3-Acetylamino-2-benzoyl-7-chloroindole

To a solution of 3-acetylamino-7-chloro-2-[(N-methoxy-N-methylamino)carbonyl]indole (step 4, 321 mg, 1.08 mmol) in diethyl ether-tetrahydrofuran (1:1, 10 ml) was added phenyl lithium (1M solution in cyclohexane, 5.4 ml, 5.42 mmol) at −78° C. After stirring for 1 h, the mixture was allowed to warm to 0° C. and stirred for an additional 2 h. The mixture was quenched with saturated aqueous ammonium chloride (20 ml) and extracted with ether (150 ml). The organic layer was washed with water (50 ml) and dried (MgSO$_4$). Removal of solvent gave an oily residue. Purification by flash column chromatography eluting with ethyl acetate/hexane (1:3) afforded yellow crystals. Recrystallization from ethyl acetate gave 87 mg, (26%) of the title compound. m.p.: 185–188° C. IR (KBr) ν: 3240, 1690, 1628, 1543, 1375, 1315, 1250, 725 cm$^1$ $^1$H-NMR (CDCl$_3$) δ: 9.77 (1 H, br s), 8.36 (1 H, br s), 8.18 (1 H, d, J=8.6 Hz), 7.87–7.83 (2 H, m), 7.71–7.57 (3 H, m), 7.40 (1 H, dd, J=1.0, 7.6 Hz), 7.10 (1 H, dd, J=7.6, 8.4 Hz), 2.26 (3 H, s).

The chemical structures of the compounds prepared in the Examples 1 to 393 are summarized in the following tables.

TABLE

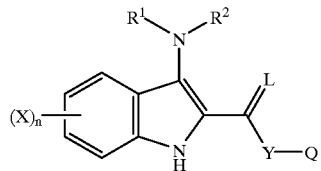

| Ex. # | L | X | Y | R¹ | R² | Q |
|---|---|---|---|---|---|---|
| 1 | O | 6-Cl | — | H | H | phenyl |
| 2 | O | 6-Cl | — | H | CH₃—C(O)— | phenyl |
| 3 | O | 6-Cl | — | H | (CH₃)₂C(O)— | phenyl |
| 4 | O | 6-Cl | — | H | phenyl-C(O)— | phenyl |
| 5 | O | 6-Cl | — | H | C₂H₅—C(O)— | phenyl |
| 6 | O | 6-Cl | — | H | CH₂=CH—C(O)— | phenyl |
| 7 | O | 6-Cl | — | H | C₃H₇—C(O)— | phenyl |
| 8 | O | 6-Cl | — | H | cyclohexyl-C(O)— | phenyl |
| 9 | O | 6-Cl | — | H | (CH₃)₃C—C(O)— | phenyl |
| 10 | O | 6-Cl | — | H | (CH₃)₂CH—CH₂—C(O)— | phenyl |
| 11 | O | 6-Cl | — | H | cyclopropyl-C(O)— | phenyl |
| 12 | O | 6-Cl | — | H | C₄H₉—C(O)— | phenyl |
| 13 | O | 6-Cl | — | H | 2-thienyl-C(O)— | phenyl |
| 14 | O | 6-Cl | — | H | phenyl-(CH₂)₂—C(O)— | phenyl |
| 15 | O | 6-Cl | — | H | F₃C—C(O)— | phenyl |
| 16 | O | 6-Cl | — | H | CH₃—O—CH₂—C(O)— | phenyl |
| 17 | O | 6-Cl | — | H | CH₃—C(O)— | 4-methoxyphenyl |
| 18 | O | 6-Cl | — | H | H | 3-methoxyphenyl |
| 19 | O | 6-Cl | — | H | CH₃—C(O)— | 3-methoxyphenyl |
| 20 | O | 6-Cl | — | H | CH₃—C(O)— | 2-methylphenyl |
| 21 | O | 6-Cl | — | H | H | 3-methylphenyl |
| 22 | O | 6-Cl | — | H | CH₃—C(O)— | 3-methylphenyl |
| 23 | O | 6-Cl | — | H | C₂H₅—C(O)— | 3-methylphenyl |
| 24 | O | 6-Cl | — | H | C₃H₇—C(O)— | 3-methylphenyl |
| 25 | O | 6-Cl | — | H | C₄H₉—C(O)— | 3-methylphenyl |
| 26 | O | 6-Cl | — | H | (CH₃)₂CH—CH₂—C(O)— | 3-methylphenyl |
| 27 | O | 6-Cl | — | H | CH₃—O—CH₂—C(O)— | 3-methylphenyl |
| 28 | O | 6-Cl | — | H | CH₃—C(O)— | 4-methylphenyl |
| 29 | O | 6-Cl | — | H | CH₃—C(O)— | 2-chlorophenyl |
| 30 | O | 6-Cl | — | H | H | 3-chlorophenyl |
| 31 | O | 6-Cl | — | H | CH₃—C(O)— | 3-chlorophenyl |
| 32 | O | 6-Cl | — | H | C₂H₅—C(O)— | 3-chlorophenyl |
| 33 | O | 6-Cl | — | H | C₃H₇—C(O)— | 3-chlorophenyl |
| 34 | O | 6-Cl | — | H | C₄H₉—C(O)— | 3-chlorophenyl |
| 35 | O | 6-Cl | — | H | (CH₃)₂CH—CH₂—C(O)— | 3-chlorophenyl |
| 36 | O | 6-Cl | — | H | CH₃—O—CH₂—C(O)— | 3-chlorophenyl |
| 37 | O | 6-Cl | — | H | CH₃—C(O)— | 4-chlorophenyl |
| 38 | O | 6-Cl | — | H | CH₃—C(O)— | 3-fluorophenyl |
| 39 | O | 6-Cl | — | H | CH₃—C(O)— | 4-fluorophenyl |
| 40 | O | 6-Cl | — | H | H | 4-CH₃S-phenyl |
| 41 | O | 6-Cl | — | H | CH₃—C(O)— | 4-CH₃S-phenyl |
| 42 | O | 6-Cl | — | H | H | 3-bromophenyl |
| 43 | O | 6-Cl | — | H | CH₃—C(O)— | 3-bromophenyl |
| 44 | O | 6-Cl | — | H | CH₃—C(O)— | 3-benzyloxyphenyl |
| 45 | O | 6-Cl | — | H | CH₃—C(O)— | 3-hyroxyphenyl |
| 46 | O | 6-Cl | — | H | CH₃—C(O)— | 3,4-dichlorophenyl |
| 47 | O | 6-Cl | — | H | H | 3,5-difluorophenyl |
| 48 | O | 6-Cl | — | H | CH₃—C(O)— | 3,5-difluorophenyl |
| 49 | O | 6-Cl | — | H | H | 3-F₃C-phenyl |
| 50 | O | 6-Cl | — | H | (CH₃)₂CH—CH₂—C(O)— | 3-F₃C-phenyl |
| 51 | O | 6-Cl | — | H | H | 4-CF₃O-phenyl |
| 52 | O | 6-Cl | — | H | CH₃—C(O)— | 4-CF₃O-phenyl |
| 53 | O | 6-Cl | — | H | H | 3-CH₃4-Cl-phenyl |
| 54 | O | 6-Cl | — | H | (CH₃)₂CH—CH₂—C(O)— | 3-CH₃4-Cl-phenyl |
| 55 | O | 6-Cl | — | H | 2-chloro-phenyl-C(O)— | phenyl |
| 56 | O | 6-Cl | — | H | C₂H₅—O—C(O)—(CH₂)₂—C(O)— | phenyl |
| 57 | O | 6-Cl | — | H | NH₂—C(O)—(CH₂)₂—C(O)— | phenyl |
| 58 | O | 6-Cl | — | H | CH₃C(O)—O—CH(CH₃)—C(O)— | phenyl |
| 59 | O | 6-Cl | — | H | CH₃CH(OH)—C(O)— | phenyl |
| 60 | O | 6-Cl | — | H | CH₃C(O)—O—(CH₃)₂C—C(O)— | phenyl |
| 61 | O | 6-Cl | — | H | (CH₃)₂(HO)C—C(O)—phenyl | |
| 62 | O | 6-Cl | — | H | CH₃—C(O)— | 2-thienyl |
| 63 | O | 6-Cl | — | H | CH₃—C(O)— | 2-furyl |
| 64 | O | 6-Cl | — | H | H | 3-pyridyl |
| 65 | O | 6-Cl | — | H | CH₃—C(O)— | 3-pyridyl |
| 66 | O | 6-Cl | — | H | H | 4-pyridyl |

TABLE-continued

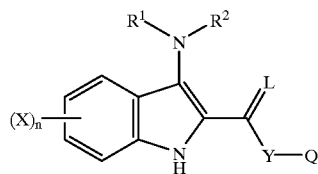

(I)

| Ex. # | L | X | Y | R¹ | R² | Q |
|---|---|---|---|---|---|---|
| 67 | O | 6-Cl | — | H | $CH_3-C(O)-$ | 4-pyridyl |
| 68 | O | 6-Cl | — | H | H | 4-Cl-2-pyridyl |
| 69 | O | 6-Cl | — | H | $CH_3-C(O)-$ | 4-Cl-2-pyridyl |
| 70 | O | 6-Cl | — | H | H | 4-$CH_3$—2-pyridyl |
| 71 | O | 6-Cl | — | H | $CH_3-C(O)-$ | 4-$CH_3$—2-pyridyl |
| 72 | O | 6-Cl | — | H | H | 4-$CH_3O$-2-pyridyl |
| 73 | O | 6-Cl | — | H | $CH_3-C(O)-$ | 4-$CH_3O$-2-pyridyl |
| 74 | O | 6-Cl | — | H | $(CH_3)_2CH-CH_2-C(O)-$ | 4-$CH_3O$-2-pyridyl |
| 75 | O | 6-Cl | — | H | H | 2-thiazolyl |
| 76 | O | 6-Cl | — | H | $CH_3-C(O)-$ | 2-thiazolyl |
| 77 | O | 6-Cl | — | H | H | 2-(5-methylfuryl) |
| 78 | O | 6-Cl | — | H | $CH_3-C(O)-$ | 2-(5-methylfuryl) |
| 79 | O | 6-Cl | — | H | H | 3-furyl |
| 80 | O | 6-Cl | — | H | $CH_3-C(O)-$ | 3-furyl |
| 81 | O | 6-Cl | — | H | H | 3-phenyl-5-isoxazolyl |
| 82 | O | 6-Cl | — | H | $CH_3-C(O)-$ | 3-phenyl-5-isoxazolyl |
| 83 | O | 6-Cl | $-CH_2-$ | H | H | phenyl |
| 84 | O | 6-Cl | $-CH_2-$ | H | $CH_3-C(O)-$ | phenyl |
| 85 | O | 6-Cl | — | H | H | methyl |
| 86 | O | 6-Cl | — | H | $CH_3-C(O)-$ | methyl |
| 87 | O | 6-Cl | — | H | H | ethyl |
| 88 | O | 6-Cl | — | H | $CH_3-C(O)-$ | ethyl |
| 89 | O | 6-Cl | — | H | H | $(CH_3)_3C-$ |
| 90 | O | 6-Cl | — | H | $CH_3-C(O)-$ | $(CH_3)_3C-$ |
| 91 | O | 6-Cl | — | H | $CH_3-C(O)-$ | 2-pyrazinyl |
| 92 | O | 6-Cl | — | H | $CH_3-C(O)-$ | 2-naphthyl |
| 93 | O | 6-Cl | — | H | H | cyclohexyl |
| 94 | O | 6-Cl | — | H | $CH_3-C(O)-$ | cyclohexyl |
| 95 | O | 6-Cl | — | H | $(CH_3)_2CH-CH_2-C(O)-$ | cyclohexyl |
| 96 | O | 5-nitro | — | H | $CH_3-C(O)-$ | phenyl |
| 97 | O | 5-nitro | — | H | $(CH_3)_2CH-CH_2-C(O)-$ | 3-chlorophenyl |
| 98 | O | 5-nitro | — | H | $CH_3-O-CH_2-C(O)-$ | 3-$CH_3$—phenyl |
| 99 | O | 5-amino | — | H | $CH_3-C(O)-$ | phenyl |
| 100 | O | 5-$H_3C$—$(O)_2S$—HN— | — | H | $CH_3-C(O)-$ | phenyl |
| 101 | O | 6-$CF_3$— | — | H | $CH_3-C(O)-$ | phenyl |
| 102 | O | 5-Br | — | H | $CH_3-C(O)-$ | phenyl |
| 103 | O | 5-Cl | — | H | $CH_3-C(O)-$ | phenyl |
| 104 | O | 5-Cl | — | H | $C_2H_5-C(O)-$ | 3-Cl-phenyl |
| 105 | O | — | — | H | $CH_3-C(O)-$ | phenyl |
| 106 | O | 4-Cl | — | H | $CH_3-C(O)-$ | phenyl |
| 107 | O | 4-F | — | H | $CH_3-C(O)-$ | phenyl |
| 108 | O | 6-F | — | H | $CH_3-C(O)-$ | phenyl |
| 109 | O | 6-$CH_3$ | — | H | $CH_3-C(O)-$ | phenyl |
| 110 | O | 6-cyano | — | H | $CH_3-C(O)-$ | phenyl |
| 111 | O | 5-Br,6-Cl | — | H | $CH_3-C(O)-$ | 2-(6-$CH_3$—pyridyl) |
| 112 | O | 6-Cl | — | H | H | 2-(6-$CH_3$—pyridyl) |
| 113 | O | 6-Cl | — | H | $CH_3-C(O)-$ | 2-(6-$CH_3$—pyridyl) |
| 114 | O | 6-Cl | — | H | 2-tetrahydrofuryl-C(O)— | phenyl |
| 115 | O | 6-Cl | — | H | $(CH_3O)(CH_3)C-C(O)-$ | phenyl |
| 116 | O | 6-Cl | — | H | $CF_3-CH_2-C(O)-$ | phenyl |
| 117 | O | 6-Cl | — | H | cyclopropyl-$CH_2$—C(O)— | phenyl |
| 118 | O | 6-Cl | — | H | $(CH_3)_2(HO)C-CH_2-C(O)-$ | phenyl |
| 119 | O | 6-Cl | — | H | $CH_3S-CH_2-C(O)-$ | phenyl |
| 120 | O | 6-Cl | — | H | $CH_3-S(O)-CH_2-C(O)-$ | phenyl |
| 121 | O | 6-Cl | — | H | $CH_3-S(O)2-CH_2-C(O)-$ | phenyl |
| 122 | O | 6-Cl | — | H | $(CH_3)_2N-CH_2-C(O)-$ | phenyl |
| 123 | O | 5,6-dimethoxy | — | H | $CH_3-C(O)-$ | phenyl |
| 124 | O | 6-Cl | — | H | $CH_3-C(O)-$ | 1-$CH_3$—imidazol-2-yl |
| 125 | O | 6-Cl | — | H | H | 2-pyridyl |
| 126 | O | 6-Cl | — | H | $CH_3-C(O)-$ | 2-pyridyl |
| 127 | O | 6-Cl | — | H | H | 3-cyano-phenyl |
| 128 | O | 6-Cl | — | H | H | 3-$NH_2$—C(O)-phenyl |
| 129 | O | 6-Cl | — | H | $CH_3-C(O)-$ | 3-$NH_2$—C(O)-phenyl |
| 130 | O | 6-Cl | — | H | $CH_3-C(O)-$ | 3-cyano-phenyl |

TABLE-continued

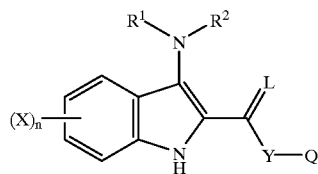

(I)

| Ex. # | L | X | Y | R$^1$ | R$^2$ | Q |
|---|---|---|---|---|---|---|
| 131 | O | 6-Cl | — | H | H | 3-HO—C(O)-phenyl |
| 132 | O | 6-Cl | — | H | CH$_3$—C(O)— | 3-HO—C(O)-phenyl |
| 133 | O | 6-Cl | — | H | H | 3-H$_3$C—O—C(O)-phenyl |
| 134 | O | 6-Cl | — | H | CH$_3$—C(O)— | 3-H$_3$C—O—C(O)-phenyl |
| 135 | O | 6-Cl | — | H | CH$_3$—C(O)— | 3-NH$_2$-phenyl |
| 136 | O | 6-Cl (hydrochloride) | — | H | CH$_3$—C(O)— | 3-NH$_2$-phenyl |
| 137 | O | 6-Cl | — | H | CH$_3$—C(O)— | 3-CH$_3$—C(O)—HN-phenyl |
| 138 | O | 6-Cl | — | H | CH$_3$—C(O)— | 3-CH$_3$—S(O)$_2$—HN-phenyl |
| 139 | O | 6-Cl | — | H | CH$_3$—C(O)— | 3-(CH$_3$)$_2$N-phenyl |
| 140 | O | 6-Cl (hydrochloride) | — | H | CH$_3$—C(O)— | 3-(CH$_3$)$_2$N-phenyl |
| 141 | O | 6-Cl | — | H | CH$_3$—C(O)— | 3,4-(HO)$_2$-phenyl |
| 142 | O | 6-Cl | — | H | H | 3-NH$_2$-S(O)$_2$-phenyl |
| 143 | O | 6-Cl | — | H | CH$_3$—C(O)— | 3-NH$_2$-S(O)$_2$-phenyl |
| 144 | O | 6-Cl | — | H | H | 3-CH$_3$—cyclohexyl |
| 145 | O | 6-Cl | — | H | CH$_3$—C(O)— | 3-CH$_3$—cyclohexyl |
| 146 | O | 6-Cl | — | CH$_3$ | CH$_3$—C(O)— | phenyl |
| 147 | O | 6-Cl | — | CH$_3$ | CH$_3$—C(O)— | 3-CH$_3$-phenyl |
| 148 | O | 6-Cl | — | CH$_3$ | CH$_3$—C(O)— | 3-chlorophenyl |
| 149 | O | 6-Cl | — | CH$_3$ | CH$_3$—C(O)— | cyclohexyl |
| 150 | O | 6-Cl | — | HO$_2$C—CH$_2$— | CH$_3$—C(O)— | phenyl |
| 151 | O | 6-Cl | — | CH$_3$ | CH$_3$ | phenyl |
| 152 | O | 6-nitro | — | H | CH$_3$—C(O)— | phenyl |
| 153 | O | 6-amino | — | H | CH$_3$—C(O)— | phenyl |
| 154 | O | 5-CH$_3$O | — | H | CH$_3$—C(O)— | phenyl |
| 155 | O | 6-CH$_3$O | — | H | CH$_3$—C(O)— | phenyl |
| 156 | O | 5-F | — | H | CH$_3$—C(O)— | phenyl |
| 157 | O | 6-Cl | — | H | (CH$_3$)$_3$C—CH$_2$—C(O)— | phenyl |
| 158 | O | 6-Cl | — | H | 2-bromophenyl-C(O)— | phenyl |
| 159 | O | 6-Cl | — | H | 3-bromophenyl-C(O)— | phenyl |
| 160 | O | 6-Cl | — | H | bromomethyl-C(O)— | phenyl |
| 161 | O | 6-Cl | — | H | 4-bromophenyl-C(O)— | phenyl |
| 162 | O | 6-Cl | — | H | C$_{16}$H$_{33}$—C(O)— | phenyl |
| 163 | O | 6-Cl | — | H | C$_{11}$H$_{23}$—C(O)— | phenyl |
| 164 | O | 6-Cl | — | H | 3,4-dichlorophenyl-C(O)— | phenyl |
| 165 | O | 6-Cl | — | H | 3,5-dichlorophenyl-C(O)— | phenyl |
| 166 | O | 6-Cl | — | H | C$_9$H$_{19}$—C(O)— | phenyl |
| 167 | O | 6-Cl | — | H | 2-furyl-C(O)— | phenyl |
| 168 | O | 6-Cl | — | H | 4-fluorophenyl-C(O)— | phenyl |
| 169 | O | 6-Cl | — | H | 2-iodophenyl-C(O)— | phenyl |
| 170 | O | 6-Cl | — | H | C$_3$F$_7$—C(O)— | phenyl |
| 171 | O | 6-Cl | — | H | 4-CF$_3$-phenyl-C(O)— | phenyl |
| 172 | O | 6-Cl | — | H | 4-methylphenyl-S(O)$_2$—N—CH-benzyl) | phenyl |
| 173 | O | 6-Cl | — | H | C$_5$H$_{11}$—C(O)— | phenyl |
| 174 | O | 6-Cl | — | H | C$_7$H$_{15}$—C(O)— | phenyl |
| 175 | O | 6-Cl | — | H | (C$_4$H$_9$)CH(C$_2$H$_5$)—C(O)— | phenyl |
| 176 | O | 6-Cl | — | H | 3-fluorophenyl-C(O)— | phenyl |
| 177 | O | 6-Cl | — | H | C$_6$H$_{13}$—C(O)— | phenyl |
| 178 | O | 6-Cl | — | H | phenoxymethyl-C(O)— | phenyl |
| 179 | O | 6-Cl | — | H | (C$_3$H$_7$)$_2$CH—C(O)— | phenyl |
| 180 | O | 6-Cl | — | H | phenyl-CH=CH—C(O)— | phenyl |
| 181 | O | 6-Cl | — | H | phenylmethyl-C(O)— | phenyl |
| 182 | O | 6-Cl | — | H | 4-CH$_3$O-phenyl-C(O)— | phenyl |
| 183 | O | 6-Cl | — | H | CH$_3$S—(CH$_2$)$_2$—C(O)— | phenyl |
| 184 | O | 6-Cl | — | H | 2-CH$_3$O-phenyl-C(O)— | phenyl |
| 185 | O | 6-Cl | — | H | C$_{15}$F$_{31}$—C(O)— | phenyl |
| 186 | O | 6-Cl | — | H | (phenoxy)(CH$_3$)CH—C(O)— | phenyl |
| 187 | O | 6-Cl | — | H | CH$_2$=C(CH$_3$)—C(O)— | phenyl |
| 188 | O | 6-Cl | — | H | 3,5-dinitrophenyl-C(O)— | phenyl |
| 189 | O | 6-Cl | — | H | phenyl-CHCl—C(O)— | phenyl |
| 190 | O | 6-Cl | — | H | (CH$_3$)$_3$C-phenyl-C(O)— | phenyl |
| 191 | O | 6-Cl | — | H | CH$_2$Cl—(CH$_2$)$_3$—C(O)— | phenyl |
| 192 | O | 6-Cl | — | H | (CH$_3$)BrCH—C(O)— | phenyl |
| 193 | O | 6-Cl | — | H | 4-nitro-2-chlorophenyl-C(O)— | phenyl |

TABLE-continued

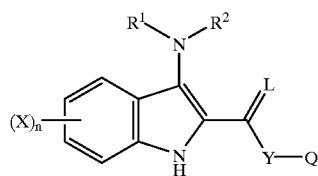

(I)

| Ex. # | L | X | Y | $R^1$ | $R^2$ | Q |
|---|---|---|---|---|---|---|
| 194 | O | 6-Cl | — | H | 4-chloromethylphenyl-C(O)— | phenyl |
| 195 | O | 6-Cl | — | H | $CH_2Cl$—$CH_2$—C(O)— | phenyl |
| 196 | O | 6-Cl | — | H | trans-$CH_3$—CH=$CH_2$—C(O)— | phenyl |
| 197 | O | 6-Cl | — | H | $(CH_3)$CHCl—C(O)— | phenyl |
| 198 | O | 6-Cl | — | H | $CH_2Cl$—$(CH_2)_2$—C(O)— | phenyl |
| 199 | O | 6-Cl | — | H | $(CH_3)_2C(CH_2Cl)$—C(O)— | phenyl |
| 200 | O | 6-Cl | — | H | $CH_2$=CH—$(CH_2)_8$—C(O)— | phenyl |
| 201 | O | 6-Cl | — | H | $C_{10}H_{21}$—C(O)— | phenyl |
| 202 | O | 6-Cl | — | H | 4-cyanophenyl-C(O)— | phenyl |
| 203 | O | 6-Cl | — | H | 4-Cl-phenyloxymethyl-C(O)— | phenyl |
| 204 | O | 6-Cl | — | H | 4-Cl-phenyl-C(O)— | phenyl |
| 205 | O | 6-Cl | — | H | $C_8H_{17}$—C(O)— | phenyl |
| 206 | O | 6-Cl | — | H | 3-nitrophenyl-C(O)— | phenyl |
| 207 | O | 6-Cl | — | H | pentafluorophenyl-C(O)— | phenyl |
| 208 | O | 6-Cl | — | H | $CCl_3$—C(O)— | phenyl |
| 209 | O | 6-Cl | — | H | 2-nitrophenoxymethyl-C(O)— | phenyl |
| 210 | O | 6-Cl | — | H | 4-nitrophenyl-C(O)— | phenyl |
| 211 | O | 6-Cl | — | H | 1-naphthyl-C(O)— | phenyl |
| 212 | O | 6-Cl | — | H | 2-naphthyl-C(O)— | phenyl |
| 213 | O | 6-Cl | — | H | 1-naphthyl-$S(O)_2$—N—CH(benzyl)-C(O)— | phenyl |
| 214 | O | 6-Cl | — | H | 4-nitrophenyl-S(O)$_2$—N—CH(benzyl)-C(O)— | phenyl |
| 215 | O | 6-Cl | — | H | $C_{17}H_{35}$—C(O)— | phenyl |
| 216 | O | 6-Cl | — | H | $C_2H_5O$—C(O)—$(CH_2)_3$—C(O)— | phenyl |
| 217 | O | 6-Cl | — | H | 2-$CF_3$-phenyl-C(O)— | phenyl |
| 218 | O | 6-Cl | — | H | 3-$CF_3$-phenyl-C(O)— | phenyl |
| 219 | O | 6-Cl | — | H | 2,4,6-trichlorophenyl-C(O)— | phenyl |
| 220 | O | 6-Cl | — | H | 3-$CH_3$—phenyl-C(O)— | phenyl |
| 221 | O | 6-Cl | — | H | 4-$CH_3$—phenyl-C(O)— | phenyl |
| 222 | O | 6-Cl | — | H | 2-$CH_3$—phenyl-C(O)— | phenyl |
| 223 | O | 6-Cl | — | H | $C_{13}H_{27}$—C(O)— | phenyl |
| 224 | O | 6-Cl | — | H | $(CH_3)_3C$—$CH_2$—$CH(CH_3)$—$CH_2$—C(O)— | phenyl |
| 225 | O | 6-Cl | — | H | 4-phenyl-phenyl-C(O)— | phenyl |
| 226 | O | 6-Cl | — | H | $(CH_3)_2C$=CH—C(O)— | phenyl |
| 227 | O | 6-Cl | — | H | 5-$CF_3$-3-F-phenyl-C(O)— | phenyl |
| 228 | O | 6-Cl | — | H | 3-$CF_3$-2-F-phenyl-C(O)— | phenyl |
| 229 | O | 6-Cl | — | H | 2,4-di$CF_3$-phenyl-C(O)— | phenyl |
| 230 | O | 6-Cl | — | H | 2-$CF_3$-4-F-phenyl-C(O)— | phenyl |
| 231 | O | 6-Cl | — | H | 3,4,5-triF-phenyl-C(O)— | phenyl |
| 232 | O | 6-Cl | — | H | $CHF_2$—$(CF_2)_3$—C(O)— | phenyl |
| 233 | O | 6-Cl | — | H | 2-chlorophenylmethyl-C(O)— | phenyl |
| 234 | O | 6-Cl | — | H | 3-$CF_3$-4-F-phenyl-C(O)— | phenyl |
| 235 | O | 6-Cl | — | H | 3,5-di$CH_3$O-phenyl-C(O)— | phenyl |
| 236 | O | 6-Cl | — | H | 2,4-difluorophenyl-C(O)— | phenyl |
| 237 | O | 6-Cl | — | H | $(C_2H_5)(CH_3)$CH—C(O)— | phenyl |
| 238 | O | 6-Cl | — | H | $C_2H_5$—CH=CH—$CH_2$—CH=CH—$CH_2$—CH=CH—$(CH_2)_7$—C(O)— | phenyl |
| 239 | O | 6-Cl | — | H | $C_{10}H_{21}$—C(O)— | phenyl |
| 240 | O | 6-Cl | — | H | $(CH_3)_3C$—$(CH_2)_5$—C(O)— | phenyl |
| 241 | O | 6-Cl | — | H | $(CH_3)_2CH$—$(CH_2)_2$—C(O)— | phenyl |
| 242 | O | 6-Cl | — | H | $CH_3CH_2C(NO_2)(CH_3)$—$(CH_2)_2$—C(O)— | phenyl |
| 243 | O | 6-Cl | — | H | $Cl_2C$=CHCl—C(O)— | phenyl |
| 244 | O | 6-Cl | — | H | 2,4,6-trifluorophenyl-C(O)— | phenyl |
| 245 | O | 6-Cl | — | H | 3-(2-Cl-6-F-phenyl)-5-methyl isoxaxol-4-yl-C(O)— | phenyl |
| 246 | O | 6-Cl | — | H | 5-$CF_3$-2-F-phenyl-C(O)— | phenyl |
| 247 | O | 6-Cl | — | H | 4-nitro-2-furyl-C(O)— | phenyl |
| 248 | O | 6-Cl | — | H | (phenoxy)(ethyl)CH—C(O)— | phenyl |
| 249 | O | 6-Cl | — | H | $CH_2Cl$—$(CH_2)_4$—C(O)— | phenyl |
| 250 | O | 6-Cl | — | H | 2-ethoxy-1-naphthyl | phenyl |
| 251 | O | 6-Cl | — | H | 2-chloro-3-pyridyl-C(O)— | phenyl |
| 252 | O | 6-Cl | — | H | 3-(2,6-diCl-phenyl)-5-methyl isoxaxol-4-yl-C(O)— | phenyl |

TABLE-continued

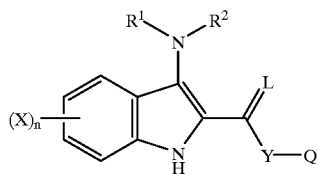

(I)

| Ex. # | L | X | Y | R¹ | R² | Q |
|---|---|---|---|---|---|---|
| 253 | O | 6-Cl | — | H | 4-CF$_3$-2-F-phenyl-C(O)— | phenyl |
| 254 | O | 6-Cl | — | H | 3-CF$_3$O-phenyl-C(O)— | phenyl |
| 255 | O | 6-Cl | — | H | (C$_3$H$_7$)(CH$_3$)CH—C(O)— | phenyl |
| 256 | O | 6-Cl | — | H | CH$_3$O—C(O)—(CH$_2$)$_4$—C(O)— | phenyl |
| 257 | O | 6-Cl | — | H | (C$_2$H$_5$)(phenyl)CH—C(O)— | phenyl |
| 258 | O | 6-Cl | — | H | 3-(2-Cl-phenyl)-5-methyl isoxaxol-4-yl-C(O)— | phenyl |
| 259 | O | 6-Cl | — | H | 4-chlorophenylmethyl-C(O)— | phenyl |
| 260 | O | 6-Cl | — | H | 4-CH$_3$—phenylmethyl-C(O)— | phenyl |
| 261 | O | 6-Cl | — | H | 1-CH$_3$—cyclohexyl-C(O)— | phenyl |
| 262 | O | 6-Cl | — | H | (CH$_2$Br)—(CH$_2$)$_2$—C(O)— | phenyl |
| 263 | O | 6-Cl | — | H | CH$_3$O—C(O)—(CH$_2$)$_2$—C(O)— | phenyl |
| 264 | O | 6-Cl | — | H | 3,4,5-tri(CH$_3$O)-phenyl-C(O)— | phenyl |
| 265 | O | 6-Cl | — | H | CH$_3$O—C(O)—(CH$_2$)$_3$—C(O)— | phenyl |
| 266 | O | 6-Cl | — | H | 2,3,4-triF-phenyl-C(O)— | phenyl |
| 267 | O | 6-Cl | — | H | 3-nitro-4-Cl-phenyl-C(O)— | phenyl |
| 268 | O | 6-Cl | — | H | 4-C$_3$H$_7$-phenyl-C(O)— | phenyl |
| 269 | O | 6-Cl | — | H | CH$_3$—C(O)—O—CH(phenyl)-C(O)— | phenyl |
| 270 | O | 6-Cl | — | H | CH$_2$Cl—CHCl—C(O)— | phenyl |
| 271 | O | 6-Cl | — | H | (CH$_2$Br)—(CH$_2$)$_3$—C(O)— | phenyl |
| 272 | O | 6-Cl | — | H | 4-CH$_3$O-phenylmethyl-C(O)— | phenyl |
| 273 | O | 6-Cl | — | H | phenyl-CH$_2$O—CH$_2$—C(O)— | phenyl |
| 274 | O | 6-Cl | — | H | 2-thienylmethyl-C(O)— | phenyl |
| 275 | O | 6-Cl | — | H | 2,3-di-F-phenyl-C(O)— | phenyl |
| 276 | O | 6-Cl | — | H | 2,5-di-F-phenyl-C(O)— | phenyl |
| 277 | O | 6-Cl | — | H | (CH$_2$Br)—CH$_2$)$_4$—C(O)— | phenyl |
| 278 | O | 6-Cl | — | H | 3,4-di(CH$_3$O)-phenyl-C(O)— | phenyl |
| 279 | O | 6-Cl | — | H | cyclobutyl-C(O)— | phenyl |
| 280 | O | 6-Cl | — | H | 3-CH$_3$O-phenyl-C(O)— | phenyl |
| 281 | O | 6-Cl | — | H | 2,6-di-F-phenyl-C(O)— | phenyl |
| 282 | O | 6-Cl | — | H | (CH$_2$Br)—CH$_2$—C(O)— | phenyl |
| 283 | O | 6-Cl | — | H | 2,3,6-triF-phenyl-C(O)— | phenyl |
| 284 | O | 6-Cl | — | H | 3-CHCl$_2$-phenyl-C(O)— | phenyl |
| 285 | O | 6-Cl | — | H | cyclopentylethyl-C(O)— | phenyl |
| 286 | O | 6-Cl | — | H | 4-butylphenyl-C(O)— | phenyl |
| 287 | O | 6-Cl | — | H | 2-CH$_3$C(O)O-phenyl-C(O)— | phenyl |
| 288 | O | 6-Cl | — | H | 3-ClCH$_2$-phenyl-C(O)— | phenyl |
| 289 | O | 6-Cl | — | H | 2-nitro-phenyl-C(O)— | phenyl |
| 290 | O | 6-Cl | — | H | 3,5-diF-phenyl-C(O)— | phenyl |
| 291 | O | 6-Cl | — | H | 3,4-di(CH$_3$O) phenyl-methyl-C(O)— | phenyl |
| 292 | O | 6-Cl | — | H | (phenyl)$_2$CH—C(O)— | phenyl |
| 293 | O | 6-Cl | — | H | 3,5-(CF$_3$)$_2$-phenyl-C(O)— | phenyl |
| 294 | O | 6-Cl | — | H | 2,4-diCl-5-F-phenyl-C(O)— | phenyl |
| 295 | O | 6-Cl | — | H | 3-methoxyphenylmethyl-C(O)— | phenyl |
| 296 | O | 6-Cl | — | H | C$_7$F$_{15}$-C(O)— | phenyl |
| 297 | O | 6-Cl | — | H | (phenyl)$_2$CCl—C(O)— | phenyl |
| 298 | O | 6-Cl | — | H | 4-C$_6$H$_{13}$-phenyl-C(O)— | phenyl |
| 299 | O | 6-Cl | — | H | 4-C$_7$H$_{15}$—O-phenyl-C(O)— | phenyl |
| 300 | O | 6-Cl | — | H | 2,5-(CF$_3$)hd 2-phenyl-C(O)— | phenyl |
| 301 | O | 6-Cl | — | H | CH$_3$O—C(O)—(CH$_2$)$_6$—C(O)— | phenyl |
| 302 | O | 6-Cl | — | H | 4-ethylphenyl-C(O)— | phenyl |
| 303 | O | 6-Cl | — | H | 2,3,4,5-tetra-F-phenyl-C(O)— | phenyl |
| 304 | O | 6-Cl | — | H | CH$_3$O—C(O)—(CH$_2$)$_8$—C(O)— | phenyl |
| 305 | O | 6-Cl | — | H | cyclopentyl-C(O)— | phenyl |
| 306 | O | 6-Cl | — | H | 3,4-diF-phenyl-C(O)— | phenyl |
| 307 | O | 6-Cl | — | H | 4-CF$_3$O-phenyl-C(O)— | phenyl |
| 308 | O | 6-Cl | — | H | 2,4,5-tri-phenyl-C(O)— | phenyl |
| 309 | O | 6-Cl | — | H | 4-butyloxyphenyl-C(O)— | phenyl |
| 310 | O | 6-Cl | — | H | 2,5-(CH$_3$O)-phenyl-methyl-C(O)— | phenyl |
| 311 | O | 6-Cl | — | H | CH$_3$—C(O)—O—CH$_2$—C(O)— | phenyl |
| 312 | O | 6-Cl | — | H | 4-pentylphenyl-C(O)— | phenyl |
| 313 | O | 6-Cl | — | H | 4-fluorophenyl-C(O)— | phenyl |
| 314 | O | 6-Cl | — | H | 4-hexyloxy-phenyl-C(O)— | phenyl |
| 315 | O | 6-Cl | — | H | 3-cyclohexenyl-C(O)— | phenyl |

TABLE-continued

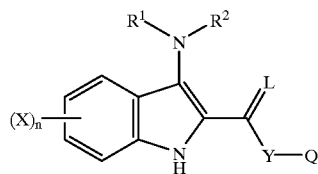

(I)

| Ex. # | L | X | Y | R¹ | R² | Q |
|---|---|---|---|---|---|---|
| 316 | O | 6-Cl | — | H | (R)-phenyl)(CF₃)(CH₃O)C—C(O)— | phenyl |
| 317 | O | 6-Cl | — | H | (S)-phenyl)(CF₃)(CH₃O)C—C(O)— | phenyl |
| 318 | O | 6-Cl | — | H | 2-fluorophenyl-C(O)— | phenyl |
| 319 | O | 6-Cl | — | H | (R)-phenyl)(NH₂)CH—C(O)— | phenyl |
| 320 | O | 6-Cl | — | H | 4-ethoxyphenyl-C(O)— | phenyl |
| 321 | O | 6-Cl | — | H | 3-chlorophenyl-C(O)— | phenyl |
| 322 | O | 6-Cl | — | H | 4-propyl)₂N—S(O)₂-phenyl-C(O)— | phenyl |
| 323 | O | 6-Cl | — | H | 1-naphthylmethyl-C(O)— | phenyl |
| 324 | O | 6-Cl | — | H | 2-F-6-CF₃-phenyl-C(O)— | phenyl |
| 325 | O | 6-Cl | — | H | CH₃O—C(O)—CH₂—C(O)— | phenyl |
| 326 | O | 6-Cl | — | H | 2-CF₃O-phenyl-C(O)— | phenyl |
| 327 | O | 6-Cl | — | H | 5-isoxazolyl-C(O)— | phenyl |
| 328 | O | 6-Cl | — | H | 2-Cl-6-F-phenyl-C(O)— | phenyl |
| 329 | O | 6-Cl | — | H | 5-tert-butyl-2-methyl-pyrazol-3-yl-C(O)— | phenyl |
| 330 | O | 6-Cl | — | H | 2,3-(CH₃)₂-phenyl-C(O)— | phenyl |
| 331 | O | 6-Cl | — | H | 2-Cl-4-F-phenyl-C(O)— | phenyl |
| 332 | O | 6-Cl | — | H | 4-Br-2-ethyl-5-methyl-pyrazol-3-yl-C(O)— | phenyl |
| 333 | O | 6-Cl | — | H | 4-methyl-1,2,3-thiadiazol-5-yl | phenyl |
| 334 | O | 6-Cl | — | H | 5-methyl-3-phenyl-isoxazol-4-yl-C(O)— | phenyl |
| 335 | O | 6-Cl | — | H | 2-chloro-5-pyridyl-C(O)— | phenyl |
| 336 | O | 6-Cl | — | H | 2-benzyl-5-tert-butyl-pyrazol-3-yl-C(O)— | phenyl |
| 337 | O | 6-Cl | — | H | 2-chloro-3-methoxy-4-thienyl-C(O)— | phenyl |
| 338 | O | 6-Cl | — | H | 3-chloro-4-(CH₃—S(O)₂-)2-thienyl-C(O)— | phenyl |
| 339 | O | 6-Cl | — | H | 1-(4-Cl-phenyl)-5-CF₃—pyrazol-4-yl-C(O)— | phenyl |
| 340 | O | 6-Cl | — | H | 5-methylisoxazol-3-yl-C(O)— | phenyl |
| 341 | O | 6-Cl | — | H | 3-chloro-2-thienyl-C(O)— | phenyl |
| 342 | O | 6-Cl | — | H | CHF₂—CF₂—C(O)— | phenyl |
| 343 | O | 6-Cl | — | H | CClF₂—CFCl—CF₂—C(O)— | phenyl |
| 344 | O | 6-Cl | — | H | CHF₂—(CF₂)₇—C(O)— | phenyl |
| 345 | O | 6-Cl | — | H | CClF₂—CF₂—C(O)— | phenyl |
| 346 | O | 6-Cl | — | H | 1-(4-Cl-phenyl)-5-propyl pyrazol-4-yl-C(O)— | phenyl |
| 347 | O | 6-Cl | — | H | trans-3-CF₃-phenyl-CH=CH—C(O)— | phenyl |
| 348 | O | 6-Cl | — | H | 4-C₅F₁₁O-phenyl-C(O)— | phenyl |
| 349 | O | 6-Cl | — | H | 4-C₇F₁₅-phenyl-C(O)— | phenyl |
| 350 | O | 6-Cl | — | H | 2,5-diCl-3-thienyl-C(O)— | phenyl |
| 351 | O | 6-Cl | — | H | 3-cyano-phenyl-C(O)— | phenyl |
| 352 | O | 6-Cl | — | H | iodoacetyl-C(O)— | phenyl |
| 353 | O | 6-Cl | — | H | 2,3-di-Cl-5-pyridyl-C(O)— | phenyl |
| 354 | O | 6-Cl | — | H | HOC(O)—(CH₂)₂—C(O)— | phenyl |
| 355 | O | 6-Cl | — | H | CH₃—C(O)—CH₂—C(O)— | phenyl |
| 356 | O | 6-Cl | — | H | CH₃CH(OH)—CH₂—C(O)— | phenyl |
| 357 | O | 6-Cl | — | H | (CH₃)₂C—CH₂—C(O)— | 3-furyl |
| 358 | O | 6-Cl | — | H | C₂H₅—C(O)— | 4-chloro-2-pyridyl |
| 359 | O | 6-Cl | — | H | (CH₃)₂C—CH₂—C(O)— | 4-chloro-2-pyridyl |
| 360 | O | 6-Cl | — | H | CH₃—C(O)—O—(CH₃)₂C—C(O)— | 4-chloro-2-pyridyl |
| 361 | O | 6-Cl | — | H | (CH₃)₂C(OH)—C(O)— | 4-chloro-2-pyridyl |
| 362 | O | 6-Cl | — | H | CH₃—C(O)—O—(CH₃)CH—C(O)— | 4-chloro-2-pyridyl |
| 363 | O | 6-Cl | — | H | CH₃CH(OH)—C(O)-4-chloro-2-pyridyl | |
| 364 | O | 6-Cl | — | CH₃ | CH₃—C(O)— | 4-chloro-2-pyridyl |
| 365 | O | 6-Cl | — | CH₃ | C₂H₅—C(O)— | 3-chloro-phenyl |
| 366 | O | 6-Cl | — | H | CH₃—C(O)— | 5-pyrimidinyl |
| 367 | O | 6-Cl | — | H | H | 3-methyl-2-pyridyl |
| 368 | O | 6-Cl | — | H | CH₃—C(O)— | 3-methyl-2-pyridyl |
| 369 | O | 6-Cl | — | H | (CH₃)₂CH—CH₂—C(O)— | 3-methyl-2-pyridyl |
| 370 | O | 6-Cl | — | H | CH₃—C(O)— | 4-hydroxymethyl-2-pyridyl |

TABLE-continued

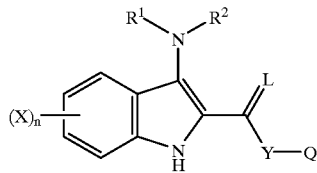

(I)

| Ex. # | L | X | Y | R¹ | R² | Q |
|---|---|---|---|---|---|---|
| 371 | O | 6-Cl (hydrochloride) | — | H | $C_2H_5$—C(O)— | 4-amino-2-pyridyl |
| 372 | O | 6-Cl | — | H | $CH_3$—C(O)— | 3-hydroxymethyl-2-furyl |
| 373 | O | 6-Cl | — | H | $(CH_3)_2CH$—$CH_2$—C(O)— | 4-hydroxymethyl-2-furyl |
| 374 | O | 6-Cl | — | H | $C_2H_5$—C(O)— | 4-hydroxymethyl-2-furyl |
| 375 | O | 6-Cl | — | H | $(CH_3)CH(OH)$—C(O)— | 4-hydroxymethyl-2-furyl |
| 376 | O | 6-Cl | — | H | H | 5-methyl-2-thiazoyl |
| 377 | O | 6-Cl | — | H | $(CH_3)_2C$=$CH_2$—C(O)— | 5-methyl-2-thiazoyl |
| 378 | O | 6-Cl | — | H | $CH_3$—C(O)— | 5-methyl-2-thioazoyl |
| 379 | O | 6-Cl | — | H | $CH_3$—C(O)— | 1-methyl-3-pyrrolyl |
| 380 | O | 6-Cl | — | H | $(AcO)(CH_3)_2C$—C(O)— | 4-methyl-2-pyridyl |
| 381 | O | 6-Cl | — | H | $(HO)(CH_3)_2C$—C(O)— | 4-methyl-2-pyridyl |
| 382 | O | 6-Cl | — | H | (S)—$(AcO)CH(CH_3)$—C(O)— | 4-methyl-2-pyridyl |
| 383 | O | 6-Cl | — | H | (S)—$(HO)CH(CH_3)$—C(O)— | 4-methyl-2-pyridyl |
| 384 | O | 6-Cl | — | H | $CH_2Cl$—C(O)— | 4-methyl-2-pyridyl |
| 385 | O | 6-Cl | — | H | $(CH_3)_2N$—$CH_2$—C(O)— | 4-methyl-2-pyridyl |
| 386 | O | 6-Cl | — | H | $CH_2Cl$—$CH_2$—C(O)— | 4-methyl-2-pyridyl |
| 387 | O | 6-Cl | — | H | $(CH_3)_2N$—$(CH_2)_2$—C(O)— | 4-methyl-2-pyridyl |
| 388 | O | 6-Cl | — | H | isopropyl-C(O)— | 3-HO-methyl-2-furyl |
| 389 | O | 6-Cl | — | H | ethyl-C(O)— | 2-$HN_2$-5-Cl-phenyl |
| 390 | O | 6-Cl (hydrochloride) | — | H | ethyl-C(O)— | 2-$HN_2$-5-Cl-phenyl |
| 391 | O | 6-Cl | — | H | ethyl-C(O)— | 2-acetylamino-5-Cl-phenyl |
| 392 | O | 6-Cl | — | H | ethyl-C(O)— | 3-HO-methyl-2-pyridyl |
| 393 | O | 7-Cl | — | H | methyl-C(O)— | phenyl |

What is claimed is:

1. A compound of the following formula:

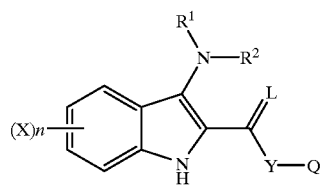

(I)

and the pharmaceutically acceptable salts thereof wherein
L is oxygen or sulfur; Y is a direct bond or $C_{1-4}$ alkylidene;
Q IS
   (a) $C_{1-6}$ alkyl or halosubstituted $C_{1-6}$ alkyl, said alkyl being optionally substituted with up to three substituents independently selected from hydroxy, $C_{1-4}$ alkoxy, amino and mono- or di-($C_{1-4}$ alkyl) amino,
   (b) $C_{3-7}$ cycloalkyl optionally substituted with up to three substituents independently selected from hydroxy, $C_{1-4}$ alkyl and $C_{1-4}$ alkoxy,
   (c) phenyl or naphthyl, said phenyl or naphthyl being optionally substituted with up to four substituents independently selected from
      (c-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_m R^3$, $SO_2NH_2$, $SO_2N(C_{1-4}$ alkyl$)_2$, amino, mono- or di-($C_{1-4}$ alkyl)amino, $NHSO_2R^3$, NHC(O)$R^3$, CN, $CO_2H$, $CO_2(C_{1-4}$ alkyl), $C_{1-4}$ alkyl-OH, $C_{1-4}$ alkyl$OR^3$, $CONH_2$, CONH($C_{1-4}$ alkyl), CON($C_{1-4}$ alkyl$)_2$ and —O—Y-phenyl, said phenyl being optionally substituted with one or two substituents independently selected from halo, $C_{1-4}$ alkyl, $CF_3$, hydroxy, $OR^3$, $S(O)_m R^3$, amino, mono- or di-($C_{1-4}$ alkyl)amino and CN,
   (d) a monocyclic aromatic group of 5 atoms, said aromatic group having one heteroatom selected from O, S and N and optionally containing up to three N atoms in addition to said heteroatom, and said aromatic group being substituted with up to three substituents independently selected from
      (d-1) halo, $C_{1-4}$ alkyl, halosubstituted $C_{1-4}$ alkyl, hydroxy, $C_{1-4}$ alkoxy, halosubstituted $C_{1-4}$ alkoxy, $C_{1-4}$ alkyl-OH, $S(O)_m R^3$, $SO_2NH_2$, $SO_2N(C_{1-4}$ alkyl$)_2$, amino, mono- or di-($C_{1-4}$ alkyl)amino, $NHSO_2R^3$, NHC(O)$R^3$, CN, $CO_2H$, $CO_2(C_{1-4}$ alkyl), $C_{1-4}$ alkyl-$OR^3$, $CONH_2$, CONH($C_{1-4}$ alkyl), CON($C_{1-4}$ alkyl$)_2$, phenyl, and mono-, di- or tri-substituted phenyl wherein the substituent is independently selected from halo, $CF_3$, $C_{1-4}$ alkyl, hydroxy, $C_{1-4}$ alkoxy, $OCF_3$, $SR^3$, $SO_2CH_3$, $SO_2NH_2$, amino, $C_{1-4}$ alkylamino and $NHSO_2R^3$,
   (e) a monocyclic aromatic group of 6 atoms, said aromatic group having one heteroatom which is N and optionally containing up to three atoms in addition to said heteroatom, and said aromatic group being substituted with up to three substituents independently selected from the above group (d-1);

$R^1$ is hydrogen or $C_{1-6}$ alkyl optionally substituted with a substituent selected independently from hydroxy, $OR^3$, nitro, amino, mono- or di-($C_{1-4}$ alkyl)amino, $CO_2H$, $CO_2(C_{1-4}$ alkyl), $CONH_2$, $CONH(C_{1-4}$ alkyl) and $CON(C_{1-4}$ alkyl)$_2$;

$R^2$ is
(a) hydrogen,
(b) $C_{1-4}$ alkyl,
(c) $C(O)R^5$ wherein $R_5$ is selected from
(c-1) $C_{1-22}$ alkyl or $C_{2-22}$ alkenyl, said alkyl or alkenyl being optionally substituted with up to four substituents independently selected from
(c-1-1) halo, hydroxy, $OR^3$, $S(O)_mR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$, $OC(O)R^3$, thienyl, naphthyl and groups of the following formulae:

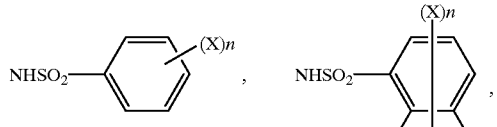

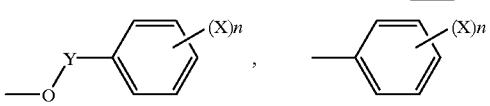

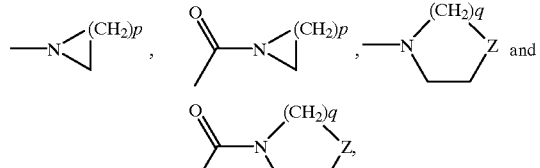

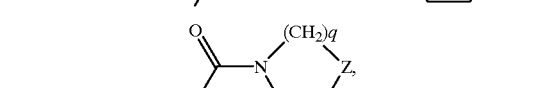

(c-2) $C_{1-22}$ alkyl or $C_{2-22}$ alkenyl, said alkyl or alkenyl being optionally substituted with five to forty-five halogen atoms,
(c-3) —Y—$C_{3-7}$ cycloalkyl or —Y—$C_{3-7}$ cycloalkenyl, said cycloalkyl or cycloalkenyl being optionally substituted with up to three substituent independently selected from
(c-3-1) $C_{1-4}$ alkyl, hydroxy, $OR^3$, $S(O)_mR^3$, amino, mono- or di-($C_{1-4}$ alkyl)amino, $CONH_2$, $CONH(C_{1-4}$ alkyl) and $CON(C_{1-4}$alkyl)$_2$,
(c-4) phenyl or naphthyl, said phenyl or naphthyl being optionally substituted with up to seven substituents independently selected from
(c-4-1) halo, $C_{1-8}$ alkyl, $C_{1-4}$ alkyl-OH, hydroxy, $C_{1-8}$alkoxy, halosubstituted $C_{1-8}$ alkyl, halosubstituted $C_{1-8}$ alkoxy, CN, nitro, $S(O)_mR^3$, $SO_2NH_2$, $SO_2NH(C_{1-4}$ alkyl), $SO_2N(C_{1-4}$ alkyl)$_2$, amino, $C_{1-4}$ alkylamino, di-($C_{1-4}$ alkyl) amino, $CONH_2$, $CONH(C_{1-4}$ alkyl), $CON(C_{1-4}$ alkyl)$_2$, $OC(O)R_3$, and phenyl optionally substituted with up to three substituents independently selected from halo, $C_{1-4}$ alkyl, hydroxy, $OCH_3$, $CF_3$, $OCF_3$, CN, nitro, amino, mono- or di-($C_{1-4}$ alkyl)amino, $CO_2H$, $CO_2(C_{1-4}$ alkyl) and $CONH_2$, (c-5) a monocyclic aromatic group as defined in (d) and (e) above, said aromatic group being optionally substituted with up to three substituents independently selected from
(c-5-1) halo, $C_{1-8}$ alkyl, $C_{1-4}$ alkyl-OH, hydroxy, $C_{1-8}$ alkoxy, $CF_3$, $OCF_3$, CN, nitro, $S(O)_mR^3$, amino, mono- or di-($C_{1-4}$ alkyl)amino, $CONH_2$, $CONH(C_{1-4}$ alkyl), $CON(C_{1-4}$ alkyl)$_2$, $CO_2H$ and $CO_2(C_{1-4}$ alkyl), and —Y-phenyl, said phenyl being optionally substituted with up to three substituents independently selected halogen, $C_{1-4}$ alkyl, hydroxy, $C_{1-4}$ alkoxy, $CF_3$, $OCF_3$, CN, nitro, $S(O)_mR^3$, amino, mono- or di-($C_{1-4}$ alkyl)amino, $CO_2H$, $CO_2$ ($C_{1-4}$ alkyl), $CONH_2$, $CONH(C_{1-4}$ alkyl) and $CON(C_{1-4}$alkyl)$_2$,
(c-6) a group of the following formula:

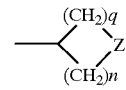

X is halo, $C_{1-4}$ alkyl, hydroxy, $C_{1-4}$ alkoxy, halosubstitued $C_{1-4}$ alkoxy, $S(O)_mR^3$, amino, mono- or di-($C_{1-4}$ alkyl)amino, $NHSO_2R^3$, nitro, halosubstitutued $C_{1-4}$ alkyl, CN, $CO_2H$, $CO_2(C_{1-4}$ alkyl), $C_{1-4}$ alkyl-OH, $C_{1-4}$ alkylOR$^3$, $CONH_2$, $CONH(C_{1-4}$ alkyl) or $CON(C_{1-4}$ alkyl)$_2$;

$R^3$ is $C_{1-4}$ alkyl or halosubstituted $C_{1-4}$ alkyl;

m is 0, 1 or 2; n is 0, 1, 2 or 3;

p is 1, 2, 3, 4 or 5; q is 2 or 3;

Z is oxygen, sulfur or $NR^4$; and $R^4$ is hydrogen, $C_{1-6}$ alkyl, halosubstitutued $C_{1-4}$ alkyl or —Y-phenyl, said phenyl being optionally substituted with up to two substituents independently selected from halo, $C_{1-4}$ alkyl, hydroxy, $C_{1-4}$ alkoxy, $S(O)_mR^3$, amino, mono- or di-($C_{1-4}$ alkyl)amino, $CF_3$, $OCF_3$, CN and nitro;

with the proviso that a group of formula —Y—Q is not methyl or ethyl when X is hydrogen; L is oxygen; $R^1$ is hydrogen; and $R^2$ is acetyl.

2. A compound according to claim 1, wherein

Y is a direct bond, methylene or ethylene;

Q is
(a) $C_{1-6}$ alkyl or halosubstituted $C_{1-6}$ alkyl, said alkyl being optionally substituted with up to two substituents independently selected from hydroxy, $C_{1-4}$alkoxy, amino and mono- or di-($C_{1-4}$alkyl) amino,
(b) $C_{3-7}$ cycloalkyl optionally substituted with up to two substituents independently selected from hydroxy, $C_{1-4}$ alkyl and $C_{1-4}$ alkoxy,
(c) phenyl or naphthyl, said phenyl or naphthyl being optionally substituted with up to four substituents independently selected from
(c-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_mR^3$, $SO_2NH_2$, $SO_2N(C_{1-4}$ alkyl)$_2$, amino, mono- or di-($C_{1-4}$ alkyl)amino, $NHSO_2R^3$, NHC (O)$R^3$, CN, $CO_2H$, $CO_2(C_{1-4}$ alkyl), $C_{1-4}$ alkyl-OH, $C_{1-4}$ alkylOR$^3$, $CONH_2$, $CONH(C_{1-4}$ alkyl) and $CON(C_{1-4}$ alkyl)$_2$,
(d) a monocyclic aromatic group of 5 atoms, said aromatic group having one heteroatom selected from O, S and N and optionally containing an N atom in addition to said heteroatom, and said aromatic group being substituted with up to three substitutents independently selected from
(d-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_mR^3$, $SO_2NH_2$, $SO_2N(C_{1-4}$ alkyl)$_2$, amino, mono- or di-($C_{1-4}$ alkyl)amino, $NHSO_2R^3$, NHC(O)$R^3$, CN, $CO_2H$, $CO_2(C_{1-4}$ alkyl), $C_{1-4}$ alkylOH, $C_{1-4}$ alkylOR$^3$, $CONH_2$, $CONH(C_{1-4}$ alkyl), $CON(C_{1-4}$ alkyl)$_2$, phenyl, and mono-, di- or tri-substituted phenyl wherein the substituent is independently selected from halo, $CF_3$, $C_{1-4}$ alkyl, hydroxy, $C_{1-4}$ alkoxy, $OCF_3$, $SR_3$, $SO_2CH_3$, $SO_2NH_2$, amino, mono- or di-($C_{1-4}$ alkyl)amino and $NHSO_2R^3$,
(e) a monocyclic aromatic group of 6 atoms, said aromatic group having one heteroatom which is N and optionally containing one or two N atoms in addition to said heteroatom, and said aromatic group being substituted with up to three substituents independently selected from the above group (d-1);

$R^1$ is hydrogen or $C_{1-6}$ alkyl optionally substituted with a substituent selected independently from hydroxy, $OR^3$, nitro, amino, mono- or di-($C_{1-4}$ alkyl)amino and $CO_2H$;

$R^2$ is
(a) hydrogen,
(b) $C_{1-4}$ alkyl,
(c) C(O)$R^5$ wherein $R^5$ is selected from
(c-1) $C_{1-17}$ alkyl or $C_{2-17}$ alkenyl, said alkyl or alkenyl being optionally substituted with up to four substituents independently selected from
(c-1-1) halo, hydroxy, $OR_3$, $S(O)_mR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$, OC(O)$R^3$, and groups of the following formulae:

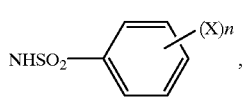 , 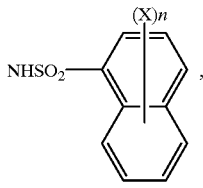 ,

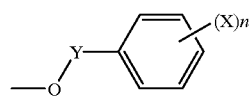 and 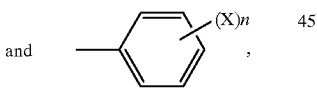 , (c-2) $C_{1-17}$ alkyl or $C_{2-17}$ alkenyl, said alkyl or alkenyl being optionally substituted with five to twenty halogen atoms,
(c-3) —Y—$C_{3-7}$ cycloalkyl or —Y—$C_{3-7}$ cycloalkenyl, said cycloalkyl or cycloalkenyl being optionally substituted with a substituent independently selected from $C_{1-4}$ alkyl, hydroxy and $OR^3$,
(c-4) phenyl or naphthyl, said phenyl or naphthyl being optionally substituted with up to three substituents independently selected from halo, $C_{1-8}$ alkyl, $C_{1-4}$ alkyl-OH, hydroxy, $C_{1-8}$ alkoxy, halosubstituted $C_{1-8}$ alkyl, halosubstituted $C_{1-8}$ alkoxy, CN, nitro, amino and mono- or di-($C_{1-4}$ alkyl) amino,
(c-5) a monocyclic aromatic group as defined in (d) and (e) above, said aromatic group being optionally substituted with up to three substituents independently selected from halo, $C_{1-8}$ alkyl, $C_{1-4}$ alkyl OH, hydroxy, $C_{1-8}$ alkoxy, $CF_3$, $OCF_3$, CN, nitro, amino and mono- or di-($C_{1-4}$alkyl)amino,
(c-6) tetrahydrofuryl, tetrahydropyrrolyl, tetrahydrothienyl or 1-methyl-tetrahydropyrrolyl;

X is halo, $C_{1-4}$ alkyl, hydroxy, $C_{1-4}$ alkoxy, halosubstitued $C_{1-4}$ alkoxy, amino, mono- or di-($C_{1-4}$ alkyl) amino, $NHSO_2R^3$, nitro, halosubstitutued $C_{1-4}$ alkyl, CN or $CO_2H$; and $R^3$ is $C_{1-4}$ alkyl or halosubstituted $C_{1-4}$ alkyl.

3. A compound according to claim 2, wherein
L is oxygen; Y is a direct bond or methylene;
Q is
(b) $C_{3-7}$ cycloalkyl optionally substituted with $C_{1-4}$ alkyl or $C_{1-4}$ alkoxy,
(c) phenyl or naphthyl, said phenyl or naphthyl being optionally substituted with up to three substituents independently selected from
(c-1) halo, $C_{1-4}$ alkyl, halosubstituted $C_{1-4}$ alkyl, hydroxy, $C_{1-4}$ alkoxy, halosubstituted $C_{1-4}$ alkoxy, amino, mono- or di-($C_{1-4}$ alkyl)amino, CN, $CO_2H$ and —$SR_3$,
(d) a monocyclic aromatic group of 5 atoms, said aromatic group having one heteroatom selected from O, S or N and optionally containing an N atom in addition to said heteroatom, and said aromatic group being substituted with up to three substitutents independently selected from
(d-1) halo, $C_{1-4}$ alkyl, halosubstituted $C_{1-4}$ alkyl, hydroxy, $C_{1-4}$ alkoxy, halosubstituted $C_{1-4}$ alkoxy, amino, mono- or di-($C_{1-4}$ alkyl)amino and $C_{1-4}$ alkyl-OH,
(e) a monocyclic aromatic group of 6 atoms, said aromatic group having one heteroatom which is N and optionally containing an N atom in addition to said heteroatom, and said aromatic group being substituted with up to three substituents independently selected from the above group (d-1);

$R^1$ is hydrogen or $C_{1-4}$ alkyl;
$R^2$ is
(a) hydrogen,
(c) C(O)$R^5$ wherein $R^5$ is selected from
(c-1) $C_{1-8}$ alkyl or $C_{2-8}$ alkenyl, said alkyl or alkenyl being optionally substituted with up to three substituents independently selected from
(c-1-1) halo, hydroxy, $OR_3$, $SOR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$ and OC(O)$R^3$,
(c-2) $C_{1-8}$ alkyl or $C_{2-8}$ alkenyl, said alkyl or alkenyl being optionally substituted with five to seventeen halogen atoms,
(c-3) —Y—$C_{3-7}$ cycloalkyl or —Y—$C_{3-7}$ cycloalkenyl, said cycloalkyl or cycloalkenyl being optionally substituted with a substituent independently selected independently from $C_{1-4}$ alkyl, hydroxy and $OR^3$,
(c-4) phenyl optionally substituted with up to three substituents independently selected from halo, $C_{1-4}$ alkyl and hydroxy,
(c-5) heteroaryl selected from pyridyl, quinolyl, thienyl, thiazolyl, pyrimidyl and indolyl, said heteroaryl being optionally substituted with up to two substituents independently selected from halo, $C_{1-4}$ alkyl, hydroxy, $C_{1-4}$ alkoxy and $CF_3$,
(c-6) tetrahydrofuryl or tetrahydrothienyl;

X is halo, $C_{1-4}$ alkyl, hydroxy, $C_{1-4}$ alkoxy, amino, nitro or CN; and $R^3$ is $C_{1-3}$ alkyl or $CF_3$.

4. A compound according to claim 3, wherein Y is a direct bond;

Q is phenyl, cyclohexyl optionally substituted with methyl, ethyl or methoxy, or a monocyclic aromatic group selected from pyridyl, pyrazinyl, thienyl, furyl, thiazolyl, imidazolyl and pyrolyl, said phenyl or aromatic group being optionally substituted with up to two substituents independently selected from halo, methyl, methoxy, amino and hydroxymethyl, $R^1$ is hydrogen or methyl;

$R^2$ is
  (a) hydrogen,
  (c) $C(O)R^5$ wherein $R^5$ is selected from
    (c-1) $C_{1-6}$ alkyl optionally substituted with up to two substituents independently selected from hydroxy, $OR^3$, $SOR^3$, nitro, amino, mono- or di-($C_{1-4}$ alkyl) amino, $NHSO_2R^3$, $CO_2H$, $CO_2(C_{1-4}$ alkyl), $CONH_2$, $CONH(C_{1-4}$ alkyl), $CON(C_{1-4}$ alkyl)$_2$, $OC(O)R^3$ and phenyl,
    (c-2) trifluoromethyl or trichloromethyl,
    (c-3) cyclopropyl or cyclohexyl,
    (c-4) phenyl or halophenyl,
    (c-5) thienyl,
    (c-6) tetrahydrofuryl;

X is chloro, fluoro or cyano; and $R^3$ is methyl, ethyl, propyl or $CF_3$.

5. A compound according to claim 4, wherein Y is a direct bond;

Q is phenyl, 3-methoxyphenyl, 3-methylphenyl, 2-chlorophenyl, 3-chlorophenyl, 3-bromophenyl, 2-pyridyl, 4-chloro-2-pyridyl, 4-methyl-2-pyridyl, 4-methoxy-2-pyridyl, 2-pyrazinyl, cyclohexyl, 3-methyl-cyclohexyl, 3-$NH_2$-phenyl, 3-methylcyclohexyl, 3-hydroxymethyl-2-furyl or 3-fluorophenyl;

$R^1$ is hydrogen or methyl;

$R^2$ is hydrogen, $CH_3$—C(O)—, $(CH_3)_2C(O)$—, phenyl-C(O)—, $C_2H_5$—C(O)—, $C_3H_7$—C(O)—, cyclohexyl-C(O)—, $(CH_3)_2CH$—$CH_2$—C(O)—, cyclopropyl-C(O)—, $CH_3$—O—$CH_2$—C(O)—, 2-chlorophenyl-C(O)—, $C_2H_5$—O—C(O)—$CH_2$—C(O)—, $(CH_3)_2CH$—C(O)—, 2-tetrahydrofuryl-C(O)—, $(CH_3O)(CH_3)C$—C(O)—, $CF_3$—$CH_2$—C(O)—, cyclopropyl-$CH_2$—C(O)—, $CH_3S$—$CH_2$—C(O)—, $(CH_3)_2N$—$CH_2$—C(O)— or $(CH_3)_2C(OH)$—C(O)—;

X is 6-chloro, 6-fluoro, 6-cyano or 6-nitro; and n is 1.

6. A compound according to claim 1 selected from 3-amino-2-benzoyl-6-chloroindole; 3-acetylamino-2-benzoyl-6-chloroindole;
2-benzoyl-6-chloro-3-(isobutyrylamino)indole;
3-(benzamido)-2-benzoyl-6-chloroindole;
2-benzoyl-6-chloro-3-(propionylamino)indole;
2-benzoyl-3-(butyrylamino)-6-chloroindole;
2-benzoyl-6-chloro-3-(cyclohexylcarboxamido)indole;
2-benzoyl-6-chloro-3-(isovalerylamino)indole;
2-benzoyl-6-chloro-3-(cyclopropylcarboxamido)indole;
2-benzoyl-6-chloro-3-(methoxyacetylamino)indole;
3-amino-6-chloro-2-(3-methoxybenzoyl)indole;
3-acetylamino-6-chloro-2-(3-methoxybenzoyl)indole;
3-amino-6-chloro-2-(3-methylbenzoyl)indole;
3-acetylamino-6-chloro-2-(3-methylbenzoyl)indole;
6-chloro-2-(3-methylbenzoyl)-3-(propionylamino)indole;
6-chloro-3-(methoxyacetylamino)-2-(3-methylbenzoyl) indole;
3-amino-6-chloro-2-(3-chlorobenzoyl)indole;
3-acetylamino-6-chloro-2-(3-chlorobenzoyl)indole;
6-chloro-2-(3-chlorobenzoyl)-3-(propionylamino)indole;
3-(butyrylamino)-6-chloro-2-(3-chlorobenzoyl)indole;
6-chloro-2-(3-chlorobenzoyl)-3-(isovalerylamino)indole;
6-chloro-2-(3-chlorobenzoyl)-3-(methoxyacetylamino) indole;
3-acetylamino-6-chloro-2-(3-fluorobenzoyl)indole;
3-amino-2-(3-bromobenzoyl)-6-chloroindole;
3-acetylamino-2-(3-bromobenzoyl)-6-chloroindole;
2-benzoyl-6-chloro-3-(2-chlorobenzamido)indole;
2-benzoyl-6-chloro-3-[(3-ethoxycarbonyl)propionylamino] indole;
(s)-(+)-2-benzoyl-6-chloro-3-[(2-hydroxypropionyl)amino] indole;
3-amino-6-chloro-2-(4-chloropyridine-2-carbonyl)indole;
3-acetylamino-6-chloro-2-(4-chloropyridine-2-carbonyl) indole;
3-amino-6-chloro-2-(4-methylpyridine-2-carbonyl)indole;
3-acetylamino-6-chloro-2-(4-methylpyridine-2-carbonyl) indole;
3-amino-6-chloro-2-(4-methoxypyridine-2-carbonyl)indole;
3-acetylamino-6-chloro-2-(4-methoxypyridine-2-carbonyl) indole;
6-chloro-3-isovalerylamino-2-(4-methoxypyridine-2-carbonyl)indole;
3-acetylamino-6-chloro-2-(pyrazine-2-carbonyl)indole;
3-acetylamino-6-chloro-2-(cyclohexanecarbonyl)indole;
3-acetylamino-2-benzoyl-6-fluoroindole;
3-acetylamino-2-benzoyl-6-cyanoindole;
2-benzoyl-6-chloro-3-[(2-tetrahydrofuryl)carboxamido) indole;
2-benzoyl-6-chloro-3-[(2-methoxypropionyl)amino]indole;
2-benzoyl-6-chloro-3-(3,3,3-trifluoropropionylamino) indole;
2-benzoyl-6-chloro-3-(cyclopropaneacetylamino)indole;
2-benzoyl-6-chloro-3-(methylthioacetylamino)indole;
2-benzoyl-6-chloro-3-[(N,N-dimethylaminoacetyl)amino] indole;
3-amino-6-chloro-2-(pyridine-2-carbonyl)indole;
3-acetylamino-6-chloro-2-(pyridine-2-carbonyl)indole;
3-acetylamino-2-(3-aminobenzoyl)-6-chloroindole hydrochloride;
3-acetylamino-6-chloro-2-(3-methylcyclohexylcarbonyl) indole;
3-(N-acetyl-N-methylamino)-6-chloro-2-(3-chlorobenzoyl) indole;
2-benzoyl-6-chloro-3-(N,N-dimethylamino)indole;
3-acetylamino-2-benzoyl-6-nitroindole;
3-actetylamino-6-chloro-2-(3-hydroxymethyl-2-furoyl) indole;
6-chloro-2-(4-chloropyridine-2-carbonyl)-3-(propionylamino)indole;
6-chloro-2-(4-chloropyridine-2-carbonyl)-3-(2-hydroxyisobutyrylamino)indole;
3-acetylamino-6-chloro-2-[2-(5-methylthiazoyl)]indole;
3-(2-acetoxyisobutyrylamino)-6-chloro-2-(4-chloropyridine-2-carbonyl)indole;
6-chloro-2-(4-chloropyridine-2-carbonyl)-3-(isovalerylamino)indole;
6-chloro-2-(4-chloropyridine-2-carbonyl)-3-[[(S)-2-hydroxypropionyl]amino]indole;
3-(N-acetyl-N-methylamino)-6-chloro-2-(4-chloropyridine-2-carbonyl)indole; and
2-(4-aminopyridine-2-carbonyl)-6-chloro-3-(propionylamino)indole hydrochloride.

7. A compound according to claim 6 selected from
3-acetylamino-2-benzoyl-6-chloroindole;
2-benzoyl-6-chloro-3-(isovalerylamino)indole;
3-acetylamino-6-chloro-2-(3-methylbenzoyl)indole;
3-acetylamino-6-chloro-2-(3-chlorobenzoyl)indole;
6-chloro-2-(3-chlorobenzoyl)-3-(propionylamino)indole;
3-acetylamino-6-chloro-2-(4-chloropyridine-2-carbonyl)indole;
3-acetylamino-6-chloro-2-(4-methylpyridine-2-carbonyl)indole;
2-benzoyl-6-chloro-3-(methylthioacetylamino)indole;
6-chloro-2-(4-chloropyridine-2-carbonyl)-3-(propionylamino)indole;
3-actetylamino-6-chloro-2-(3-hydroxymethyl-2-furoyl)indole;
6-chloro-2-(4-chloropyridine-2-carbonyl)-3-(2-hydroxyisobutyrylamino)indole; and
3-acetylamino-6-chloro-2-[2-(5-methylthiazoyl)]indole.

8. A compound according to claim 7 selected from 3-acetylamino-2-benzoyl-6-chloroindole;
2-benzoyl-6-chloro-3-(isovalerylamino)indole;
3-acetylamino-6-chloro-2-(3-methylbenzoyl)indole;
3-acetylamino-6-chloro-2-(3-chlorobenzoyl)indole;
6-chloro-2-(3-chlorobenzoyl)-3-(propionylamino)indole;
3-acetylamino-6-chloro-2-(4-methylpyridine-2-carbonyl)indole;
2-benzoyl-6-chloro-3-(methylthioacetylamino)indole;
6-chloro-2-(4-chloropyridine-2-carbonyl)-3-(propionylamino)indole; and
6-chloro-2-(4-chloropyridine-2-carbonyl)-3-(2-hydroxyisobutyrylamino)indole.

9. A pharmaceutical composition useful for the treatment of a medical condition in which prostaglandins are implicated as pathogens, which comprises a compound of the formula (I) of claim 1, and a pharmaceutically inert carrier.

10. A pharmaceutical composition useful for the treatment of a medical condition in which prostaglandins are implicated as pathogens, which comprises a compound of the formula (I):

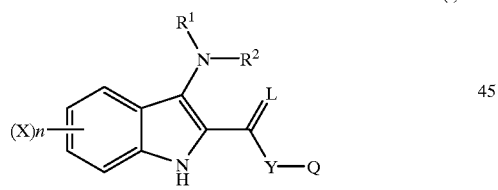

(I)

and the pharmaceutically acceptable salts thereof wherein
L is oxygen or sulfur; Y is a direct bond or $C_{1-4}$ alkylidene;
Q is
(a) $C_{1-6}$ alkyl or halosubstituted $C_{1-6}$ alkyl, said alkyl being optionally substituted with up to three substituents independently selected from hydroxy, $C_{1-4}$alkoxy, amino and mono- or di-($C_{1-4}$alkyl)amino,
(b) $C_{3-7}$ cycloalkyl optionally substituted with up to three substituents independently selected from hydroxy, $C_{1-4}$ alkyl and $C_{1-4}$ alkoxy,
(c) phenyl or naphthyl, said phenyl or naphthyl being optionally substituted with up to four substituents independently selected from
(c-1) halo, $C_{1-4}$ alkyl, halosubstituted $C_{1-4}$ alkyl, hydroxy, $C_{1-4}$ alkoxy, halosubstituted $C_{1-4}$ alkoxy, $S(O)_mR^3$, $SO_2NH_2$, $SO_2N(C_{1-4}$ alkyl$)_2$, amino, mono- or di-($C_{1-4}$ alkyl)amino, $NHSO_2R^3$, $NHC(O)R^3$, CN, $CO_2H$, $CO_2(C_{1-4}$ alkyl), $C_{1-4}$ alkyl-OH, $C_{1-4}$ alkylOR$^3$, $CONH_2$, $CONH(C_{1-4}$ alkyl), $CON(C_{1-4}$ alkyl$)_2$ and —O—Y-phenyl, said phenyl being optionally substituted with one or two substituents independently selected from halo, $C_{1-4}$ alkyl, $CF_3$, hydroxy, $OR^3$, $S(O)_mR^3$, amino, mono- or di-($C_{1-4}$ alkyl)amino and CN, (d) a monocyclic aromatic group of 5 atoms, said aromatic group having one heteroatom selected from O, S and N and optionally containing up to three N atoms in addition to said heteroatom, and said aromatic group being substituted with up to three substitutents independently selected from
(d-1) halo, $C_{1-4}$ alkyl, halosubstituted $C_{1-4}$ alkyl, hydroxy, $C_{1-4}$ alkoxy, halosubstituted $C_{1-4}$ alkoxy, $C_{1-4}$ alkyl-OH, $S(O)_mR^3$, $SO_2NH_2$, $SO_2N(C_{1-4}$ alkyl$)_2$, amino, mono- or di-($C_{1-4}$ alkyl)amino, $NHSO_2R^3$, $NHC(O)R^3$, CN, $CO_2H$, $CO_2(C_{1-4}$ alkyl), $C_{1-4}$ alkyl-OR$^3$, $CONH_2$, $CONH(C_{1-4}$ alkyl), $CON(C_{1-4}$ alkyl$)_2$, phenyl, and mono-, di- or tri-substituted phenyl wherein the substituent is independently selected from halo, $CF_3$, $C_{1-4}$ alkyl, hydroxy, $C_{1-4}$ alkoxy, $OCF_3$, $SR^3$, $SO_2CH_3$, $SO_2NH_2$, amino, $C_{1-4}$ alkylamino and $NHSO_2R^3$, (e) a monocyclic aromatic group of 6 atoms, said aromatic group having one heteroatom which is N and optionally containing up to three atoms in addition to said heteroatom, and said aromatic group being substituted with up to three substituents independently selected from the above group (d-1);

$R^1$ is hydrogen or $C_{1-6}$ alkyl optionally substituted with a substituent selected independently from hydroxy, $OR^3$, nitro, amino, mono- or di-($C_{1-4}$ alkyl)amino, $CO_2H$, $CO_2(C_{1-4}$ alkyl), $CONH_2$, $CONH(C_{1-4}$ alkyl) and $CON(C_{1-4}$ alkyl$)_2$;

$R^2$ is
(a) hydrogen, (b) $C_{1-4}$ alkyl,
(c) $C(O)R^5$ wherein $R^5$ is selected from
(c-1) $C_{1-22}$ alkyl or $C_{2-22}$ alkenyl, said alkyl or alkenyl being optionally substituted with up to four substituents independently selected from
(c-1-1) halo, hydroxy, $OR^3$, $S(O)_mR^3$, nitro, amino, mono- or di-($C_{1-4}$ alkyl)amino, $NHSO_2R^3$, $CO_2H$, $CO_2(C_{1-4}$ alkyl), $CONH_2$, $CONH(C_{1-4}$ alkyl), $CON(C_{1-4}$ alkyl$)_2$, $OC(O)R^3$, thienyl, naphthyl and groups of the following formulae:

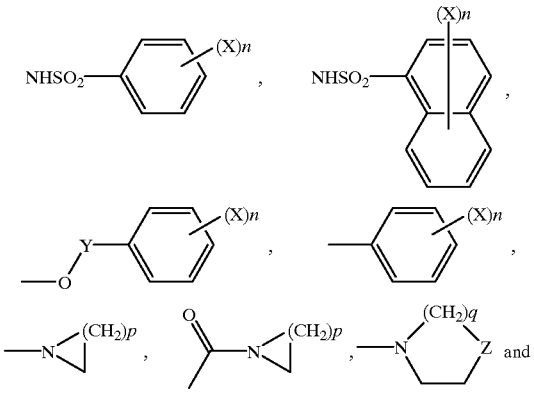

-continued

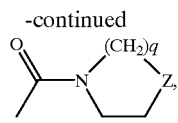

(c-2) $C_{1-22}$ alkyl or $C_{2-22}$ alkenyl, said alkyl or alkenyl being optionally substituted with five to forty-five halogen atoms, (c-3) —Y—$C_{3-7}$ cycloalkyl or —Y—$C_{3-7}$ cycloalkenyl, said cycloalkyl or cycloalkenyl being optionally substituted with up to three substituent independently selected from (c-3-1) $C_{1-4}$ alkyl, hydroxy, $OR^3$, $S(O)_mR^3$, amino, mono- or di($C_{1-4}$ alkyl)amino, $CONH_2$, $CONH(C_{1-4}$ alkyl) and $CON(C_{1-4}$alkyl$)_2$, (c-4) phenyl or naphthyl, said phenyl or naphthyl being optionally substituted with up to seven substituents independently selected from (c-4-1) halo, $C_{1-8}$ alkyl, $C_{1-4}$ alkyl-OH, hydroxy, $C_{1-8}$alkoxy, halosubstituted $C_{1-8}$ alkyl, halosubstituted $C_{1-8}$ alkoxy, CN, nitro, $S(O)_mR^3$, $SO_2NH_2$, $SO_2NH(C_{1-4}$ alkyl), $SO_2N(C_{1-4}$ alkyl$)_2$, amino, $C_{1-4}$ alkylamino, di-($C_{1-4}$ alkyl)amino, $CONH_2$, $CONH(C_{1-4}$ alkyl), $CON(C_{1-4}$ alkyl$)_2$, $OC(O)R_3$, and phenyl optionally substituted with up to three substituents independently selected from halo, $C_{1-4}$ alkyl, hydroxy, $OCH_3$, $CF_3$, $OCF_3$, CN, nitro, amino, mono- or di-($C_{1-4}$ alkyl)amino, $CO_2H$, $CO_2(C_{1-4}$ alkyl) and $CONH_2$, (c-5) a monocyclic aromatic group as defined in (d) and (e) above, said aromatic group being optionally substituted with up to three substituents independently selected from (c-5-1) halo, $C_{1-8}$ alkyl, $C_{1-4}$ alkyl-OH, hydroxy, $C_{1-8}$ alkoxy, $CF_3$, $OCF_3$, CN, nitro, $S(O)_mR^3$, amino, mono- or di-($C_{1-4}$ alkyl)amino, $CONH_2$, $CONH(C_{1-4}$ alkyl), $CON(C_{1-4}$ alkyl$)_2$, $CO_2H$ and $CO_2(C_{1-4}$ alkyl), and —Y-phenyl, said phenyl being optionally substituted with up to three substituents independently selected halogen, $C_{1-4}$ alkyl, hydroxy, $C_{1-4}$ alkoxy, $CF_3$, $OCF_3$, CN, nitro, $S(O)_mR^3$, amino, mono- or di-($C_{1-4}$ alkyl)amino, $CO_2H$, $CO_2(C_{1-4}$ alkyl), $CONH_2$, $CONH(C_{1-4}$ alkyl) and $CON(C_{1-4}$ alkyl$)_2$, (c-6) a group of the following formula:

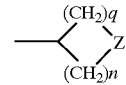

X is halo, $C_{1-4}$ alkyl, hydroxy, $C_{1-4}$ alkoxy, halosubstitutued $C_{1-4}$ alkoxy, $S(O)_mR^3$ amino, mono- or di-($C_{1-4}$ alkyl)amino, $NHSO_2R^3$, nitro, halosubstitutued $C_{1-4}$ alkyl, CN, $CO_2H$, $CO_2(C_{1-4}$ alkyl), $C_{1-4}$ alkyl-OH, $C_{1-4}$ alkyl$OR^3$, $CONH_2$, $CONH(C_{1-4}$ alkyl) or $CON(C_{1-4}$ alkyl$)_2$;

$R^3$ is $C_{1-4}$ alkyl or halosubstituted $C_{1-4}$ alkyl; m is 0, 1 or 2; n is 0, 1, 2 or 3; p is 1, 2, 3, 4 or 5; q is 2 or 3; Z is oxygen, sulfur or $NR^4$; and $R^4$ is hydrogen, $C_{1-6}$ alkyl, halosubstitutued $C_{1-4}$ alkyl or —Y-phenyl, said phenyl being optionally substituted with up to two substituents independently selected from halo, $C_{1-4}$ alkyl, hydroxy, $C_{1-4}$ alkoxy, $S(O)_mR^3$, amino, mono- or di-($C_{1-4}$ alkyl)amino, $CF_3$, $OCF_3$, CN and nitro, and a pharmaceutically inert carrier.

11. A method for the treatment of a medical condition in which prostaglandin E2 is implicated as a pathogen, in a mammalian subject, which comprises administering said pharmaceutical composition of claim 10.

\* \* \* \* \*